US011986475B1

(12) United States Patent
Lim et al.

(10) Patent No.: US 11,986,475 B1
(45) Date of Patent: May 21, 2024

(54) COMPOSITIONS AND METHODS FOR TREATING CANCER

(71) Applicants: A2A Pharmaceuticals, Inc., New York, NY (US); OncoCube Therapeutics LLC, Wilmington, DE (US)

(72) Inventors: Chaemin Lim, New York, NY (US); Sridhar Vempati, Edison, NJ (US); Erden Banoglu, Ankara (TR); Burcu Caliskan, Ankara (TR); Ozgur Sahin, Charleston, SC (US)

(73) Assignees: A2A Pharmaceuticals, Inc., New York, NY (US); OncoCube Therapeutics LLC, Wilmington, DE (US)

( * ) Notice: Subject to any disclaimer, the term of this patent is extended or adjusted under 35 U.S.C. 154(b) by 0 days.

(21) Appl. No.: 18/389,078

(22) Filed: Nov. 13, 2023

Related U.S. Application Data

(63) Continuation of application No. PCT/US2023/016132, filed on Mar. 23, 2023.

(60) Provisional application No. 63/323,339, filed on Mar. 24, 2022.

(51) Int. Cl.
*A61K 31/501* (2006.01)
*A61P 35/00* (2006.01)

(52) U.S. Cl.
CPC ............ *A61K 31/501* (2013.01); *A61P 35/00* (2018.01)

(58) Field of Classification Search
CPC .. C07D 401/12; C07D 401/14; C07D 403/14; C07D 413/12; C07D 413/14; C07D 471/10; C07D 487/02; C07D 491/08; C07D 491/107; A61K 31/506; A61K 31/5377; A61K 31/541; A61P 35/04
See application file for complete search history.

(56) References Cited

U.S. PATENT DOCUMENTS

| | | | |
|---|---|---|---|
| 9,630,953 B2 | 4/2017 | Yao et al. | |
| 11,622,966 B2 | 4/2023 | Banoglu et al. | |
| 2006/0069110 A1* | 3/2006 | Andersen ............ | C07D 239/48 544/328 |
| 2016/0332989 A1 | 11/2016 | Wu et al. | |
| 2019/0337926 A1 | 11/2019 | Hashizume et al. | |
| 2021/0220369 A1 | 7/2021 | Banoglu et al. | |
| 2023/0183520 A1 | 6/2023 | Fujita et al. | |

FOREIGN PATENT DOCUMENTS

| | | |
|---|---|---|
| CN | 107089968 A | 8/2017 |
| EP | 2857392 A1 | 4/2015 |
| JP | 2016/065869 A | 4/2016 |
| WO | WO-03/018022 A1 | 3/2003 |
| WO | WO-2006/037117 A1 | 4/2006 |
| WO | WO-2007/026251 A2 | 3/2007 |
| WO | WO-2008/005538 A2 | 1/2008 |
| WO | WO-2011/120026 A1 | 9/2011 |
| WO | WO-2012/117059 A1 | 9/2012 |
| WO | WO-2013/102431 A1 | 7/2013 |
| WO | WO-2015/082583 A1 | 6/2015 |
| WO | WO-2016/146220 A1 | 9/2016 |
| WO | WO-2016/173557 A1 | 11/2016 |
| WO | WO-2016/196776 A2 | 12/2016 |
| WO | WO-2017/136315 A1 | 8/2017 |
| WO | WO-2018/002217 A1 | 1/2018 |
| WO | WO-2018/045957 A1 | 3/2018 |
| WO | WO-2018/231910 A1 | 12/2018 |
| WO | WO-2019/101843 A1 | 5/2019 |
| WO | WO-2019/161224 A1 | 8/2019 |
| WO | WO-2019/177374 A1 | 9/2019 |
| WO | WO-2020/018039 A2 | 1/2020 |
| WO | WO-2021/030623 A1 | 2/2021 |
| WO | WO-2021/097352 A1 | 5/2021 |
| WO | WO-2022/221194 A1 | 10/2022 |
| WO | WO-2023/183520 A1 | 9/2023 |

OTHER PUBLICATIONS

CAS Registry No. 499142-07-3 CA Index Name: 5-Pryimidinecarboxylic acid, 2-(methylthio)-4-[(3-phenyl-5-isoxazolyl)amino]-, ethyl ester Entered STN: Mar. 14, 2003.
Extended European Search Report for EP Application No. 20888312.4 dated Nov. 28, 2023.
ClinicalTrials, NCT06136884, "A First-In-Human, Phase 1 Study Evaluating Oral TACC3 PPI Inhibitor, AO-252, in Advanced Solid Tumors", National Institute of Health, 13 pages (Record updated Nov. 18, 2023).
Akbulut et al., "A Highly Potent TACC3 Inhibitor as a Novel Anticancer Drug Candidate," Molecular Cancer Therapeutics, 19(6): 1243-1254 (2020).
Akbulut et al., "A novel TACC3 inhibitor as an anti-cancer agent in breast cancer [abstract]," Cancer Research, 79(13): 4 pages (2019).
Akbulut et al., "A novel TACC3 inhibitor as an anti-cancer agent in breast cancer [abstract]," European Journal of Cancer, 103(S1): e71 Abstract 200(PB-051)(2018).
Campo et al., "Inhibition of TACC3 by a small molecule inhibitor in breast cancer," Biochemical and Biophysical Research Communications, 498(4): 1085-1092 (2018).
CAS Registry No. 2322029-91-2; CA Index Name: 4-Pyrimidinamine, 6-ethyl-5-fluoro-N-[3-(2-thienyl)-5-isoxazolyl]-; Entered STN: May 31, 2019.
CAS Registry No. 2326659-25-8; CA Index Name: 4-Pyrimidinamine, N-[3-(2-thienyl)-5-isoxazolyl]-6-(trifluoromethyl)-; Entered STN: Jun. 9, 2019.
CAS Registry No. 2328417-44-1; CA Index Name: 4-Pyrimidinamine, 2-cyclopropyl-6-methyl-N-[3-(2-thienyl)-5-isoxazolyl]-; Entered STN: Jun. 11, 2019.
CAS Registry No. 2329636-00-0; CA Index Name: 4-Pyrimidinamine, 6-ethyl-N-[3-(2-thienyl)-5-isoxazolyl]-; Entered STN: Jun. 11, 2019.

(Continued)

Primary Examiner — James D. Anderson
(74) Attorney, Agent, or Firm — Foley Hoag LLP; Lucas P. Watkins; Alexander J. Chatterley

(57) ABSTRACT

Disclosed herein are inhibitors of TACC and methods of treating certain diseases and disorders (e.g., diseases and disorders related to TACC).

28 Claims, 1 Drawing Sheet

(56) References Cited

OTHER PUBLICATIONS

CAS Registry No. 2329672-37-7; CA Index Name: 4-Pyrimidinamine, 2-methyl-N-[3-(2-thienyl)-5-isoxazolyl]-6-(trifluoromethyl) -; Entered STN: Jun. 11, 2019.
CAS Registry No. 2329697-20-1; CA Index Name: 2-Pyridinecarboxylic acid, 4-[[3-(2-thienyl)-5-isoxazolyl]amino]-, methyl ester; Entered STN: Jun. 11, 2019.
CAS Registry No. 2329701-76-8; CA Index Name: 4-Pyrimidinamine, 5,6-dimethyl-N-[3-(2-thienyl)-5-isoxazolyl]-; Entered STN: Jun. 11, 2019.
CAS Registry No. 2329961-45-5; CA Index Name: 4-Pyrimidinamine, 2-(1-methylethyl)- N-[3-(2-thienyl)-5-isoxazolyl]-; Entered STN: Jun. 12, 2019.
CAS Registry No. 2330400-57-0; CA Index Name: 4-Pyrimidinamine, 2-methyl-N-[3-(2-thienyl)-5-isoxazolyl]-; Entered STN: Jun. 12, 2019.
CAS Registry No. 2330488-91-8; CA Index Name: 4-Pyrimidinamine, 2,6-dimethyl-N-[3-(2-thienyl)-5-isoxazolyl]-; Entered STN: Jun. 12, 2019.
CAS Registry No. 2330625-68-6; CA Index Name: 4-Pyrimidinamine, 6-methyl-N-[3-(2-thienyl)-5-isoxazolyl]-; Entered STN: Jun. 12, 2019.
Chu-Farseeva et al., "Design and synthesis of potent dual inhibitors of JAK2 and HDAC based on fusing the pharmacophores of XL019 and vorinostat", *European journal of medicinal chemistry* 158: 593-619 (2018).
Extended European Search Report for EP Application No. 19209120.5 dated Mar. 17, 2020.
Extended European Search Report for EP Application No. EP 19837587 dated Mar. 9, 2022.
Ha et al., "TACC3 deregulates the DNA damage response and confers sensitivity to radiation and PARP inhibition", Oncogene, 34: 1667-1678, (2015).
Ha et al., "Transforming acidic coiled-coil proteins (TACCs) in human cancer", Cancer Letters, 336(1): 24-33, (2013).
International Search Report and Written Opinion for International Application No. PCT/TR2019/050164 dated Feb. 21, 2020.
International Search Report and Written Opinion for International Application No. PCT/TR2019/050951 dated Aug. 14, 2020.
International Search Report and Written Opinion for International Application No. PCT/US2020/060588 dated Mar. 4, 2021.
International Search Report and Written Opinion for International Application No. PCT/US2023/016132 dated May 15, 2023.
Lengerli et al., "Studies On the Synthesis and Anticancer Potential of Novel 2,4-Diaminopyrimidine Derivatives," EFMC-YMSC Abstract: 1 page (Sep. 8, 2022).
Lengerli, D., Akbulut O., Caliskan, B., Sahin, O., Banoglu, E ?nh?b?töru yen? 2,4-D?am?nop?r?m?d?n Türevler?n?n sentez?, Ant?— Kanser Etk? Potans?Yeller? ve ?laç Benzer? Özell?kler?n?n De?Erlend? r?lmes? üzer?ne ali?Malar. VI. Ulusal Farmasötik Kimya Kongresi (UMFKK2022), Istanbul—Türkiye, Aug. 26-29, 2022 (National Congress, Oral Presentation).
Lengerli, D., Akbulut O., Caliskan, B., Sahin, O., Banoglu, E., *Studies on the Synthesis and Anticancer Potential of Novel 2,4-Diaminopyrimidine Derivatives*. The 9th Young Medicinal Chemist Symposium (EFMC-YMCS 2022), Nice-France, Sep. 8-9, 2022 (International Congress, Oral Presentation). Scientific Programme.
Lin et al., "Discovery and evaluation of 3-phenyl-1 H-5-pyrazolylamine-based derivatives as potent, selective and efficacious inhibitors of FMS-like tyrosine kinase-3 (FLT3). Bioorganic & medicinal chemistry", 19(14): 4173-4182, (2011).
Saacti et al., "Targeting TACC3 represents a novel vulnerability in highly aggressive breast cancers with centrosome amplification" CDD press, 15 pages (2023).
Turk et al., "From cancer to pain target by automated selectivity inversion of a clinical candidate", Journal of Medicinal Chemistry, 61(11): 4851-4859, (2018).
Turkish Examination Report for TR application No. 2018/07464 dated Jun. 28, 2020.
Turkish Search Report for TR application No. 2018/07464 dated Feb. 21, 2020.
Wurdak et al., "A small molecule accelerates neuronal differentiation in the adult rat," PNAS, 107(38): 16542-16547 (2010).
Yao et al. "A small compound targeting TACC3 revealed its different spatiotemporal contributions for spindle assembly in cancer cells," Oncogene, 33(33): 4242-4252 (2013).
U.S. Appl. No. 17/058,982, Issued.
U.S. Appl. No. 18/286,469, Pending.
Lengerli, "Studies on the Synthesis and Investigation of Their Mechanisms of Action of Anti-Cancer-Active 2,4-Diamineprimidine Derivative Compounds" Gazi University, 362 Pages (2021).

\* cited by examiner

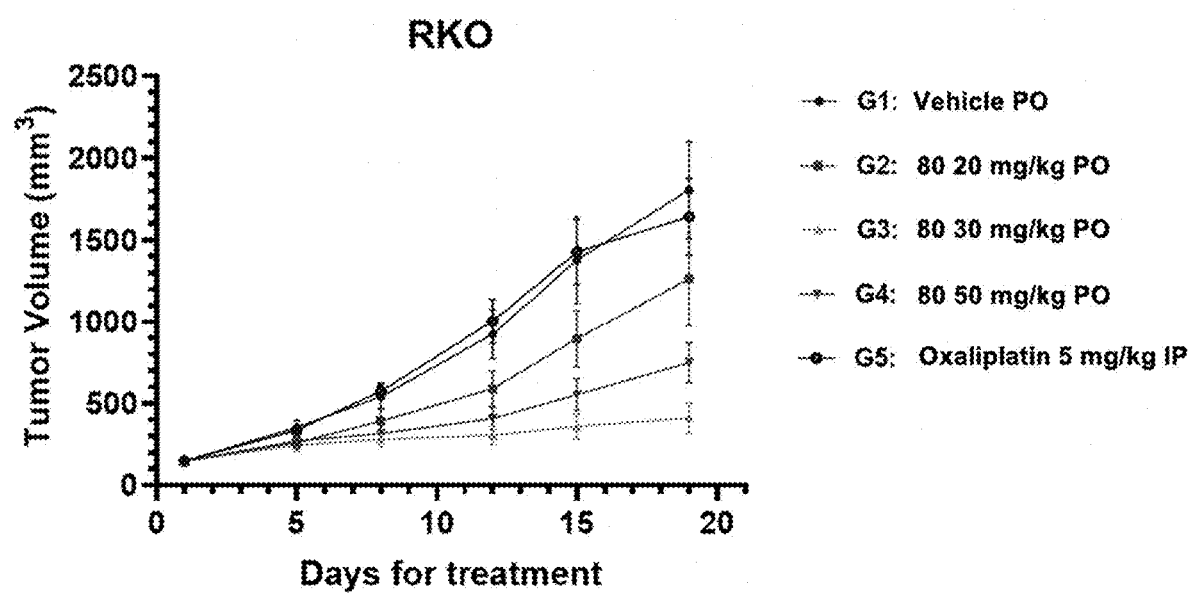

COMPOSITIONS AND METHODS FOR TREATING CANCER

RELATED APPLICATIONS

This application is a continuation of International Application No. PCT/US2023/016132, filed Mar. 23, 2023, which claims the benefit of U.S. Provisional Application No. 63/323,339, filed Mar. 24, 2022; the contents of which are hereby incorporated by reference in their entirety.

BACKGROUND

Cancer is a complex disease characterized by uncontrolled cell division. In the USA, among cancer types, breast cancer, lung cancer and colorectal cancer account for 50% of all cases in women while prostate, lung, and colorectal cancers account for 46% of all newly diagnosed cases in men (Siegel et al., 2021). Moreover, available treatments have numerous drawbacks and are of limited efficacy, such that new treatments for cancer are needed.

SUMMARY OF THE INVENTION

In one aspect, the present disclosure provides compounds of formula I or a pharmaceutically acceptable salt thereof:

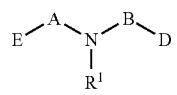

I wherein,
E and B are each independently aryl, heteroaryl, or heterocyclyl;
D is amino or heterocyclyl;
A is a six-membered heteroaryl; and
$R^1$ is H, alkyl, or benzyl.

In another aspect, the present disclosure provides a pharmaceutical composition comprising a compound disclosed herein and a pharmaceutically acceptable excipient.

In yet another aspect, the present disclosure provides methods of treating a disease or disorder mediated by Transforming acidic coiled-coil proteins (TACC) in a subject comprising administering a compound disclosed herein or a pharmaceutically acceptable salt thereof to the subject.

BRIEF DESCRIPTION OF THE DRAWINGS

FIG. 1 shows the exemplary biological activity of an exemplary compound of the disclosure. Compound 80 shows superior tumor growth inhibition in a xenograft model as compared to the standard of care.

DETAILED DESCRIPTION OF THE INVENTION

Transforming acidic coiled-coil proteins (TACC) family members are emerging as important proteins for microtubule and centrosome related functions. Vertebrates express 3 different isoforms of TACC: TACC1, TACC2, and TACC3. TACC plays a critical role in gene regulation, cell growth and differentiation, mRNA processing, transcription, migration and so on by interacting with different molecules involved in microtubule/centrosome dynamics/transcription (Ha et al., 2013). Members share a conserved domain, called the TACC domain, which is required for TACC proteins to interact with spindles and the centrosome apparatus (Gergely et al., 2000). Although the members of TACC family were described as centrosomal proteins, they are also distributed throughout the cell during interphase. For instance, TACC3 and TACC2 form a complex with different histone acetyltransferases, including hGCN5L2 and pCAF showing their regulatory function in transcription (Gangisetty et al., 2004). Noticeably, TACC3 interacts with MBD2 (mCpG-binding domain 2) in the interphase nucleus where it facilitates the association of MBD2 with histone acetyltransferases to reactivate methylated promoters.

TACC proteins levels are elevated in many cancer types including prostate cancer, hepatocellular carcinoma, non-small cell lung cancer and breast cancer and so on. TACC1, first member of TACC family, was independently discovered as a breast cancer amplicon 8p11 (Still et al., 1999) and later found to be able to promote mammary tumorigenesis possibly through the activation of Ras/PI3K signaling pathways (Cully et al., 2005). TACC2 has been found to promote androgen mediated growth in the prostate cancer and is associated with poor prognosis (Takayama et al., 2012). Furthermore, the overexpression of TACC2 leads to proliferation of breast cancer cells (Cheng et al., 2010). TACC3, when disrupted, also causes a range of different cellular outcomes including multi-polar spindle formation leading to mitotic arrest (Yao et al., 2012), chromosome misalignment resulting in caspase-dependent apoptosis (Schneider et al., 2007) and, in some cases, senescence (Schmidt et al., 2010). Moreover, knockdown of TACC3 suppresses tumorigenesis and cell growth in renal cell carcinoma (RCC) (Guo & Liu, 2018). The aforementioned studies show that the TACC family of proteins are critical molecules enrolled in spindle assembly of cancer cells, which makes them important and potential targets for cancer targeted therapy.

However, to date, there is no available inhibitor for TACC1 and TACC2 and there are merely two inhibitors targeting TACC3. KHS101, a small molecule TACC3 inhibitor, was first identified to promote neuronal differentiation in rats (Wurdak et al., 2010). Although tumor growth of glioblastoma (GBM) xenografts was suppressed through KHS101 treatment (Polson et al., 2018), KHS101 has many drawbacks, such as low oral systemic stability and high working doses (Wurdak et al., 2010). Another TACC3 inhibitor, SPL-B, has been shown to inhibit the centrosome microtubule nucleation in ovarian cancer cells and suppress tumor growth in ovarian cancer xenografts (Yao et al., 2014). However, like KHS101, SPL-B has not been approved for the treatment of cancer.

In view of the foregoing, there is a clear, unmet need, for new TACC inhibitors for the treatment of cancer and other TACC mediated diseases.

In one aspect, the present disclosure provides compounds of formula I or a pharmaceutically acceptable salt thereof:

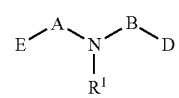

I wherein,
E and B are each independently aryl, heteroaryl, or heterocyclyl;
D is amino or heterocyclyl;
A is a six-membered heteroaryl; and
$R^1$ is H, alkyl, or benzyl.

In certain embodiments, A is pyridyl, pyridazinyl, pyrimidinyl, or pyrazinyl. In certain preferred embodiments, A is pyridyl. In other preferred embodiments, A is pyridazinyl.

In certain embodiments, the compound is represented by formula Ia or a pharmaceutically acceptable salt thereof:

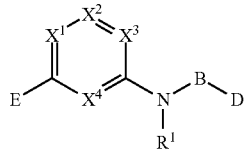

Ia wherein,

E and B are each independently aryl, heteroaryl, or heterocyclyl;

D is amino or heterocyclyl;

$X^1$ is N or $CR^2$;

$X^2$ is N or $CR^3$;

$X^3$ is N or $CR^4$;

$X^4$ is N or $CR^5$;

$R^1$ is H, alkyl, or benzyl; and $R^2$, $R^3$, $R^4$, and $R^5$ are each independently H, alkyl, alkenyl, alkynyl, halo, hydroxyl, carboxyl, acyl, acetyl, ester, thioester, alkoxy, phosphoryl, amino, amido, cyano, nitro, azido, alkylthio, alkenyl, alkynyl, cycloalkyl, alkylsulfonyl, or sulfonamido.

In certain embodiments, the compound is represented by formula IIb or a pharmaceutically acceptable salt thereof:

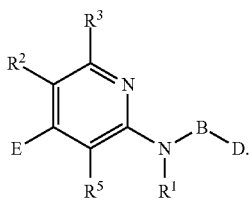

IIa

In certain preferred embodiments, $R^3$ is halo (e.g., fluoro).

In certain embodiments, the compound is represented by formula IIb or a pharmaceutically acceptable salt thereof:

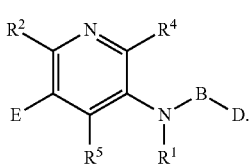

IIb

In certain preferred embodiments, $R^4$ is halo (e.g., fluoro). In other embodiments, $R^4$ is hydroxyl or alkoxy (e.g., methoxy).

In certain embodiments, the compound s represented by formula IIc or a pharmaceutically acceptable salt thereof:

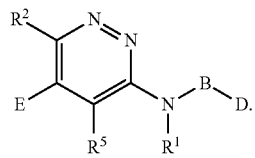

IIc

In certain embodiments, $R^2$ is H, alkyl (e.g., methyl or ethyl), halo (e.g., chloro), hydroxyl, alkoxy (e.g., methoxy), amino (e.g., amino alkyl, such as methylamino), amido (e.g., N-methyl amido), acetyl, carboxy, or ester (e.g., methyl ester). In certain preferred embodiments, $R^2$ is halo (e.g., fluoro). In other preferred embodiments, $R^2$ is H.

In certain embodiments, $R^5$ is H or alkyl (e.g., methyl). In certain preferred embodiments, $R^2$ is H.

In certain embodiments, $R^1$ is H. In certain embodiments, $R^1$ is alkyl (e.g., methyl or ethyl).

In certain embodiments, B is heteroaryl (e.g., pyridinyl, pyrimidinyl, or triazinyl). In certain preferred embodiments, B is pyrimidinyl.

In certain embodiments, B is substituted with at least one $R^4$ and each $R^4$ is independently selected from alkyl, alkenyl, alkynyl, halo, hydroxyl, oxo, carboxyl, acyl, acetyl, ester, thioester, alkoxy, phosphoryl, amino, amido, cyano, nitro, azido, alkylthio, alkenyl, alkynyl, cycloalkyl, alkylsulfonyl, and sulfonamido. In certain embodiments, B is substituted with at least one $R^4$ and each $R^4$ is independently selected from alkyl (e.g., methyl), oxo, and halo (e.g., chloro or fluoro). In certain preferred embodiments, B is substituted with 1 or 2 $R^4$.

In certain embodiments, the compound is represented by formula Ia or a pharmaceutically acceptable salt thereof:

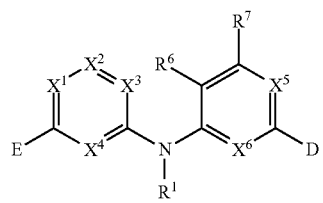

Ib wherein,

E and B are each independently aryl, heteroaryl, or heterocyclyl;

D is amino or heterocyclyl;

$X^1$ is N or $CR^2$;

$X^2$ is N or $CR^3$;

$X^3$ is N or $CR^4$;

$X^4$ is N or $CR^5$;

$X^5$ is N or $CR^8$;

$X^6$ is N or $CR^9$;

$R^1$ is H, alkyl, or benzyl; and $R^2$, $R^3$, $R^4$, $R^5$, $R^6$, $R^7$, $R^8$, and $R^9$ are each independently H, alkyl, alkenyl, alkynyl, halo, hydroxyl, oxo, carboxyl, acyl, acetyl, ester, thioester, alkoxy, phosphoryl, amino, amido, cyano, nitro, azido, alkylthio, alkenyl, alkynyl, cycloalkyl, alkylsulfonyl, or sulfonamido.

In certain embodiments, the compound is represented by formula IIIa or a pharmaceutically acceptable salt thereof:

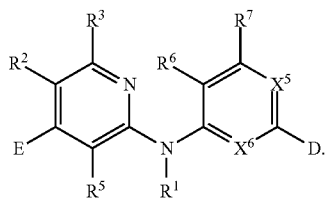

IIIa

In certain embodiments, the compound is represented by formula IIIb or a pharmaceutically acceptable salt thereof:

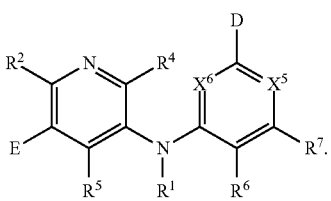

IIIb

In certain embodiments, the compound is represented by formula IIIc or a pharmaceutically acceptable salt thereof:

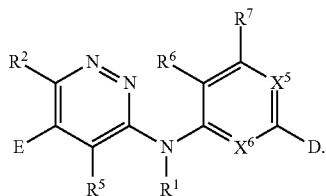

IIIc

In certain embodiments, $X^5$ is $CR^8$.

In certain embodiments, $R^8$ is H or halo (e.g., fluoro). In certain preferred embodiments, $R^8$ is fluoro.

In certain embodiments, $X^5$ is N.

In certain embodiments, $X^6$ is $CR^9$. In other embodiments, $X^6$ is N.

In certain embodiments, $R^9$ is H or halo (e.g., fluoro). In certain preferred embodiments, $R^9$ is fluoro.

In certain embodiments, the compound is represented by formula IVa or a pharmaceutically acceptable salt thereof:

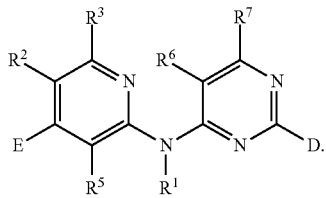

IVa

In certain embodiments, the compound is represented by formula IVb or a pharmaceutically acceptable salt thereof:

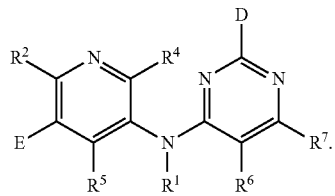

IVb

In certain embodiments, the compound is represented by formula IVc or a pharmaceutically acceptable salt thereof:

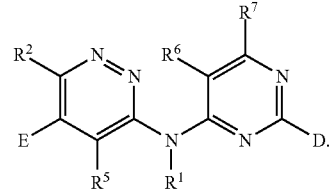

IVc

In certain embodiments, the compound is represented by formula IVd or a pharmaceutically acceptable salt thereof:

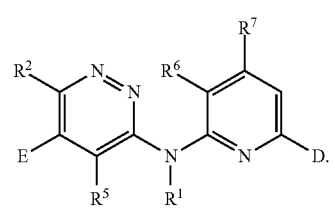

IVd

In certain embodiments, the compound is represented by formula IVe or a pharmaceutically acceptable salt thereof:

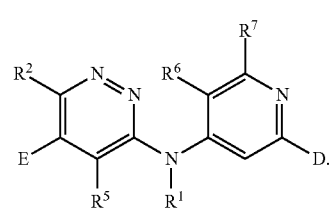

IVe

In certain embodiments, $R^6$ is H, hydroxyl, oxo, halo (e.g., fluoro), alkyl (e.g., methyl, hydroxyalkyl, such as hydroxymethyl, or alkyloxyalkyl, such as methoxyethyl), or alkoxy (e.g., methoxy). In certain preferred embodiments, $R^6$ is halo (e.g., fluoro). In other preferred embodiments, $R^6$ is H.

In certain embodiments, $R^7$ is H, alkyl (e.g., methyl), halo (e.g., fluoro), acyl (e.g., acetyl), or amido (e.g., methylamido). In certain preferred embodiments, $R^7$ is halo (e.g., fluoro).

In certain embodiments, D is amino. In certain embodiments, D is N-linked heterocyclyl (e.g., azetidinyl, pyrrolidinyl, piperidinyl, piperazinyl, morpholinyl, thiomorpholinyl, dioxidethiomorpholinyl, azabicyclooctanyl, oxaazabicyclooctane, hexahydrofuropyrrolyl, or azabicyclohexanyl).

In certain embodiments, D is substituted with at least one $R^{10}$ and each $R^{10}$ is independently selected from H, deuterium, alkyl, alkenyl, alkynyl, halo, hydroxyl, carboxyl, acyl, acetyl, ester, thioester, alkoxy, phosphoryl, amino, amido, cyano, nitro, azido, alkylthio, alkenyl, alkynyl, cycloalkyl, alkylsulfonyl, and sulfonamido; or D is substituted with at least two $R^5$s and two of the $R^5$s combine to complete a bicyclic heterocyclyl.

In certain embodiments, D is substituted with at least one $R^{10}$ and each $R^{10}$ is independently selected from alkyl (e.g., methyl, fluoromethyl, difluoromethyl, or trifluoromethyl), halo (e.g., fluoro), cycloalkyl (e.g., cyclopropyl or cyclobutyl), or heterocyclyl (e.g., oxetanyl). In certain embodiments, D is substituted with 1 or 2 $R^{10}$. In certain preferred embodiments, D is substituted with 2 $R^{10}$.

In certain embodiments, D has a structure represented by formula V or a pharmaceutically acceptable salt thereof:

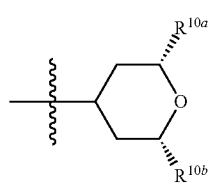

wherein, $R^{10a}$ and $R^{10b}$ are each independently selected from H, deuterium, alkyl, alkenyl, alkynyl, halo, hydroxyl, carboxyl, acyl, acetyl, ester, thioester, alkoxy, phosphoryl, amino, amido, cyano, nitro, azido, alkylthio, alkenyl, alkynyl, cycloalkyl, alkylsulfonyl, and sulfonamido.

In certain embodiments, $R^{10a}$ is alkyl (e.g., methyl, fluoromethyl, difluoromethyl, or trifluoromethyl), halo (e.g., fluoro), cycloalkyl (e.g., cyclopropyl or cyclobutyl), or heterocyclyl (e.g., oxetanyl). In certain preferred embodiments, $R^{10a}$ is methyl.

In certain embodiments, $R^{10b}$ is alkyl (e.g., methyl, fluoromethyl, difluoromethyl, or trifluoromethyl), halo (e.g., fluoro), cycloalkyl (e.g., cyclopropyl or cyclobutyl), or heterocyclyl (e.g., oxetanyl). In certain preferred embodiments, $R^{10b}$ is methyl.

In certain preferred embodiments, D is

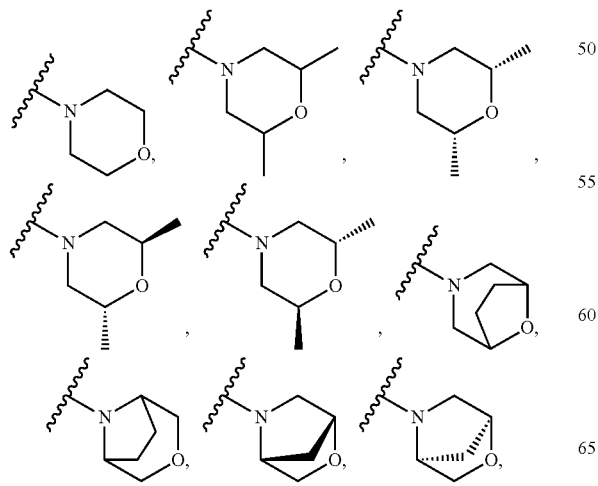

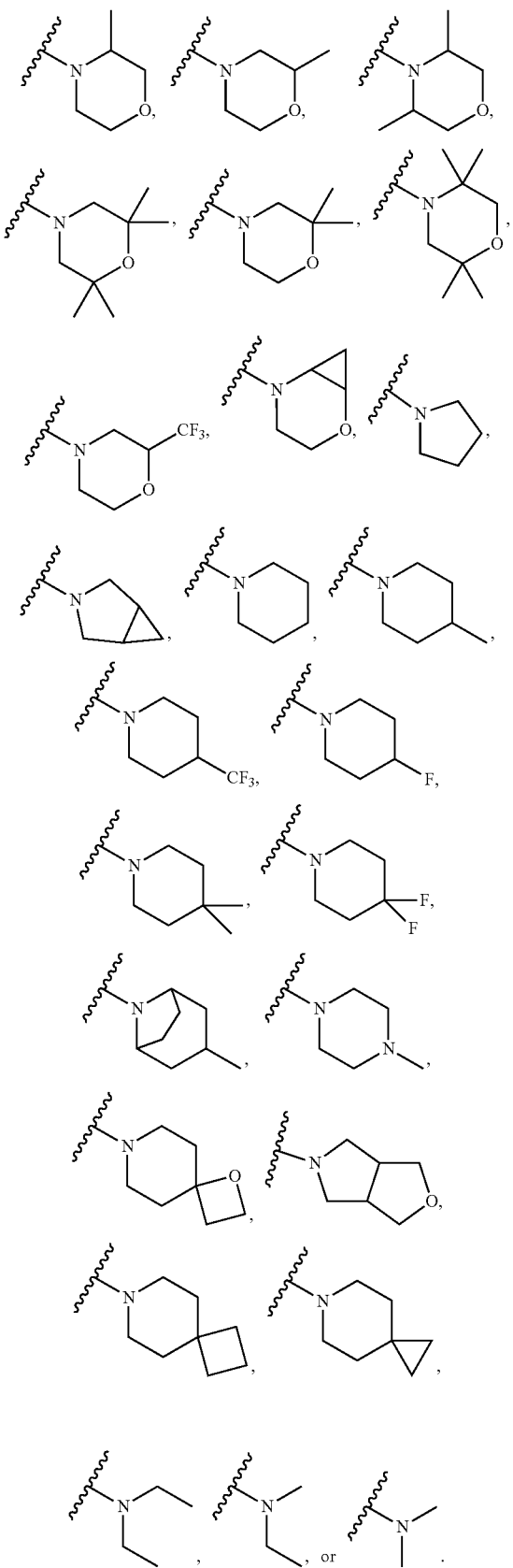

In certain embodiments, D is

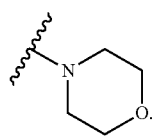

In certain embodiments, D is

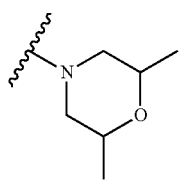

In a more preferred embodiment, D is

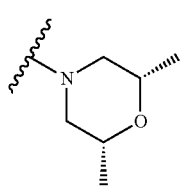

In another more preferred embodiment, D is

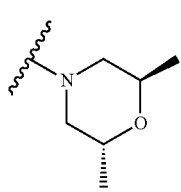

In another more preferred embodiment, D is

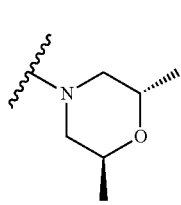

In certain embodiments, D is

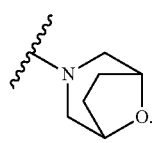 [SMILES: *N1CC2CCC(C1)O2]

In certain embodiments, D is

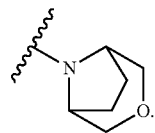 [SMILES: *N1C2CCC1COC2]

In certain embodiments, D is

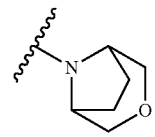

In certain embodiments, D is

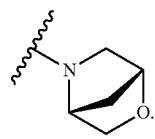 [SMILES: *N1C[C@H]2C[C@@H]1CO2]

In certain embodiments, D is

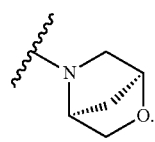 [SMILES: *N1C[C@@H]2C[C@H]1CO2]

In certain embodiments, D is

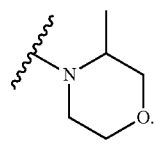 [SMILES: *N1CCOCC1C]

In certain embodiments, D is

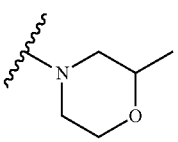

In certain embodiments, D is

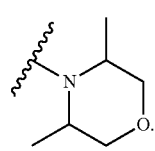 [SMILES: *N1C(C)COCC1C]

In certain embodiments, D is
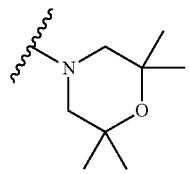
In certain embodiments, D is
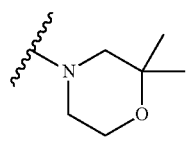
In certain embodiments, D is
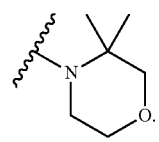 [SMILES: *N1CCOCC1(C)C]
In certain embodiments, D is
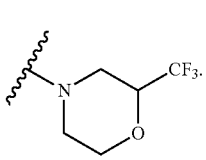 [SMILES: *N1CCOC(C(F)(F)F)C1]
In certain embodiments, D is
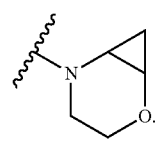 [SMILES: *N1CCOC2CC21]
In certain embodiments, D is
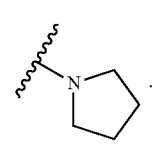 [SMILES: *N1CCCC1]
In certain embodiments, D is
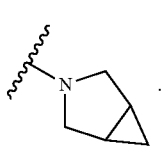 [SMILES: *N1CC2CC2C1]
In certain embodiments, D is
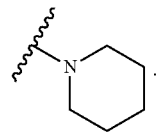 [SMILES: *N1CCCCC1]
In certain embodiments, D is
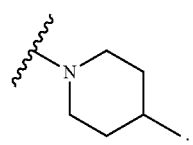 [SMILES: *N1CCC(C)CC1]
In certain embodiments, D is
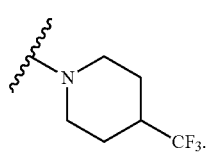
In certain embodiments, D is
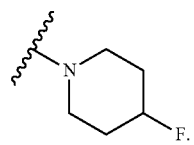 [SMILES: *N1CCC(F)CC1]
In certain embodiments, D is
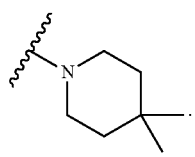 [SMILES: *N1CCC(C)(C)CC1]
In certain embodiments, D is
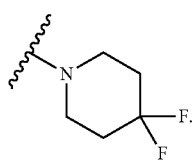 [SMILES: *N1CCC(F)(F)CC1]

In certain embodiments, D is

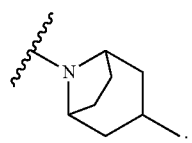 [SMILES: *N1C2CCC1CC(C)C2]

In certain embodiments, D is


In certain embodiments, D is

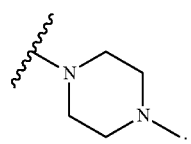 [SMILES: *N1CCN(C)CC1]

In certain embodiments, D is

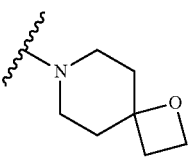

In certain embodiments, D is

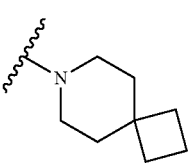

In certain embodiments, D is

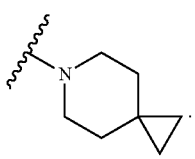 [SMILES: *N1CCC2(CC1)CC2]

In certain embodiments, D is

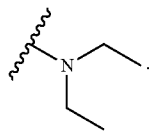 [SMILES: *N(CC)CC]

In certain embodiments, D is

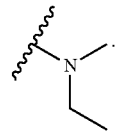 [SMILES: *N(C)CC]

In certain embodiments, D is

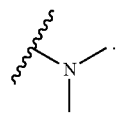 [SMILES: *N(C)C]

In certain embodiments, E is aryl (e.g., phenyl, dihydrobenzofuran, or benzodioxole). In certain preferred embodiments, E is phenyl. In other embodiments, E is heteroaryl (e.g., pyridinyl, pyrazinyl, benzofuranyl, or benzodioxyl). In certain preferred embodiments, E is pyridinyl. In other preferred embodiments, E is pyrazinyl.

In certain embodiments, E is substituted with at least one $R^{11}$ and each $R^{11}$ is independently selected from alkyl with alkyl, alkenyl, alkynyl, halo, hydroxyl, carboxyl, acyl, acetyl, ester, thioester, alkoxy, phosphoryl, amino, amido, cyano, nitro, azido, alkylthio, alkenyl, alkynyl, cycloalkyl, alkylsulfonyl, and sulfonamido. In certain embodiments, E is substituted with at least one $R^6$ and each $R^{11}$ is independently selected from alkyl (e.g., deuteroalkyl, methyl, ethyl, butyl, isopropyl, fluoromethyl, difluoromethyl, difluoroethyl, trifluoromethyl, or difluoroethyl), alkyloxy (e.g., deuteroalkyloxy, methoxy, ethoxy, fluoromethoxy, difluoromethoxy, or trifluoromethoxy), alkylthio (e.g., methylthio), amino (e.g., dimethylamino), hydroxyl, halo (e.g., fluoro or chloro), cyano, heterocyclyl (e.g., azetidinyl), and hydroxyl.

In certain preferred embodiments, E is substituted with 1 $R^{11}$. In other preferred embodiments, E is substituted with 2 $R^{11}$. In yet other embodiments, E is substituted with 3 $R^{11}$.

In certain embodiments, E has a structure represented by formula VIa, VIb, or VIc:

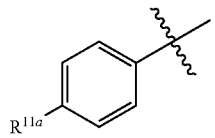

VIa

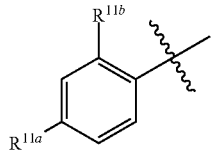

VIb

-continued

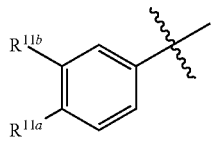
Vlc

Wherein $R^{11a}$ and $R^{11b}$ are each independently selected from hydrogen, deuterium, alkyl, alkenyl, alkynyl, halo, hydroxyl, carboxyl, acyl, acetyl, ester, thioester, alkoxy, phosphoryl, amino, amido, cyano, nitro, azido, alkylthio, alkenyl, alkynyl, cycloalkyl, alkylsulfonyl, and sulfonamido.

In certain embodiments, E has a structure represented by formula VIa:

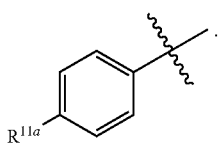
VIa

In certain embodiments, E has a structure represented by formula VIb:

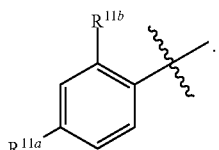
VIb

In certain embodiments, E has a structure represented by formula VIc:

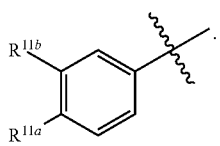
VIc

In certain embodiments, $R^{11a}$ is selected from alkyl (e.g., deuteroalkyl, methyl, ethyl, butyl, isopropyl, difluoromethyl, trifluoromethyl, or difluoroethyl), alkyloxy (e.g., deuteroalkyloxy, methoxy, ethoxy, difluoromethoxy, or trifluoromethoxy), alkylthio (e.g., methylthio), amino (e.g., dimethylamino), halo (e.g., fluoro or chloro), cyano, heterocyclyl (e.g., azetidinyl), and hydroxyl. In certain preferred embodiments, $R^{11a}$ is difluoromethoxy.

In certain embodiments, $R^{11b}$ is selected from alkyl (e.g., deuteroalkyl, methyl, ethyl, butyl, isopropyl, difluoromethyl, trifluoromethyl, or difluoroethyl), alkyloxy (e.g., deuteroalkyloxy, methoxy, ethoxy, difluoromethoxy, or trifluoromethoxy), alkylthio (e.g., methylthio), amino (e.g., dimethylamino), halo (e.g., fluoro or chloro), cyano, heterocyclyl (e.g., azetidinyl), and hydroxyl.

In certain preferred embodiments, E is

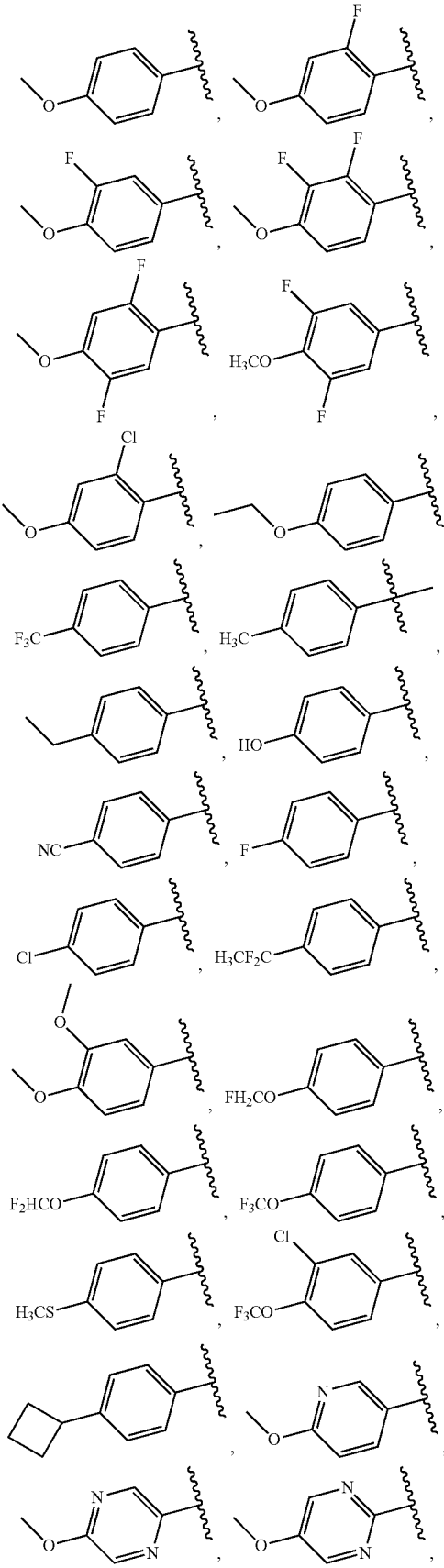

-continued
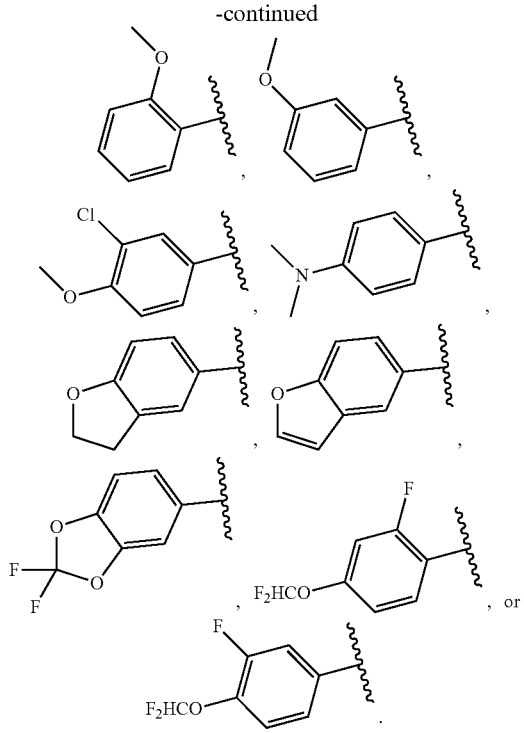, or
In certain embodiments, E is
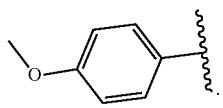 [SMILES: *c1ccc(OC)cc1]
In certain embodiments, E is
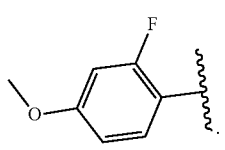 [SMILES: *c1ccc(OC)cc1F]
In certain embodiments, E is
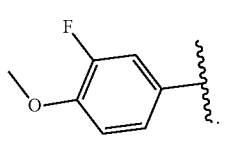 [SMILES: *c1ccc(OC)c(F)c1]
In certain embodiments, E is
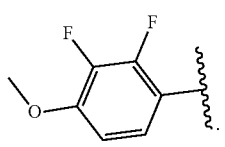 [SMILES: *c1ccc(OC)c(F)c1F]
In certain embodiments, E is
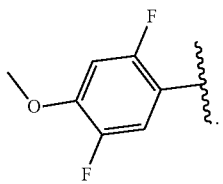 [SMILES: *c1cc(F)c(OC)cc1F]
In certain embodiments, E is
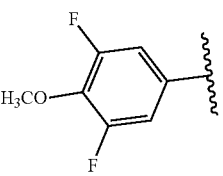
In certain embodiments, E is
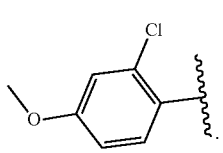 [SMILES: *c1ccc(OC)cc1Cl]
In certain embodiments, E is
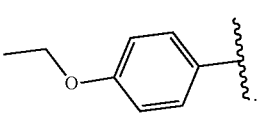 [SMILES: *c1ccc(OCC)cc1]
In certain embodiments, E is
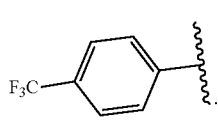
In certain embodiments, E is
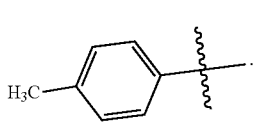
In certain embodiments, E is
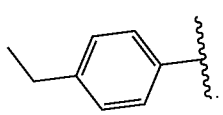 [SMILES: *c1ccc(CC)cc1]

In certain embodiments, E is

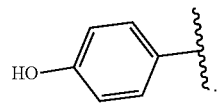 [SMILES: *c1ccc(C#N)cc1]

In certain embodiments, E is

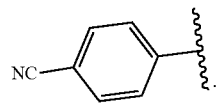

In certain embodiments, E is

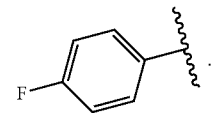

In certain embodiments, E is

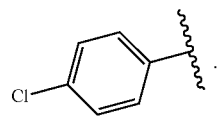

In certain embodiments, E is

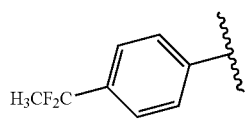

In certain embodiments, E is

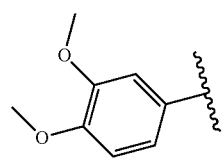

In certain preferred embodiments, E is

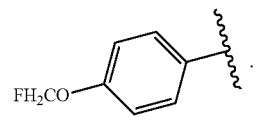

In even more preferred embodiments, E is

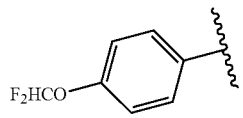

In certain embodiments,

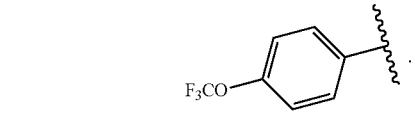

In certain embodiments, E is

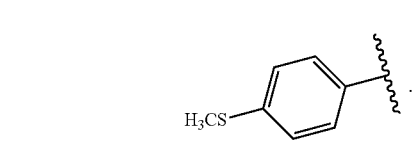

In certain embodiments, E is

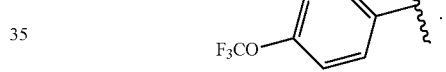

In certain embodiments, E is

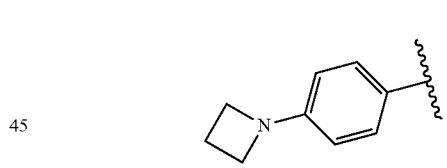

In certain embodiments, E is

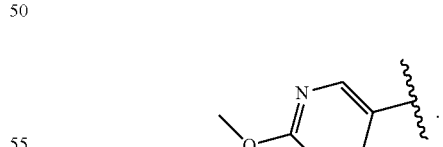

In certain embodiments, E is

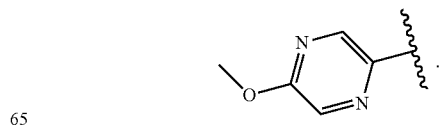

In certain embodiments, E is

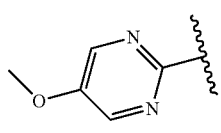

In certain embodiments, E is

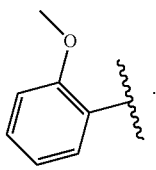 [SMILES: *c1ccccc1OC]

In certain embodiments, E is

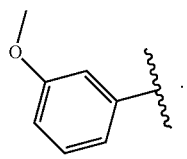 [SMILES: *c1cccc(OC)c1]

In certain embodiments, E is

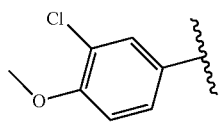

In certain embodiments, E is

In certain embodiments, E is

In certain embodiments, E is

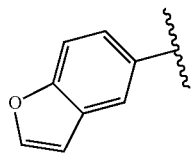

In certain embodiments, E is

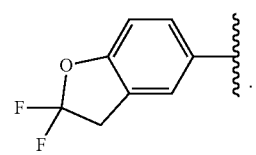 [SMILES: *c1ccc2c(c1)CC(F)(F)O2]

In certain embodiments, E is

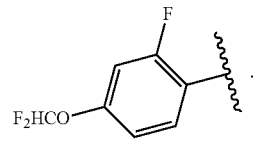 [SMILES: *c1ccc(OC(F)F)cc1F]

In certain embodiments, E is

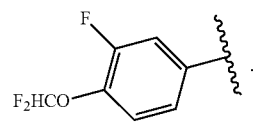

In certain embodiments, the compound is represented by formula VIIa, VIIb, or a pharmaceutically acceptable salt thereof:

VIIa

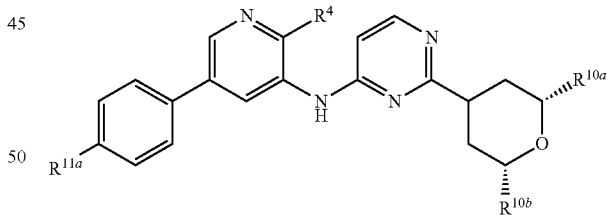

VIIb

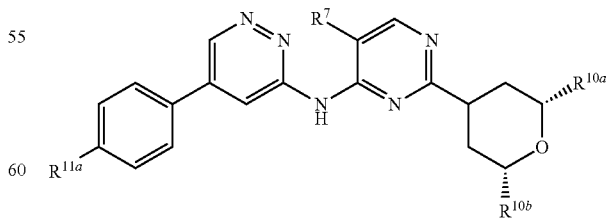

wherein;

$R^4$ and $R^7$ are each independently H, alkyl, alkenyl, alkynyl, halo, hydroxyl, oxo, carboxyl, acyl, acetyl, ester, thioester, alkoxy, phosphoryl, amino, amido, cyano, nitro, azido, alkylthio, alkenyl, alkynyl, cycloalkyl, alkylsulfonyl, or sulfonamide;

$R^{10a}$ and $R^{10b}$ are each H, deuterium, alkyl, alkenyl, alkynyl, halo, hydroxyl, carboxyl, acyl, acetyl, ester, thioester, alkoxy, phosphoryl, amino, amido, cyano, nitro, azido, alkylthio, alkenyl, alkynyl, cycloalkyl, alkylsulfonyl, and sulfonamide; and $R^{11a}$ is hydrogen, deuterium, alkyl, alkenyl, alkynyl, halo, hydroxyl, carboxyl, acyl, acetyl, ester, thioester, alkoxy, phosphoryl, amino, amido, cyano, nitro, azido, alkylthio, alkenyl, alkynyl, cycloalkyl, alkylsulfonyl, or sulfonamido.

In certain embodiments, the compound is represented by formula VIIa or a pharmaceutically acceptable salt thereof:

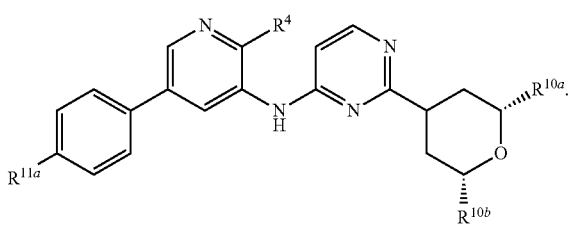

VIIa

In certain embodiments of formula VIIa, $R^4$ is alkyl (e.g., methyl), oxo, or halo (e.g., chloro or fluoro). In certain preferred embodiments of formula VIIa, $R^4$ is halo (e.g., chloro or fluoro).

In certain embodiments, the compound is represented by formula VIIb, or a pharmaceutically acceptable salt thereof:

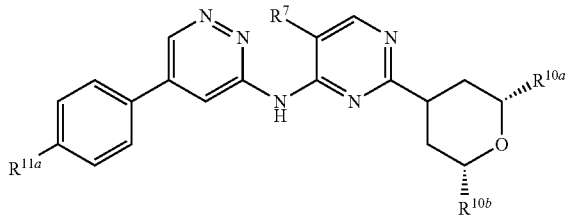

VIIb

In certain embodiments of formula VIIb, $R^7$ is H, hydroxyl, oxo, alkyl (e.g., methyl), halo (e.g., fluoro), acyl (e.g., acetyl), or amido (e.g., methylamido). In certain embodiments of formula VIIb, $R^7$ is H, alkyl (e.g., methyl), halo (e.g., fluoro), acyl (e.g., acetyl), or amido (e.g., methylamido). In certain preferred embodiments of formula VIIb, $R^7$ is halo (e.g., fluoro).

In certain preferred embodiments of formula VIIa or VIIb, $R^{10a}$ is alkyl (e.g., methyl).

In certain preferred embodiments of formula VIIa or VIIb, $R^{10b}$ is alkyl (e.g., methyl).

In certain embodiments of formula VIIa or VIIb, $R^{11a}$ is alkyl (e.g., deuteroalkyl, methyl, ethyl, butyl, isopropyl, fluoromethyl, difluoromethyl, difluoroethyl, trifluoromethyl, or difluoroethyl), alkyloxy (e.g., deuteroalkyloxy, methoxy, ethoxy, fluoromethoxy, difluoromethoxy, or trifluoromethoxy), alkylthio (e.g., methylthio), amino (e.g., dimethylamino), hydroxyl, halo (e.g., fluoro or chloro), cyano, heterocyclyl (e.g., azetidinyl), and hydroxyl. In certain preferred embodiments of formula VIIa or VIIb, $R^{11a}$ is difluoromethyl.

In certain embodiments, the compound is selected from a compound recited in Table 1 or a pharmaceutically acceptable salt thereof:

TABLE 1

Exemplary Compounds of the Present Disclosure

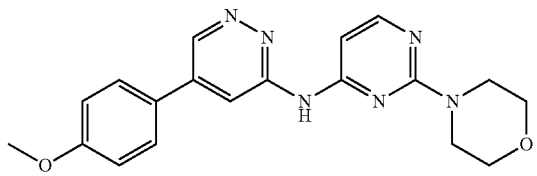

1

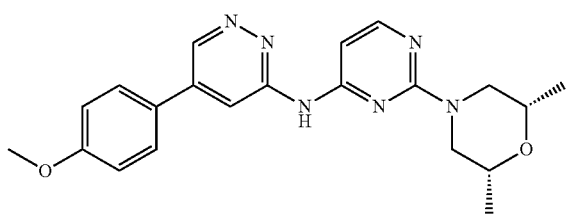

2

TABLE 1-continued
Exemplary Compounds of the Present Disclosure
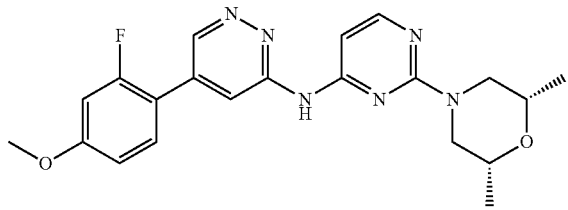
3
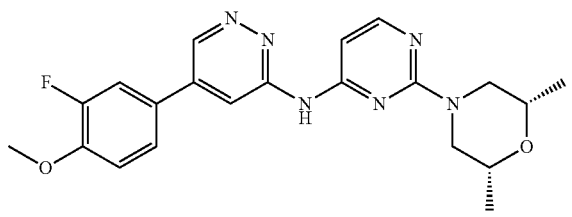
4
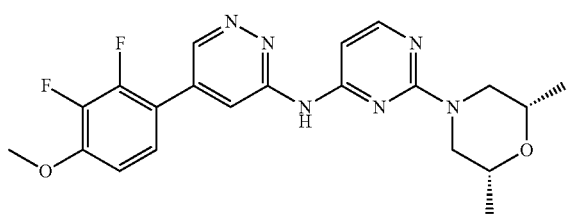
5
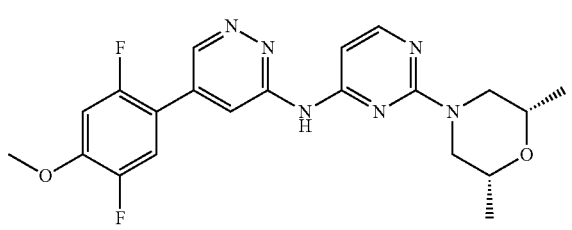
6
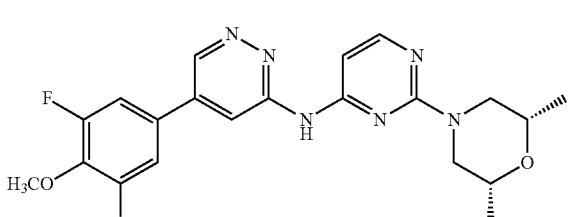
7
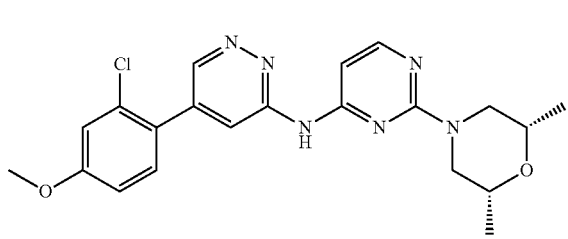
8

TABLE 1-continued
Exemplary Compounds of the Present Disclosure
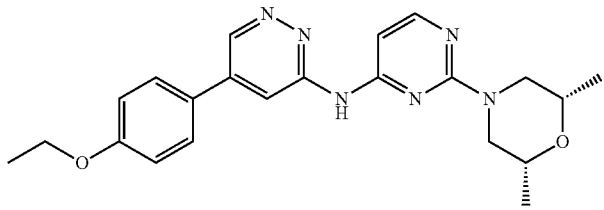
9
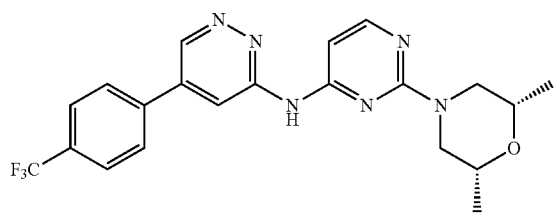
10
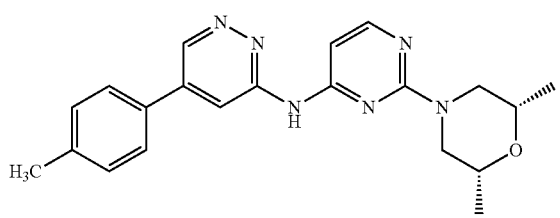
11
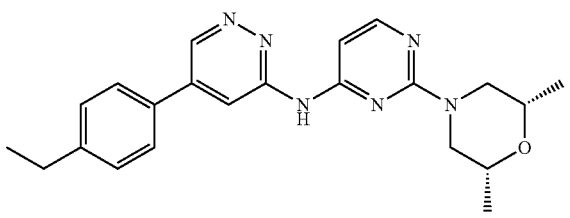
12
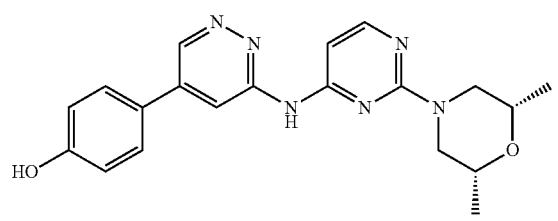
13
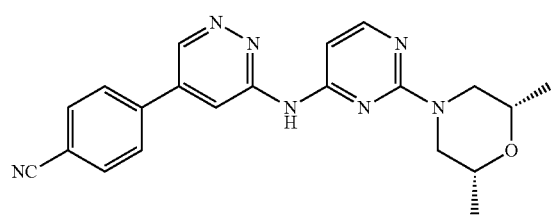
14

TABLE 1-continued
Exemplary Compounds of the Present Disclosure
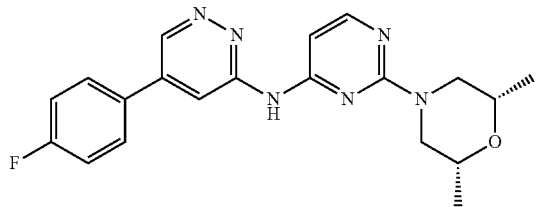
15
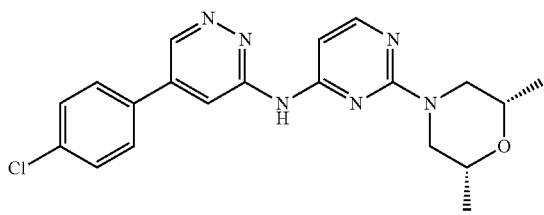
16
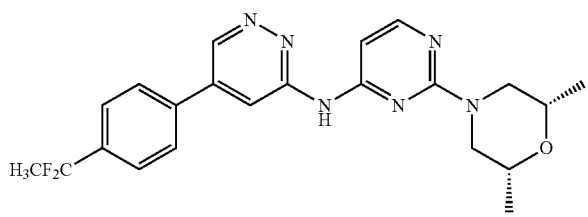
17
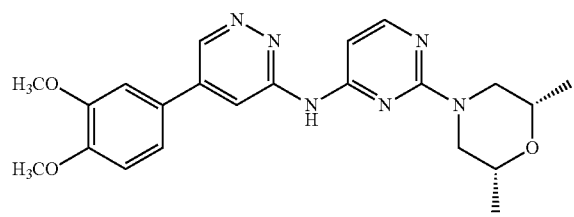
18
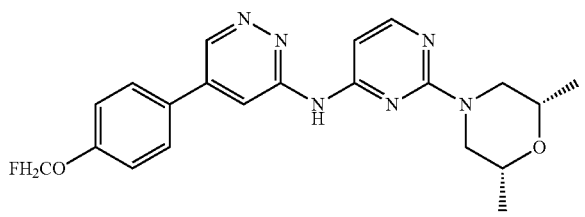
19
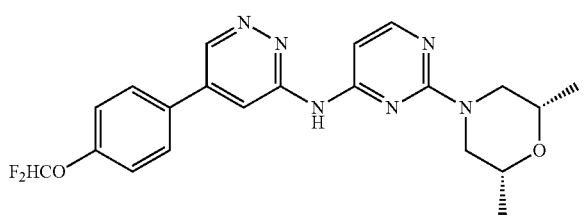
20

TABLE 1-continued
Exemplary Compounds of the Present Disclosure
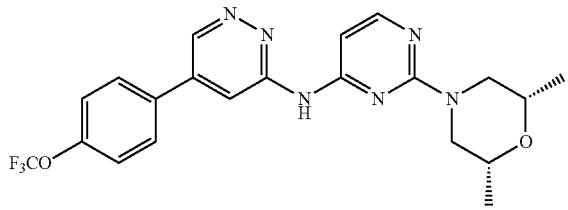
21
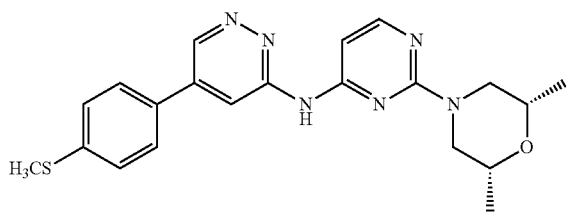
22
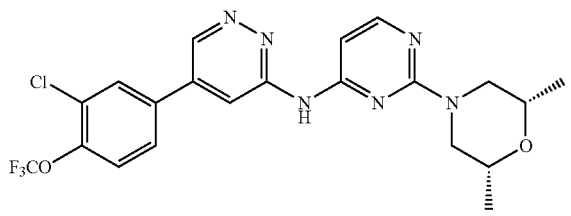
23
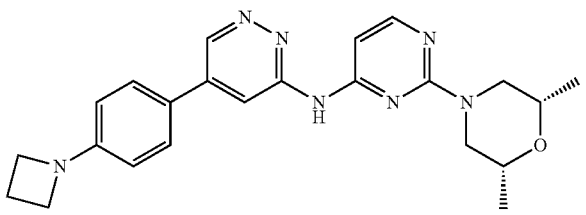
24
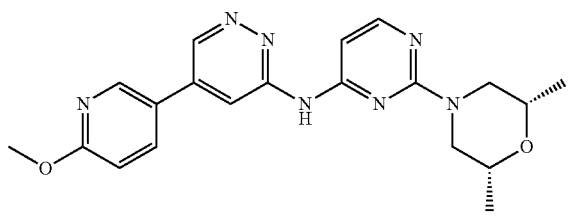
25
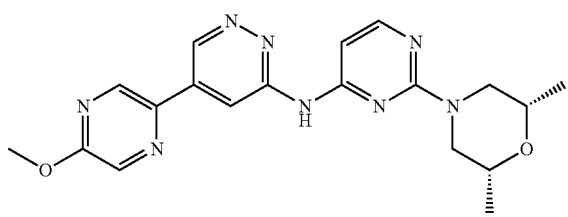
26

TABLE 1-continued
Exemplary Compounds of the Present Disclosure
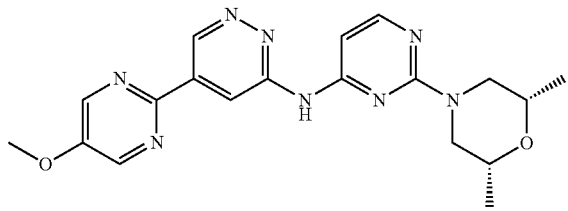
27
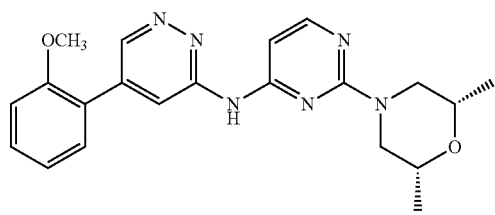
28
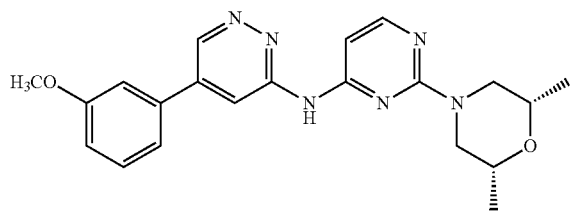
29
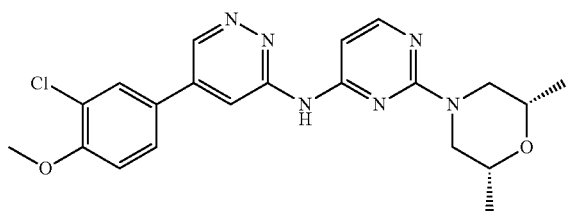
30
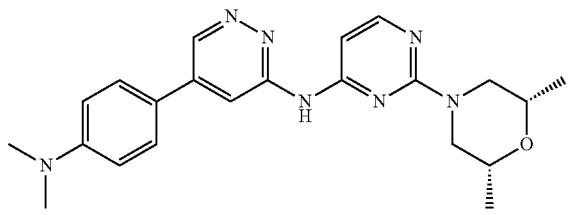
31
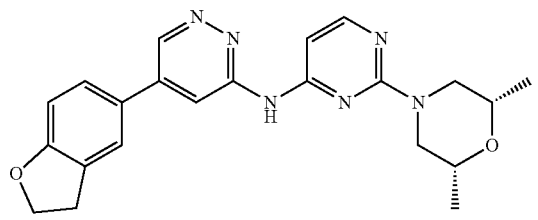
32

TABLE 1-continued
Exemplary Compounds of the Present Disclosure
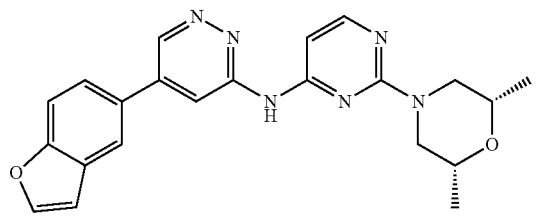
33
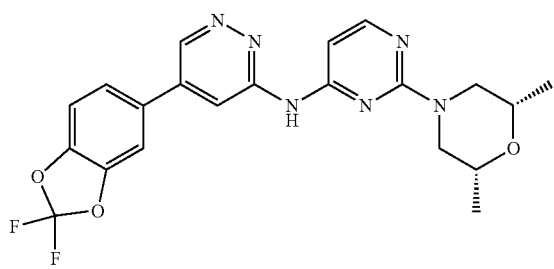
34
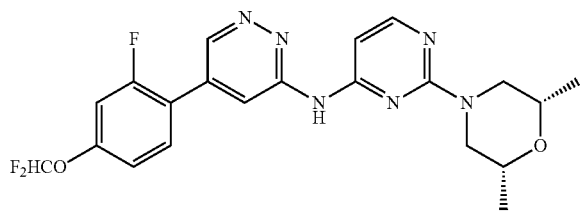
35
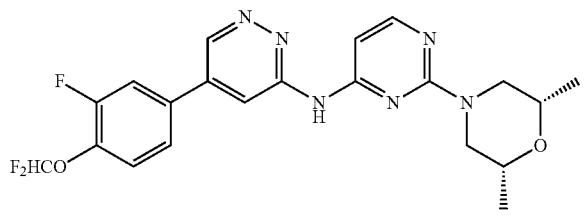
36
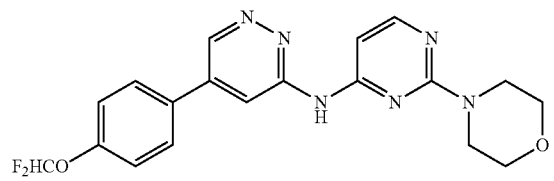
37
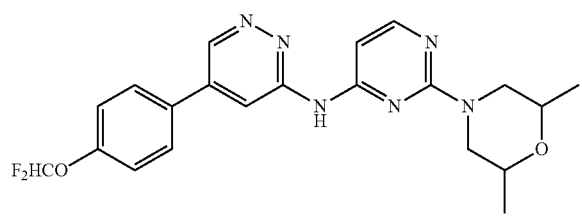
38

TABLE 1-continued
Exemplary Compounds of the Present Disclosure
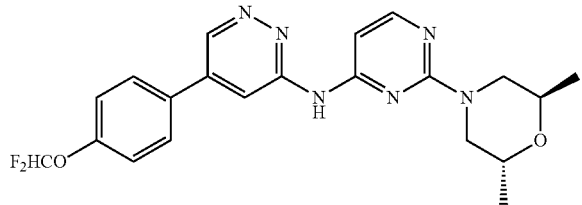
39
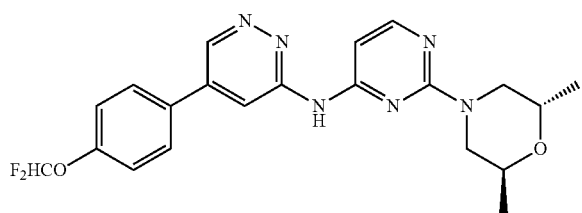
40
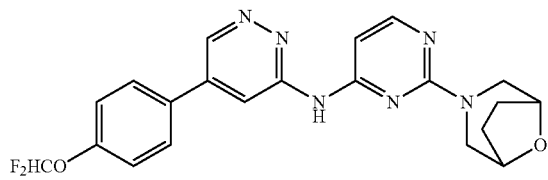
41
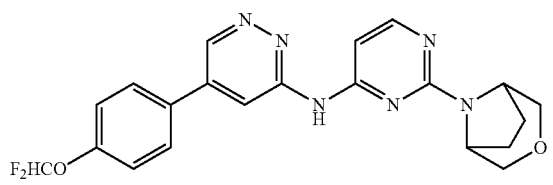
42
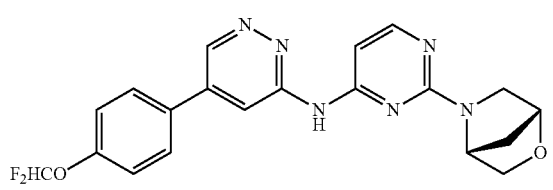
43
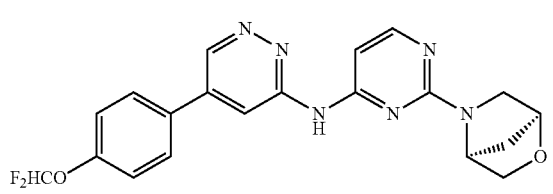
44

TABLE 1-continued
Exemplary Compounds of the Present Disclosure
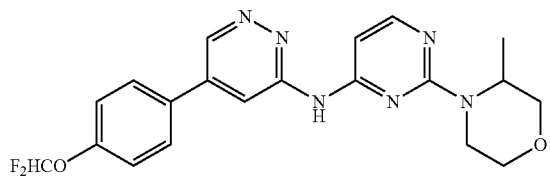
45
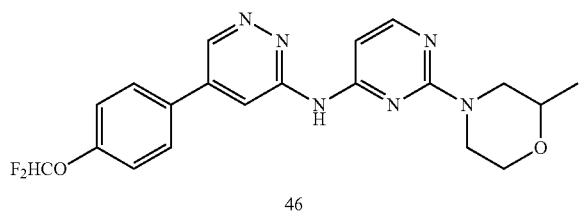 [SMILES: CC1CN(c2nccc(Nc3cc(-c4ccc(OC(F)F)cc4)cnn3)n2)CCO1]
46
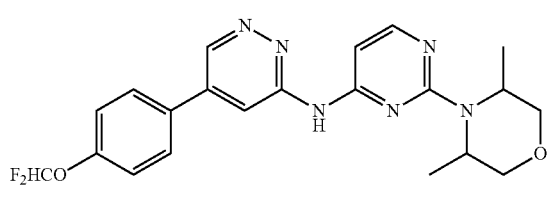
47
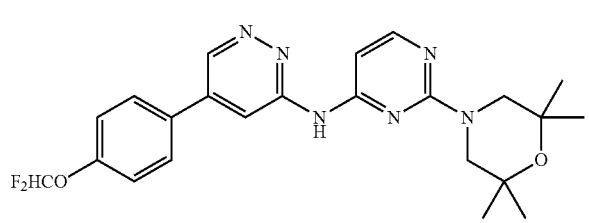
48
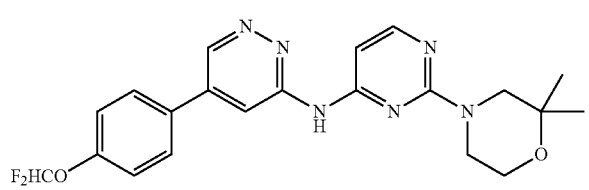
49
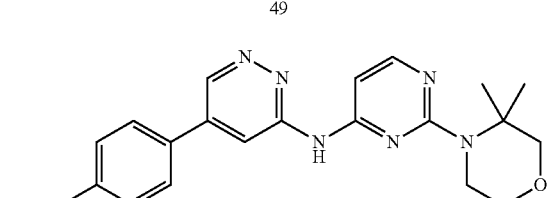
50
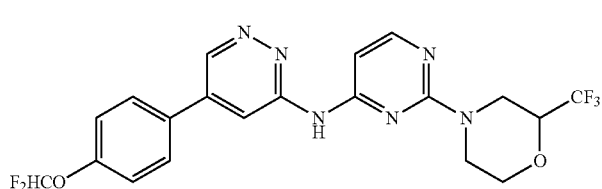
51

TABLE 1-continued
Exemplary Compounds of the Present Disclosure
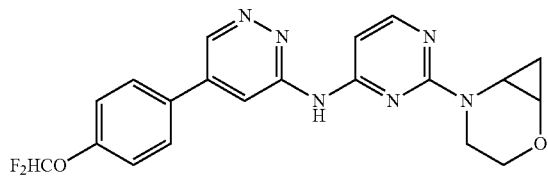
52
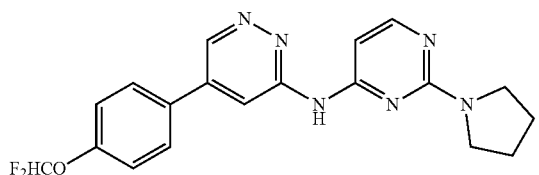
53
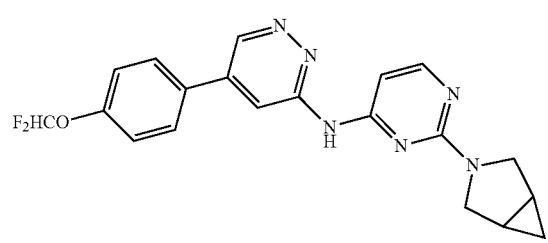
54
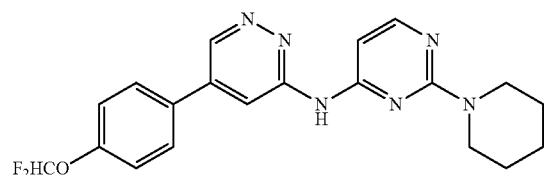
55
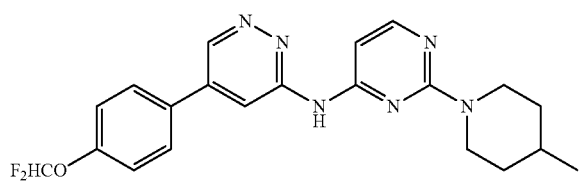
56
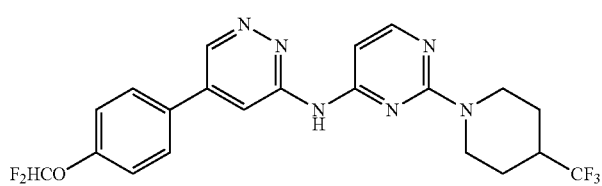
57

TABLE 1-continued
Exemplary Compounds of the Present Disclosure
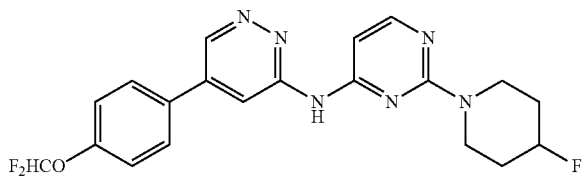
58
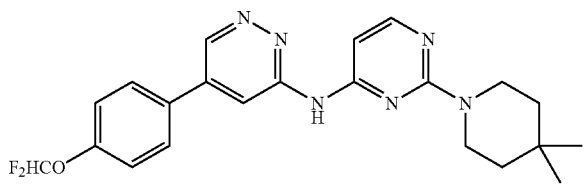
59
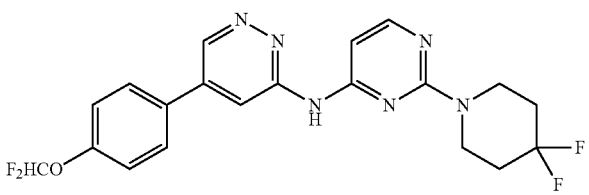
60
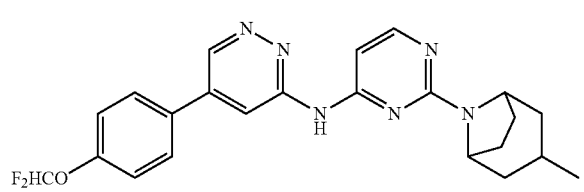
61
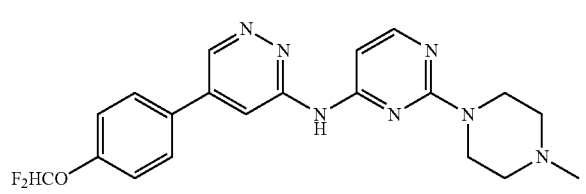
62
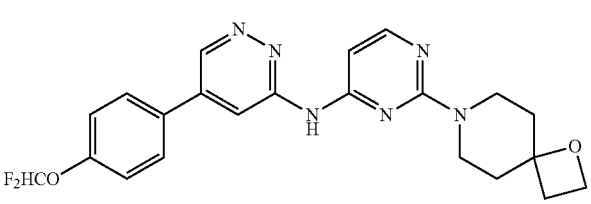
63
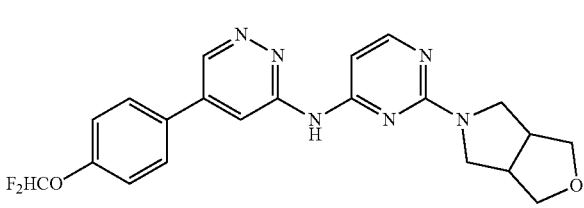
64

TABLE 1-continued
Exemplary Compounds of the Present Disclosure
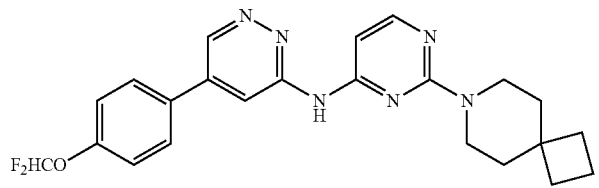
65
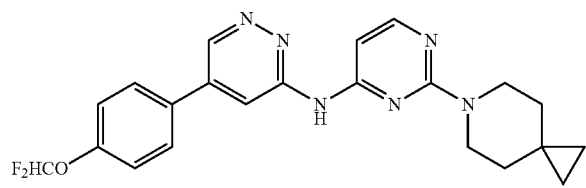
66
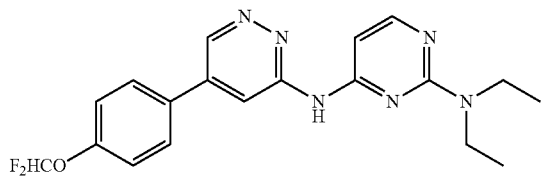
67
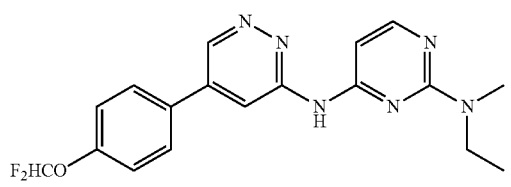
68
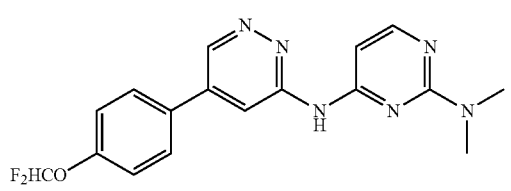
69
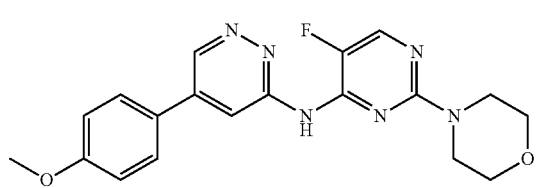
70

TABLE 1-continued
Exemplary Compounds of the Present Disclosure
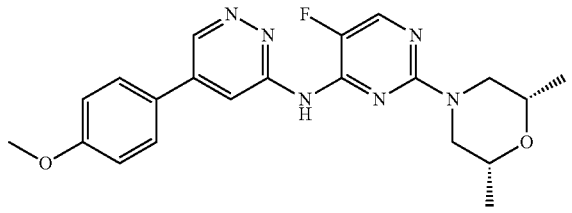
71
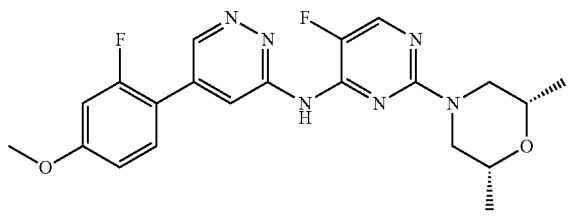
72
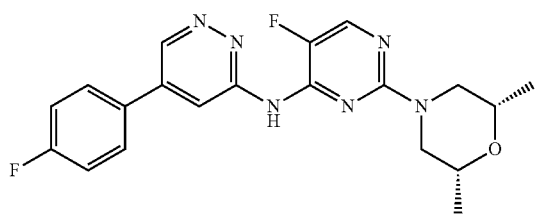
73
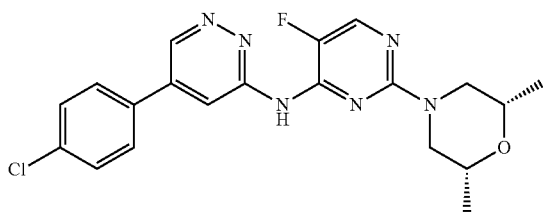 [SMILES: C[C@@H]1CN(c2ncc(F)c(Nc3cc(-c4ccc(Cl)cc4)cnn3)n2)C[C@H](C)O1]
74
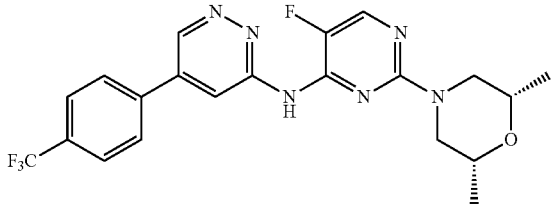 [SMILES: C[C@@H]1CN(c2ncc(F)c(Nc3cc(-c4ccc(C(F)(F)F)cc4)cnn3)n2)C[C@H](C)O1]
75
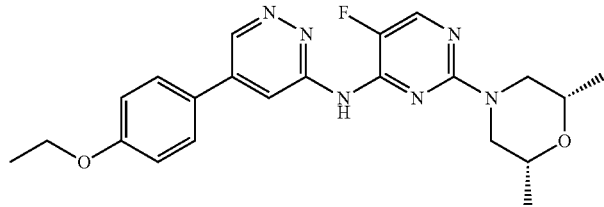 [SMILES: CCOc1ccc(-c2cnnc(Nc3nc(N4C[C@@H](C)O[C@@H](C)C4)ncc3F)c2)cc1]
76

TABLE 1-continued
Exemplary Compounds of the Present Disclosure
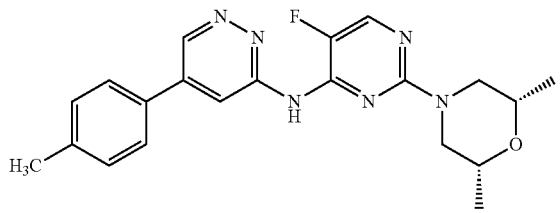
77
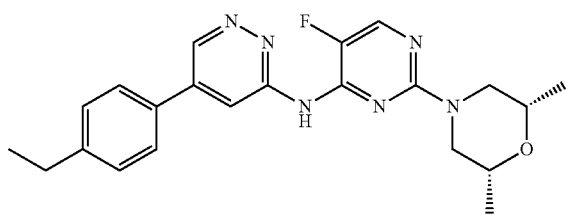
78
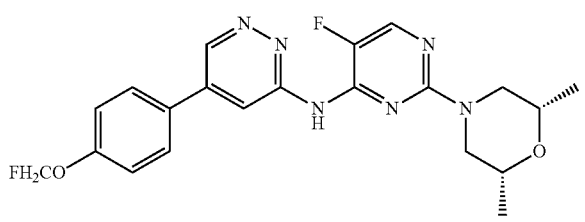
79
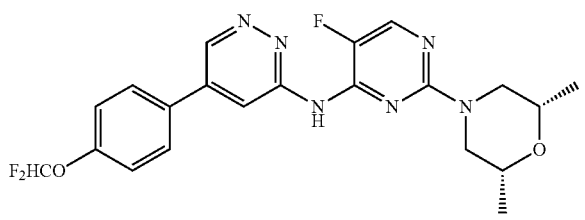
80
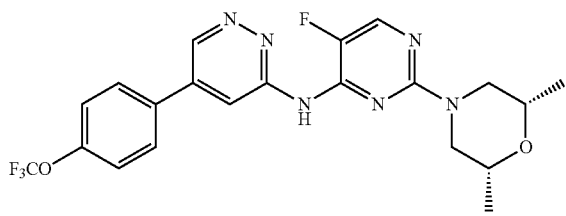
81
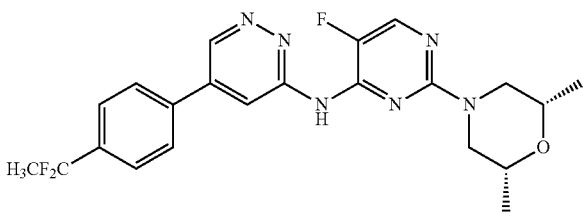
82

TABLE 1-continued
Exemplary Compounds of the Present Disclosure
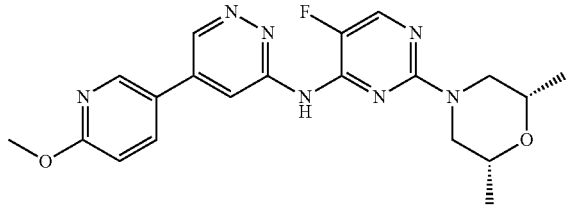
83
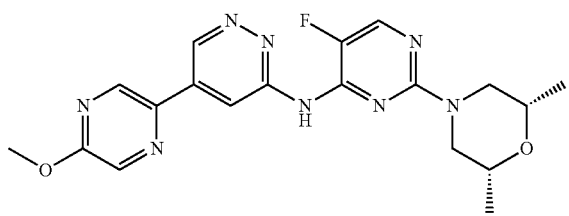
84
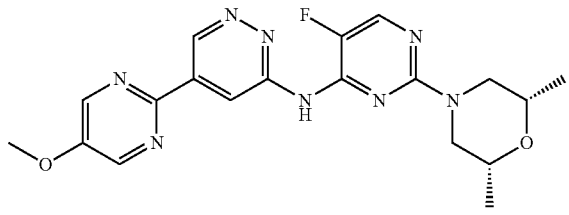
85
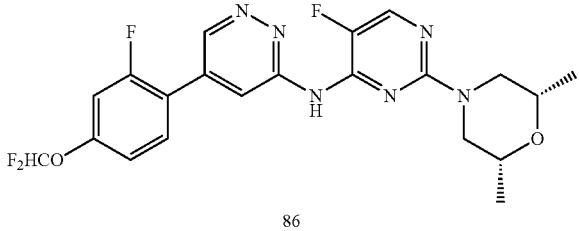
86
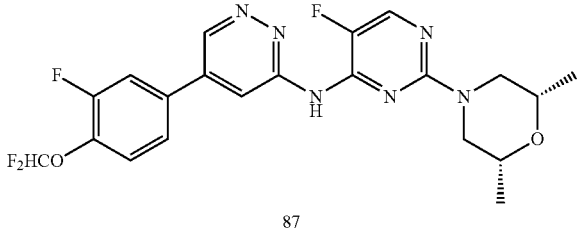
87
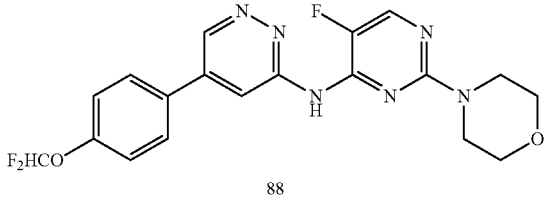
88

TABLE 1-continued
Exemplary Compounds of the Present Disclosure
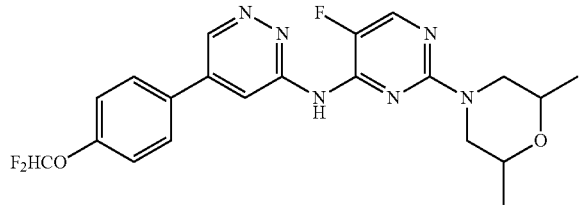
89
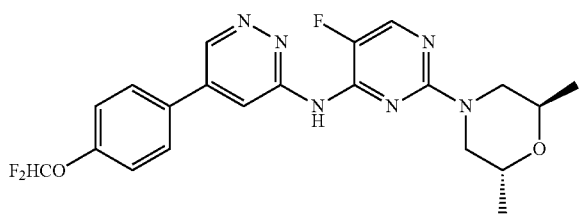
90
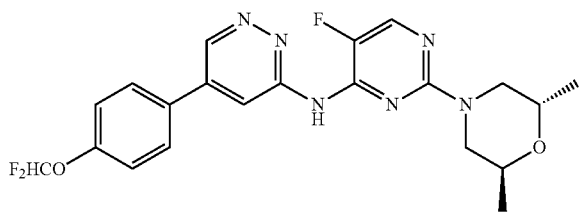
91
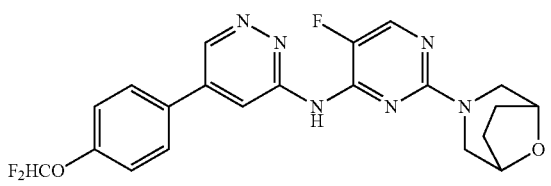
92
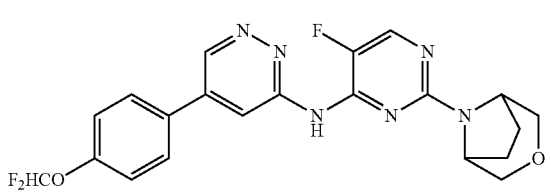
93
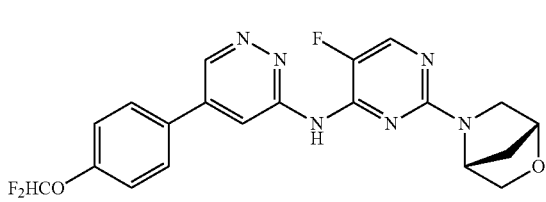
94

TABLE 1-continued
Exemplary Compounds of the Present Disclosure
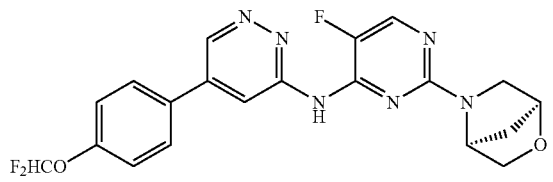
95
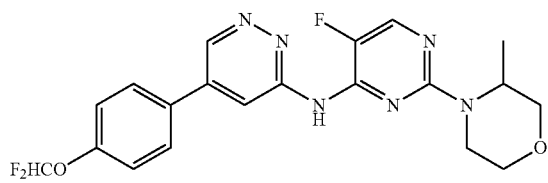
96
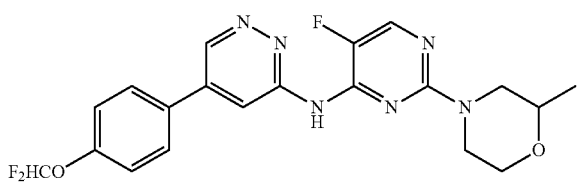
97
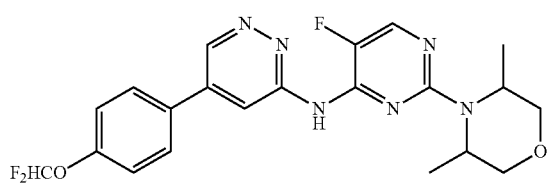
98
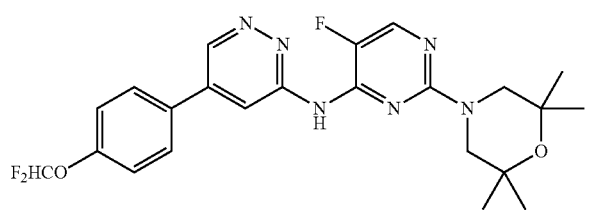
99
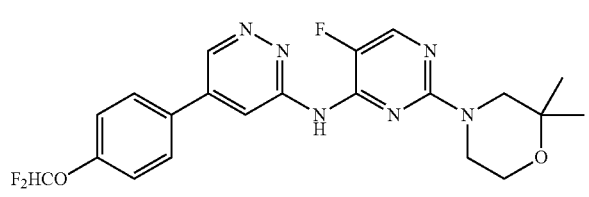
100
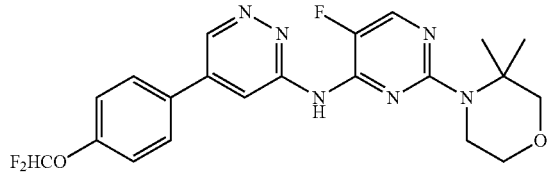
101

TABLE 1-continued
Exemplary Compounds of the Present Disclosure
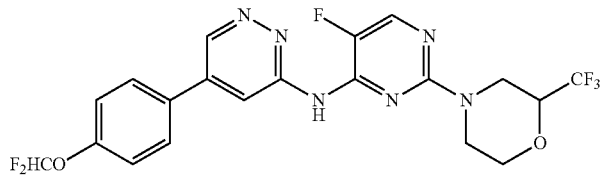
102
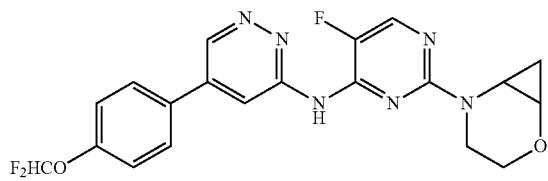
103
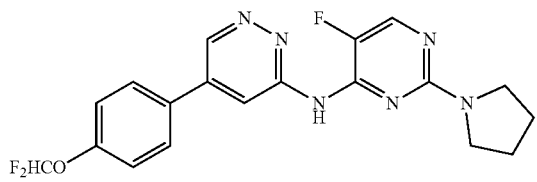
104
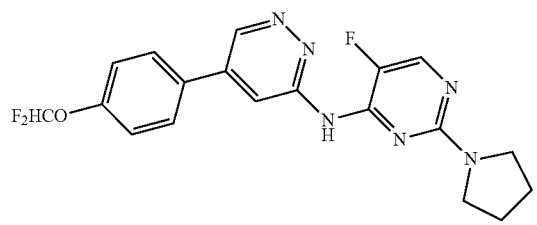
105
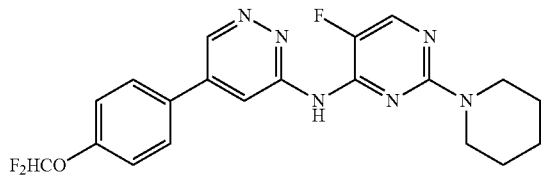
106
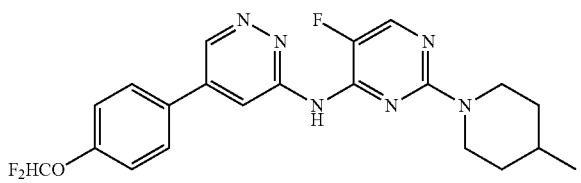
107

TABLE 1-continued
Exemplary Compounds of the Present Disclosure
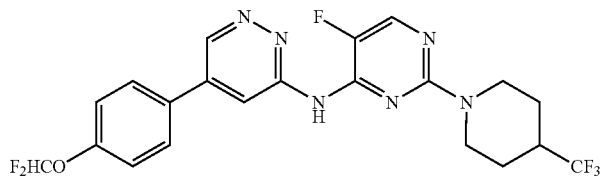
108
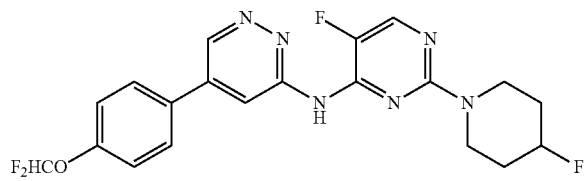
109
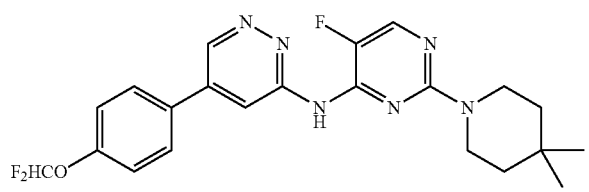
110
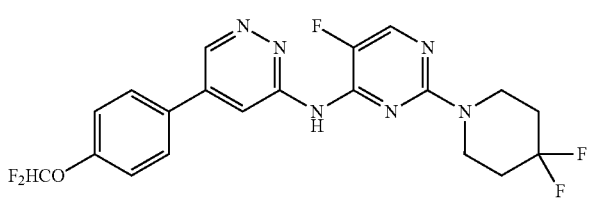
111
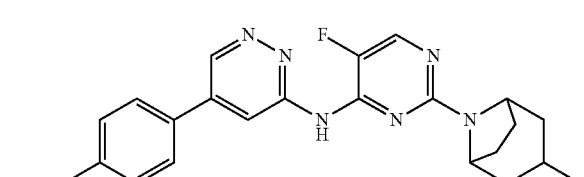
112
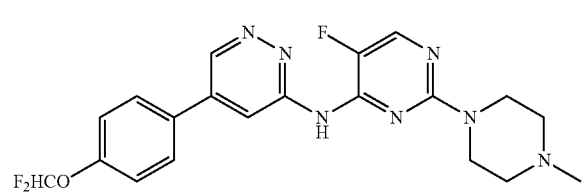
113
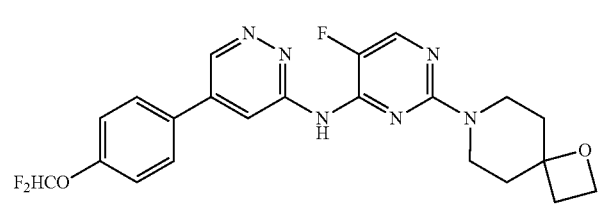
114

US 11,986,475 B1
TABLE 1-continued
Exemplary Compounds of the Present Disclosure
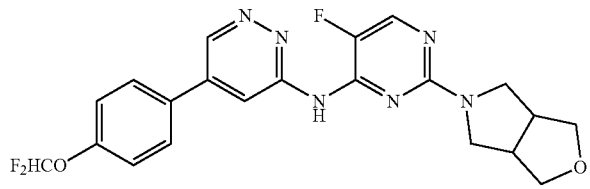
115
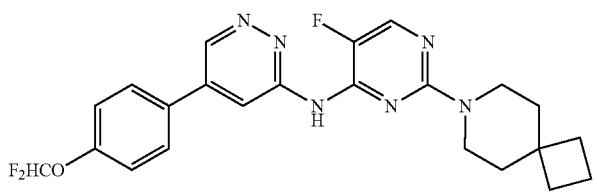
116
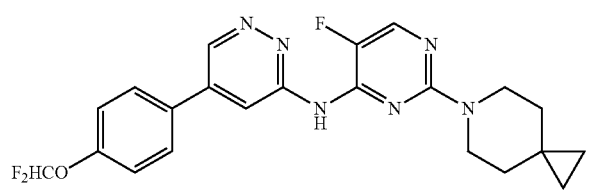
117
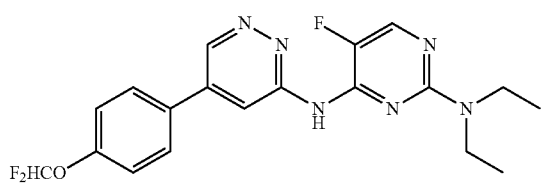
118
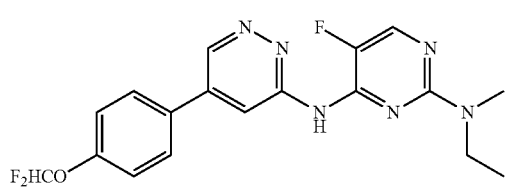
119
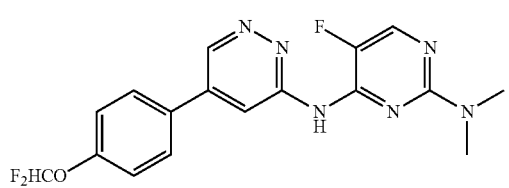
120

TABLE 1-continued
Exemplary Compounds of the Present Disclosure
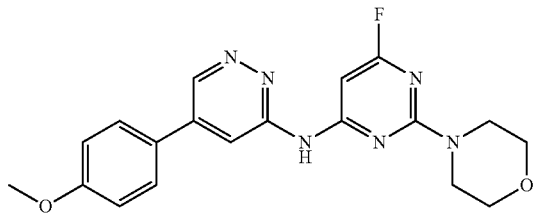
121
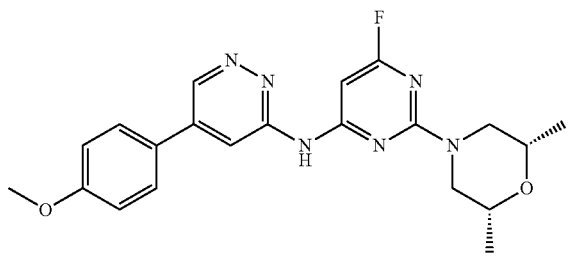
122
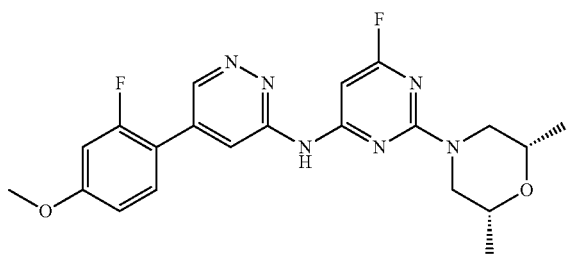
123
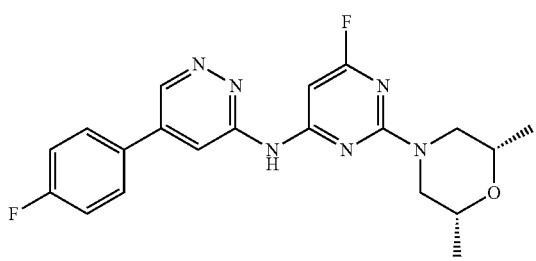
124
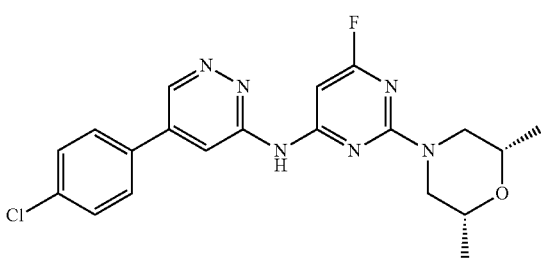
125

TABLE 1-continued
Exemplary Compounds of the Present Disclosure
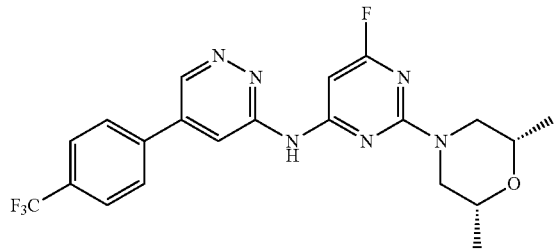
126
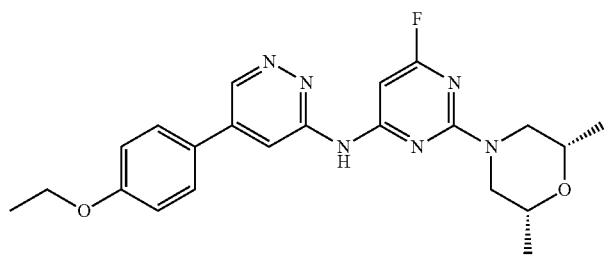
127
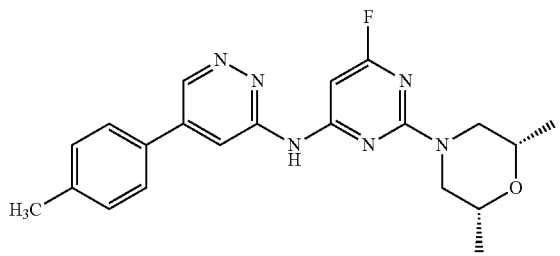
128
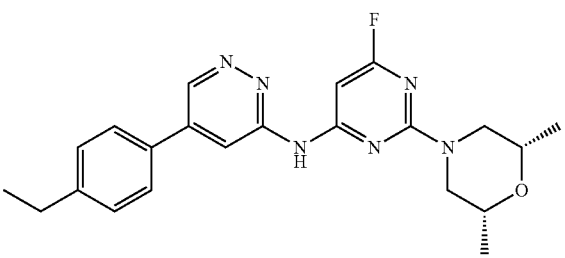
129
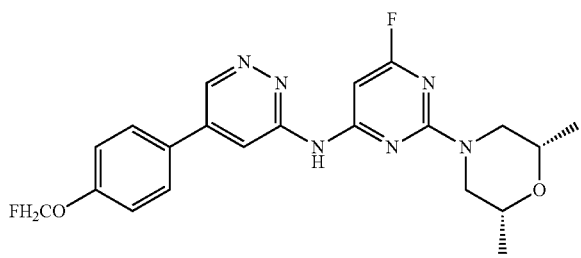
130

TABLE 1-continued
Exemplary Compounds of the Present Disclosure
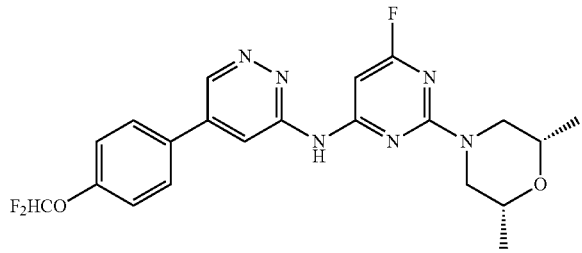
131
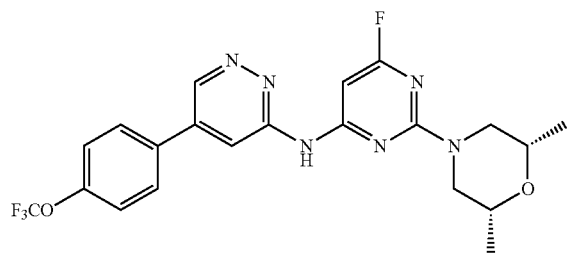
132
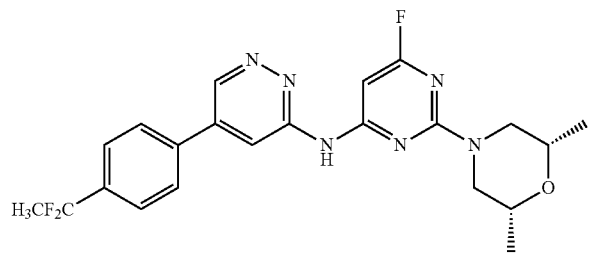
133
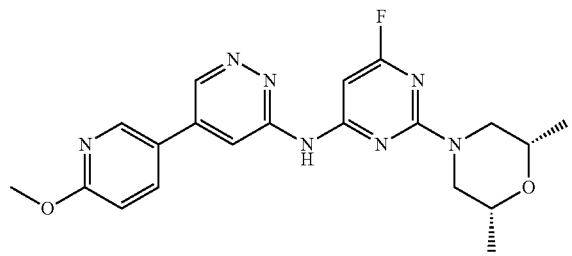
134
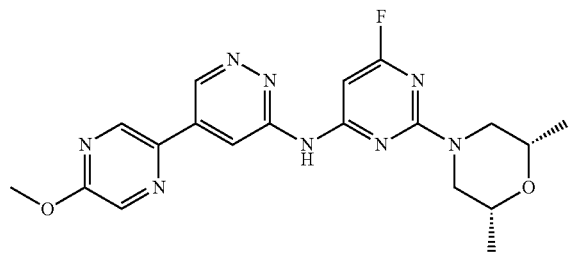
135

TABLE 1-continued
Exemplary Compounds of the Present Disclosure
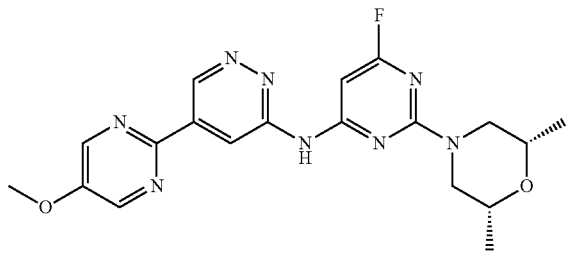
136
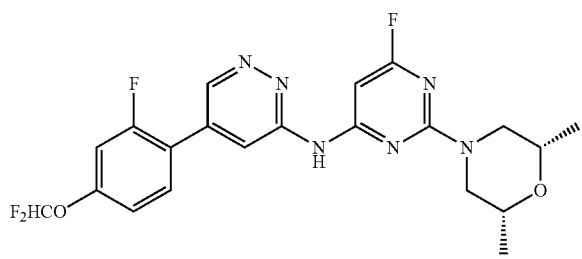
137
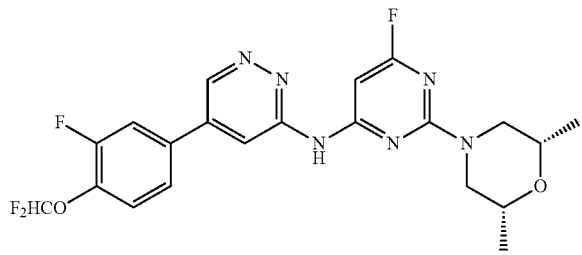
138
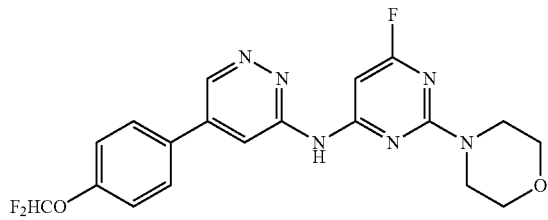
139
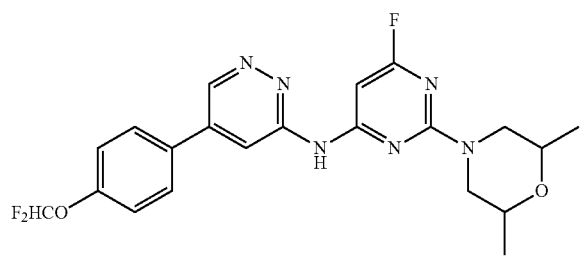
140

TABLE 1-continued
Exemplary Compounds of the Present Disclosure
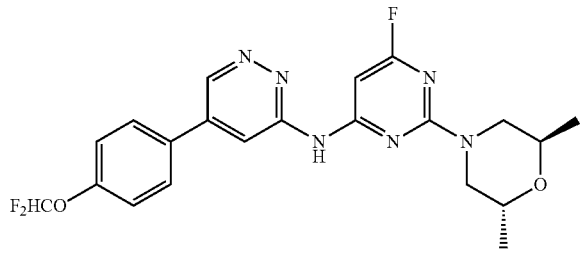
141
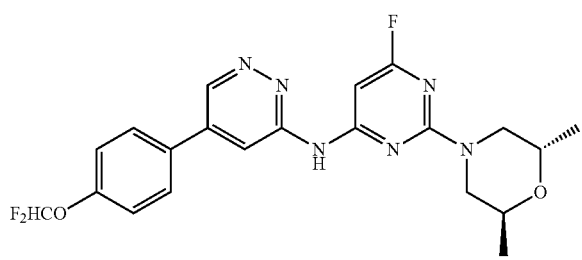
142
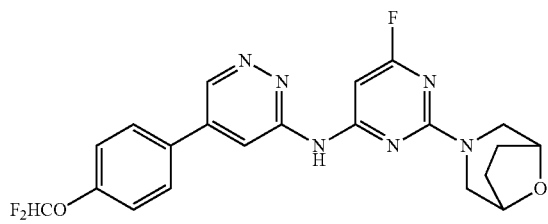
143
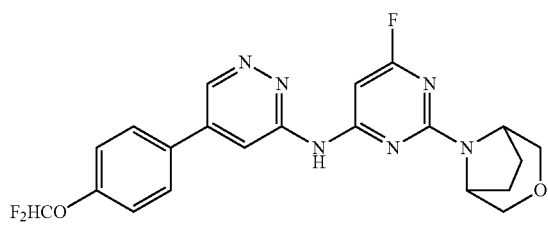
144
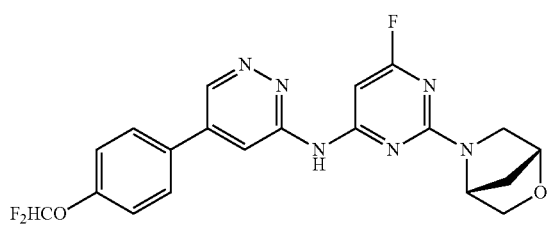
145

TABLE 1-continued
Exemplary Compounds of the Present Disclosure
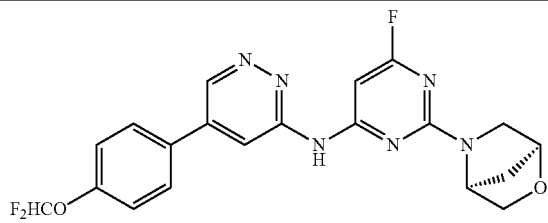
146
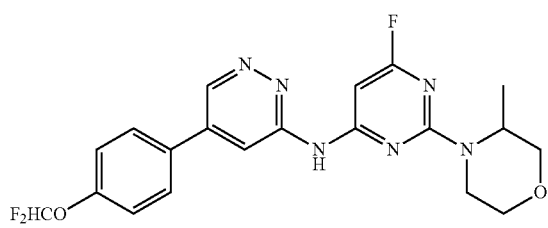
147
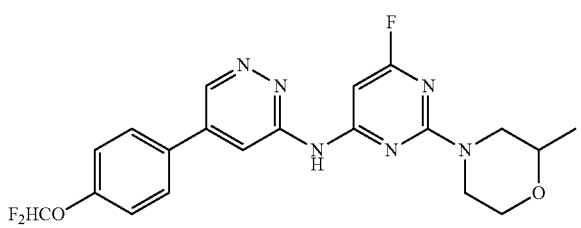
148
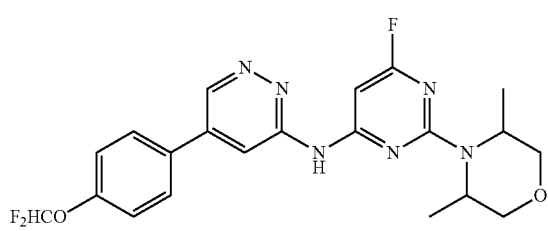
149
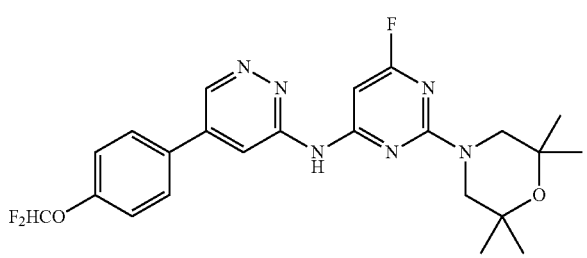
150
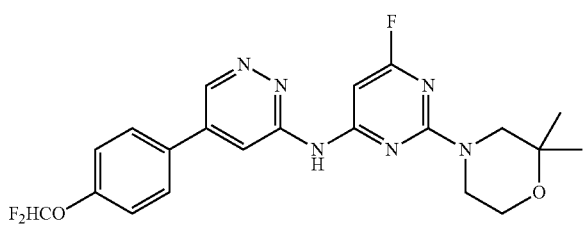
151

TABLE 1-continued
Exemplary Compounds of the Present Disclosure
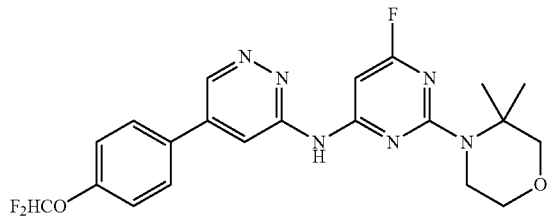
152
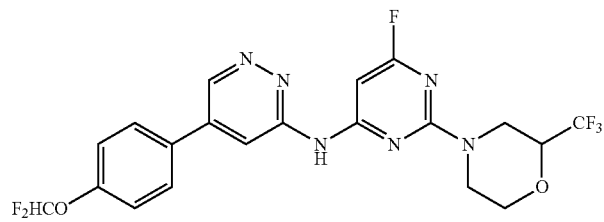
153
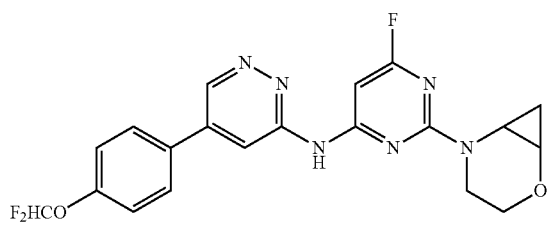
154
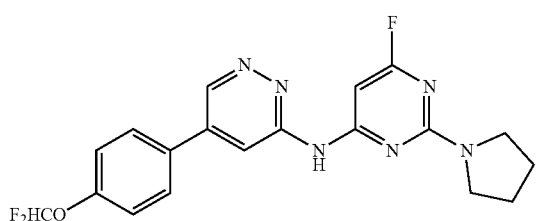
155
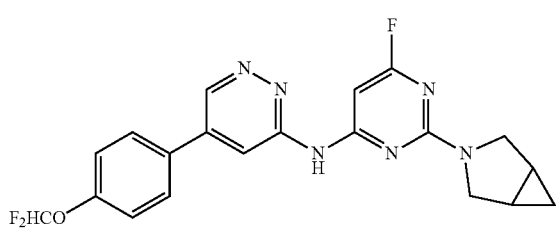
156

TABLE 1-continued
Exemplary Compounds of the Present Disclosure
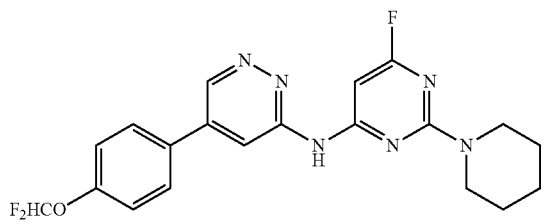
157
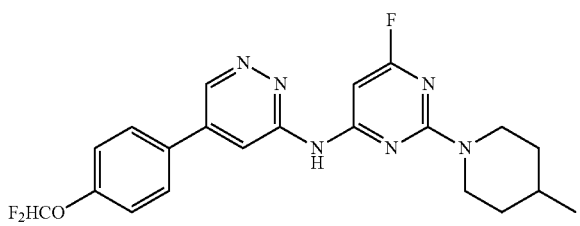
158
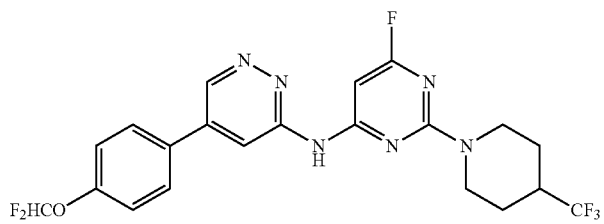
159
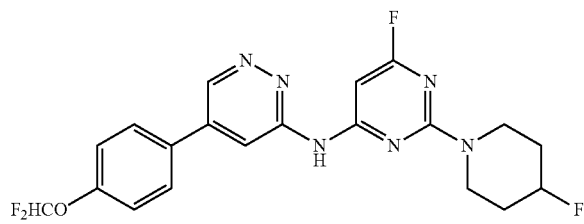
160
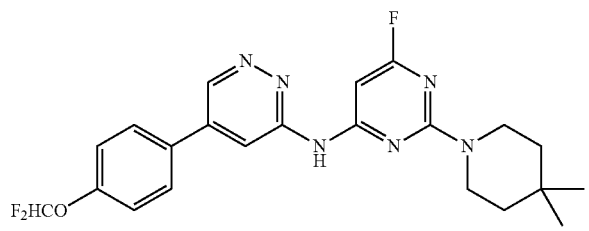
161
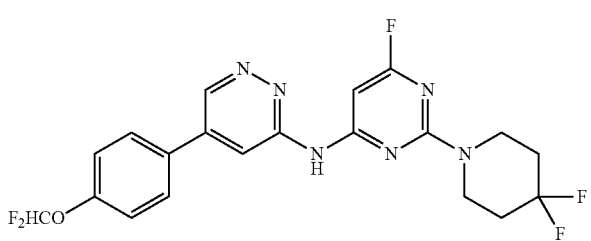
162

TABLE 1-continued
Exemplary Compounds of the Present Disclosure
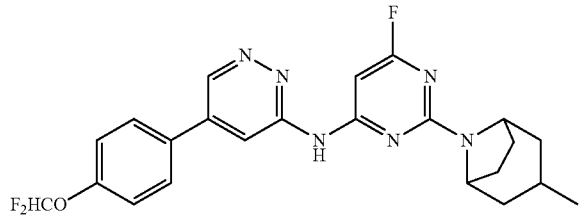
163
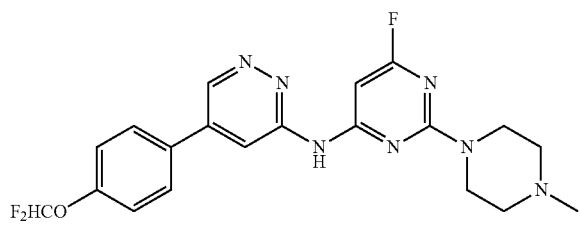
164
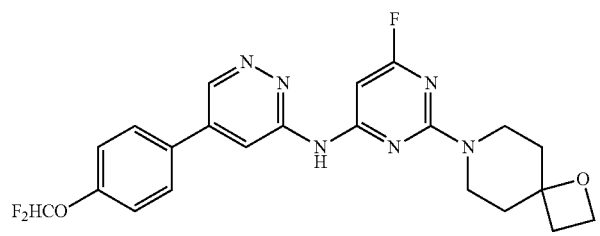
165
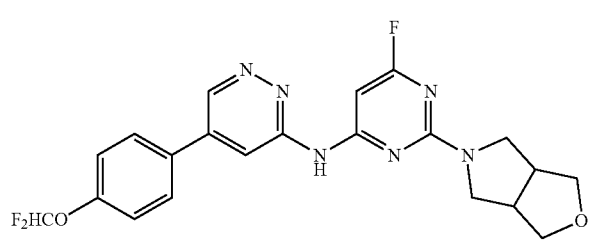
166
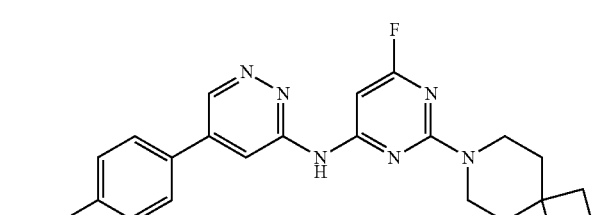
167

TABLE 1-continued
Exemplary Compounds of the Present Disclosure
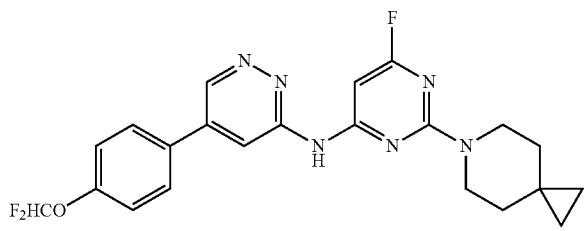
168
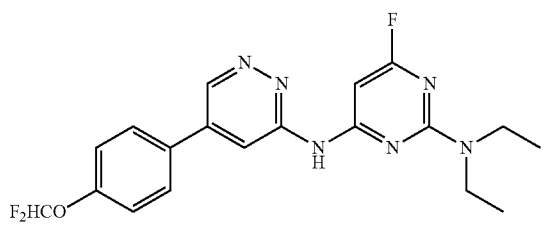
169
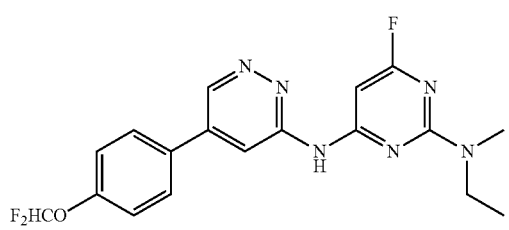
170
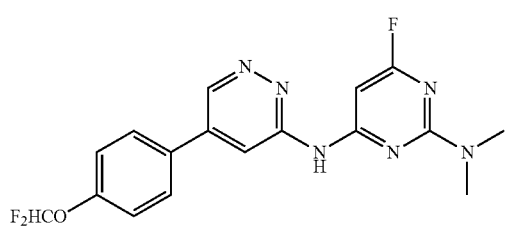
171
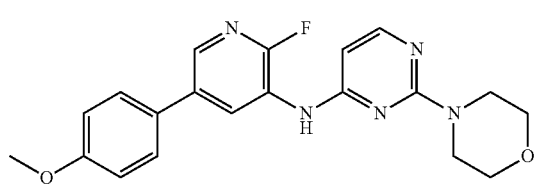
172
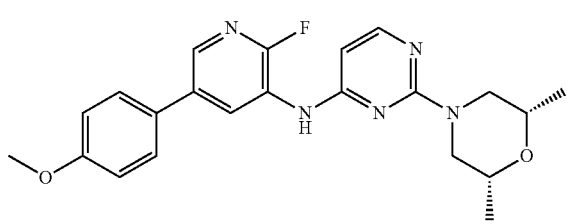
173

TABLE 1-continued
Exemplary Compounds of the Present Disclosure
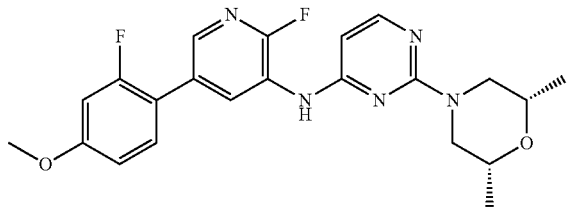
174
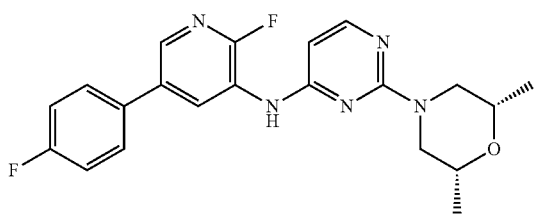
175
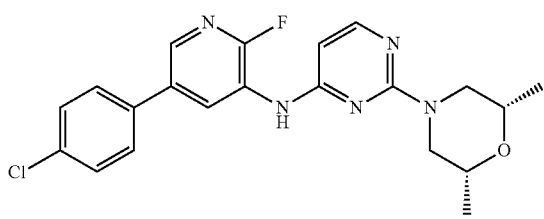
176
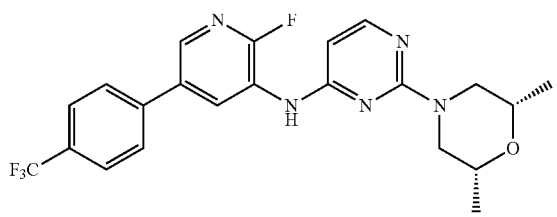
177
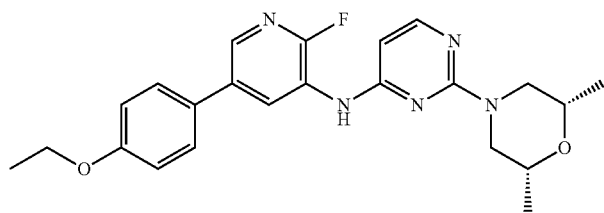
178
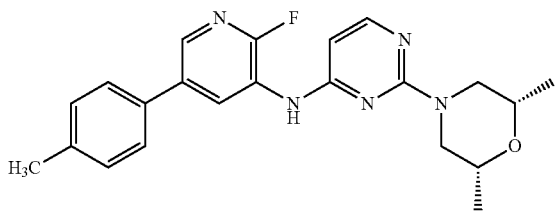
179

TABLE 1-continued
Exemplary Compounds of the Present Disclosure
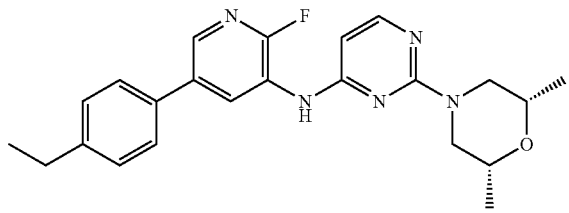
180
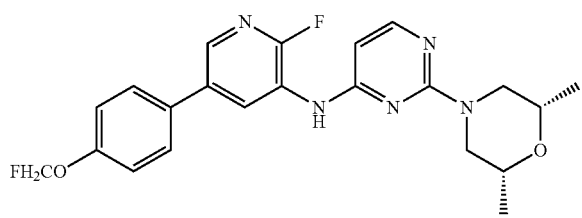
181
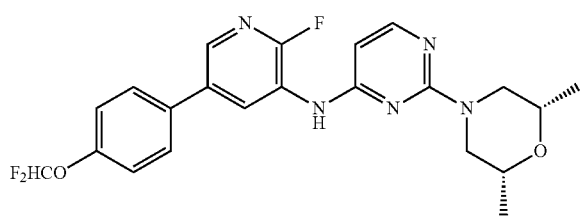
182
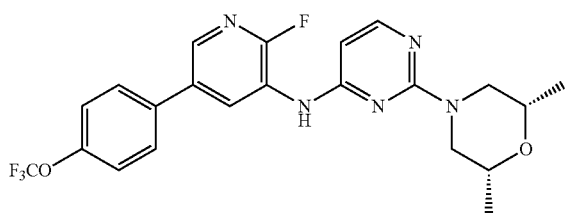
183
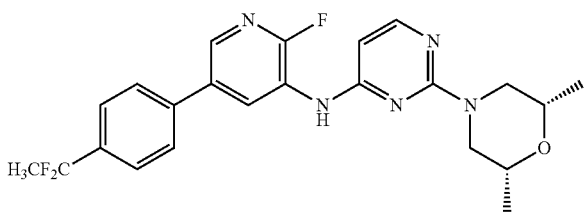
184
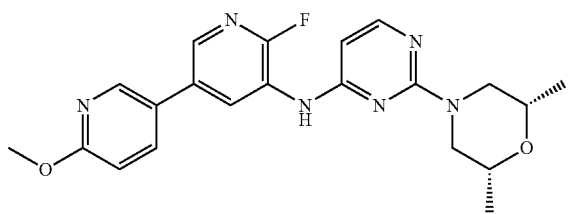
185

US 11,986,475 B1
TABLE 1-continued
Exemplary Compounds of the Present Disclosure
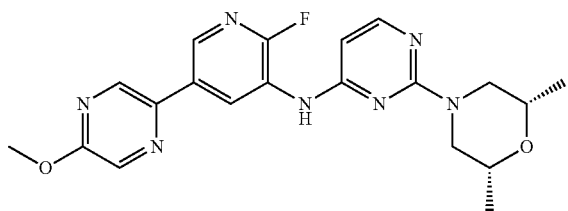
186
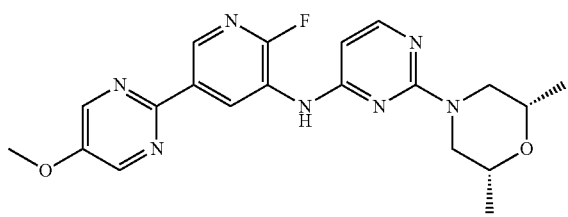
187
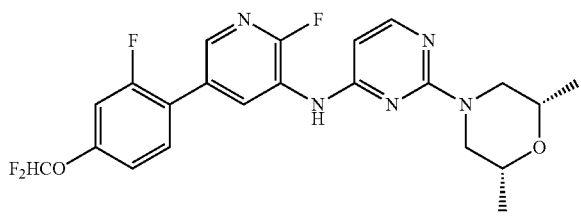
188
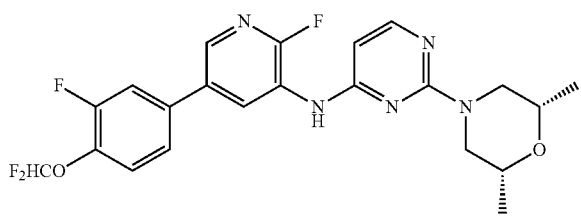
189
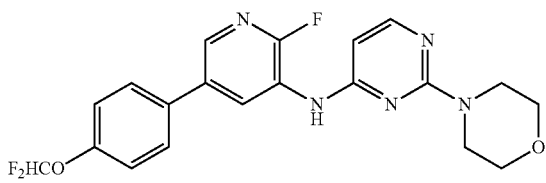
190
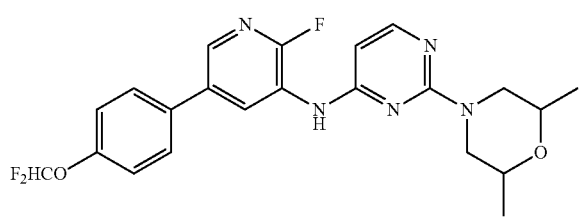
191

TABLE 1-continued
Exemplary Compounds of the Present Disclosure
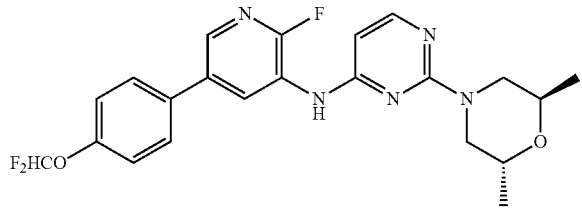
192
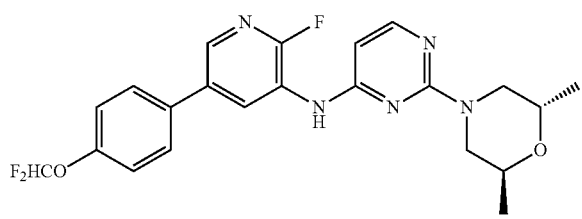
193
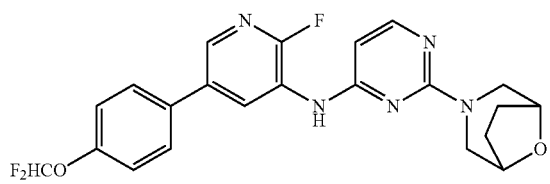
194
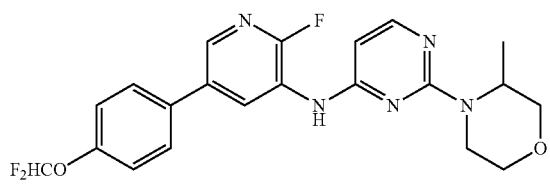
195
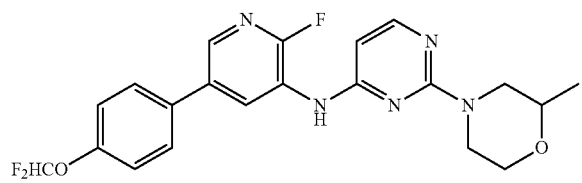
196
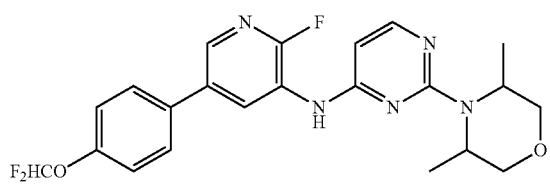
197

TABLE 1-continued
Exemplary Compounds of the Present Disclosure
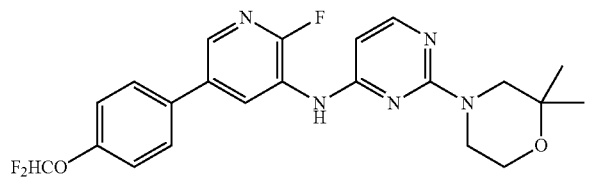
198
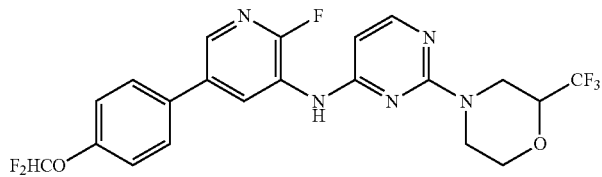
199
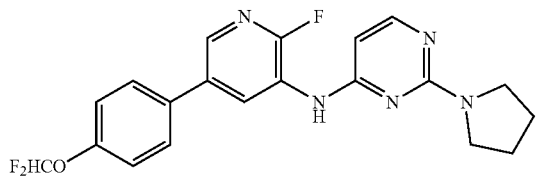
200
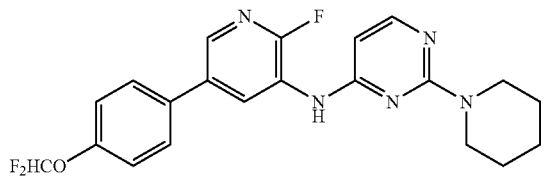
201
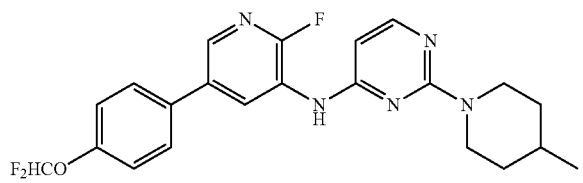
202
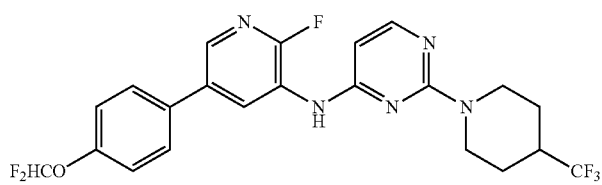
203
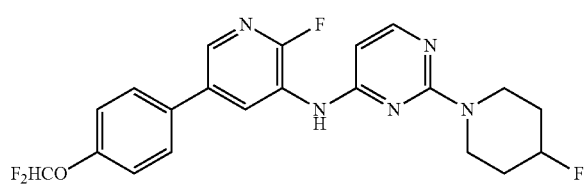
204

TABLE 1-continued
Exemplary Compounds of the Present Disclosure
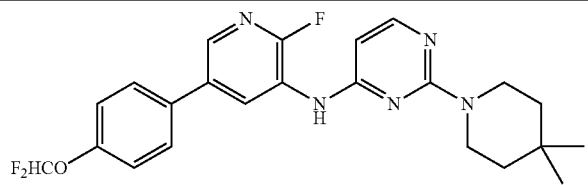
205
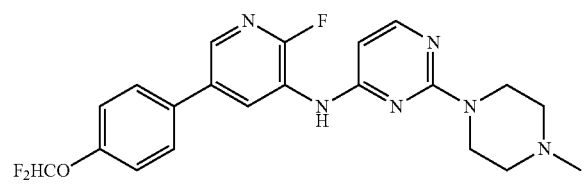
206
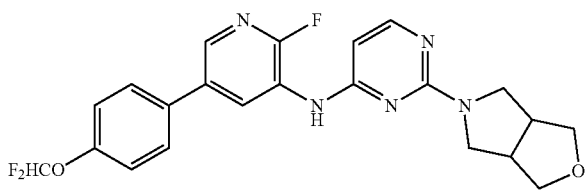
207
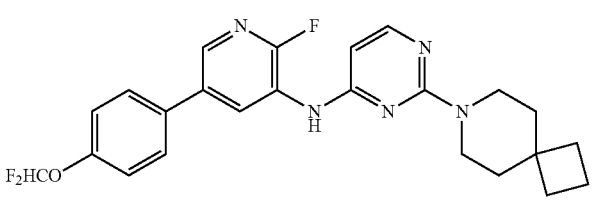
208
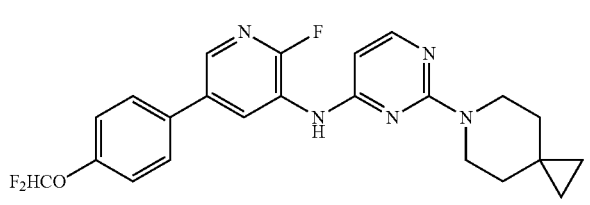
209
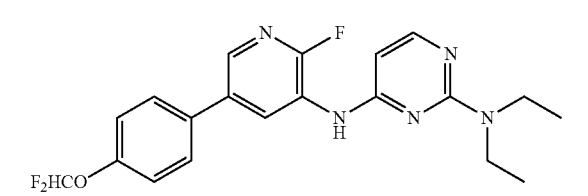
210
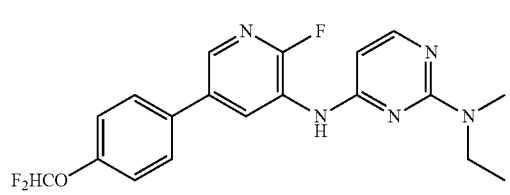
211

TABLE 1-continued
Exemplary Compounds of the Present Disclosure
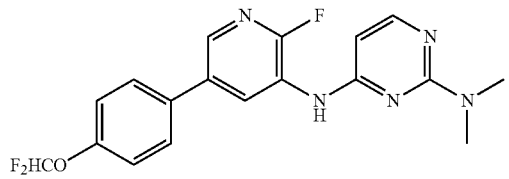
212
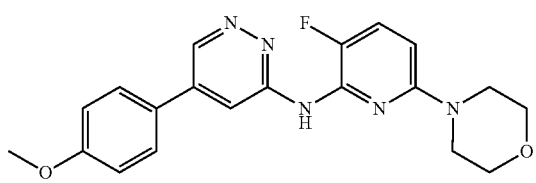
213
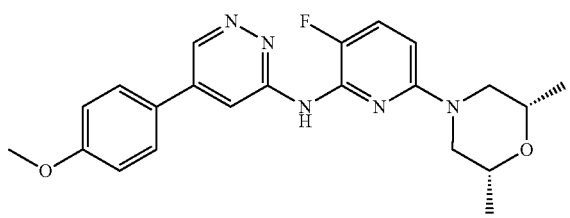
214
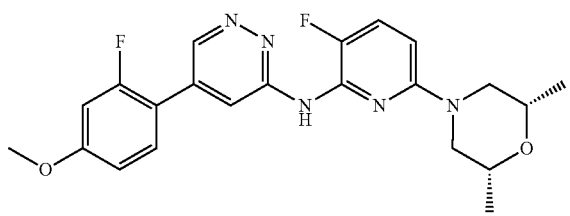
215
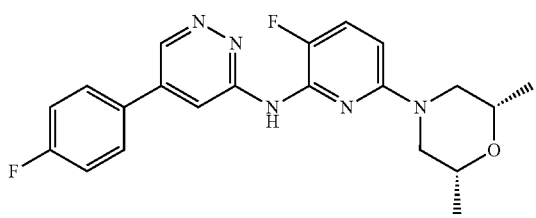
216
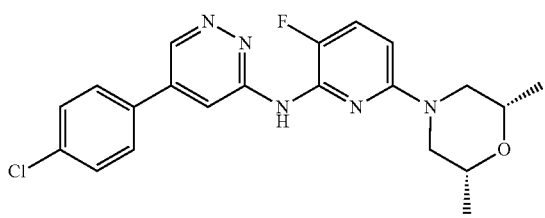
217

TABLE 1-continued
Exemplary Compounds of the Present Disclosure
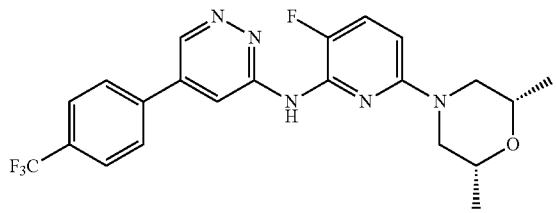
218
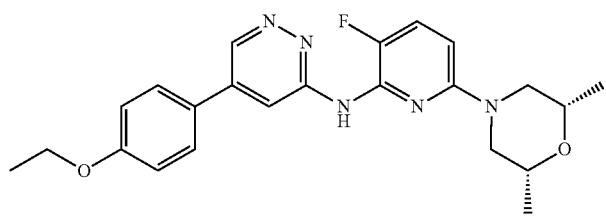
219
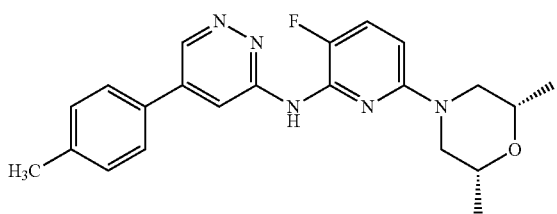
220
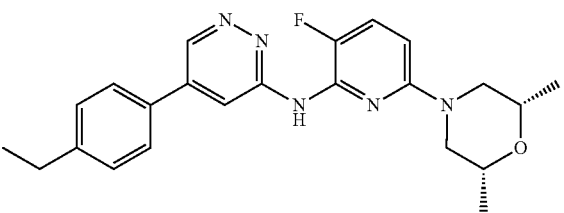 [SMILES: CCc1ccc(-c2cnnc(Nc3nc(N4C[C@@H](C)O[C@@H](C)C4)ncc3F)c2)cc1]
221
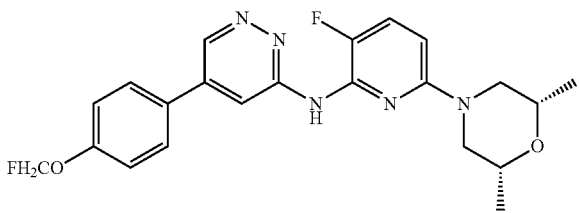
222
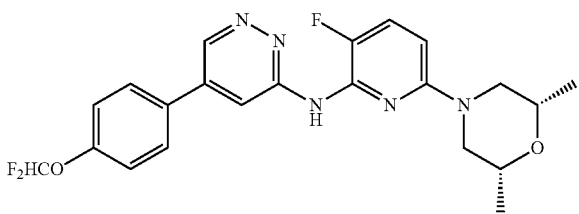 [SMILES: C[C@@H]1CN(c2ncc(F)c(Nc3cc(-c4ccc(OC(F)F)cc4)cnn3)n2)C[C@H](C)O1]
223

TABLE 1-continued
Exemplary Compounds of the Present Disclosure
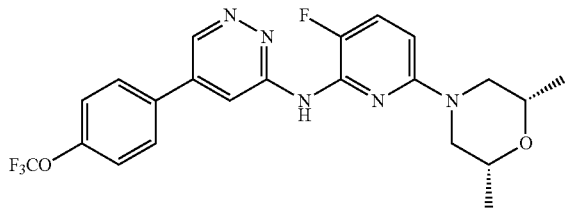 [SMILES: C[C@@H]1CN(c2ncc(F)c(Nc3cc(-c4ccc(OC(F)(F)F)cc4)cnn3)n2)C[C@H](C)O1]
224
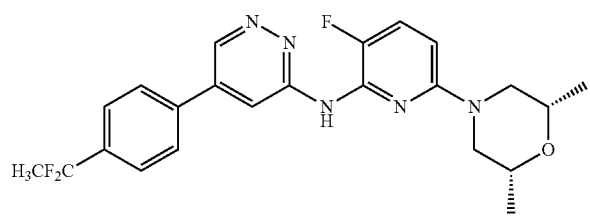
225
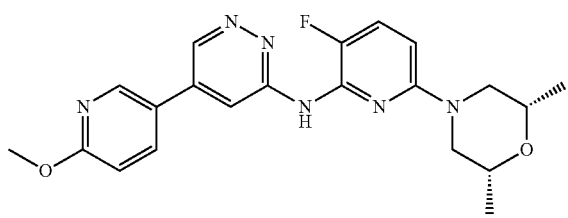
226
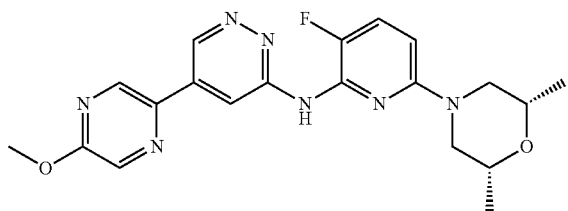
227
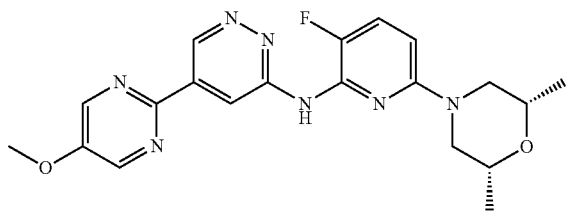
228
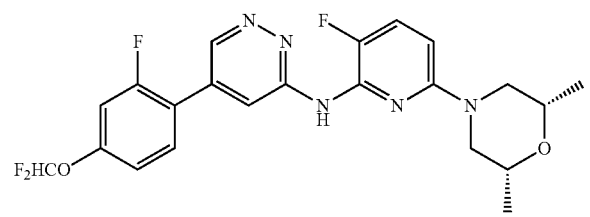 [SMILES: C[C@@H]1CN(c2ncc(F)c(Nc3cc(-c4ccc(OC(F)F)cc4F)cnn3)n2)C[C@H](C)O1]
229

TABLE 1-continued
Exemplary Compounds of the Present Disclosure
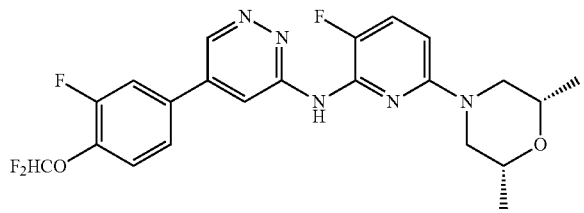 [SMILES: C[C@@H]1CN(c2ncc(F)c(Nc3cc(-c4ccc(OC(F)F)c(F)c4)cnn3)n2)C[C@H](C)O1]
230
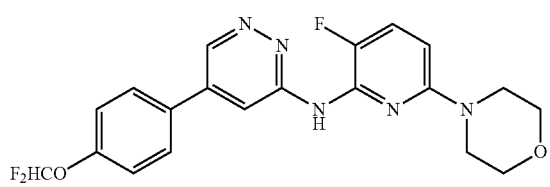
231
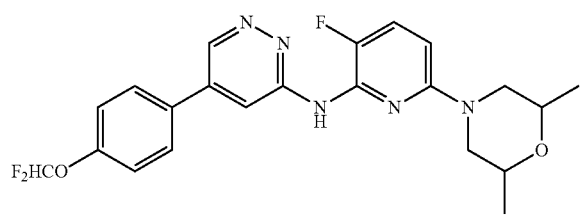
232
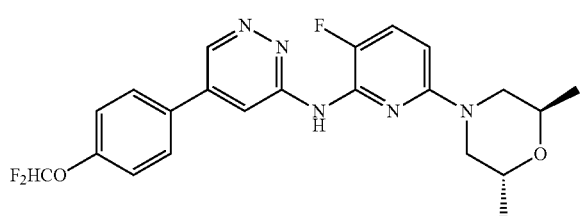
233
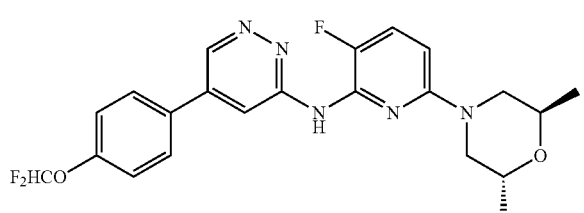
234
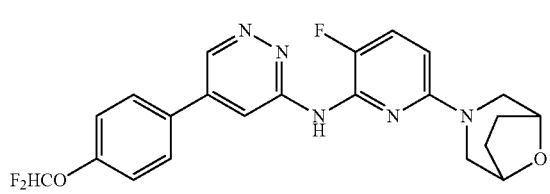
235

TABLE 1-continued
Exemplary Compounds of the Present Disclosure
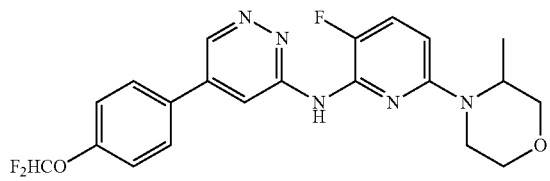 [SMILES: Fc1cnc(N2CCOCC2)nc1Nc1cc(-c2ccc(OC(F)F)cc2)cnn1]
236
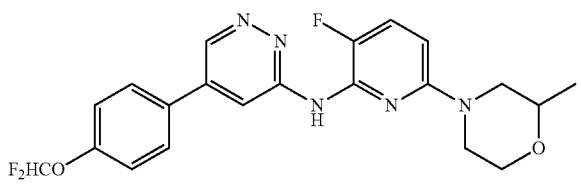
237
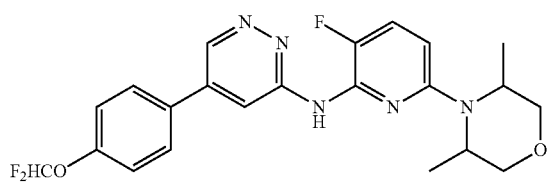
238
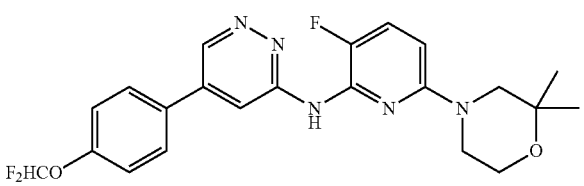
239
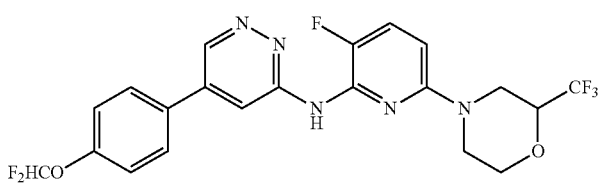
240
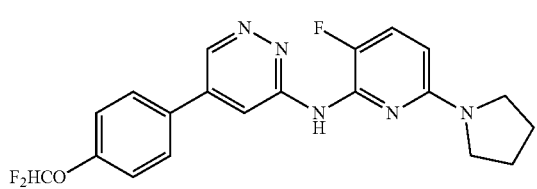
241
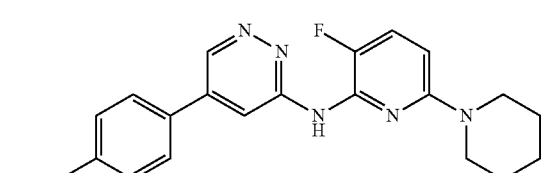
242

TABLE 1-continued
Exemplary Compounds of the Present Disclosure
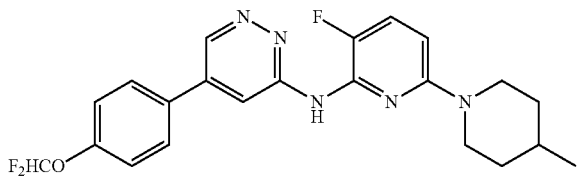
243
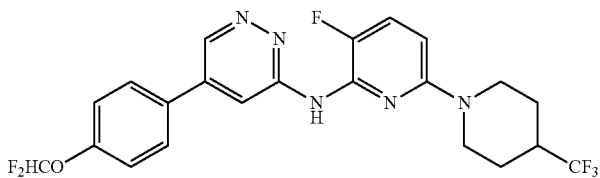
244
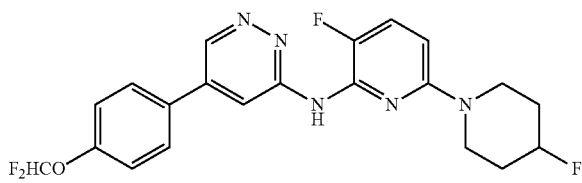
245
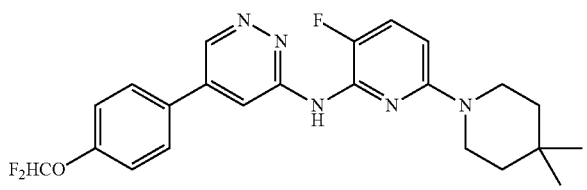
246
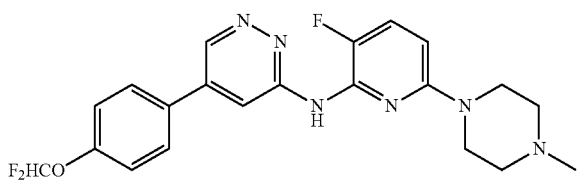
247
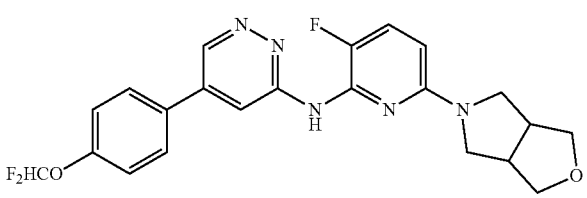
248
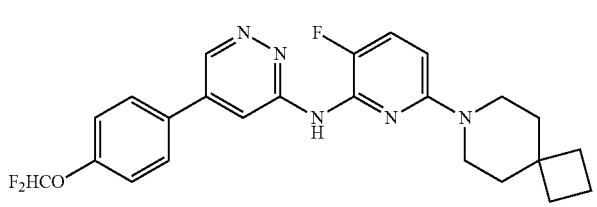
249

TABLE 1-continued
Exemplary Compounds of the Present Disclosure
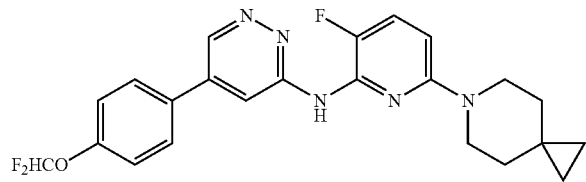
250
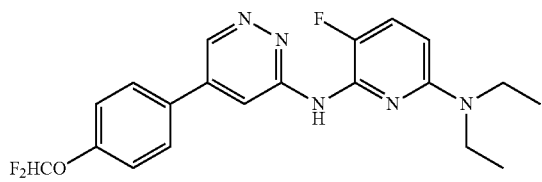
251
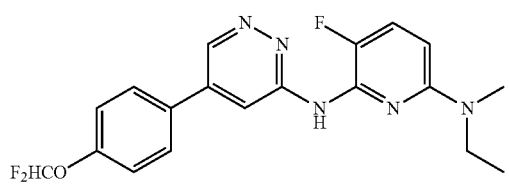
252
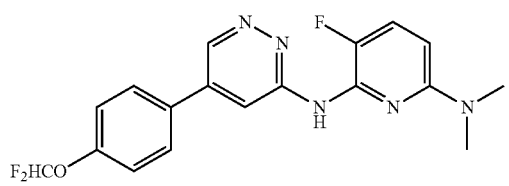
253
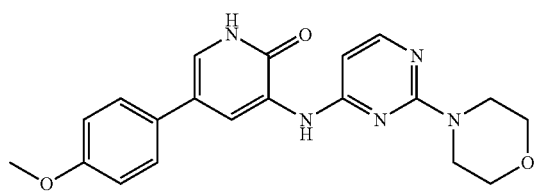
254
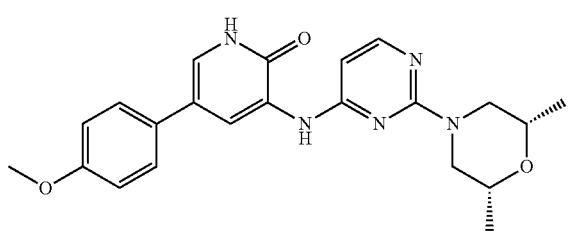
255

TABLE 1-continued
Exemplary Compounds of the Present Disclosure
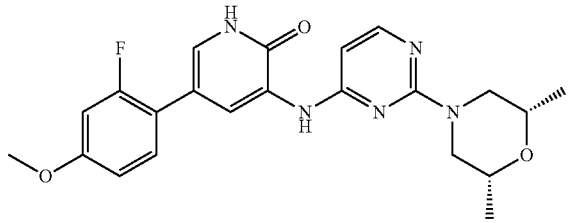
256
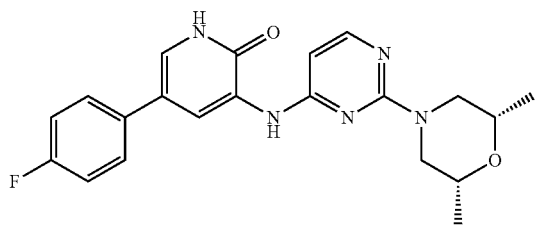
257
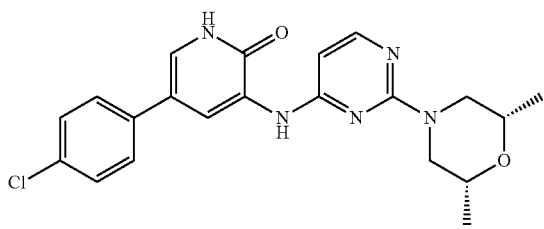
258
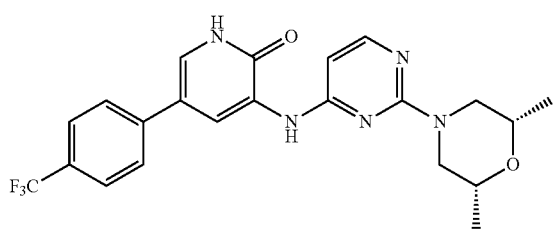
259
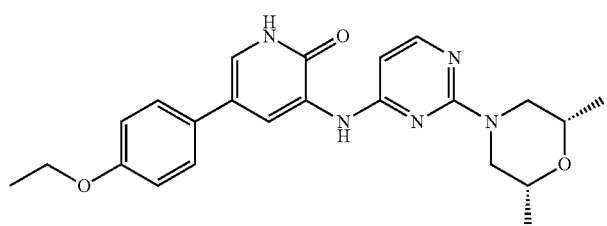
260

TABLE 1-continued
Exemplary Compounds of the Present Disclosure
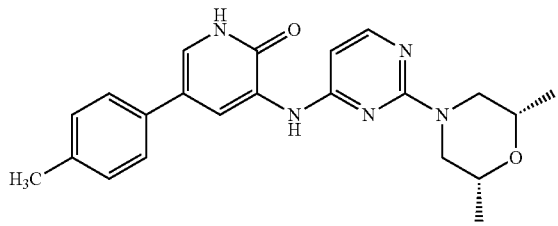
261
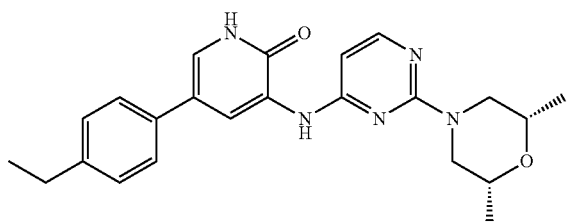
262
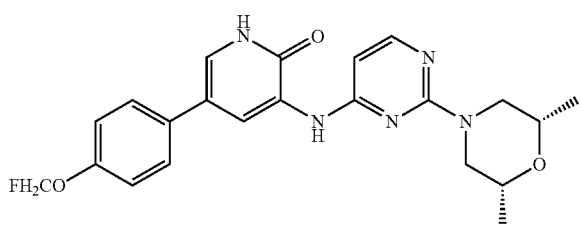
263
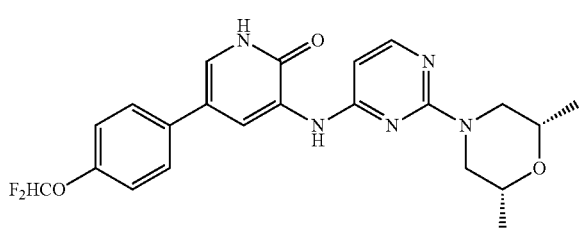
264
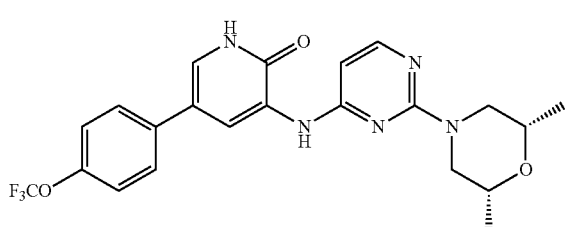
265

TABLE 1-continued
Exemplary Compounds of the Present Disclosure
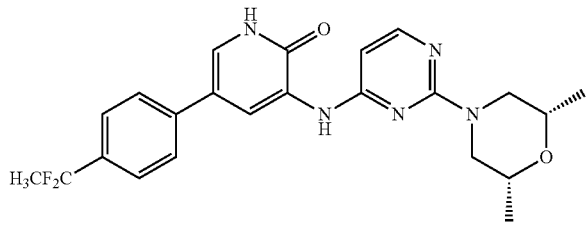
266
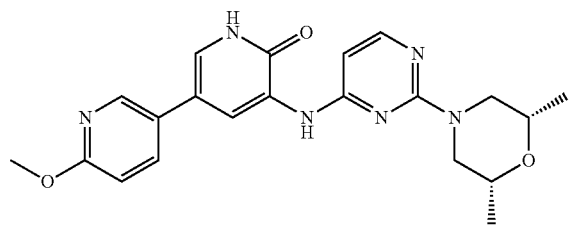
267
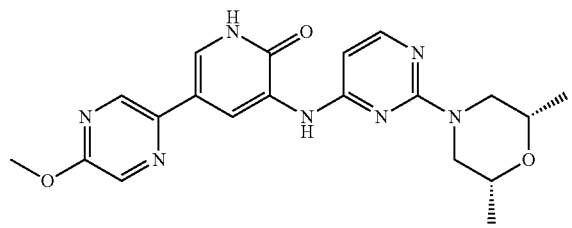
268
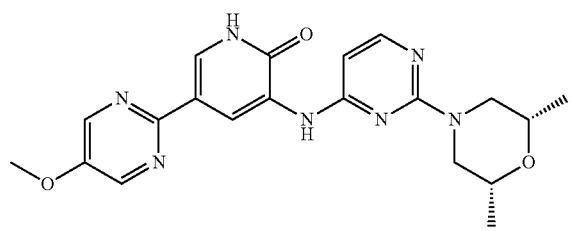
269
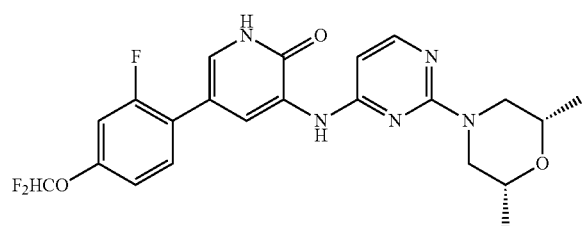
270

TABLE 1-continued
Exemplary Compounds of the Present Disclosure
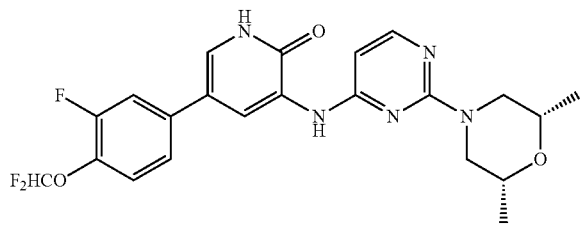
271
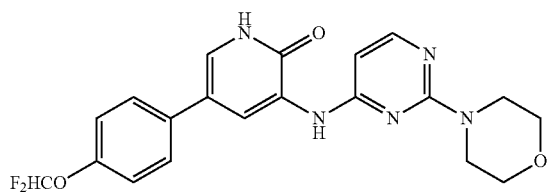
272
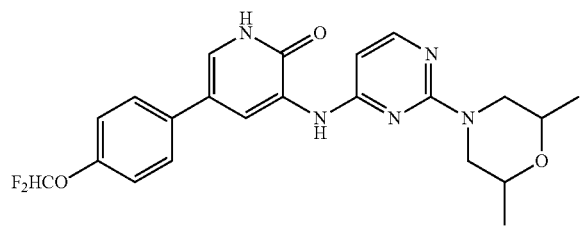 [SMILES: CN1CCN(c2nccc(Nc3cc(-c4ccc(OC(F)F)cc4)c[nH]c3=O)n2)CC1]
273
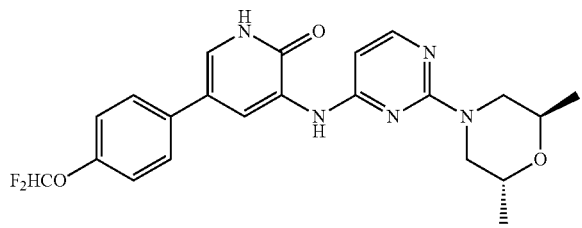
274
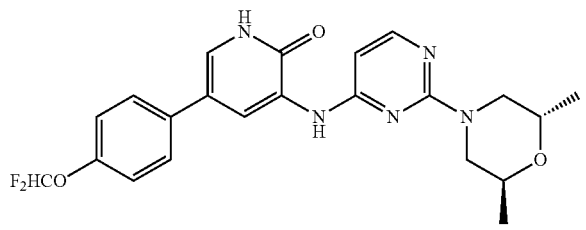
275
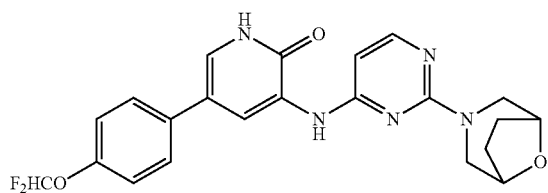
276

TABLE 1-continued
Exemplary Compounds of the Present Disclosure
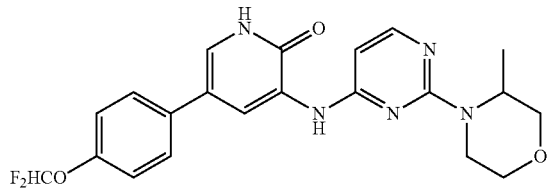
277
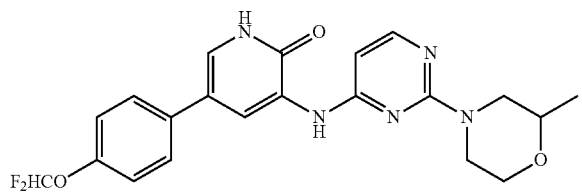
278
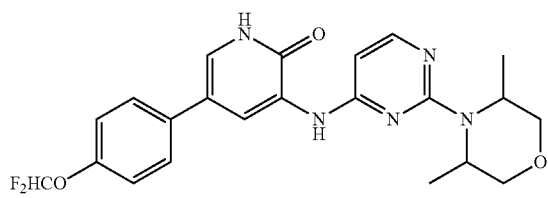
279
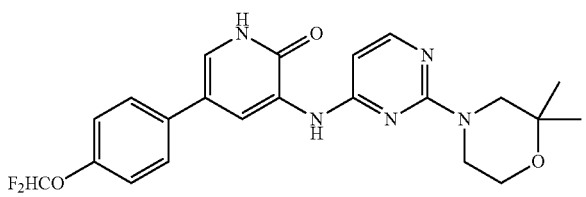
280
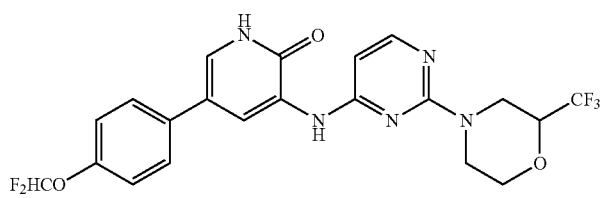
281
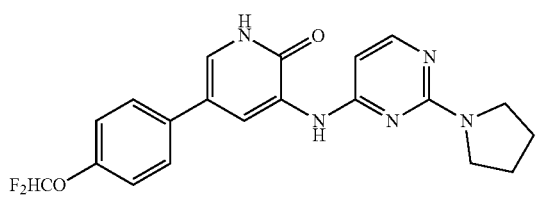
282

TABLE 1-continued
Exemplary Compounds of the Present Disclosure
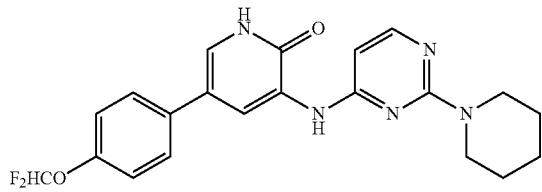
283
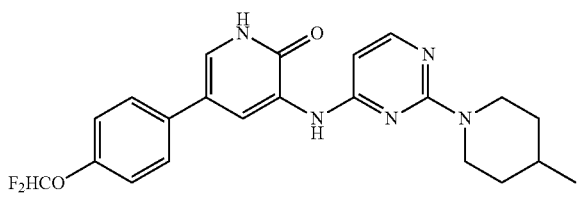
284
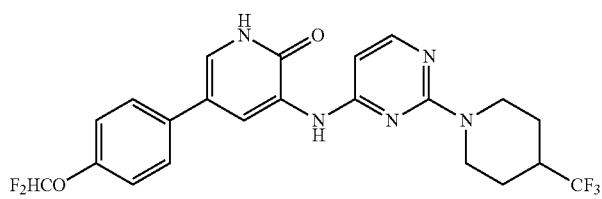
285
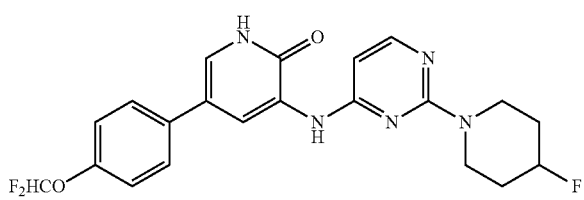
286
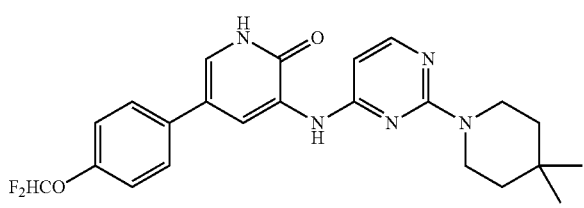
287
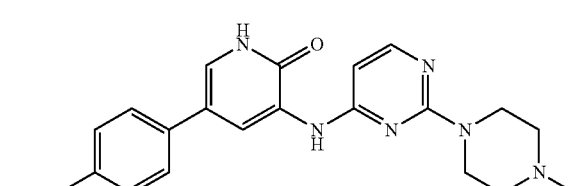
288

121
TABLE 1-continued
Exemplary Compounds of the Present Disclosure
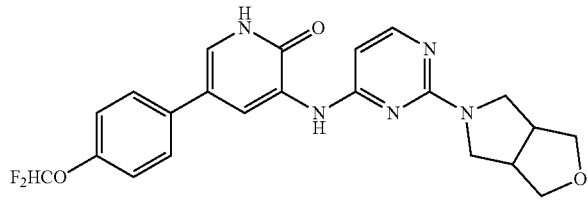
289
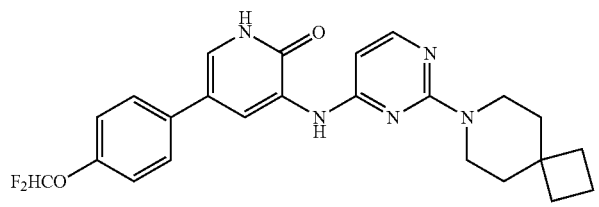
290
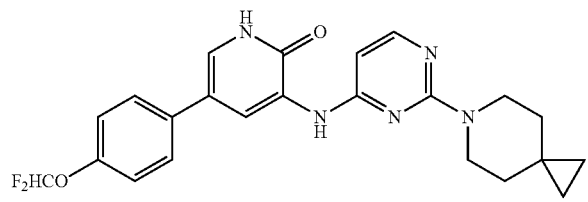
291
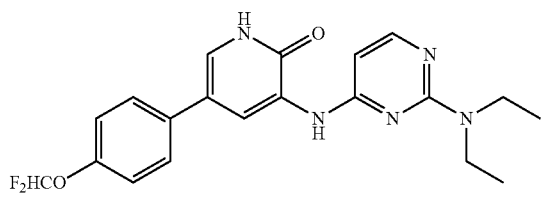
292
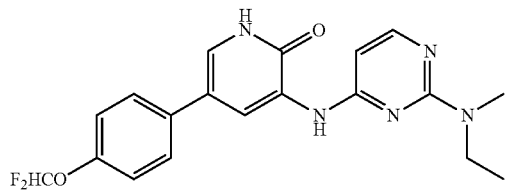
293
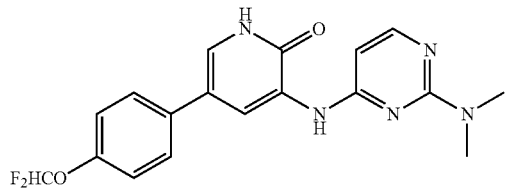
294

TABLE 1-continued
Exemplary Compounds of the Present Disclosure
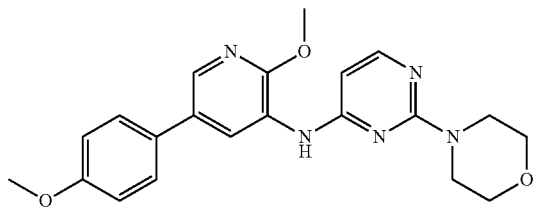
295
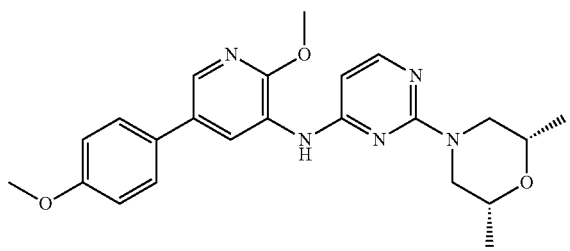
296
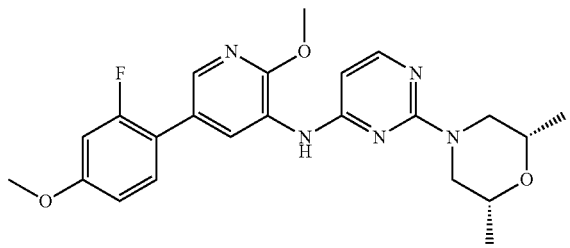
297
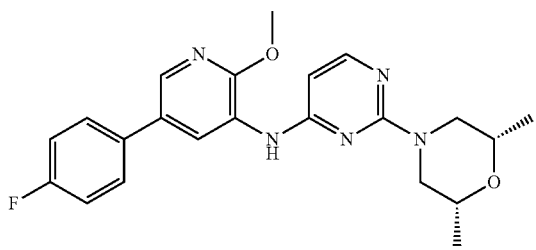
298
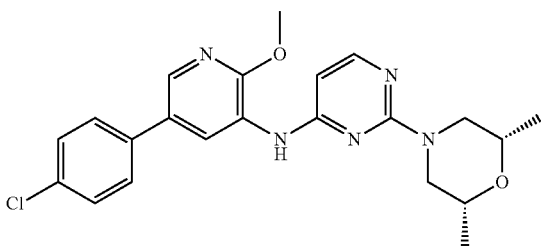
299

TABLE 1-continued
Exemplary Compounds of the Present Disclosure
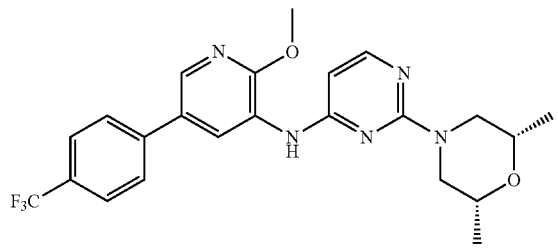
300
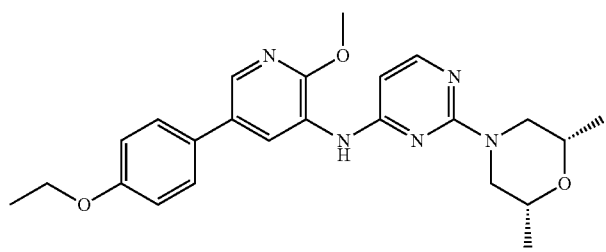
301
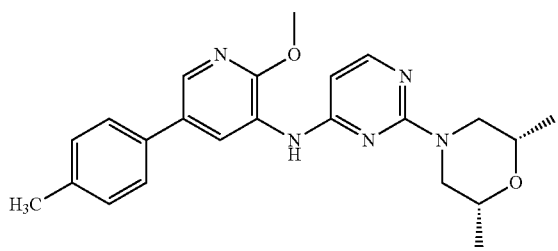
302
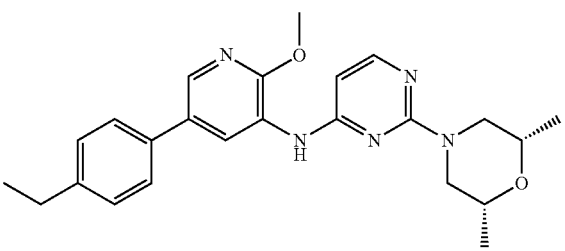
303
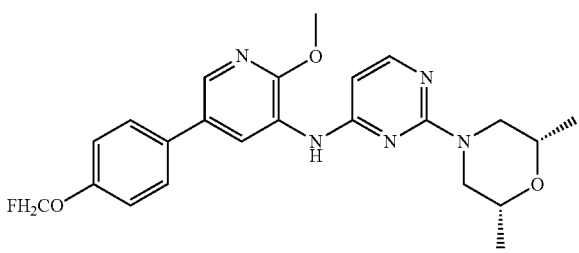
304

TABLE 1-continued
Exemplary Compounds of the Present Disclosure
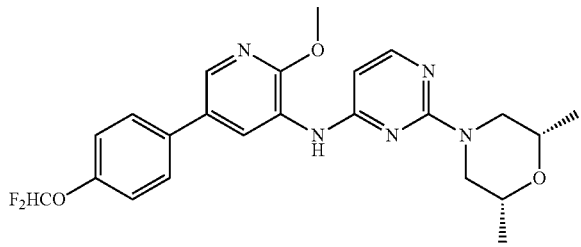
305
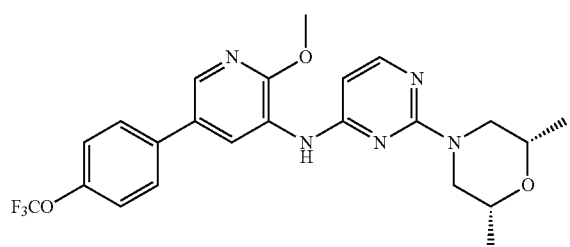
306
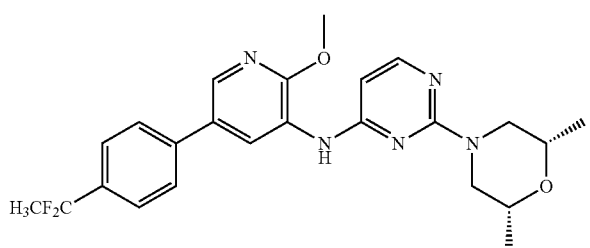
307
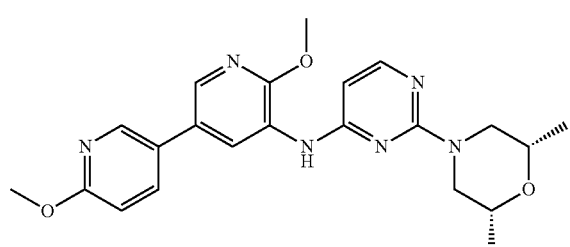
308
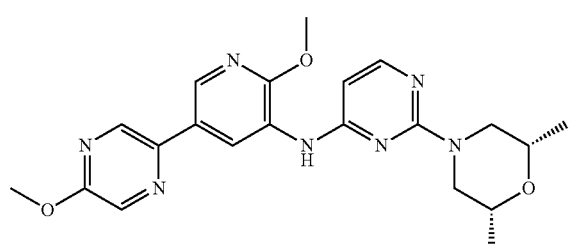
309

TABLE 1-continued
Exemplary Compounds of the Present Disclosure
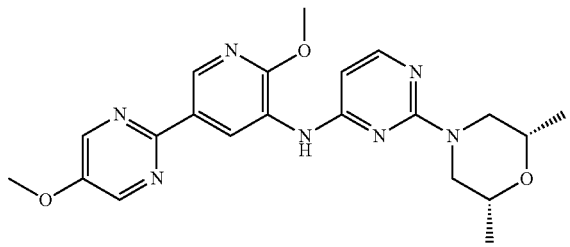
310
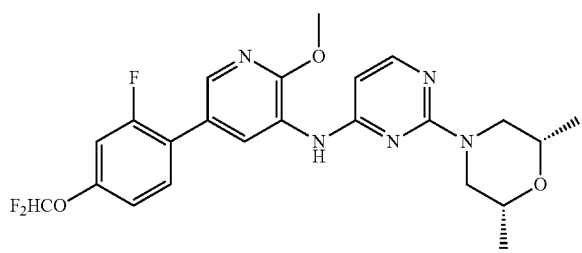
311
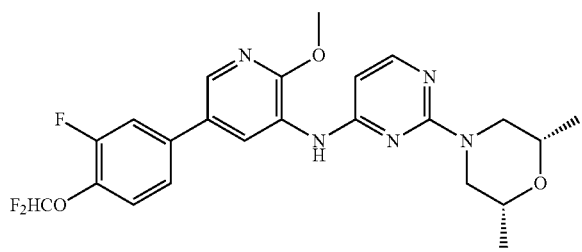
312
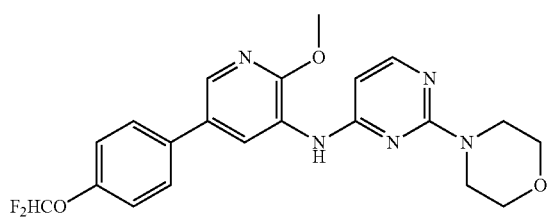
313
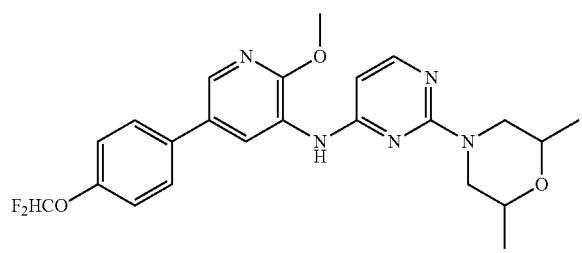 [SMILES: COc1ncc(-c2ccc(OC(F)F)cc2)cc1Nc1ccnc(N2CCOC(C)C2)n1]
314

TABLE 1-continued
Exemplary Compounds of the Present Disclosure
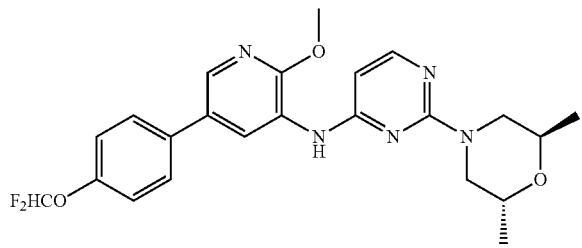
315
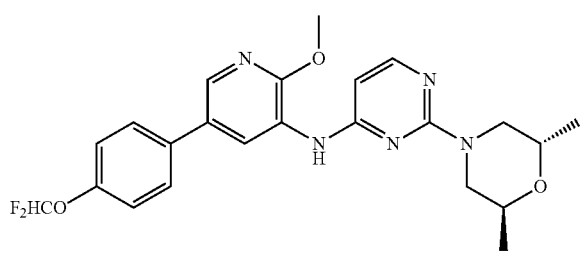
316
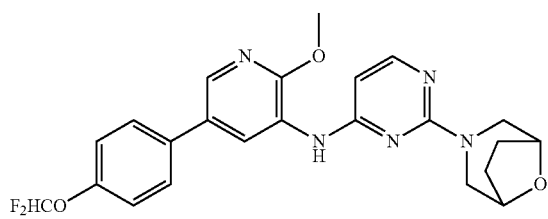
317
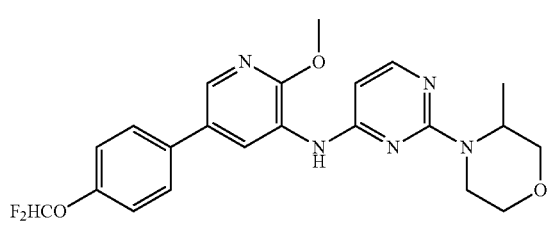
318
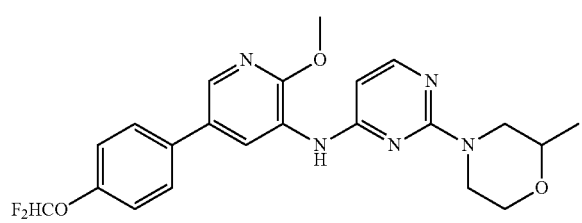
319

TABLE 1-continued
Exemplary Compounds of the Present Disclosure
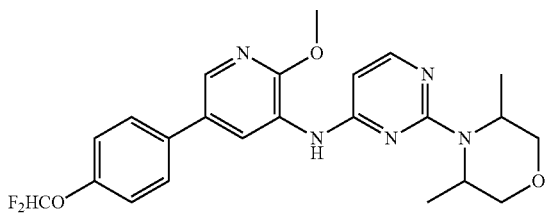
320
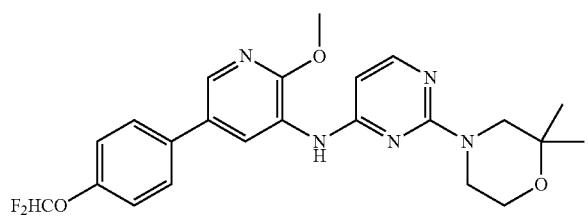
321
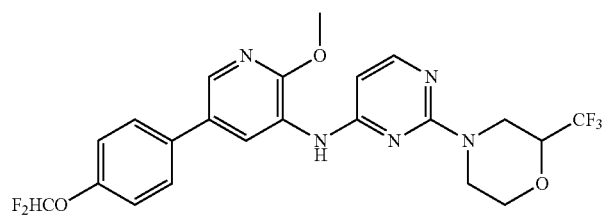
322
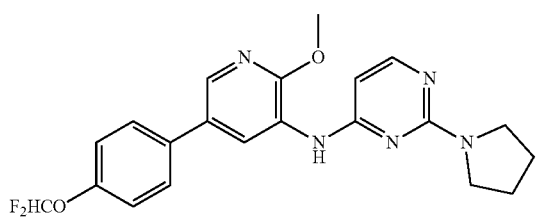
323
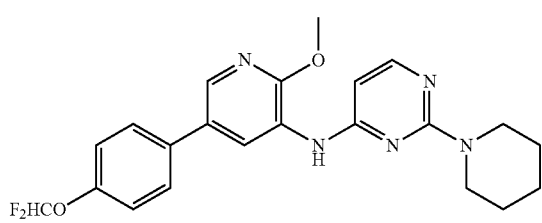
324
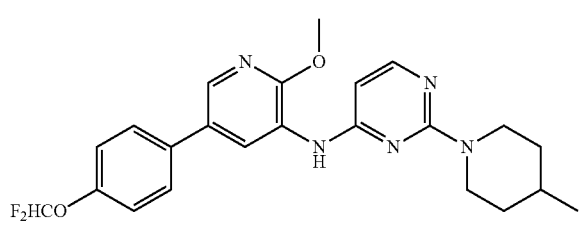
325

TABLE 1-continued
Exemplary Compounds of the Present Disclosure
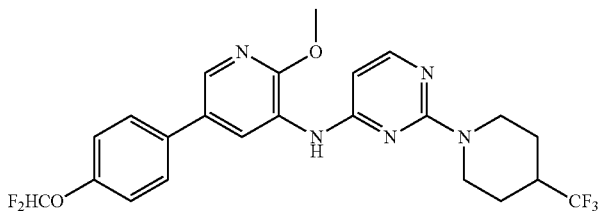
326
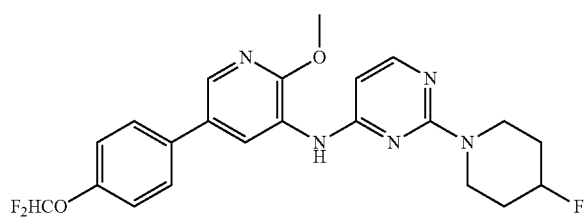
327
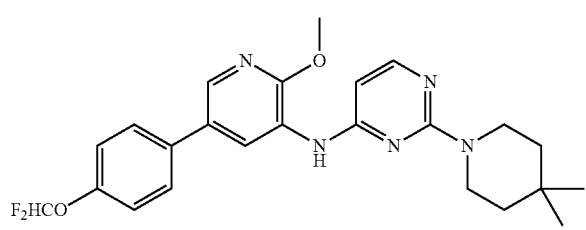
328
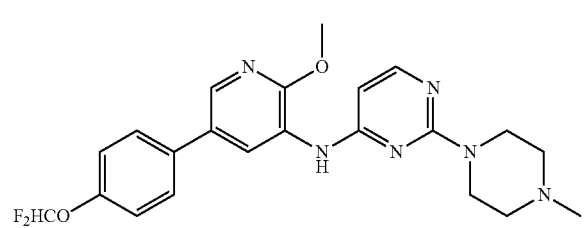
329
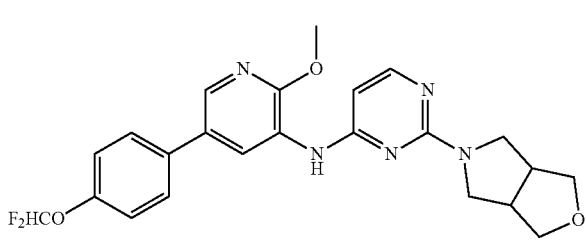
330
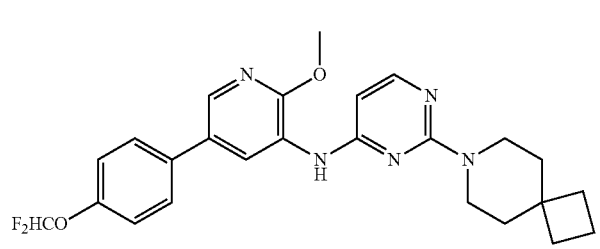
331

TABLE 1-continued
Exemplary Compounds of the Present Disclosure
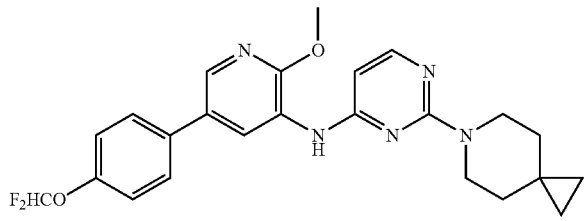
332
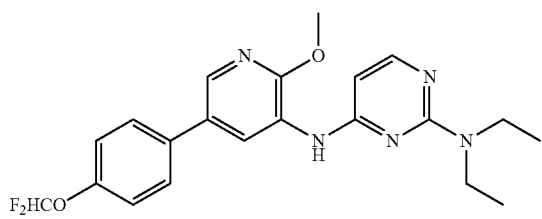
333
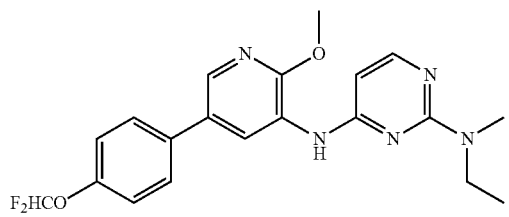
334
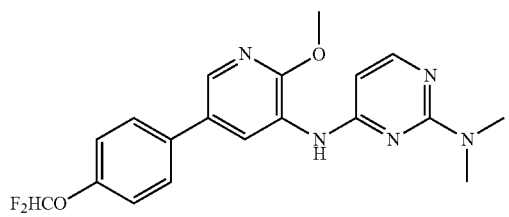
335
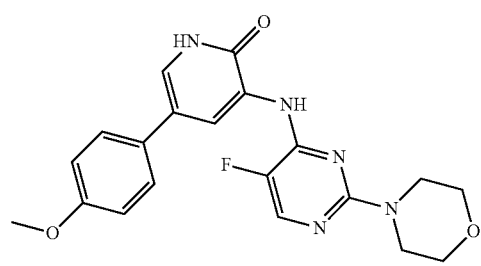
336

TABLE 1-continued
Exemplary Compounds of the Present Disclosure
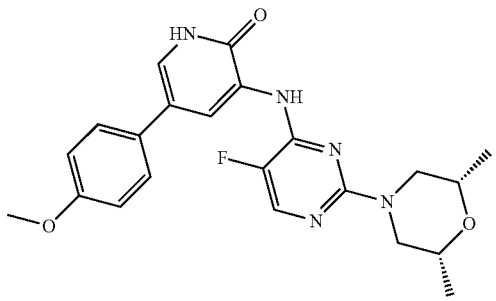
337
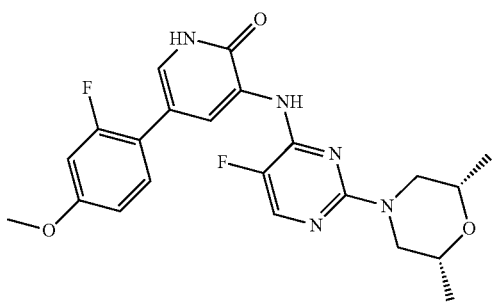
338
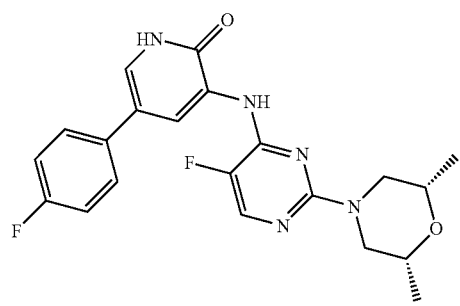
339
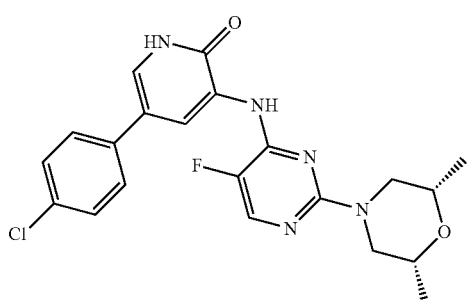
340

141 142
TABLE 1-continued
Exemplary Compounds of the Present Disclosure
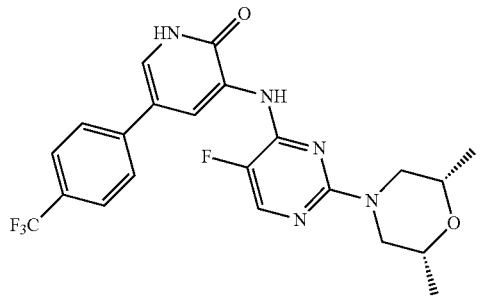
341
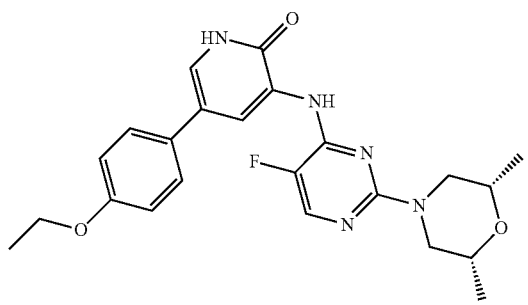
342
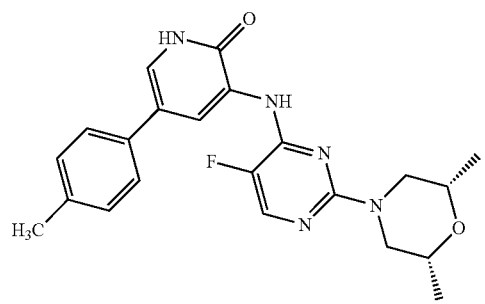
343
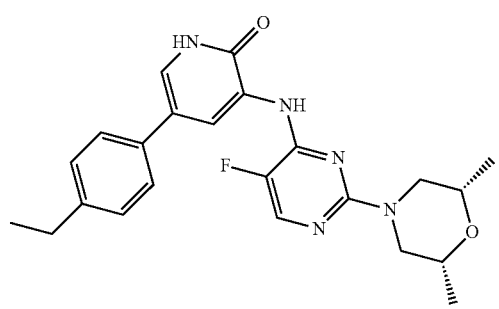
344

TABLE 1-continued
Exemplary Compounds of the Present Disclosure
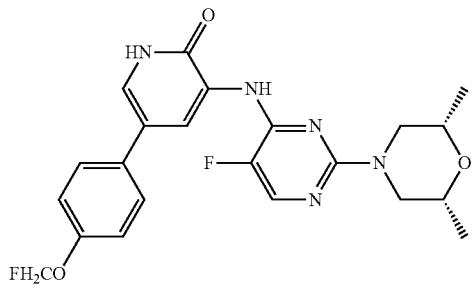
345
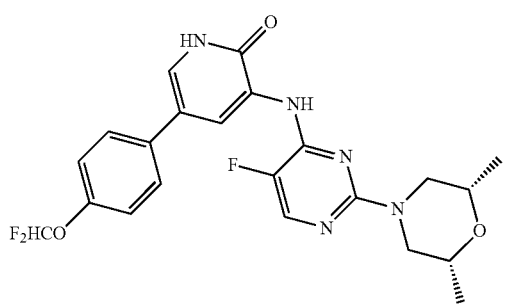
346
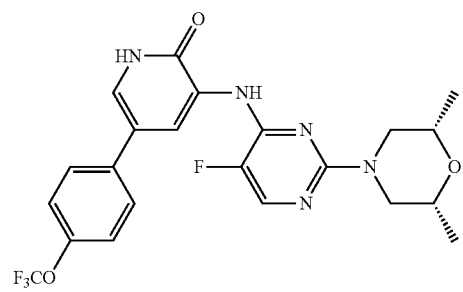
347
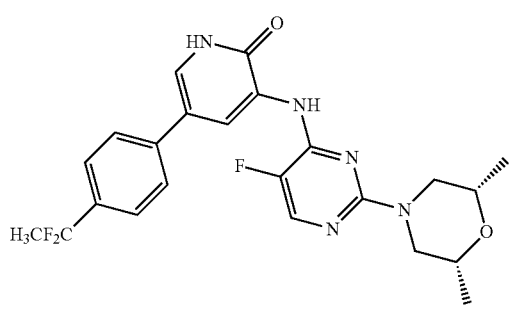
348

TABLE 1-continued
Exemplary Compounds of the Present Disclosure
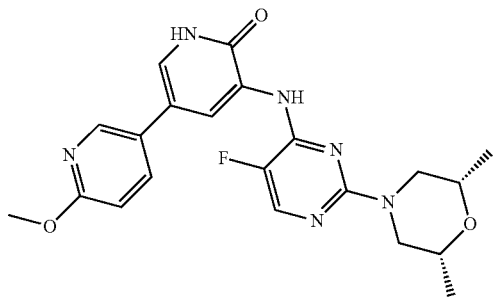
349
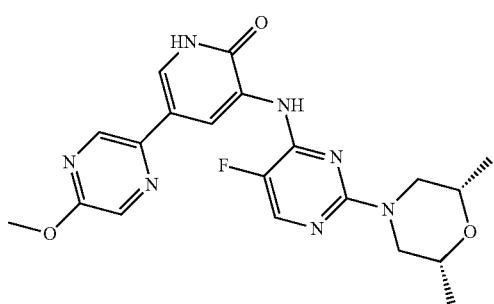
350
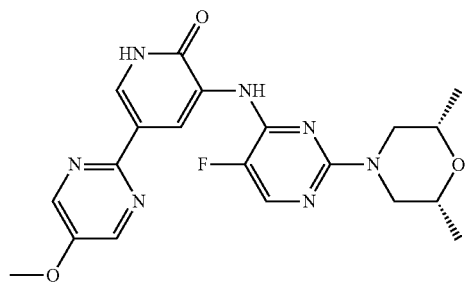
351
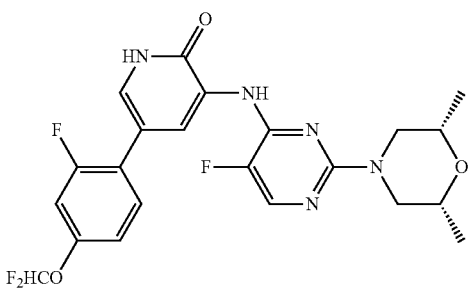
352

TABLE 1-continued
Exemplary Compounds of the Present Disclosure
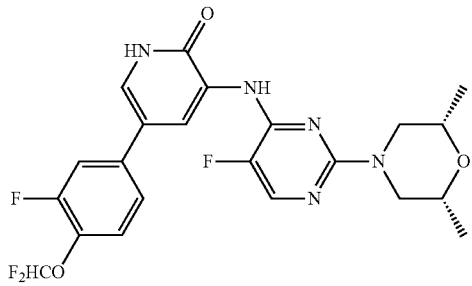
353
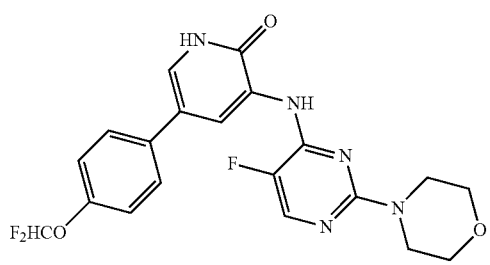
354
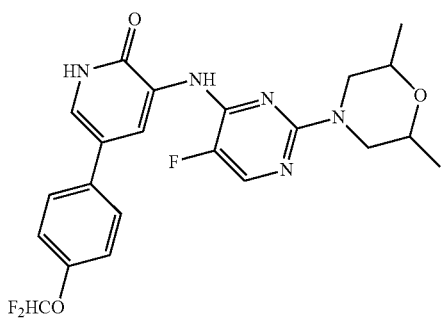
355
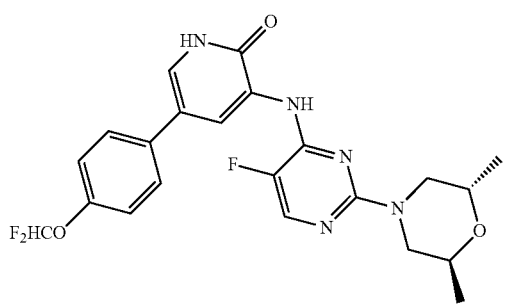
356

TABLE 1-continued
Exemplary Compounds of the Present Disclosure
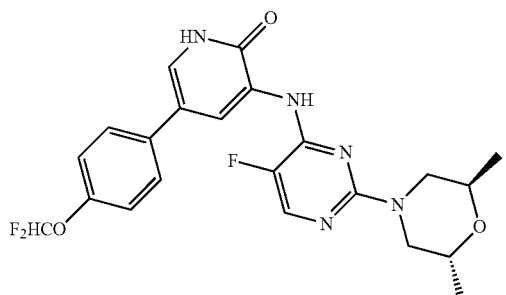
357
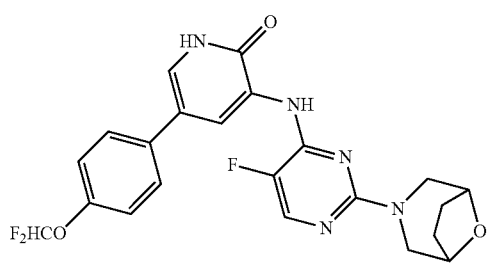
358
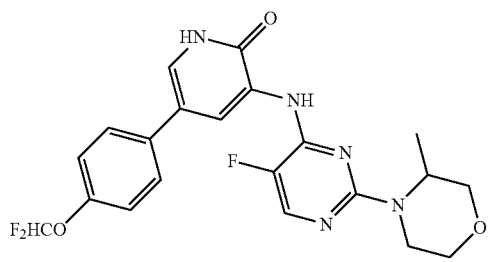
359
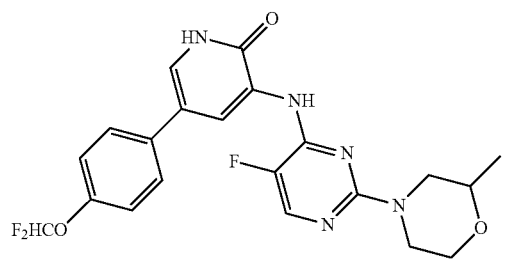
360
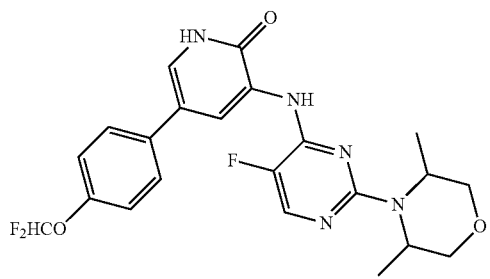
361

TABLE 1-continued
Exemplary Compounds of the Present Disclosure
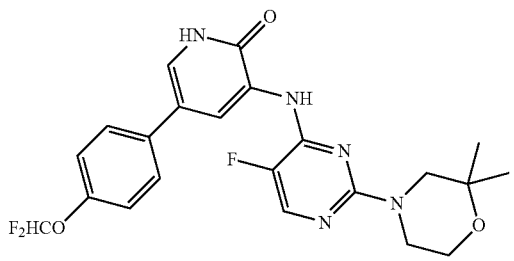
362
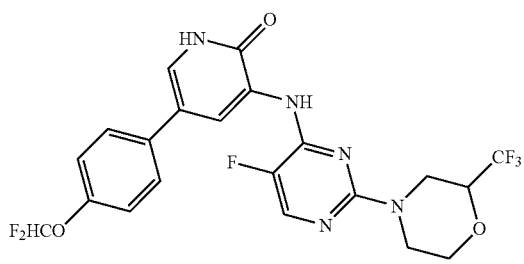
363
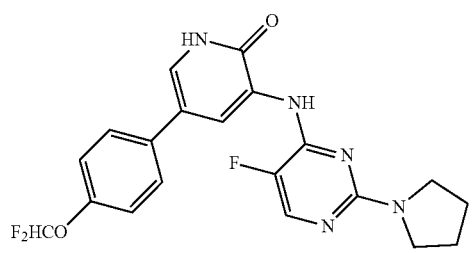
364
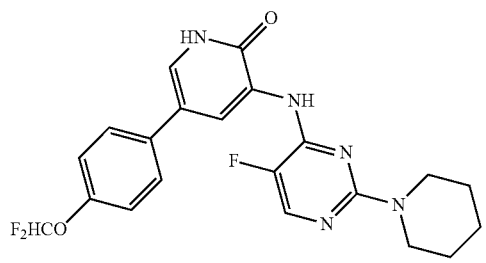
365
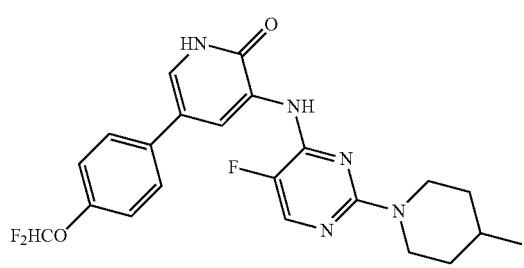
366

TABLE 1-continued
Exemplary Compounds of the Present Disclosure
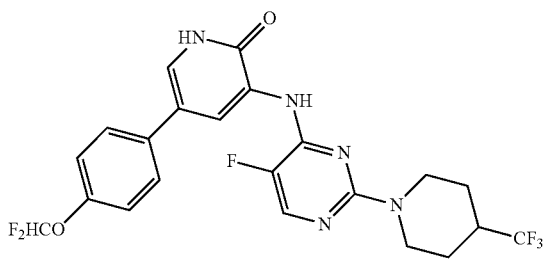
367
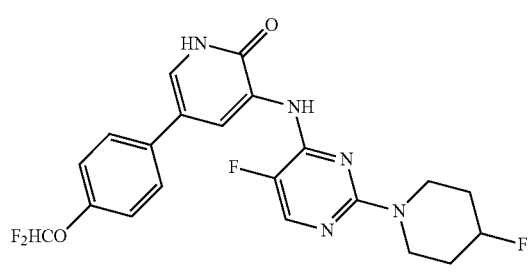
368
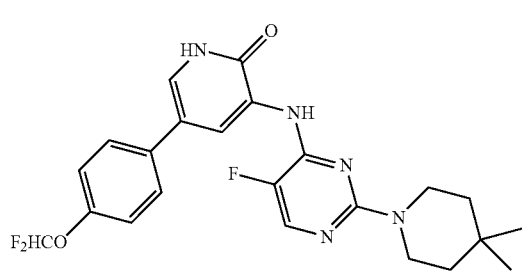
369
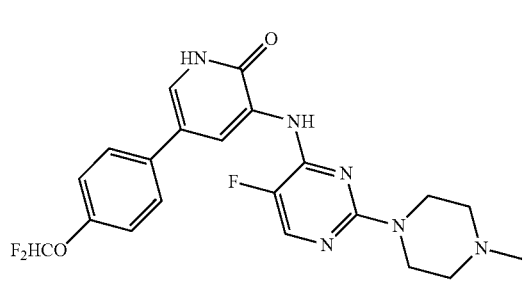
370
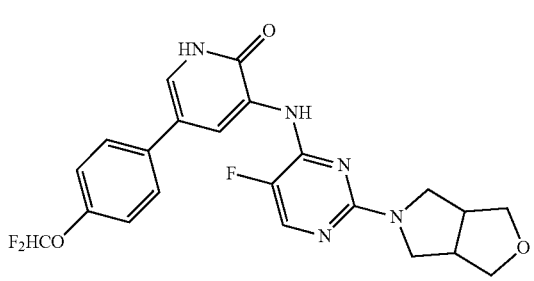
371

US 11,986,475 B1
155
156
TABLE 1-continued
Exemplary Compounds of the Present Disclosure
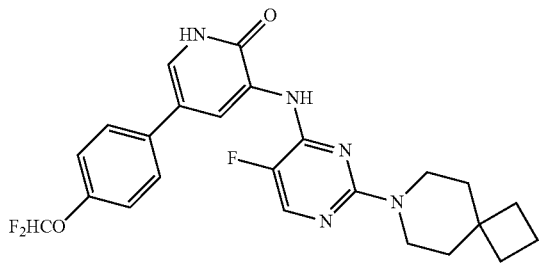
372
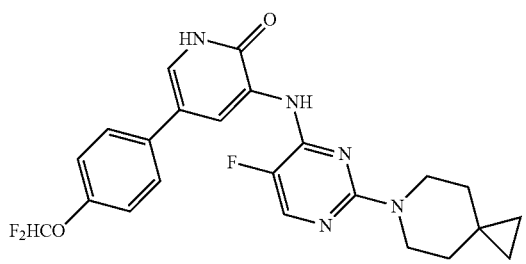
373
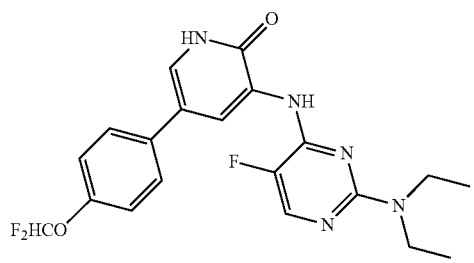
374
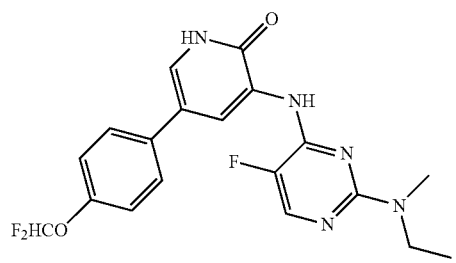
375
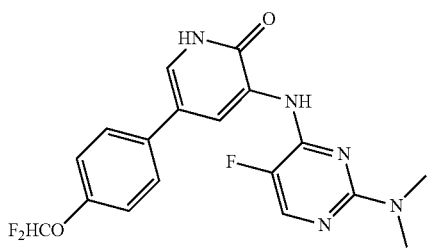
376

TABLE 1-continued
Exemplary Compounds of the Present Disclosure
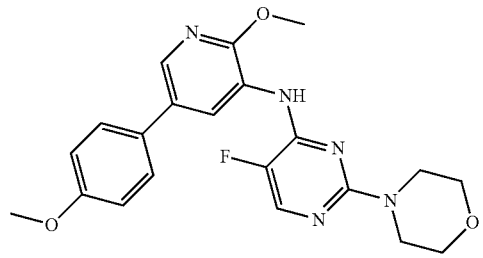
377
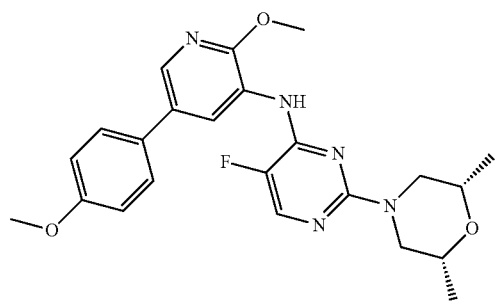
378
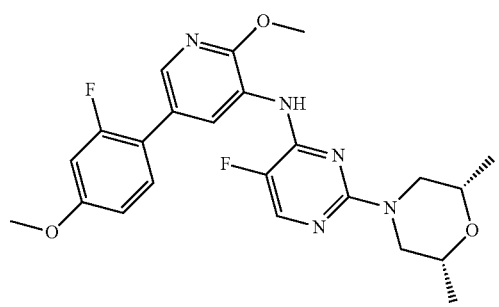
379
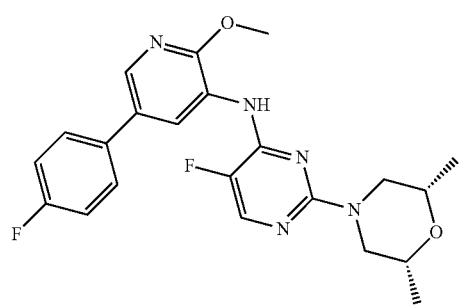
380

TABLE 1-continued
Exemplary Compounds of the Present Disclosure
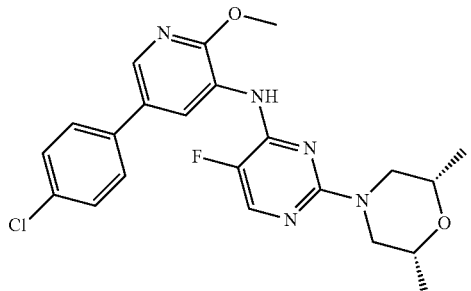
381
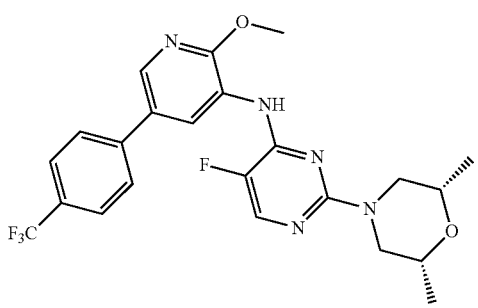
382
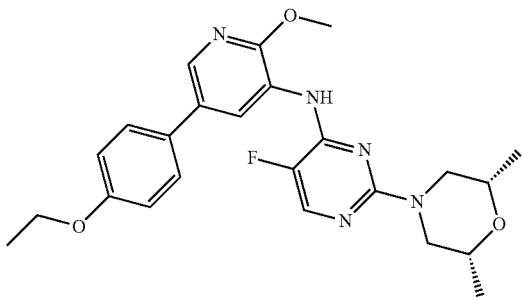
383
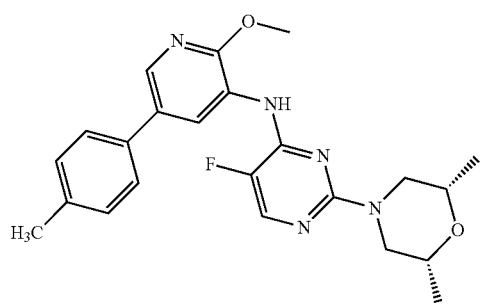
384

TABLE 1-continued
Exemplary Compounds of the Present Disclosure
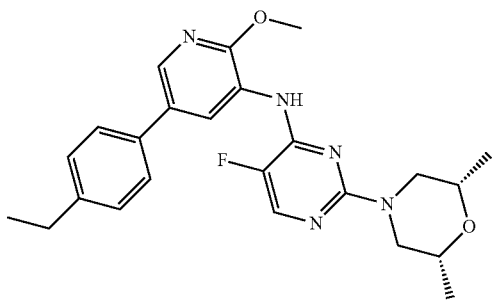
385
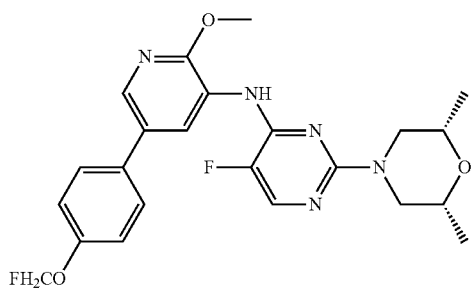
386
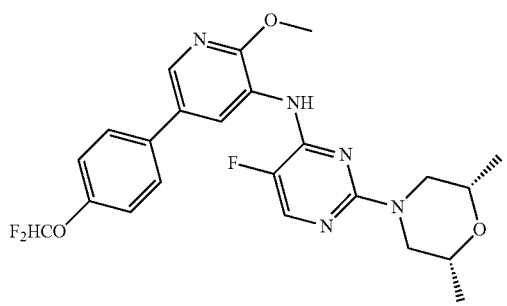
387
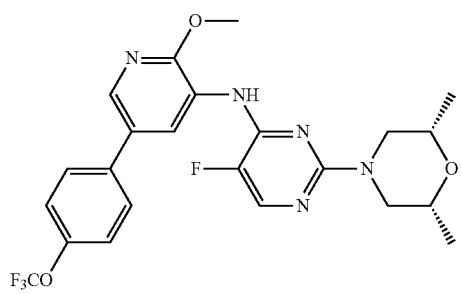
388

TABLE 1-continued
Exemplary Compounds of the Present Disclosure
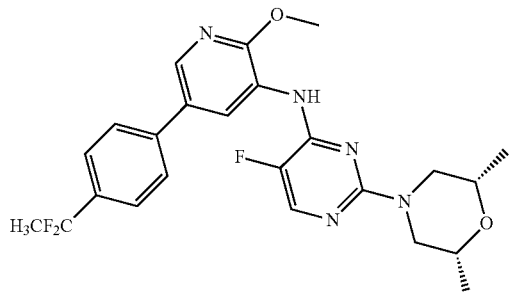
389
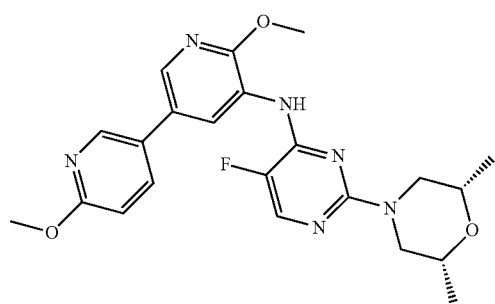
390
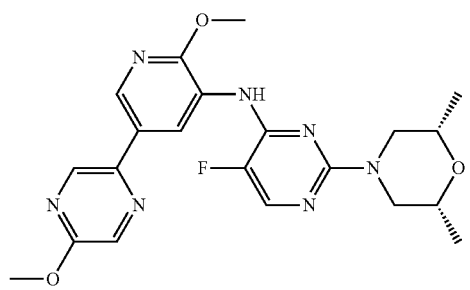
391
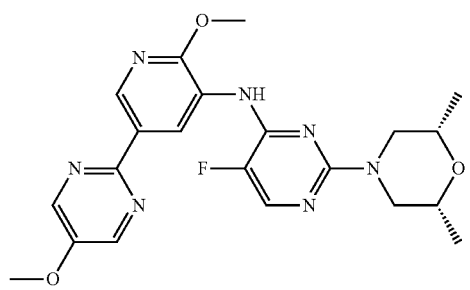
392

TABLE 1-continued
Exemplary Compounds of the Present Disclosure
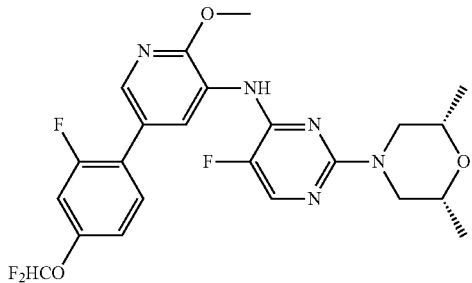
393
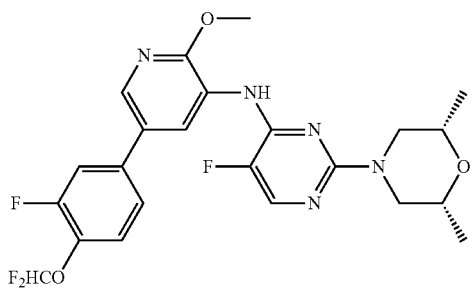
394
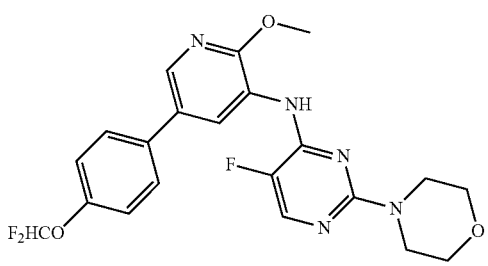
395
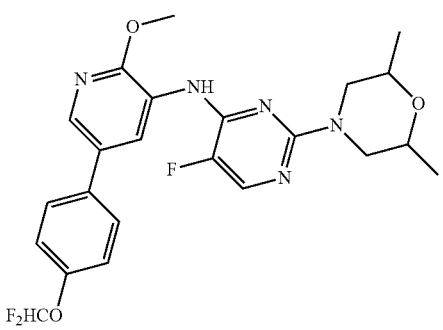
396

TABLE 1-continued
Exemplary Compounds of the Present Disclosure
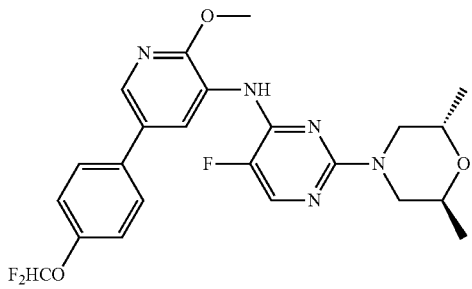
397
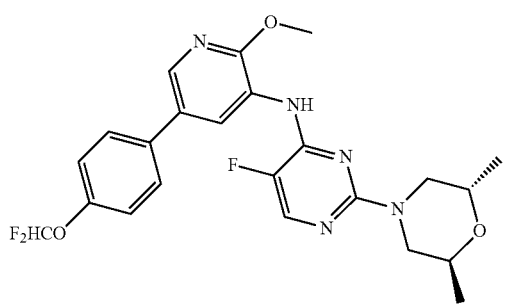
398
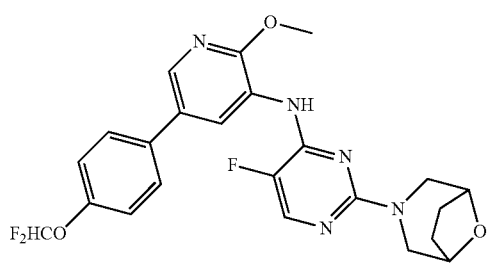
399
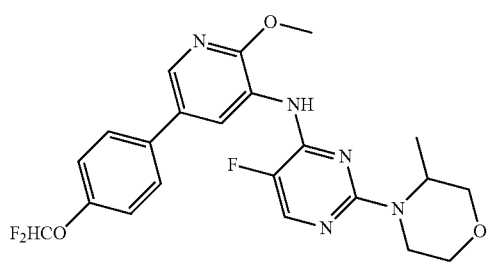
400
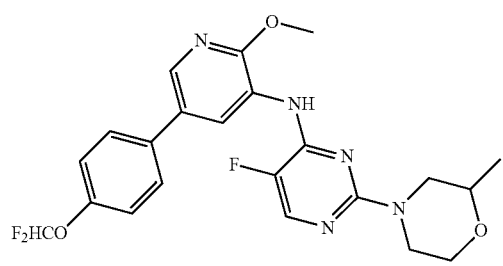
401

TABLE 1-continued
Exemplary Compounds of the Present Disclosure
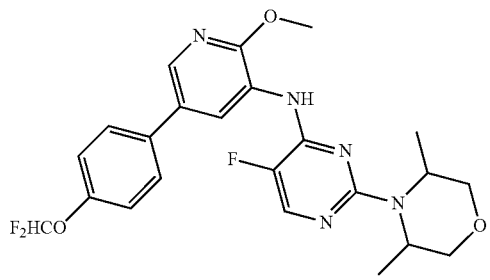
402
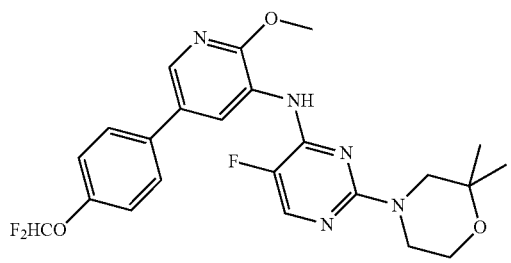
403
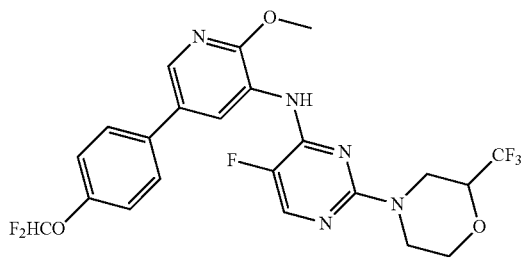
404
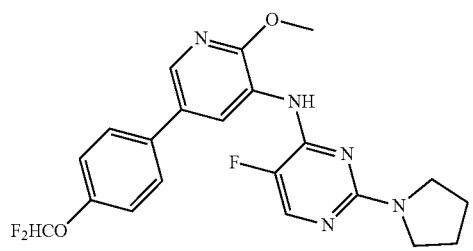
405
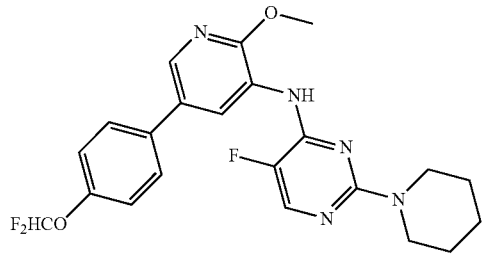
406

TABLE 1-continued
Exemplary Compounds of the Present Disclosure
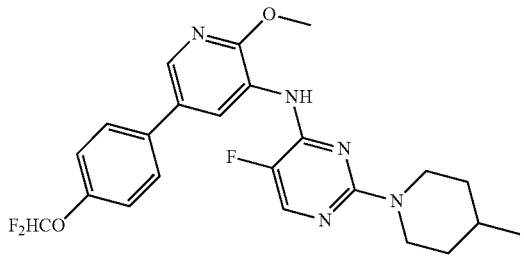
407
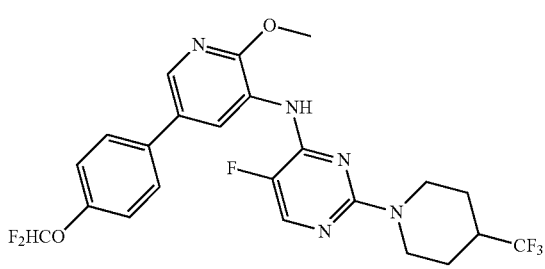
408
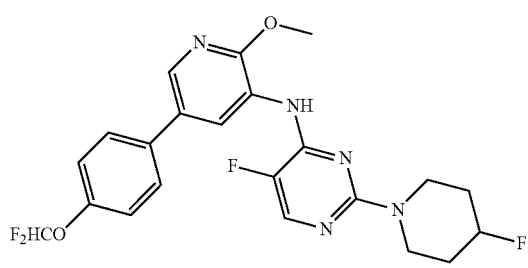
409
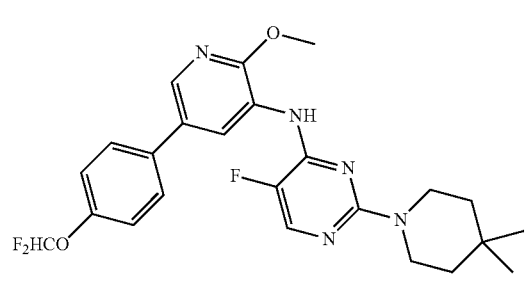
410
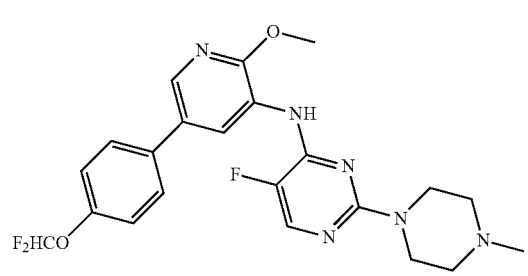
411

TABLE 1-continued
Exemplary Compounds of the Present Disclosure
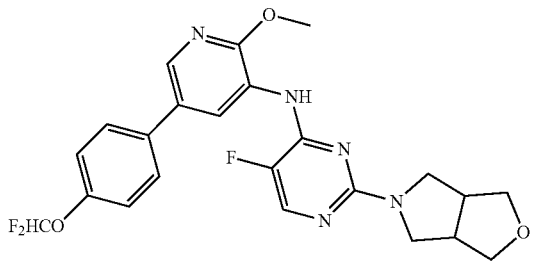
412
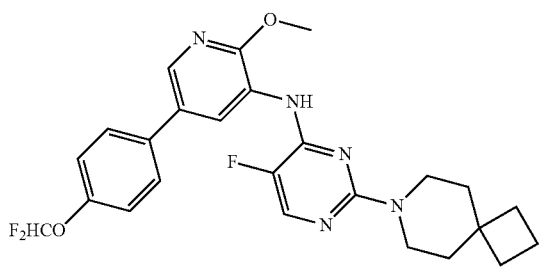
413
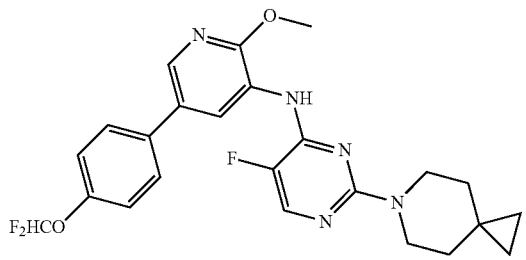
414
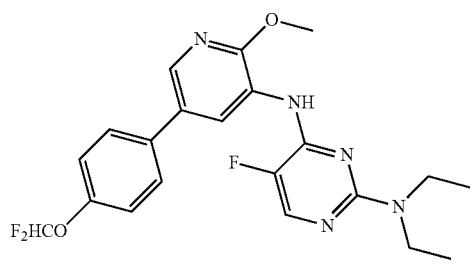
415
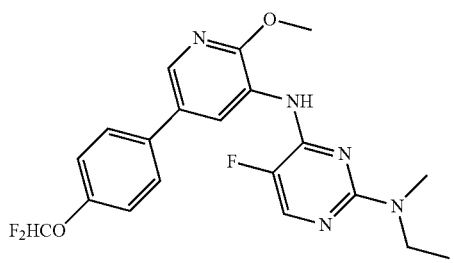
416

TABLE 1-continued
Exemplary Compounds of the Present Disclosure
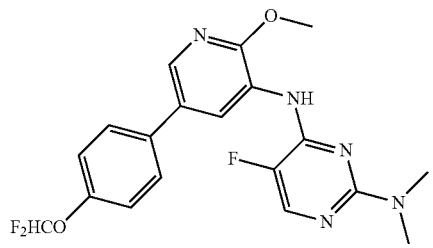
417
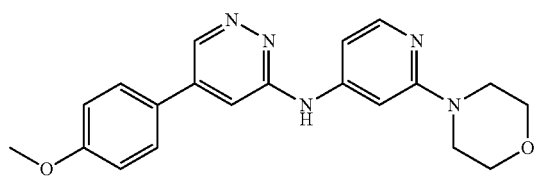
418
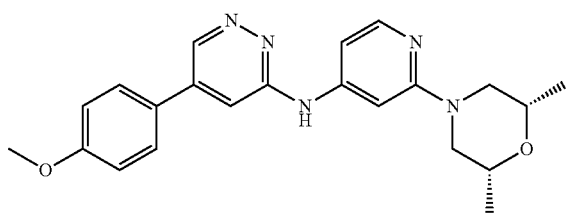
419
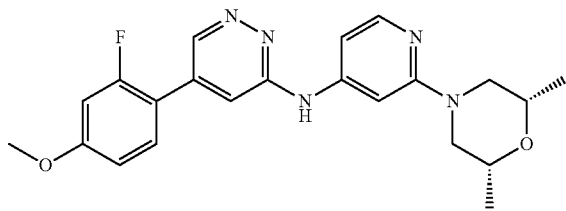
420
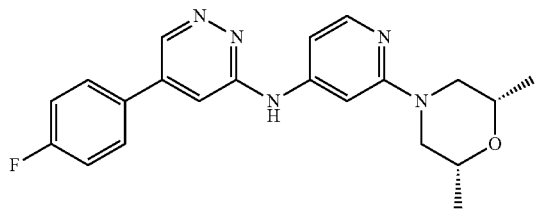
421
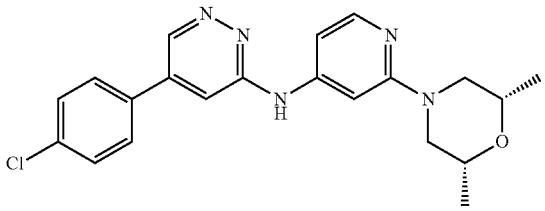
422

TABLE 1-continued
Exemplary Compounds of the Present Disclosure
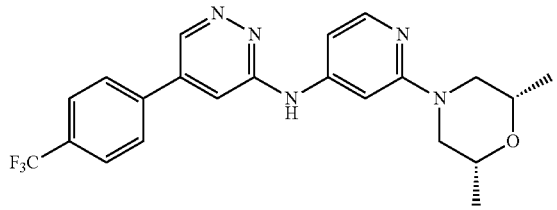
423
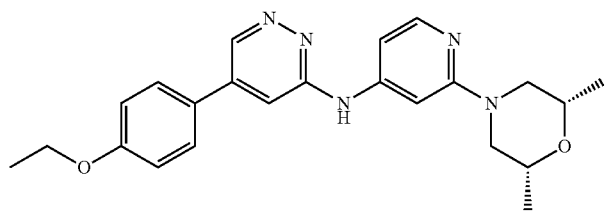
424
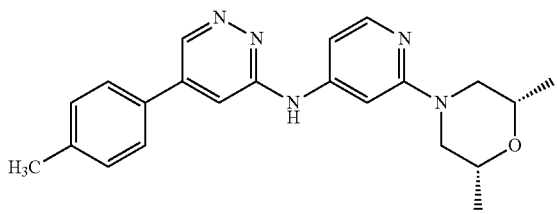
425
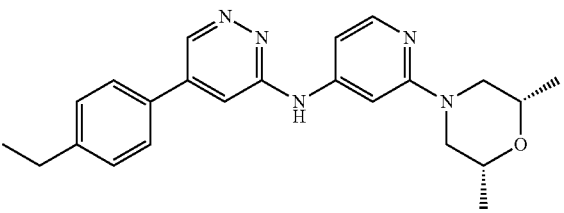
426
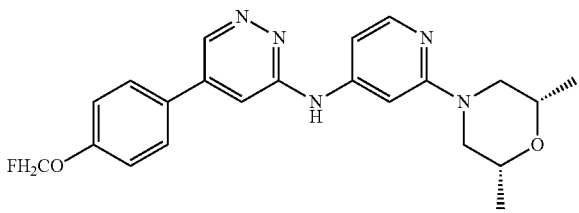
427
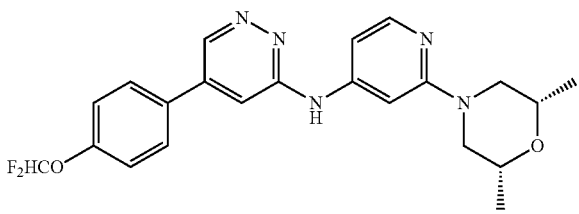
428

TABLE 1-continued
Exemplary Compounds of the Present Disclosure
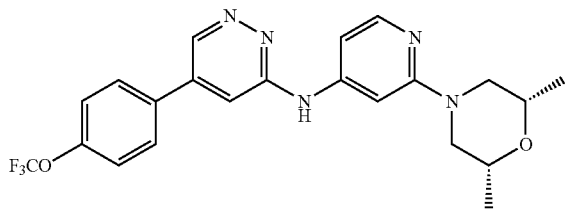
429
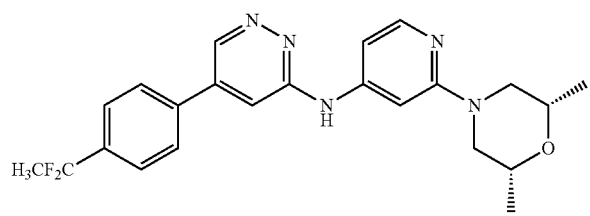
430
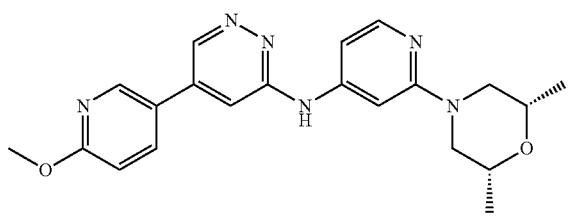
431
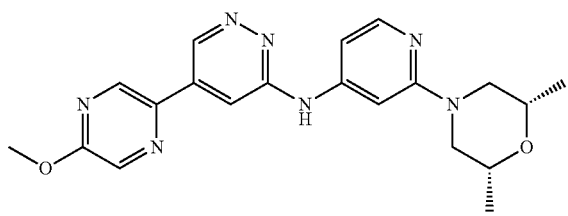
432
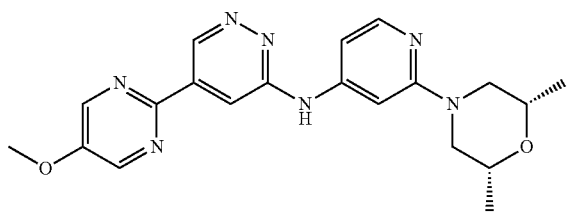
433
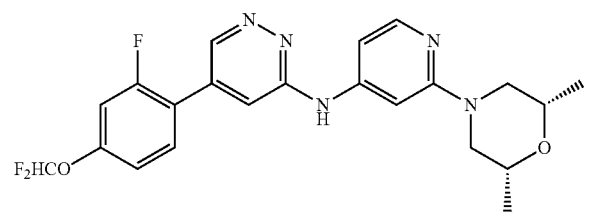
434

TABLE 1-continued
Exemplary Compounds of the Present Disclosure
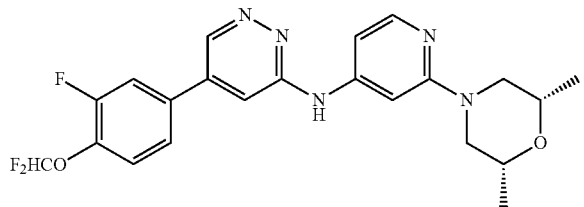
435
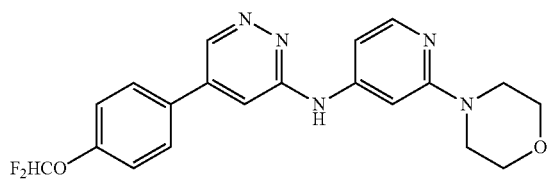
436
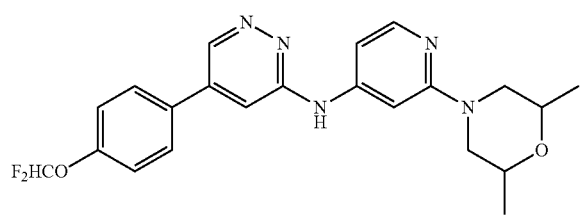
437
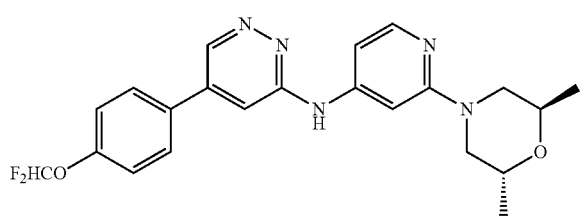
438
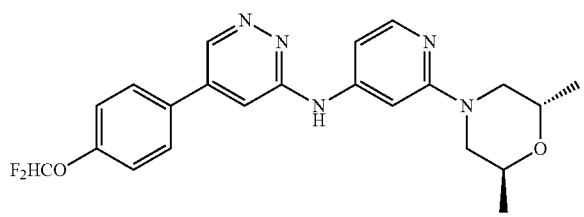
439
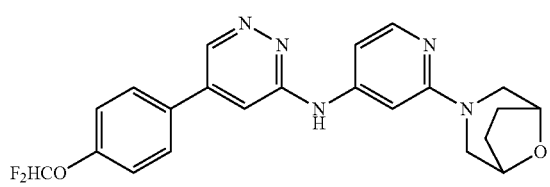
440

TABLE 1-continued
Exemplary Compounds of the Present Disclosure
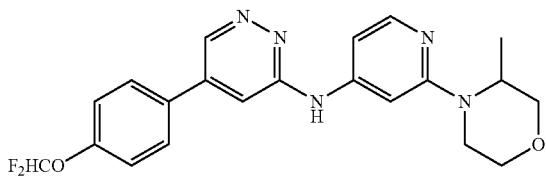
441
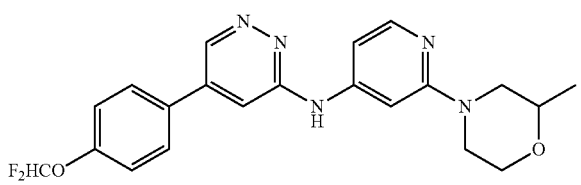
442
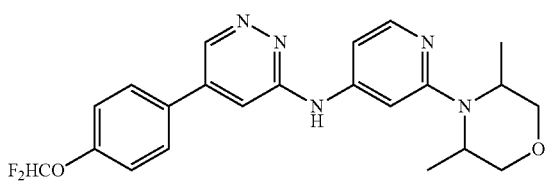
443
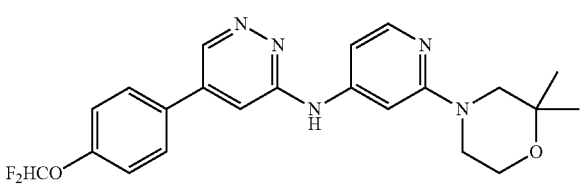
444
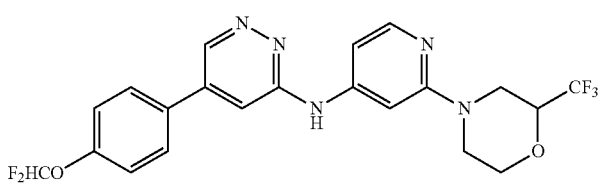
445
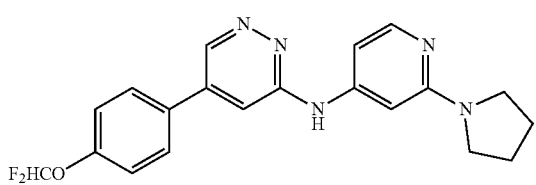
446
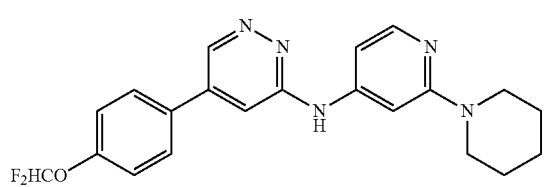
447

TABLE 1-continued
Exemplary Compounds of the Present Disclosure
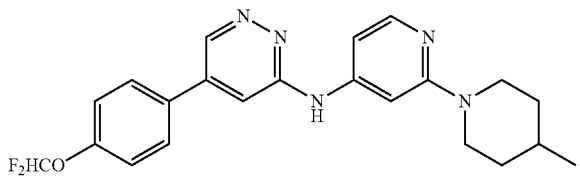
448
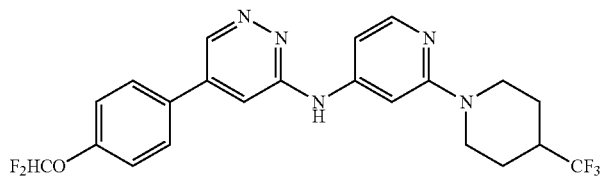
449
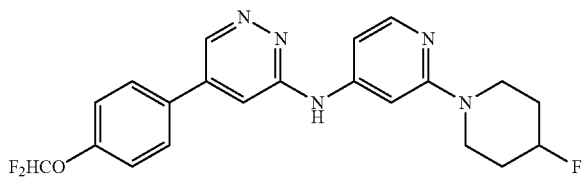
450
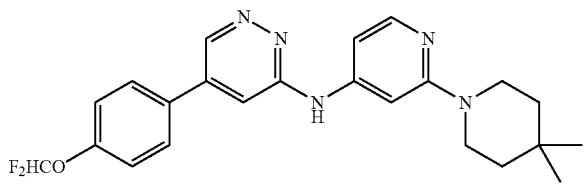
451
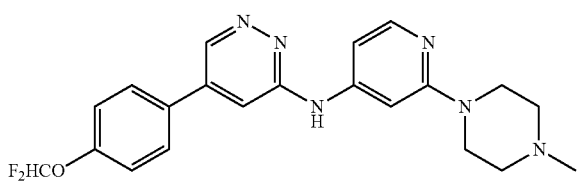
452
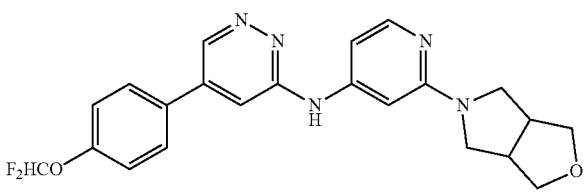
453
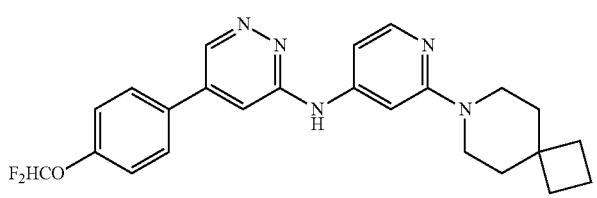
454

TABLE 1-continued
Exemplary Compounds of the Present Disclosure
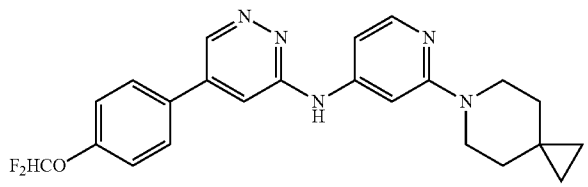
455
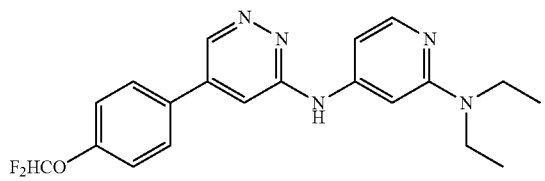
456
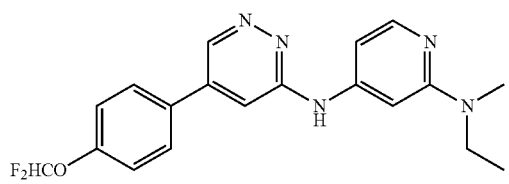
457
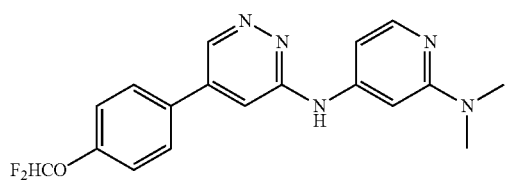
458
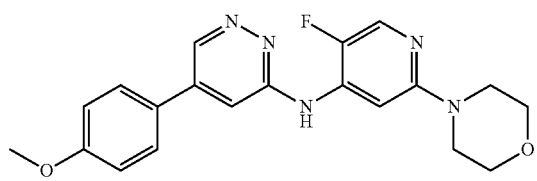
459
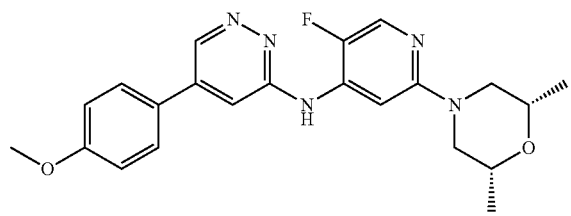
460

189
TABLE 1-continued
Exemplary Compounds of the Present Disclosure
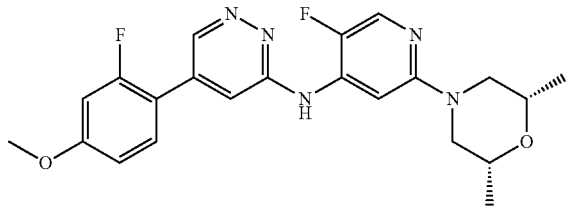
461
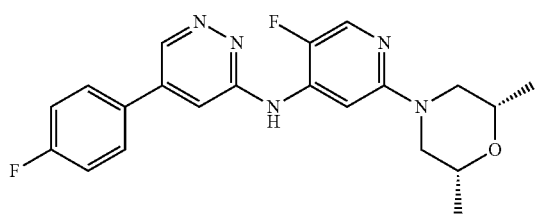
462
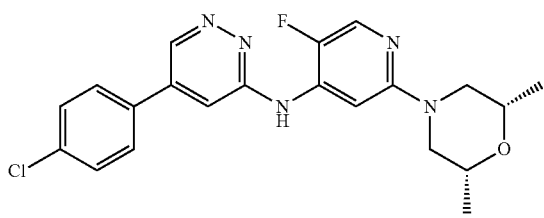
463
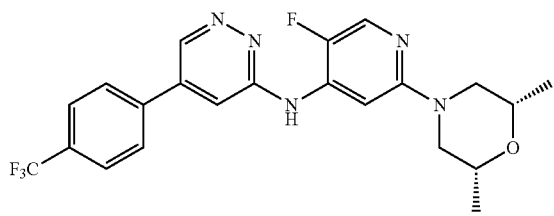
464
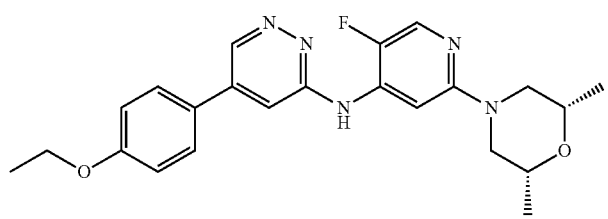
465
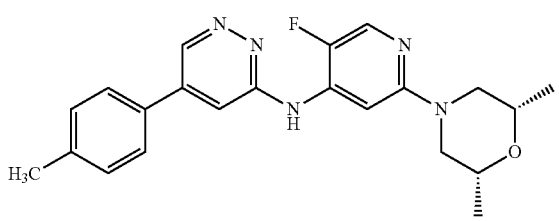
466

TABLE 1-continued
Exemplary Compounds of the Present Disclosure
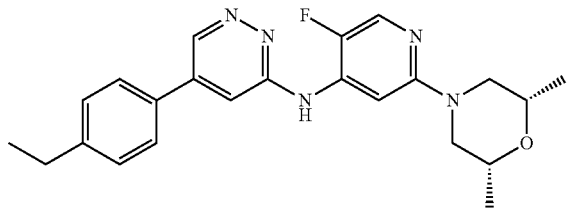
467
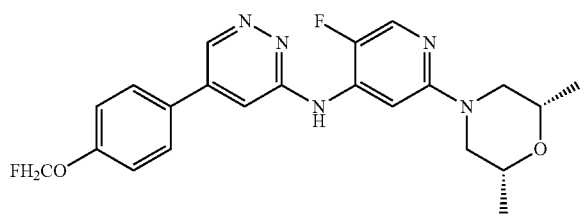
468
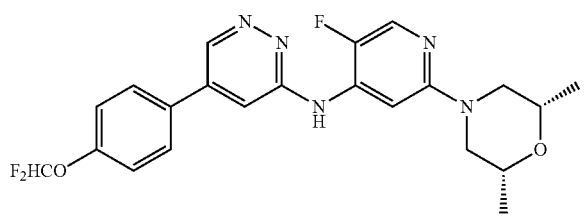
469
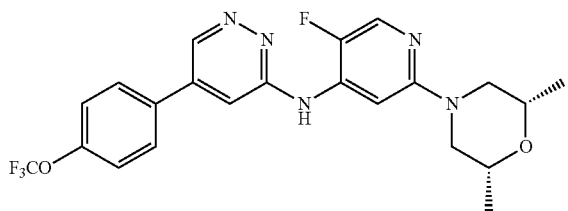
470
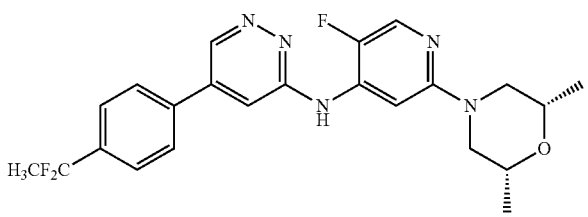
471
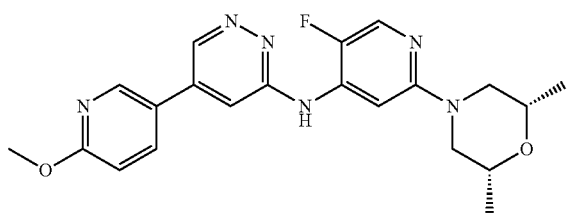
472

TABLE 1-continued
Exemplary Compounds of the Present Disclosure
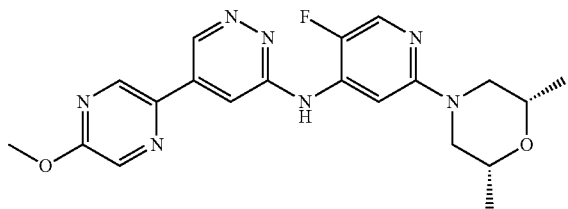
473
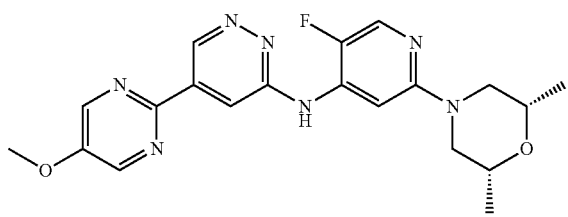
474
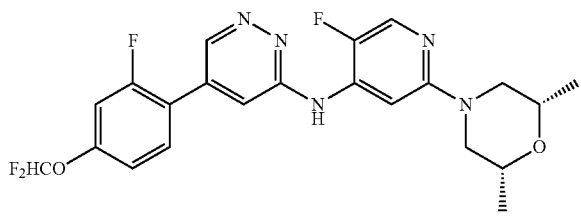
475
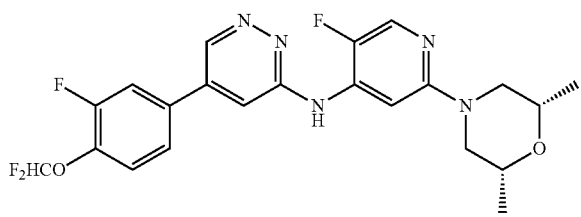
476
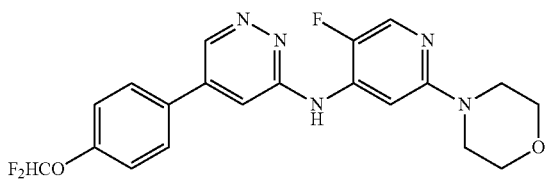
477
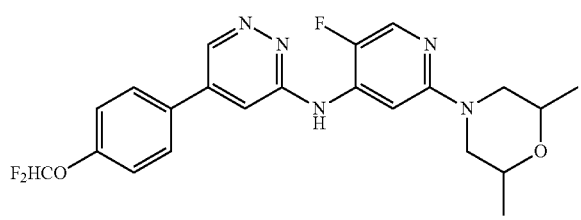
478

TABLE 1-continued
Exemplary Compounds of the Present Disclosure
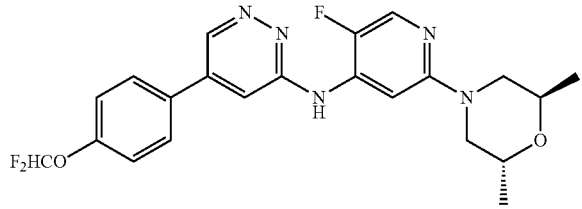
479
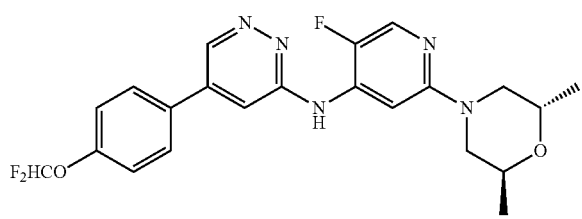
480
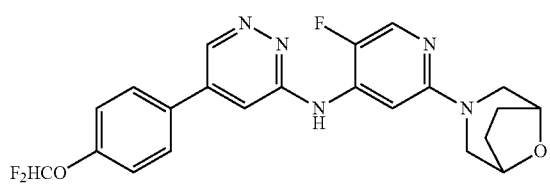
481
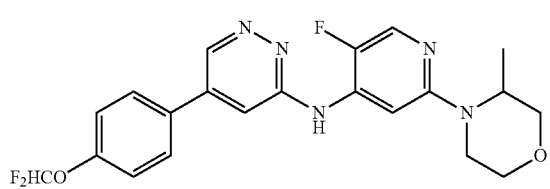
482
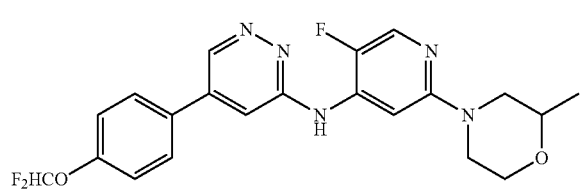
483
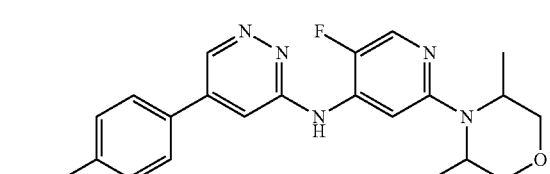
484

TABLE 1-continued
Exemplary Compounds of the Present Disclosure
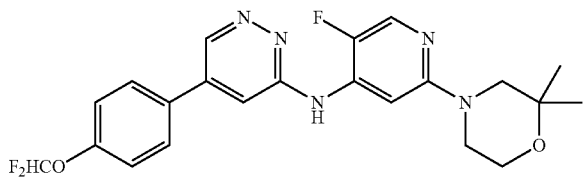
485
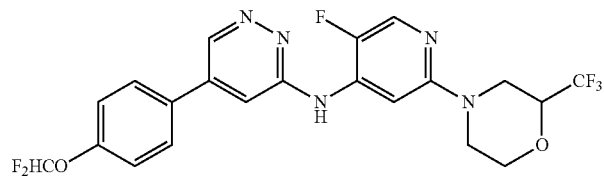
486
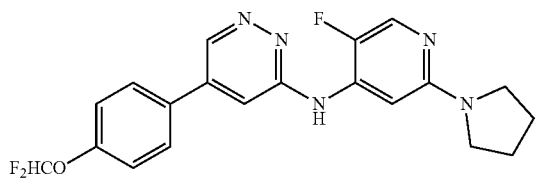
487
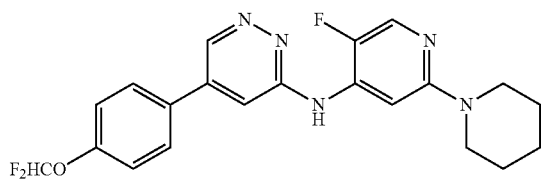
488
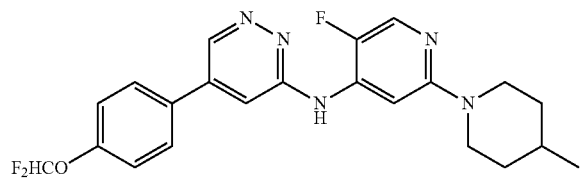
489
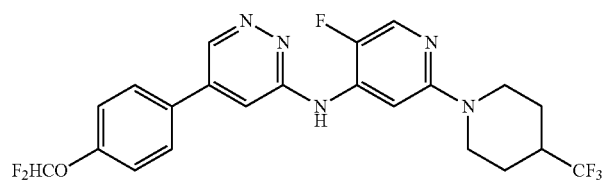
490
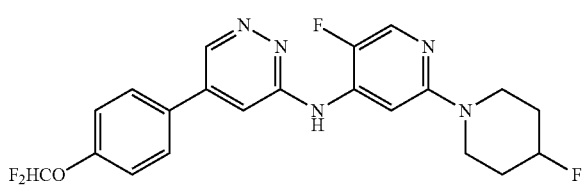
491

TABLE 1-continued
Exemplary Compounds of the Present Disclosure
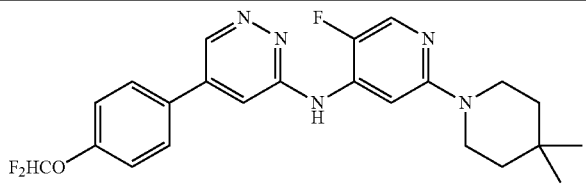
492
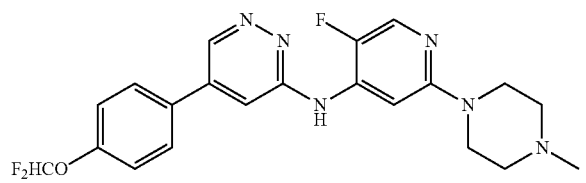
493
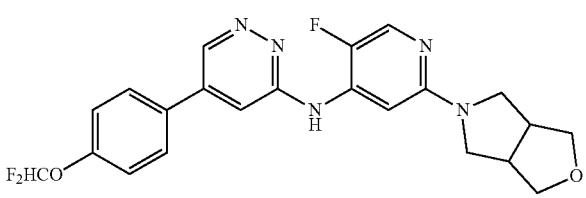
494
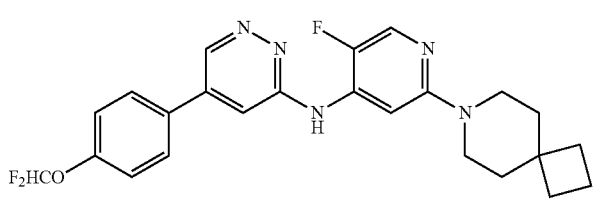
495
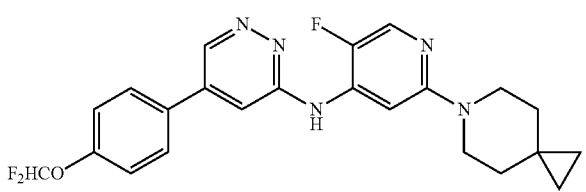
496
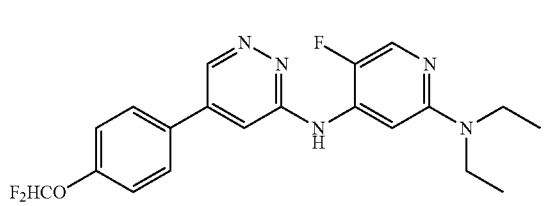
497
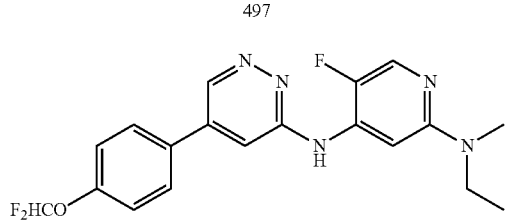
498

TABLE 1-continued
Exemplary Compounds of the Present Disclosure
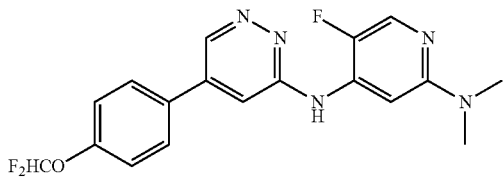
499
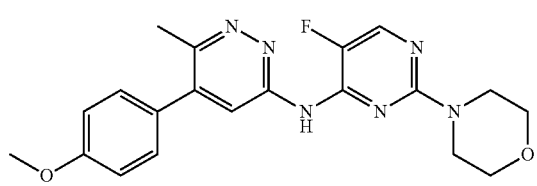
500
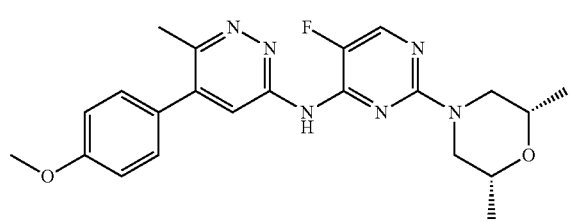
501
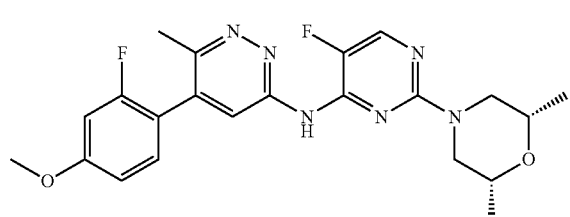
502
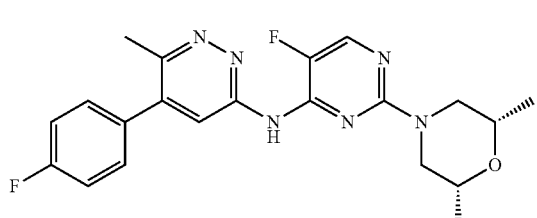
503
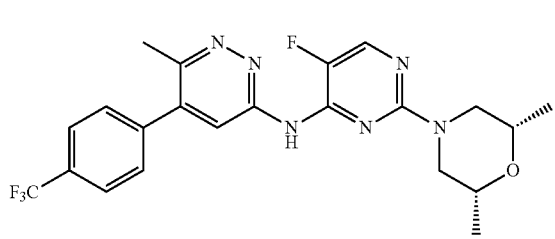
504

TABLE 1-continued
Exemplary Compounds of the Present Disclosure
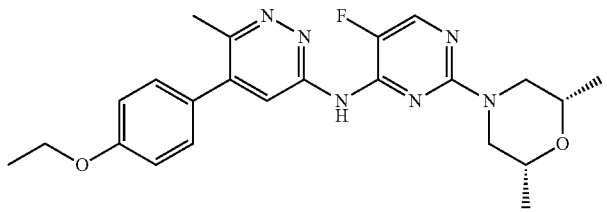
505
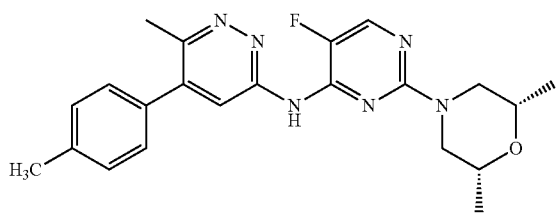
506
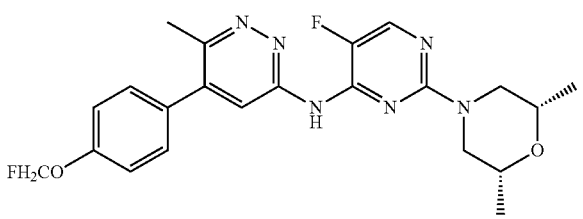
507
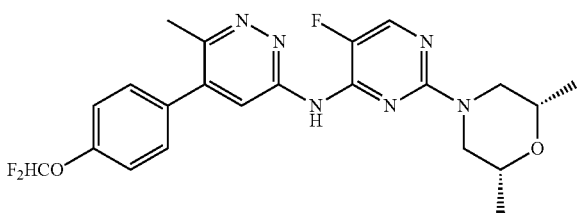
508
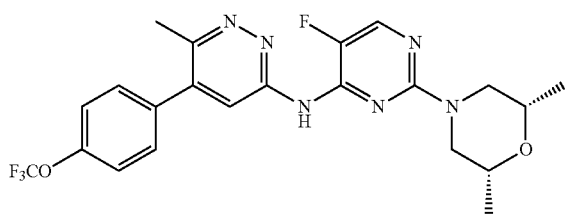
509
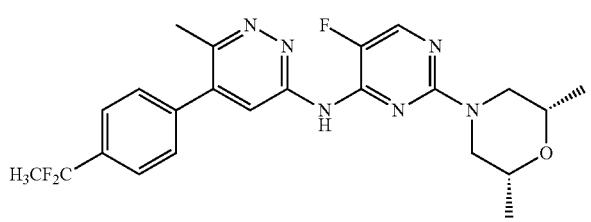
510

TABLE 1-continued
Exemplary Compounds of the Present Disclosure
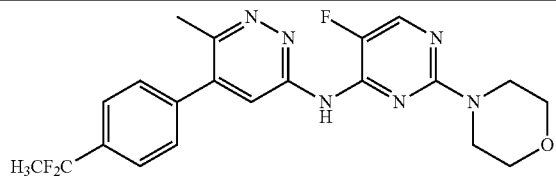
511
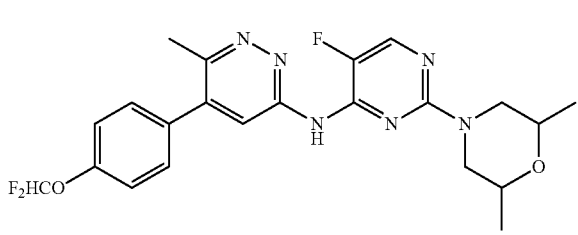
512
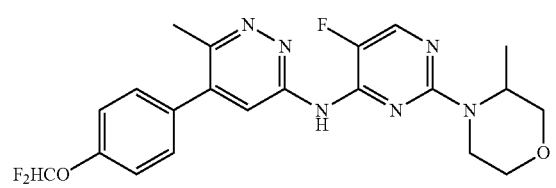
513
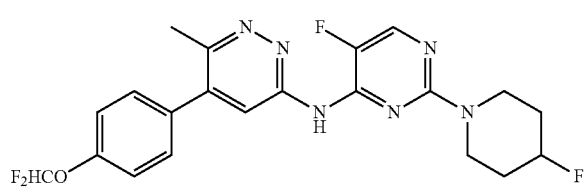
514
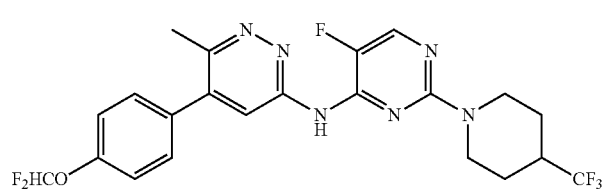
515
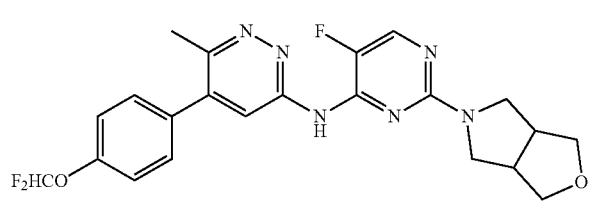
516
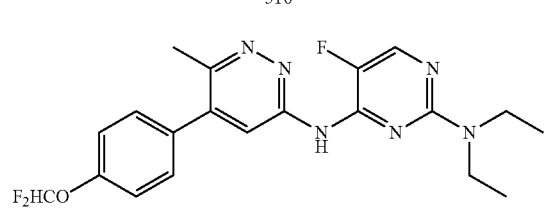
517

TABLE 1-continued
Exemplary Compounds of the Present Disclosure
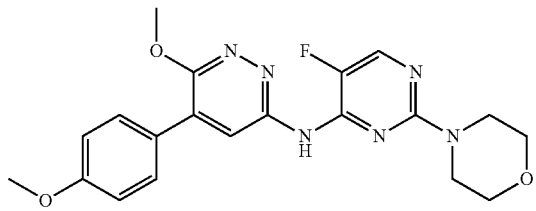
518
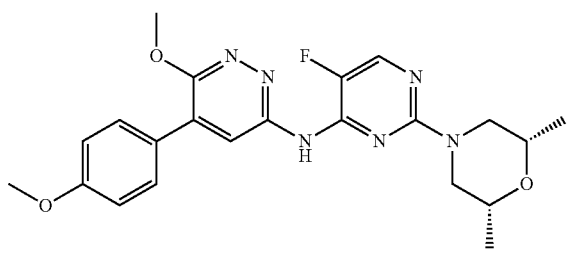
519
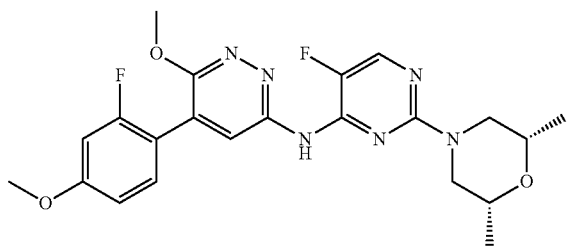
520
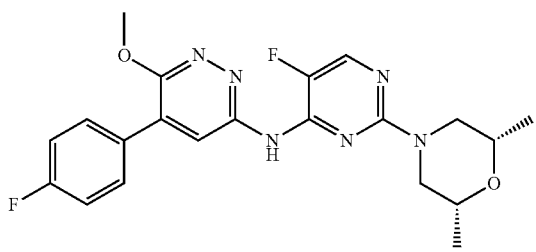
521
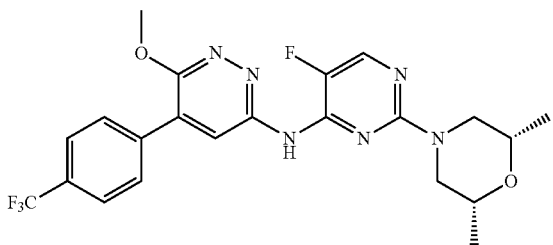
522

TABLE 1-continued
Exemplary Compounds of the Present Disclosure
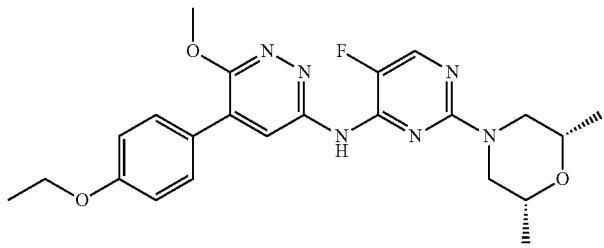
523
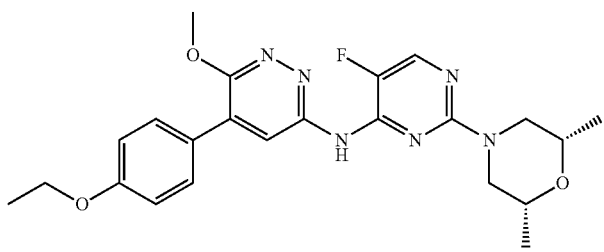
524
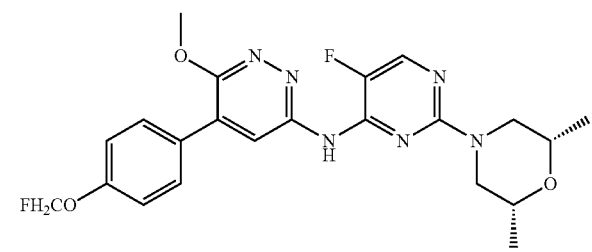
525
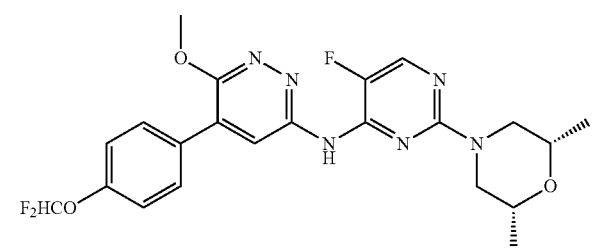
526
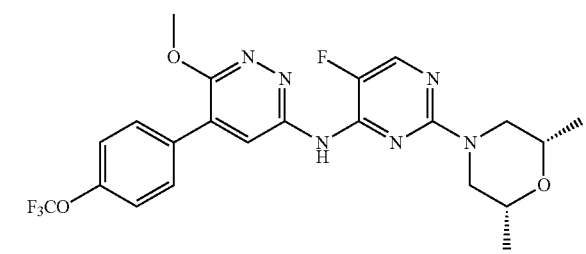
527

TABLE 1-continued
Exemplary Compounds of the Present Disclosure
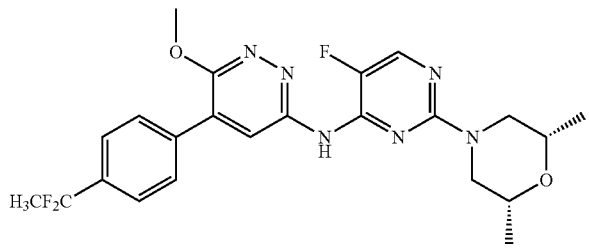
528
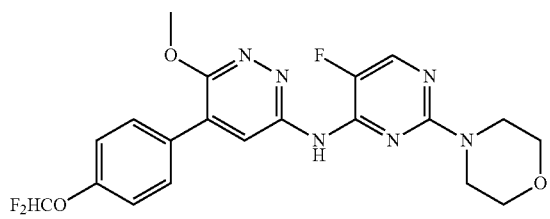
529
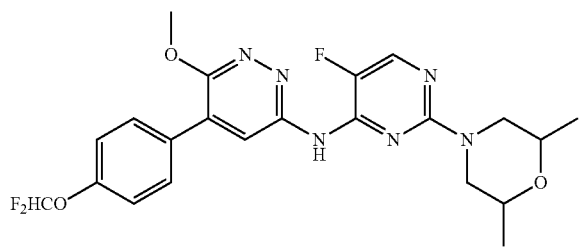
530
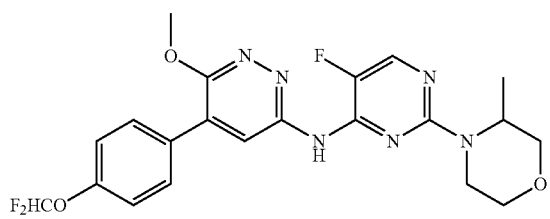
531
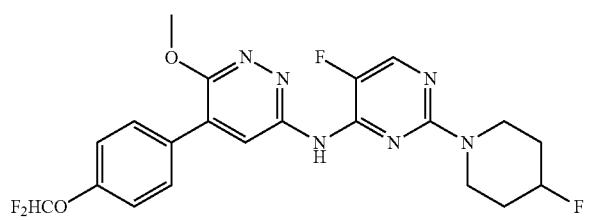
532

TABLE 1-continued
Exemplary Compounds of the Present Disclosure
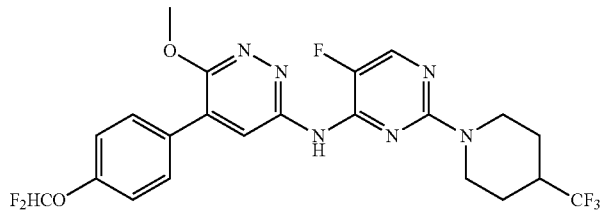
533
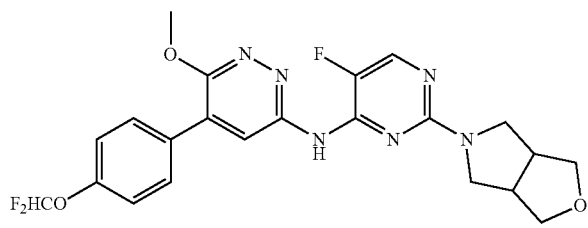
534
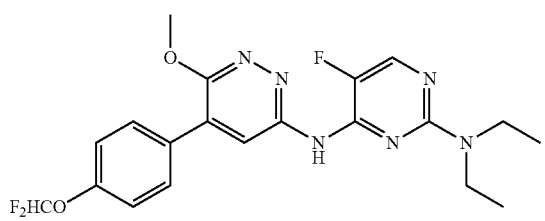
535
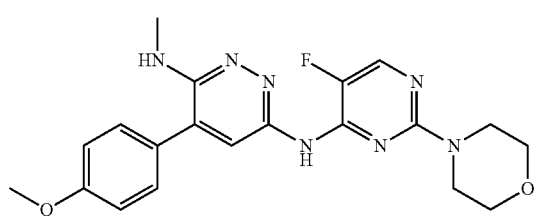
536
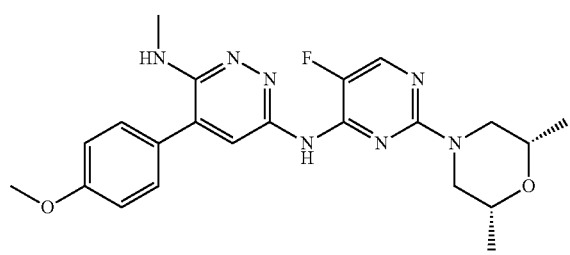
537

TABLE 1-continued
Exemplary Compounds of the Present Disclosure
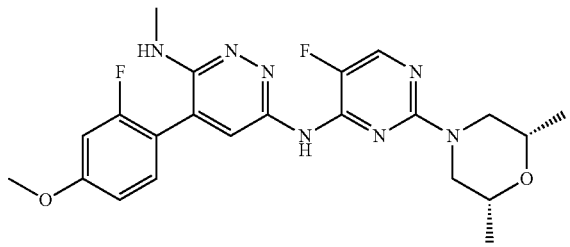
538
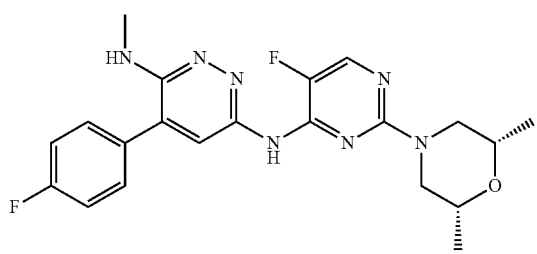
539
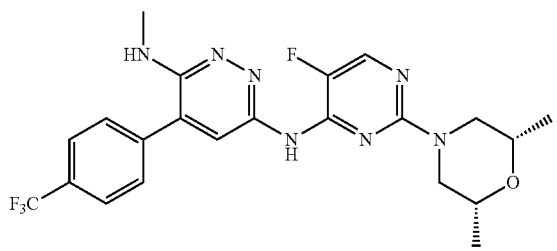
540
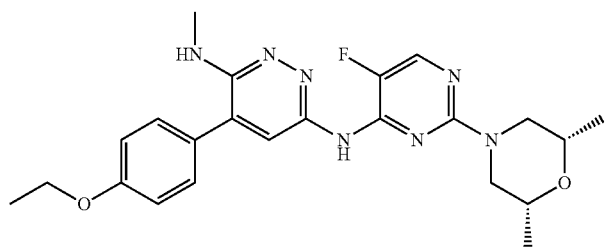
541
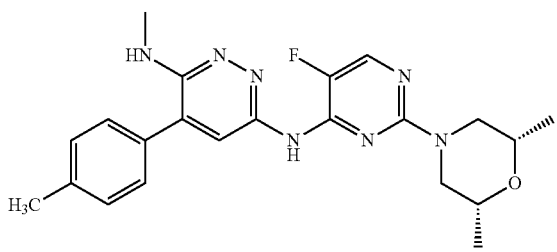
542

TABLE 1-continued
Exemplary Compounds of the Present Disclosure
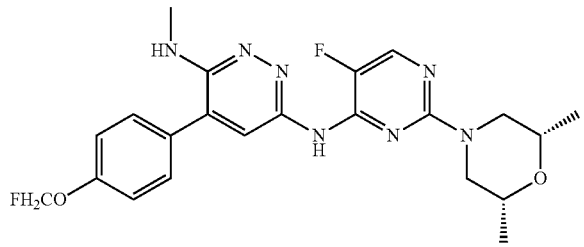
543
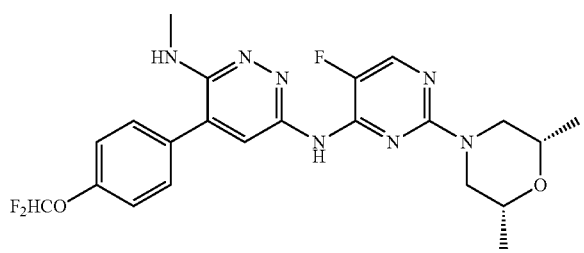
544
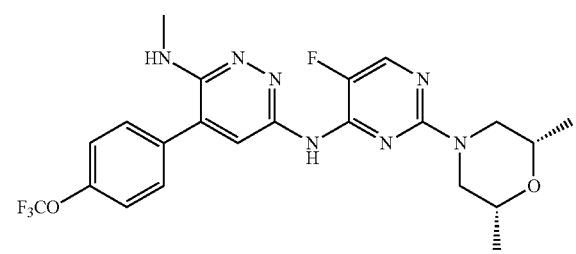
545
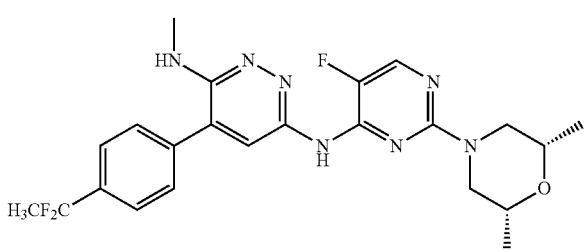
546
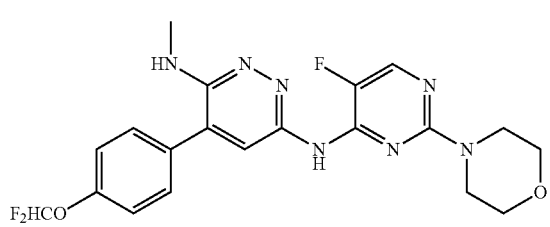
547

TABLE 1-continued
Exemplary Compounds of the Present Disclosure
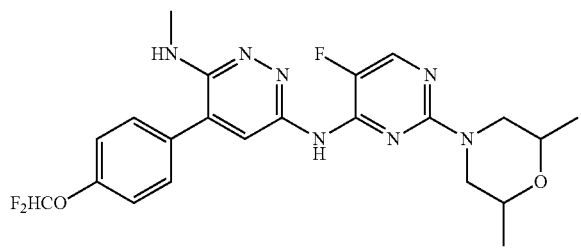
548
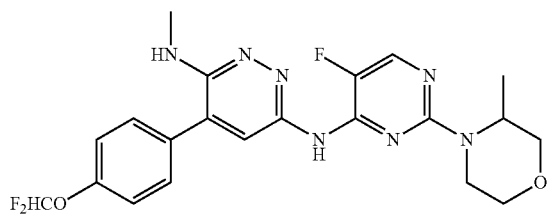
549
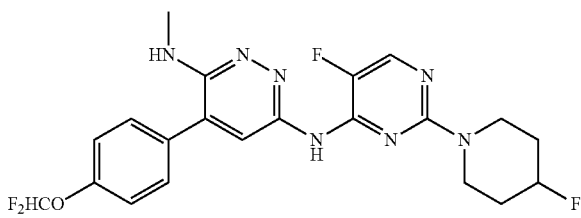
550
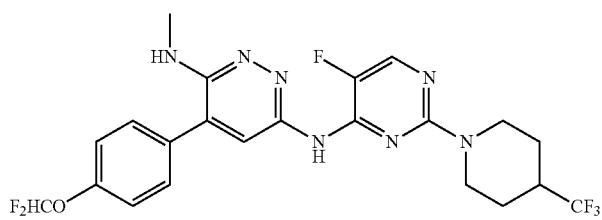
551
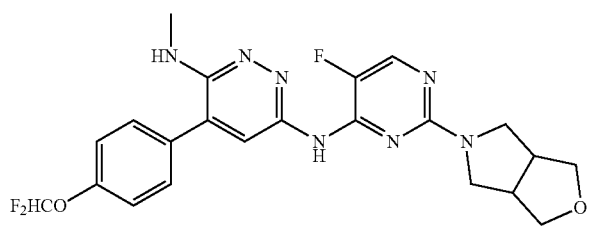
552
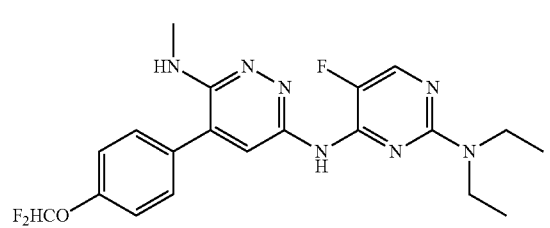
553

TABLE 1-continued
Exemplary Compounds of the Present Disclosure
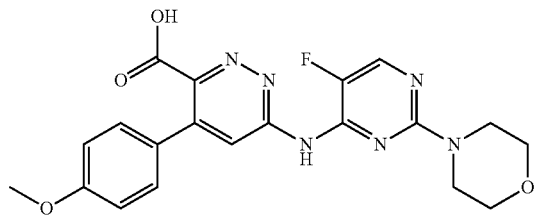
554
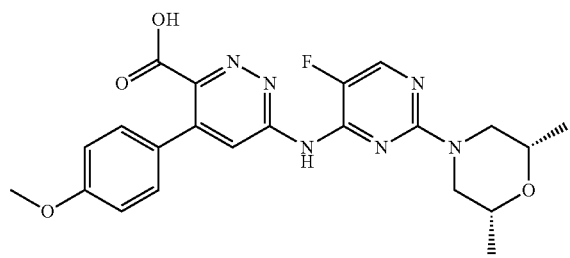
555
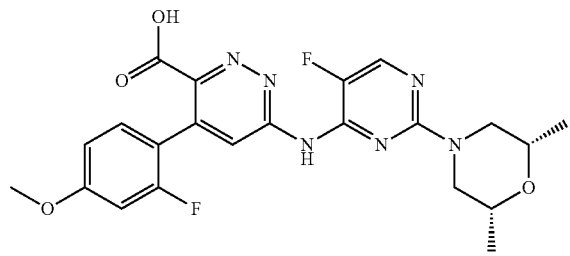
556
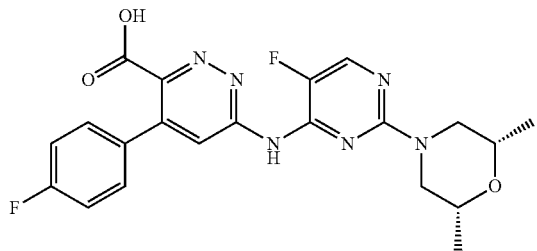
557
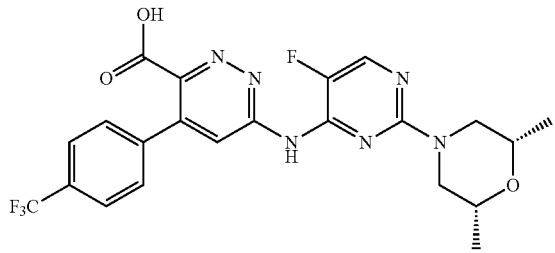
558

TABLE 1-continued
Exemplary Compounds of the Present Disclosure
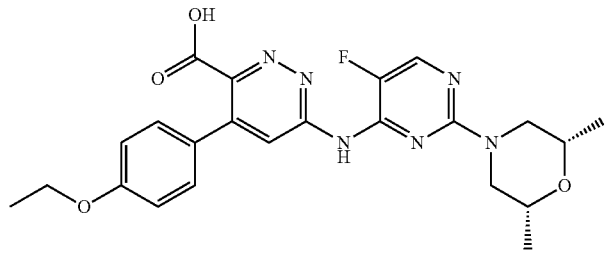
559
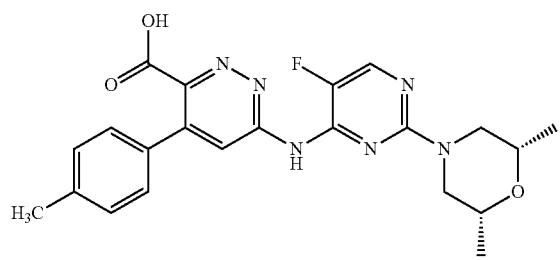
560
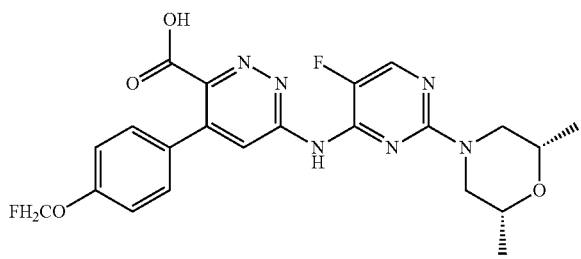
561
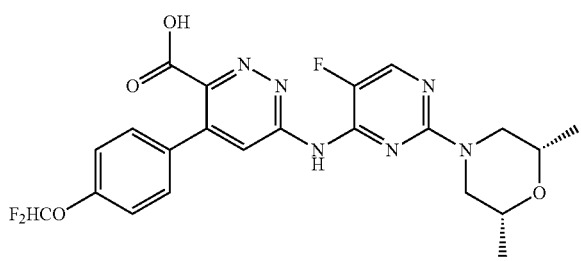
562
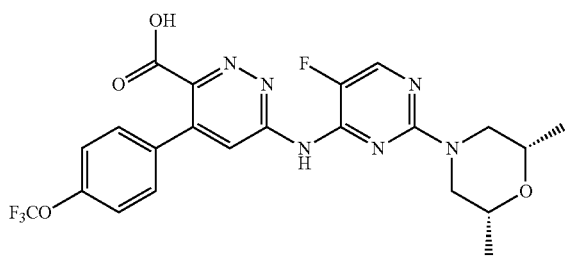
563

TABLE 1-continued
Exemplary Compounds of the Present Disclosure
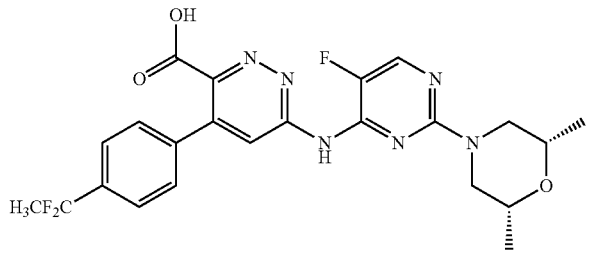
564
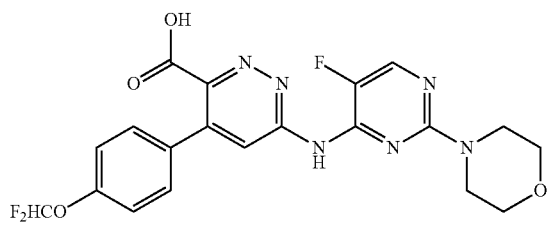
565
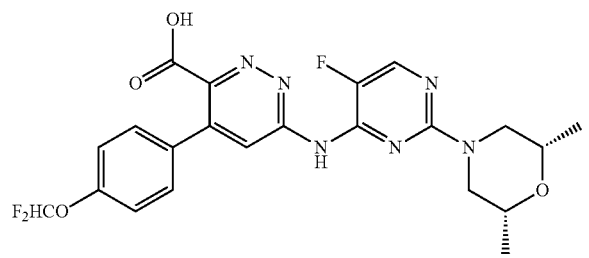 [SMILES: O=C(O)c1nnc(Nc2nc(N3CCC(F)CC3)ncc2F)cc1-c1ccc(OC(F)F)cc1]
566
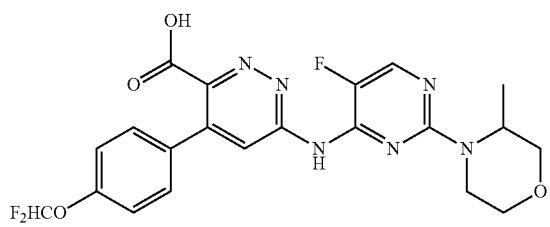
567
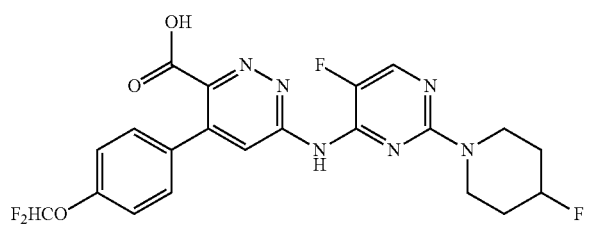
568

TABLE 1-continued
Exemplary Compounds of the Present Disclosure
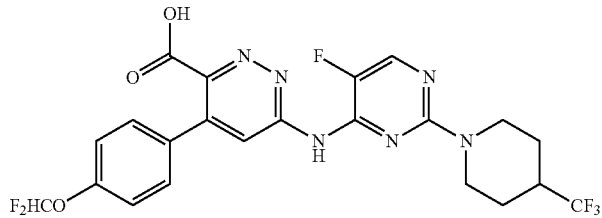
569
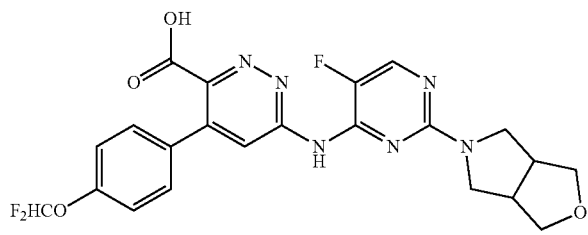
570
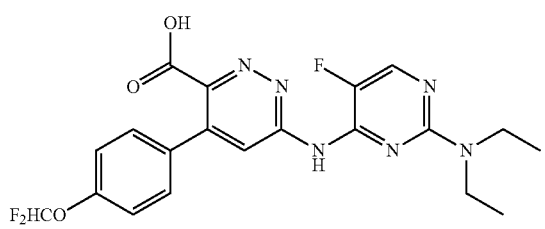
571
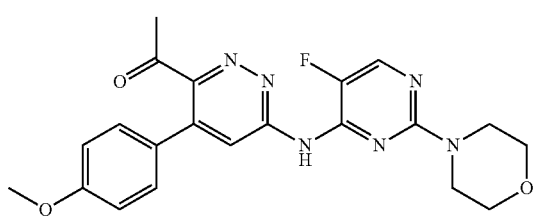
572
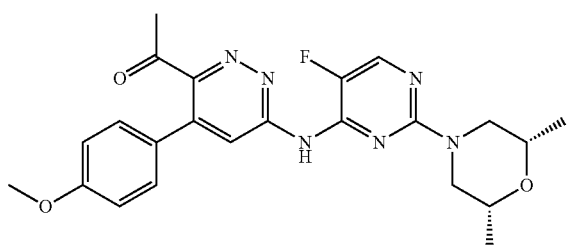
573

TABLE 1-continued
Exemplary Compounds of the Present Disclosure
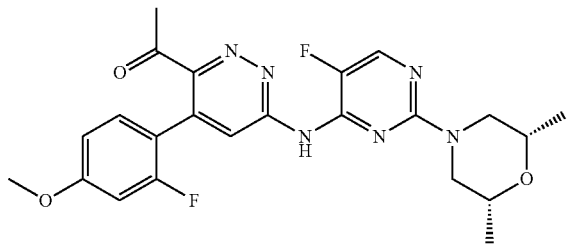
574
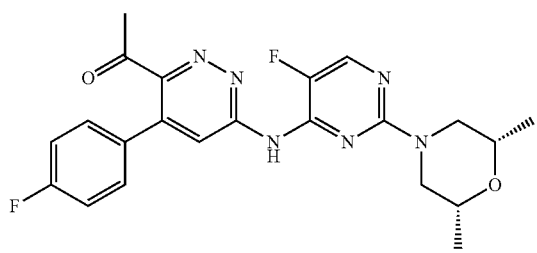
575
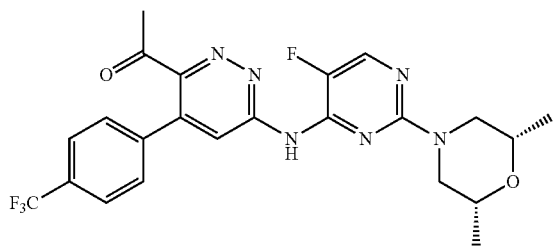
576
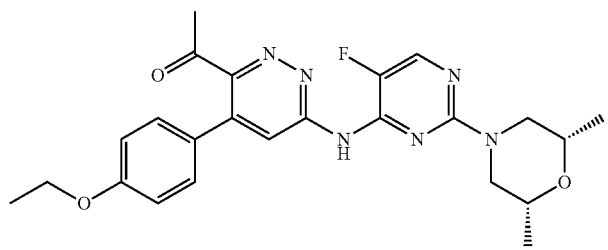
577
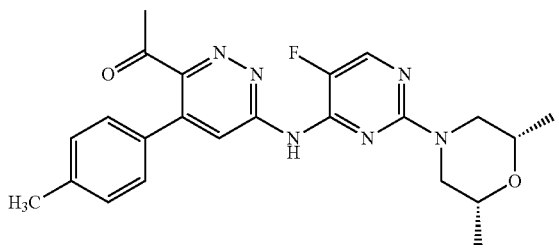
578

TABLE 1-continued
Exemplary Compounds of the Present Disclosure
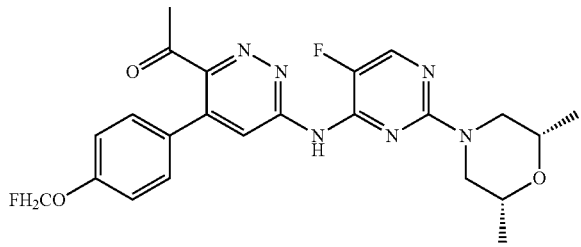
579
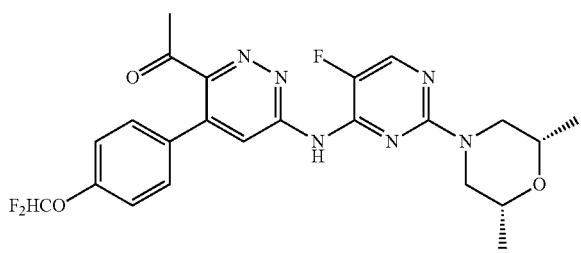
580
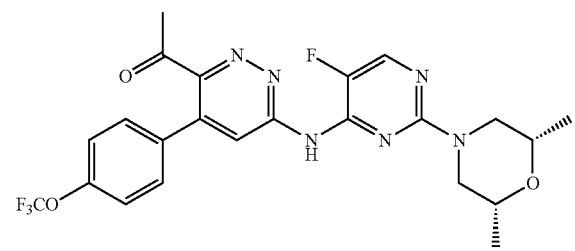
581
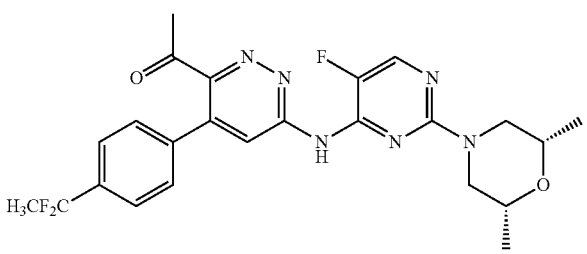
582
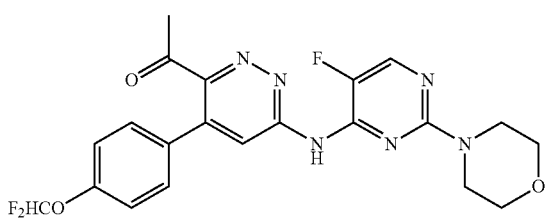
583

TABLE 1-continued
Exemplary Compounds of the Present Disclosure
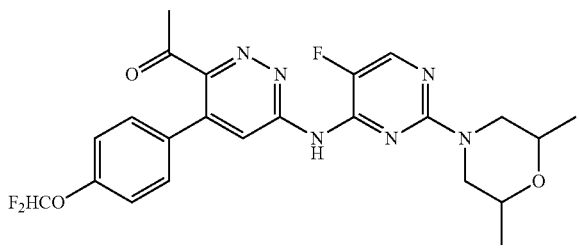
584
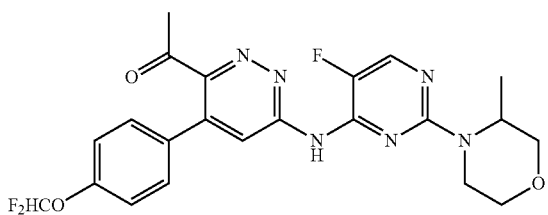
585
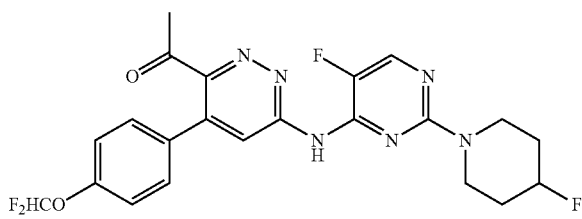
586
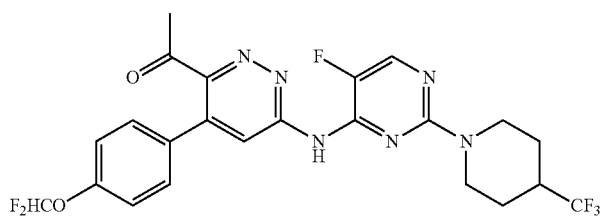
587
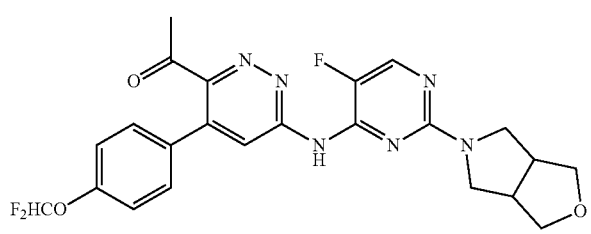
588
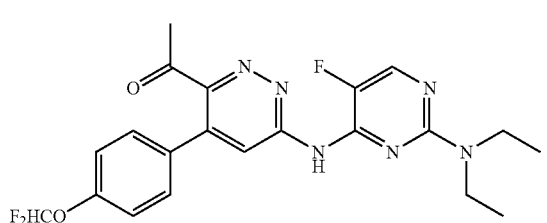
589

TABLE 1-continued
Exemplary Compounds of the Present Disclosure
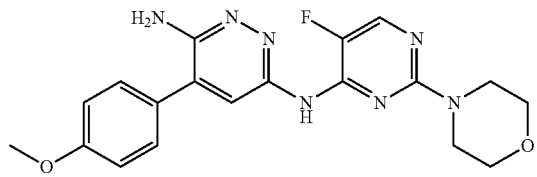
590
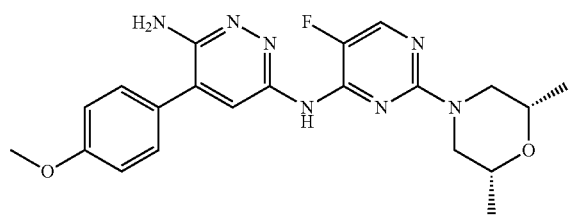
591
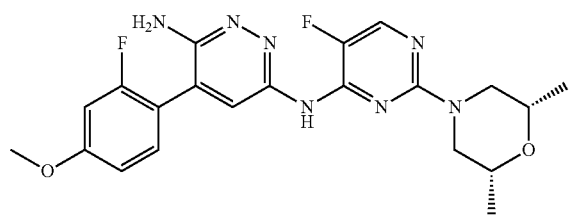
592
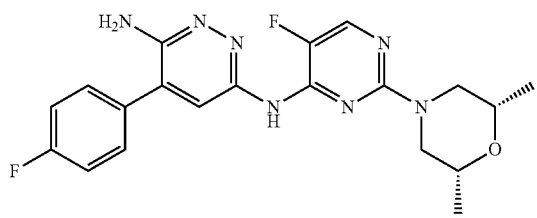
593
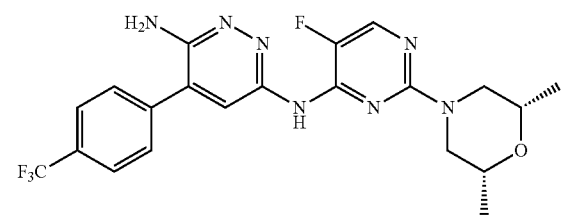
594
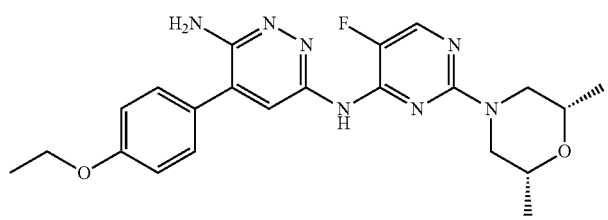
595

TABLE 1-continued
Exemplary Compounds of the Present Disclosure
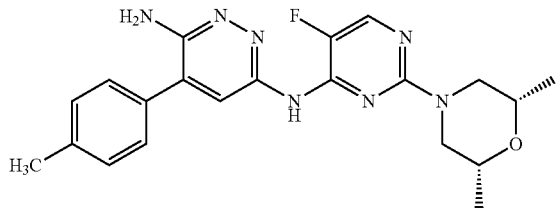
596
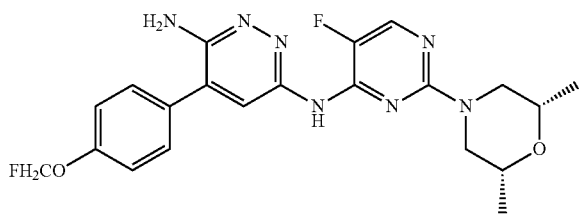
597
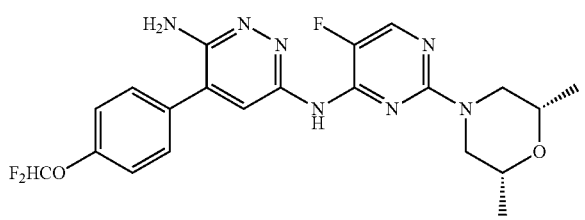
598
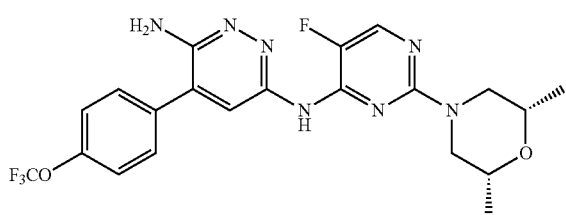
599
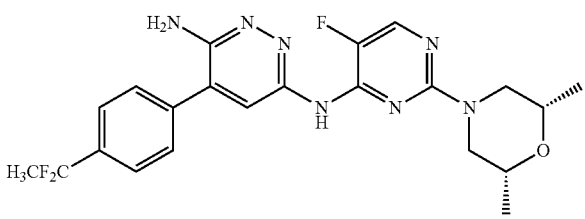
600
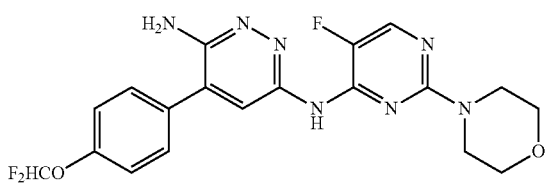
601

TABLE 1-continued
Exemplary Compounds of the Present Disclosure
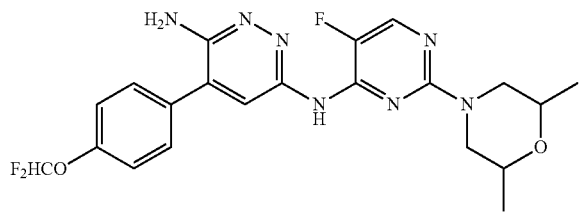
602
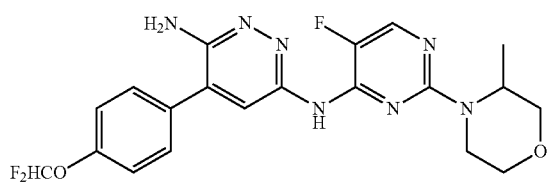
603
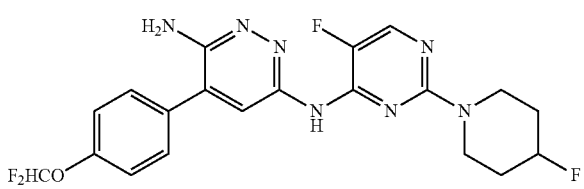
604
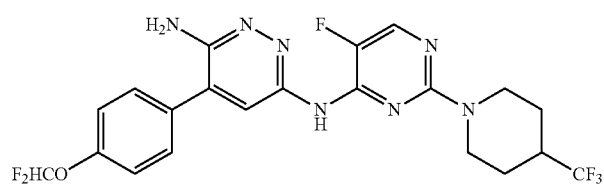
605
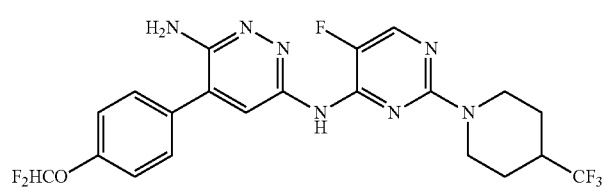
606
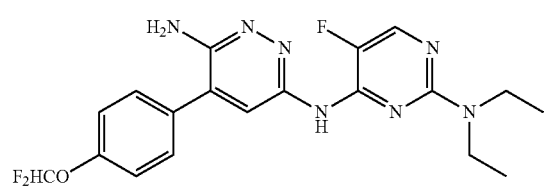
607

TABLE 1-continued
Exemplary Compounds of the Present Disclosure
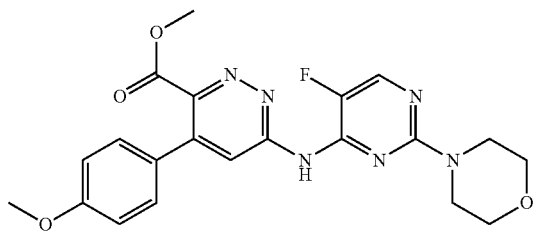
608
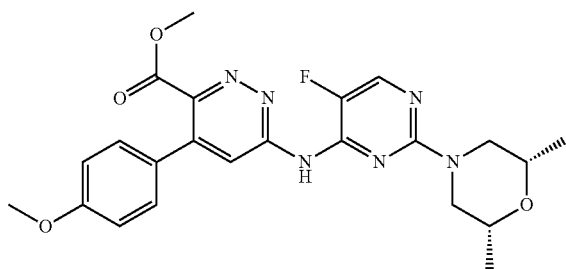
609
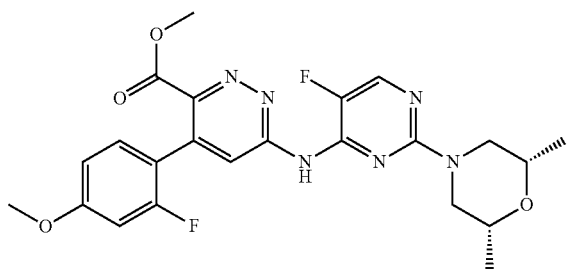
610
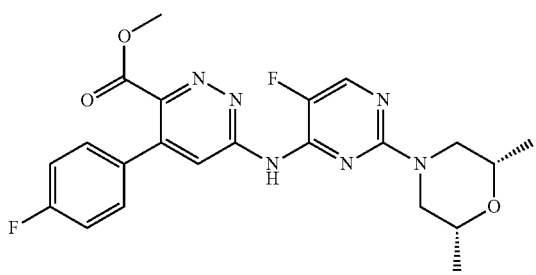
611
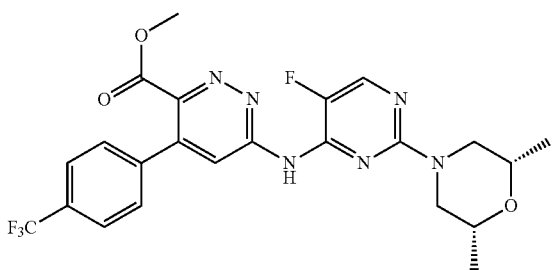
612

TABLE 1-continued
Exemplary Compounds of the Present Disclosure
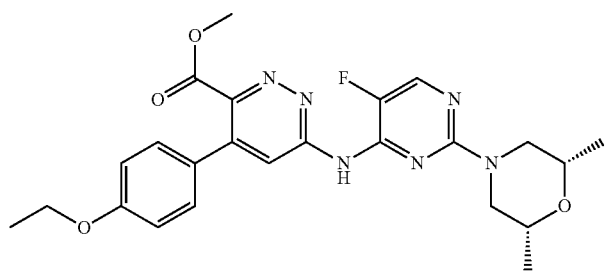
613
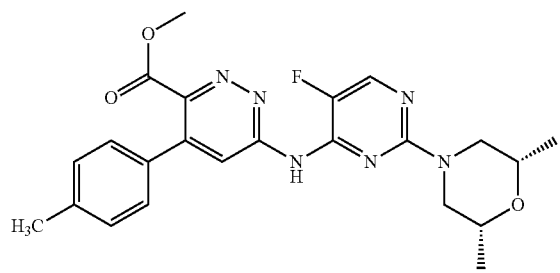
614
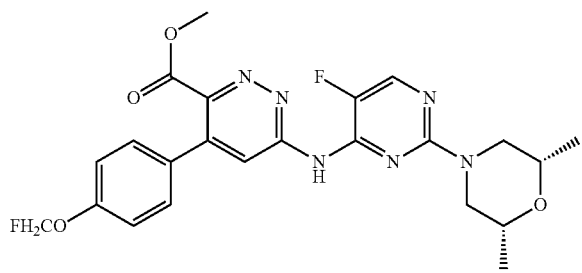 [SMILES: COC(=O)c1nnc(Nc2nc(N3CCC(F)CC3)ncc2F)cc1-c1ccc(OC(F)F)cc1]
615
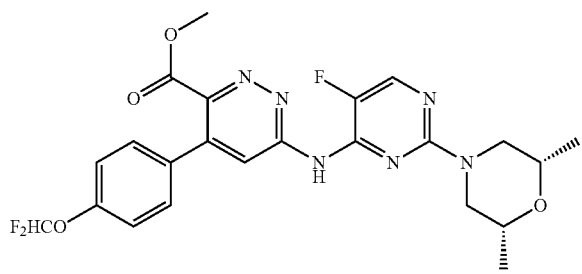
616
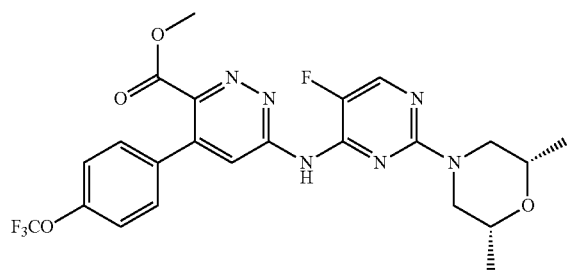
617

TABLE 1-continued
Exemplary Compounds of the Present Disclosure
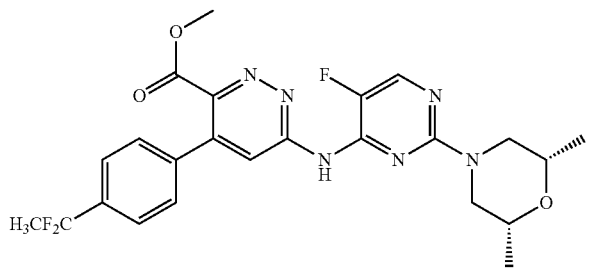
618
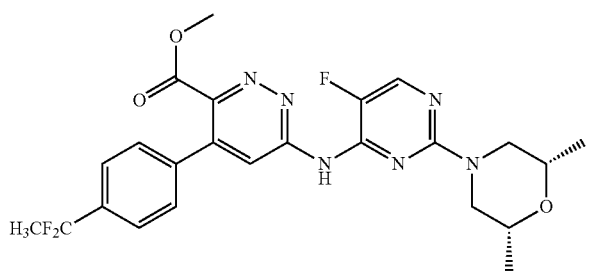
619
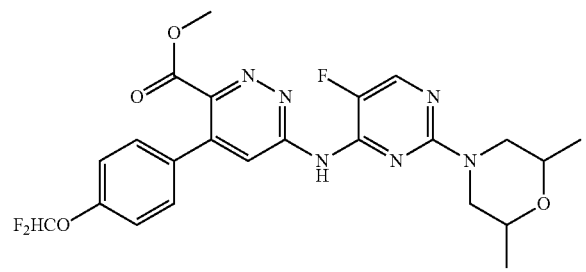
620
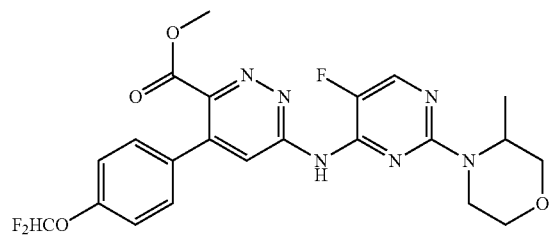
621
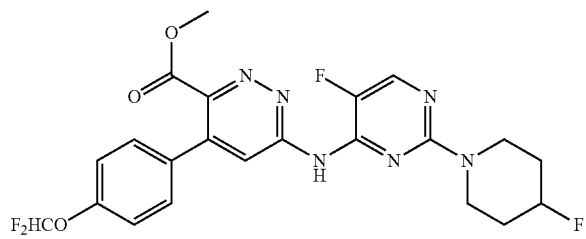
622

TABLE 1-continued
Exemplary Compounds of the Present Disclosure
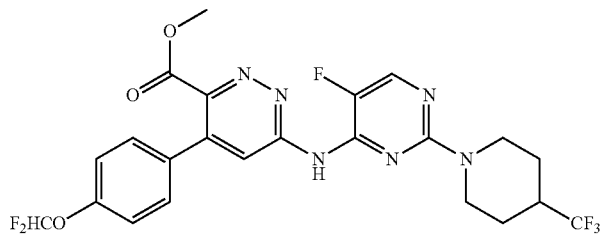
623
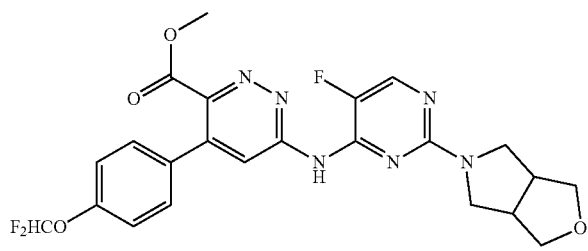
624
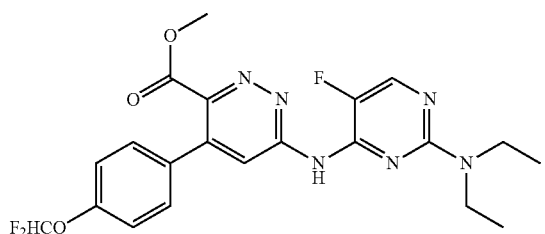
625
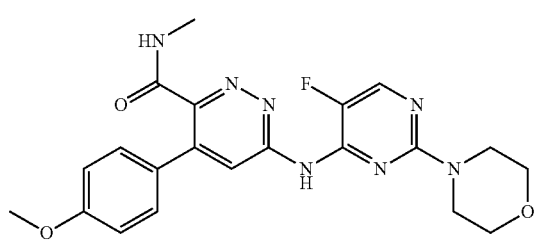
626
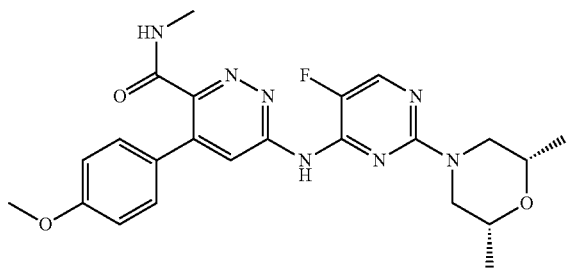
627

TABLE 1-continued
Exemplary Compounds of the Present Disclosure
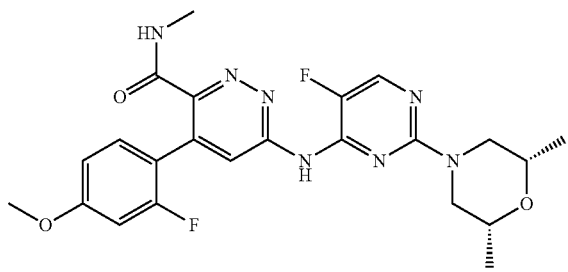
628
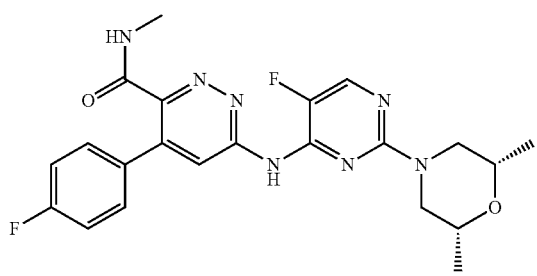
629
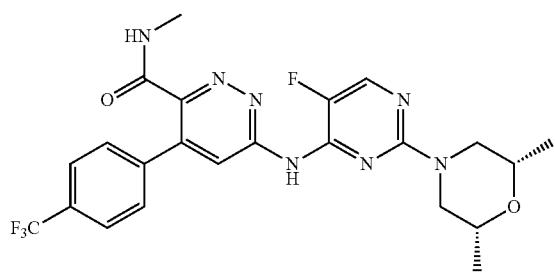
630
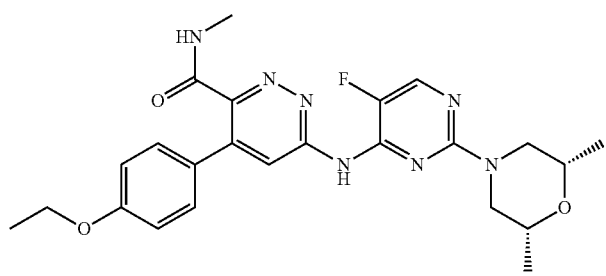
631
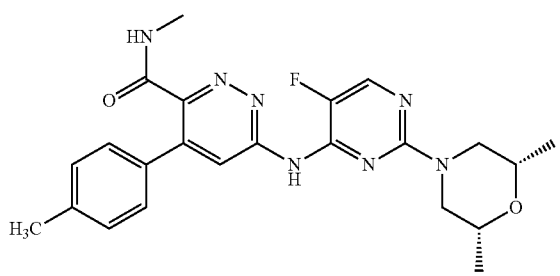
632

TABLE 1-continued
Exemplary Compounds of the Present Disclosure
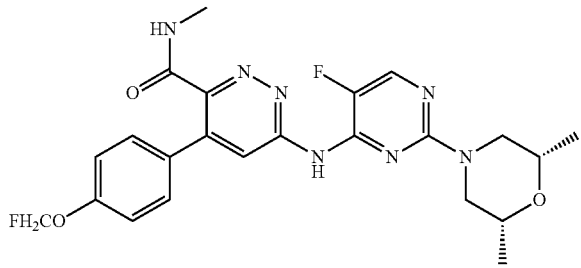
633
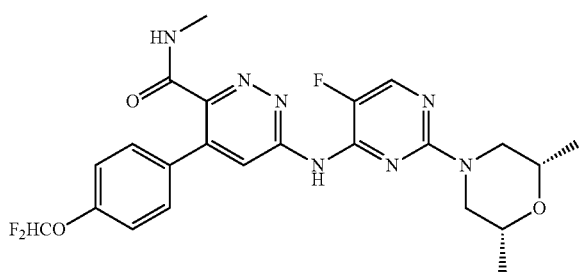
634
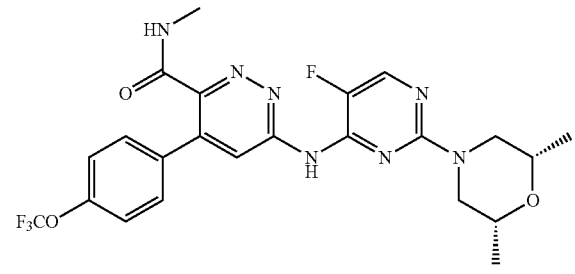
635
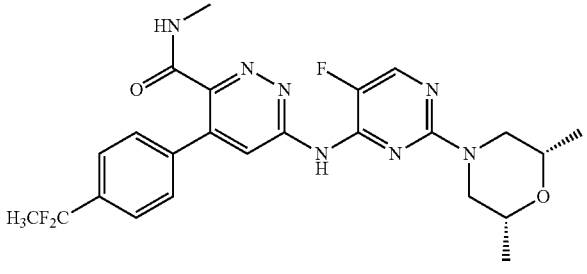
636
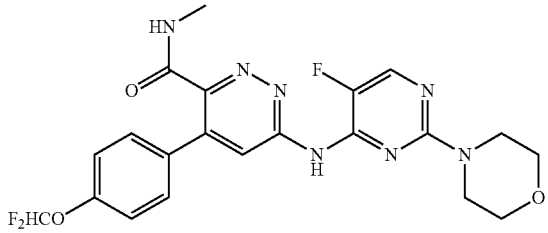
637

TABLE 1-continued
Exemplary Compounds of the Present Disclosure
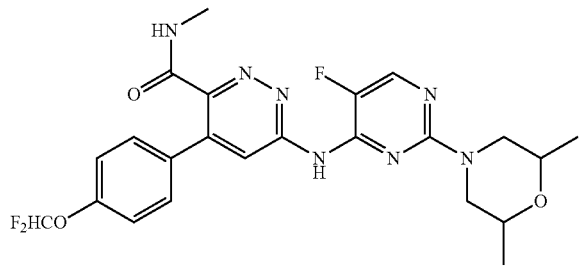
638
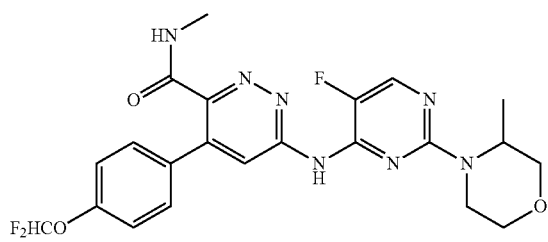
639
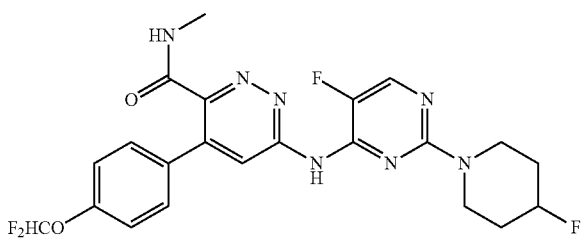
640
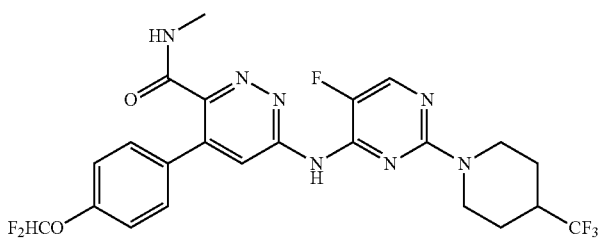
641
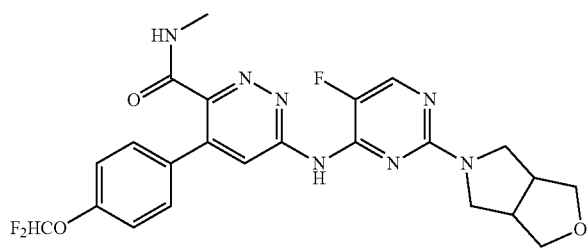
642

TABLE 1-continued

Exemplary Compounds of the Present Disclosure

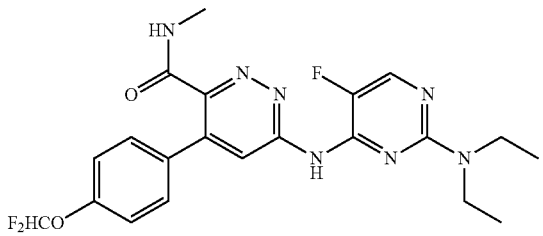

643

Some of the compounds disclosed herein may also exist in tautomeric forms. Such forms, although not explicitly indicated in the formulae described herein, are intended to be included within the scope of the present disclosure.

This disclosure also includes all suitable isotopic variations of a compound of the disclosure. An isotopic variation of a compound of the invention is defined as one in which at least one atom is replaced by an atom having the same atomic number but an atomic mass different from the atomic mass usually or predominantly found in nature. Examples of isotopes that can be incorporated into a compound of the invention include isotopes of hydrogen, carbon, nitrogen, oxygen, phosphorus, sulfur, fluorine, chlorine, bromine and iodine, such as $^{2}$H (deuterium), $^{3}$H (tritium), $^{11}$C, $^{13}$C, $^{14}$C, $^{15}$N, $^{17}$O, $^{18}$O, $^{32}$P, $^{33}$P, $^{33}$S, $^{34}$S, $^{35}$S, $^{36}$S, $^{18}$F, $^{36}$Cl, $^{82}$Br, $^{123}$I, $^{124}$I, $^{129}$I and $^{131}$I, respectively. Accordingly, recitation of "hydrogen" or "H" should be understood to encompass $^{1}$H (protium), $^{2}$H (deuterium), and $^{3}$H (tritium) unless otherwise specified. Certain isotopic variations of a compound of the invention, for example, those in which one or more radioactive isotopes such as $^{3}$H or $^{14}$C are incorporated, are useful in drug and/or substrate tissue distribution studies. Tritiated and carbon-14, i.e., $^{14}$C, isotopes are particularly preferred for their ease of preparation and detectability. Further, substitution with isotopes such as deuterium may afford certain therapeutic advantages resulting from greater metabolic stability, for example, increased in vivo half-life or reduced dosage requirements and hence may be preferred in some circumstances. Such variants may also have advantageous optical properties arising, for example, from changes to vibrational modes due to the heavier isotope. Isotopic variations of a compound of the invention can generally be prepared by conventional procedures known by a person skilled in the art such as by the illustrative methods or by the preparations described in the examples hereafter using appropriate isotopic variations of suitable reagents.

In another aspect, the present disclosure provides a pharmaceutical composition comprising a compound disclosed herein and a pharmaceutically acceptable excipient.

In yet another aspect, the present disclosure provides methods of treating a TACC mediated disease or disorder in a subject comprising administering a compound disclosed herein or a pharmaceutically acceptable salt thereof to the subject.

In yet another aspect, the present disclosure provides methods of treating a disease or disorder characterized by the dysregulation of TACC in a subject comprising administering a compound disclosed herein or a pharmaceutically acceptable salt thereof to the subject.

In certain embodiments, the TACC is TACC1. In other embodiments, the TACC is TACC2. In other preferred embodiments, the TACC is TACC3.

In certain embodiments, the TACC mediated disease or disorder is cancer. In certain embodiments, the cancer is breast cancer, colon cancer, melanoma cancer, lung cancer, central nervous system cancer, ovarian cancer, leukemia, renal cancer or prostate cancer. In certain embodiments, the cancer is breast cancer, ovarian cancer, esophageal cancer, endometrial cancer, prostate cancer, colon cancer, pancreatic cancer, head and neck cancer, or lung cancer.

In yet another aspect, the present disclosure provides methods of treating cancer in a subject comprising administering a compound disclosed herein or a pharmaceutically acceptable salt thereof to the subject. In certain embodiments, the cancer is breast cancer, colon cancer, melanoma cancer, lung cancer, central nervous system cancer, ovarian cancer, leukemia, renal cancer or prostate cancer. In certain embodiments, the cancer is breast cancer, ovarian cancer, esophageal cancer, endometrial cancer, prostate cancer, colon cancer, pancreatic cancer, head and neck cancer, or lung cancer.

Pharmaceutical Compositions

The compositions and methods of the present invention may be utilized to treat an individual in need thereof. In certain embodiments, the individual is a mammal such as a human, or a non-human mammal. When administered to an animal, such as a human, the composition or the compound is preferably administered as a pharmaceutical composition comprising, for example, a compound of the invention and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil, or injectable organic esters. In preferred embodiments, when such pharmaceutical compositions are for human administration, particularly for invasive routes of administration (i.e., routes, such as injection or implantation, that circumvent transport or diffusion through an epithelial barrier), the aqueous solution is pyrogen-free, or substantially pyrogen-free. The excipients can be chosen, for example, to effect delayed release of an agent or to selectively target one or more cells, tissues or organs. The pharmaceutical composition can be in dosage unit form such as tablet, capsule (including sprinkle capsule and gelatin capsule), granule, lyophile for reconstitution, powder, solution, syrup, suppository, injection or the like. The composition can also be present in a transdermal delivery system, e.g., a skin patch. The composition can also be present in a solution suitable for topical administration, such as a lotion, cream, or ointment.

A pharmaceutically acceptable carrier can contain physiologically acceptable agents that act, for example, to stabilize, increase solubility or to increase the absorption of a compound such as a compound of the invention. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The preparation or pharmaceutical composition can be a selfemulsifying drug delivery system or a selfmicroemulsifying drug delivery system. The pharmaceutical composition (preparation) also can be a liposome or other polymer matrix, which can have incorporated therein, for example, a compound of the invention. Liposomes, for example, which comprise phospholipids or other lipids, are nontoxic, physiologically acceptable and metabolizable carriers that are relatively simple to make and administer.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

A pharmaceutical composition (preparation) can be administered to a subject by any of a number of routes of administration including, for example, orally (for example, drenches as in aqueous or non-aqueous solutions or suspensions, tablets, capsules (including sprinkle capsules and gelatin capsules), boluses, powders, granules, pastes for application to the tongue); absorption through the oral mucosa (e.g., sublingually); subcutaneously; transdermally (for example as a patch applied to the skin); and topically (for example, as a cream, ointment or spray applied to the skin). The compound may also be formulated for inhalation. In certain embodiments, a compound may be simply dissolved or suspended in sterile water. Details of appropriate routes of administration and compositions suitable for same can be found in, for example, U.S. Pat. Nos. 6,110,973, 5,763,493, 5,731,000, 5,541,231, 5,427,798, 5,358,970 and 4,172,896, as well as in patents cited therein.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an active compound, such as a compound of the invention, with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules (including sprinkle capsules and gelatin capsules), cachets, pills, tablets, lozenges (using a flavored basis, usually sucrose and acacia or tragacanth), lyophile, powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. Compositions or compounds may also be administered as a bolus, electuary or paste.

To prepare solid dosage forms for oral administration (capsules (including sprinkle capsules and gelatin capsules), tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; (10) complexing agents, such as, modified and unmodified cyclodextrins; and (11) coloring agents. In the case of capsules (including sprinkle capsules and gelatin capsules), tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions, such as dragees, capsules (including sprinkle capsules and gelatin capsules), pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms useful for oral administration include pharmaceutically acceptable emulsions, lyophiles for reconstitution, microemulsions, solutions, suspensions, syrups and elixirs. In addition to the active ingredient, the liquid dosage forms may contain inert diluents commonly used in the art, such as, for example, water or other solvents, cyclodextrins and derivatives thereof, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Dosage forms for the topical or transdermal administration include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the active compound in the proper medium. Absorption enhancers can also be used to increase the flux of the compound across the skin. The rate of such flux can be controlled by either providing a rate controlling membrane or dispersing the compound in a polymer matrix or gel.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion. Pharmaceutical compositions suitable for parenteral administration comprise one or more active compounds in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

For use in the methods of this invention, active compounds can be given per se or as a pharmaceutical composition containing, for example, 0.1 to 99.5% (more preferably, 0.5 to 90%) of active ingredient in combination with a pharmaceutically acceptable carrier.

Methods of introduction may also be provided by rechargeable or biodegradable devices. Various slow release polymeric devices have been developed and tested in vivo in recent years for the controlled delivery of drugs, including proteinaceous biopharmaceuticals. A variety of biocompatible polymers (including hydrogels), including both biodegradable and non-degradable polymers, can be used to form an implant for the sustained release of a compound at a particular target site.

Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound or combination of compounds employed, or the ester, salt or amide thereof, the route of administration, the time of administration, the rate of excretion of the particular compound(s) being employed, the duration of the treatment, other drugs, compounds and/or materials used in combination with the particular compound(s) employed, the age, sex, weight, condition, general health and prior medical history of the patient being treated, and like factors well known in the medical arts.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. By "therapeutically effective amount" is meant the concentration of a compound that is sufficient to elicit the desired therapeutic effect. It is generally understood that the effective amount of the compound will vary according to the weight, sex, age, and medical history of the subject. Other factors which influence the effective amount may include, but are not limited to, the severity of the patient's condition, the disorder being treated, the stability of the compound, and, if desired, another type of therapeutic agent being administered with the compound of the invention. A larger total dose can be delivered by multiple administrations of the agent. Methods to determine efficacy and dosage are known to those skilled in the art (Isselbacher et al. (1996) Harrison's Principles of Internal Medicine 13 ed., 1814-1882, herein incorporated by reference).

In general, a suitable daily dose of an active compound used in the compositions and methods of the invention will be that amount of the compound that is the lowest dose effective to produce a therapeutic effect. Such an effective dose will generally depend upon the factors described above.

If desired, the effective daily dose of the active compound may be administered as one, two, three, four, five, six or more sub-doses administered separately at appropriate intervals throughout the day, optionally, in unit dosage forms. In certain embodiments of the present invention, the active compound may be administered two or three times daily. In preferred embodiments, the active compound will be administered once daily.

The patient receiving this treatment is any animal in need, including primates, in particular humans; and other mammals such as equines, cattle, swine, sheep, cats, and dogs; poultry; and pets in general.

In certain embodiments, compounds of the invention may be used alone or conjointly administered with another type of therapeutic agent.

The present disclosure includes the use of pharmaceutically acceptable salts of compounds of the invention in the compositions and methods of the present invention. In certain embodiments, contemplated salts of the invention include, but are not limited to, alkyl, dialkyl, trialkyl or tetra-alkyl ammonium salts. In certain embodiments, contemplated salts of the invention include, but are not limited to, L-arginine, benenthamine, benzathine, betaine, calcium hydroxide, choline, deanol, diethanolamine, diethylamine, 2-(diethylamino)ethanol, ethanolamine, ethylenediamine, N-methylglucamine, hydrabamine, 1H-imidazole, lithium, L-lysine, magnesium, 4-(2-hydroxyethyl)morpholine, piperazine, potassium, 1-(2-hydroxyethyl)pyrrolidine, sodium, triethanolamine, tromethamine, and zinc salts. In certain embodiments, contemplated salts of the invention include, but are not limited to, Na, Ca, K, Mg, Zn or other metal salts. In certain embodiments, contemplated salts of the invention include, but are not limited to, 1-hydroxy-2-naphthoic acid, 2,2-dichloroacetic acid, 2-hydroxyethanesulfonic acid, 2-oxoglutaric acid, 4-acetamidobenzoic acid, 4-aminosalicylic acid, acetic acid, adipic acid, 1-ascorbic acid, 1-aspartic acid, benzenesulfonic acid, benzoic acid, (+)-camphoric acid, (+)-camphor-10-sulfonic acid, capric acid (decanoic acid), caproic acid (hexanoic acid), caprylic acid (octanoic acid), carbonic acid, cinnamic acid, citric acid, cyclamic acid, dodecylsulfuric acid, ethane-1,2-disulfonic acid, ethanesulfonic acid, formic acid, fumaric acid, galactaric acid, gentisic acid, d-glucoheptonic acid, d-gluconic acid, d-glucuronic acid, glutamic acid, glutaric acid, glycerophosphoric acid, glycolic acid, hippuric acid, hydrobromic acid, hydrochloric acid, isobutyric acid, lactic acid, lactobionic acid, lauric acid, maleic acid, 1-malic acid, malonic acid, mandelic acid, methanesulfonic acid, naphthalene-1,5-disulfonic acid, naphthalene-2-sulfonic acid, nicotinic acid, nitric acid, oleic acid, oxalic acid, palmitic acid, pamoic acid, phosphoric acid, proprionic acid, 1-pyroglutamic acid, salicylic acid, sebacic acid, stearic acid, succinic acid, sulfuric acid, 1-tartaric acid, thiocyanic acid, p-toluenesulfonic acid, trifluoroacetic acid, and undecylenic acid acid salts.

The pharmaceutically acceptable acid addition salts can also exist as various solvates, such as with water, methanol, ethanol, dimethylformamide, and the like. Mixtures of such solvates can also be prepared. The source of such solvate can be from the solvent of crystallization, inherent in the solvent of preparation or crystallization, or adventitious to such solvent.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

Definitions

Unless otherwise defined herein, scientific and technical terms used in this application shall have the meanings that are commonly understood by those of ordinary skill in the art. Generally, nomenclature used in connection with, and techniques of, chemistry, cell and tissue culture, molecular biology, cell and cancer biology, neurobiology, neurochemistry, virology, immunology, microbiology, pharmacology, genetics and protein and nucleic acid chemistry, described herein, are those well known and commonly used in the art.

The methods and techniques of the present disclosure are generally performed, unless otherwise indicated, according to conventional methods well known in the art and as described in various general and more specific references that are cited and discussed throughout this specification. See, e.g. "Principles of Neural Science", McGraw-Hill Medical, New York, N.Y. (2000); Motulsky, "Intuitive Biostatistics", Oxford University Press, Inc. (1995); Lodish et al., "Molecular Cell Biology, 4th ed.", W. H. Freeman & Co., New York (2000); Griffiths et al., "Introduction to Genetic Analysis, 7th ed.", W. H. Freeman & Co., N.Y. (1999); and Gilbert et al., "Developmental Biology, 6th ed.", Sinauer Associates, Inc., Sunderland, MA (2000).

Chemistry terms used herein, unless otherwise defined herein, are used according to conventional usage in the art, as exemplified by "The McGraw-Hill Dictionary of Chemical Terms", Parker S., Ed., McGraw-Hill, San Francisco, C.A. (1985).

All of the above, and any other publications, patents and published patent applications referred to in this application are specifically incorporated by reference herein. In case of conflict, the present specification, including its specific definitions, will control.

The term "agent" is used herein to denote a chemical compound (such as an organic or inorganic compound, a mixture of chemical compounds), a biological macromolecule (such as a nucleic acid, an antibody, including parts thereof as well as humanized, chimeric and human antibodies and monoclonal antibodies, a protein or portion thereof, e.g., a peptide, a lipid, a carbohydrate), or an extract made from biological materials such as bacteria, plants, fungi, or animal (particularly mammalian) cells or tissues. Agents include, for example, agents whose structure is known, and those whose structure is not known.

A "patient," "subject," or "individual" are used interchangeably and refer to either a human or a non-human animal. These terms include mammals, such as humans, primates, livestock animals (including bovines, porcines, etc.), companion animals (e.g., canines, felines, etc.) and rodents (e.g., mice and rats).

"Treating" a condition or patient refers to taking steps to obtain beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment.

The term "preventing" is art-recognized, and when used in relation to a condition, such as a local recurrence (e.g., pain), a disease such as cancer, a syndrome complex such as heart failure or any other medical condition, is well understood in the art, and includes administration of a composition which reduces the frequency of, or delays the onset of, symptoms of a medical condition in a subject relative to a subject which does not receive the composition. Thus, prevention of cancer includes, for example, reducing the number of detectable cancerous growths in a population of patients receiving a prophylactic treatment relative to an untreated control population, and/or delaying the appearance of detectable cancerous growths in a treated population versus an untreated control population, e.g., by a statistically and/or clinically significant amount.

"Administering" or "administration of" a substance, a compound or an agent to a subject can be carried out using one of a variety of methods known to those skilled in the art. For example, a compound or an agent can be administered, intravenously, arterially, intradermally, intramuscularly, intraperitoneally, subcutaneously, ocularly, sublingually, orally (by ingestion), intranasally (by inhalation), intraspinally, intracerebrally, and transdermally (by absorption, e.g., through a skin duct). A compound or agent can also appropriately be introduced by rechargeable or biodegradable polymeric devices or other devices, e.g., patches and pumps, or formulations, which provide for the extended, slow or controlled release of the compound or agent. Administering can also be performed, for example, once, a plurality of times, and/or over one or more extended periods.

Appropriate methods of administering a substance, a compound or an agent to a subject will also depend, for example, on the age and/or the physical condition of the subject and the chemical and biological properties of the compound or agent (e.g., solubility, digestibility, bioavailability, stability and toxicity). In some embodiments, a compound or an agent is administered orally, e.g., to a subject by ingestion. In some embodiments, the orally administered compound or agent is in an extended release or slow release formulation, or administered using a device for such slow or extended release.

As used herein, the phrase "conjoint administration" refers to any form of administration of two or more different therapeutic agents such that the second agent is administered while the previously administered therapeutic agent is still effective in the body (e.g., the two agents are simultaneously effective in the patient, which may include synergistic effects of the two agents). For example, the different therapeutic compounds can be administered either in the same formulation or in separate formulations, either concomitantly or sequentially. Thus, an individual who receives such treatment can benefit from a combined effect of different therapeutic agents.

A "therapeutically effective amount" or a "therapeutically effective dose" of a drug or agent is an amount of a drug or an agent that, when administered to a subject will have the intended therapeutic effect. The full therapeutic effect does not necessarily occur by administration of one dose, and may occur only after administration of a series of doses.

Thus, a therapeutically effective amount may be administered in one or more administrations. The precise effective amount needed for a subject will depend upon, for example, the subject's size, health and age, and the nature and extent of the condition being treated, such as cancer or MDS. The skilled worker can readily determine the effective amount for a given situation by routine experimentation.

As used herein, the terms "optional" or "optionally" mean that the subsequently described event or circumstance may occur or may not occur, and that the description includes instances where the event or circumstance occurs as well as instances in which it does not. For example, "optionally substituted alkyl" refers to the alkyl may be substituted as well as where the alkyl is not substituted.

It is understood that substituents and substitution patterns on the compounds of the present invention can be selected by one of ordinary skilled person in the art to result chemically stable compounds which can be readily synthesized by techniques known in the art, as well as those methods set forth below, from readily available starting materials. If a substituent is itself substituted with more than one group, it is understood that these multiple groups may be on the same carbon or on different carbons, so long as a stable structure results.

As used herein, the term "optionally substituted" refers to the replacement of one to six hydrogen radicals in a given structure with the radical of a specified substituent including, but not limited to: hydroxyl, hydroxyalkyl, alkoxy, halogen, alkyl, nitro, silyl, acyl, acyloxy, aryl, cycloalkyl, heterocyclyl, amino, aminoalkyl, cyano, haloalkyl, haloalkoxy, —OCO—$CH_2$—O-alkyl, —OP(O)(O-alkyl)$_2$ or —$CH_2$—OP(O)(O-alkyl)$_2$. Preferably, "optionally substituted" refers to the replacement of one to four hydrogen radicals in a given structure with the substituents mentioned above. More preferably, one to three hydrogen radicals are replaced by the substituents as mentioned above. It is understood that the substituent can be further substituted.

As used herein, the term "alkyl" refers to saturated aliphatic groups, including but not limited to $C_1$-$C_{10}$ straight-chain alkyl groups or $C_1$-$C_{10}$ branched-chain alkyl groups. Preferably, the "alkyl" group refers to $C_1$-$C_6$ straight-chain alkyl groups or $C_1$-$C_6$ branched-chain alkyl groups. Most preferably, the "alkyl" group refers to $C_1$-$C_4$ straight-chain alkyl groups or $C_1$-$C_4$ branched-chain alkyl groups. Examples of "alkyl" include, but are not limited to, methyl, ethyl, 1-propyl, 2-propyl, n-butyl, sec-butyl, tert-butyl, 1-pentyl, 2-pentyl, 3-pentyl, neo-pentyl, 1-hexyl, 2-hexyl, 3-hexyl, 1-heptyl, 2-heptyl, 3-heptyl, 4-heptyl, 1-octyl, 2-octyl, 3-octyl or 4-octyl and the like. The "alkyl" group may be optionally substituted.

The term "acyl" is art-recognized and refers to a group represented by the general formula hydrocarbylC(O)—, preferably alkylC(O)—.

The term "acylamino" is art-recognized and refers to an amino group substituted with an acyl group and may be represented, for example, by the formula hydrocarbylC(O)NH—.

The term "acyloxy" is art-recognized and refers to a group represented by the general formula hydrocarbylC(O)O—, preferably alkylC(O)O—.

The term "alkoxy" refers to an alkyl group having an oxygen attached thereto. Representative alkoxy groups include methoxy, ethoxy, propoxy, tert-butoxy and the like.

The term "alkoxyalkyl" refers to an alkyl group substituted with an alkoxy group and may be represented by the general formula alkyl-O-alkyl.

The term "alkyl" refers to saturated aliphatic groups, including straight-chain alkyl groups, branched-chain alkyl groups, cycloalkyl (alicyclic) groups, alkyl-substituted cycloalkyl groups, and cycloalkyl-substituted alkyl groups. In preferred embodiments, a straight chain or branched chain alkyl has 30 or fewer carbon atoms in its backbone (e.g., $C_{1-30}$ for straight chains, $C_{3-30}$ for branched chains), and more preferably 20 or fewer.

Moreover, the term "alkyl" as used throughout the specification, examples, and claims is intended to include both unsubstituted and substituted alkyl groups, the latter of which refers to alkyl moieties having substituents replacing a hydrogen on one or more carbons of the hydrocarbon backbone, including haloalkyl groups such as trifluoromethyl and 2,2,2-trifluoroethyl, etc.

The term "$C_{x-y}$" or "$C_x$-$C_y$", when used in conjunction with a chemical moiety, such as, acyl, acyloxy, alkyl, alkenyl, alkynyl, or alkoxy is meant to include groups that contain from x to y carbons in the chain. $C_0$alkyl indicates a hydrogen where the group is in a terminal position, a bond if internal. A $C_{1-6}$alkyl group, for example, contains from one to six carbon atoms in the chain.

The term "alkylamino", as used herein, refers to an amino group substituted with at least one alkyl group.

The term "alkylthio", as used herein, refers to a thiol group substituted with an alkyl group and may be represented by the general formula alkylS—.

The term "amido", as used herein, refers to a group

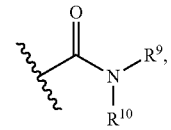

wherein $R^9$ $R^{10}$ each independently represent a hydrogen or hydrocarbyl group, or $R^9$ and $R^{10}$ taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

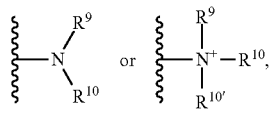

wherein $R^9$, $R^{10}$, and $R^{10\prime}$ each independently represent a hydrogen or a hydrocarbyl group, or $R^9$ and $R^{10}$ taken together with the N atom to which they are attached complete a heterocycle having from 4 to 8 atoms in the ring structure.

The term "aminoalkyl", as used herein, refers to an alkyl group substituted with an amino group.

The term "aralkyl", as used herein, refers to an alkyl group substituted with an aryl group.

The term "aryl" as used herein include substituted or unsubstituted single-ring aromatic groups in which each atom of the ring is carbon. Preferably the ring is a 5- to 7-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The term "carbamate" is art-recognized and refers to a group

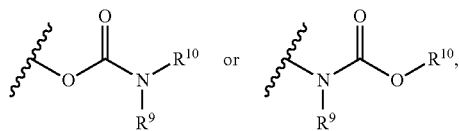

wherein $R^9$ and $R^{10}$ independently represent hydrogen or a hydrocarbyl group.

The term "carbocyclylalkyl", as used herein, refers to an alkyl group substituted with a carbocycle group.

The term "carbocycle" includes 5-7 membered monocyclic and 8-12 membered bicyclic rings. Each ring of a bicyclic carbocycle may be selected from saturated, unsaturated and aromatic rings. Carbocycle includes bicyclic molecules in which one, two or three or more atoms are shared between the two rings. The term "fused carbocycle" refers to a bicyclic carbocycle in which each of the rings shares two adjacent atoms with the other ring. Each ring of a fused carbocycle may be selected from saturated, unsaturated and aromatic rings. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, is included in the definition of carbocyclic. Exemplary "carbocycles" include cyclopentane, cyclohexane, bicyclo[2.2.1]heptane, 1,5-cyclooctadiene, 1,2,3,4-tetrahydronaphthalene, bicyclo[4.2.0]oct-3-ene, naphthalene and adamantane. Exemplary fused carbocycles include decalin, naphthalene, 1,2,3,4-tetrahydronaphthalene, bicyclo[4.2.0]octane, 4,5,6,7-tetrahydro-1H-indene and bicyclo[4.1.0]hept-3-ene. "Carbocycles" may be substituted at any one or more positions capable of bearing a hydrogen atom.

The term "carbocyclylalkyl", as used herein, refers to an alkyl group substituted with a carbocycle group.

The term "carbonate" is art-recognized and refers to a group —OCO$_2$—.

The term "carboxy", as used herein, refers to a group represented by the formula —CO$_2$H.

The term "cycloalkyl" includes substituted or unsubstituted non-aromatic single ring structures, preferably 4- to 8-membered rings, more preferably 4- to 6-membered rings. The term "cycloalkyl" also includes polycyclic ring systems having two or more cyclic rings in which two or more carbons are common to two adjoining rings wherein at least one of the rings is cycloalkyl and the substituent (e.g., $R^{100}$) is attached to the cycloalkyl ring, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, pyrimidine, denzodioxane, tetrahydroquinoline, and the like.

The term "ester", as used herein, refers to a group —C(O)OR$^9$ wherein R$^9$ represents a hydrocarbyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

The terms "halo" and "halogen" as used herein means halogen and includes chloro, fluoro, bromo, and iodo.

The terms "hetaralkyl" and "heteroaralkyl", as used herein, refers to an alkyl group substituted with a hetaryl group.

The terms "heteroaryl" and "hetaryl" include substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The term "heteroatom" as used herein means an atom of any element other than carbon or hydrogen. Preferred heteroatoms are nitrogen, oxygen, and sulfur.

The term "heterocyclylalkyl", as used herein, refers to an alkyl group substituted with a heterocycle group.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and even trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to, aryl, heteroaryl, carbocycle, heterocycle, alkyl, alkenyl, alkynyl, and combinations thereof.

The term "hydroxyalkyl", as used herein, refers to an alkyl group substituted with a hydroxy group.

The term "lower" when used in conjunction with a chemical moiety, such as, acyl, acyloxy, alkyl, alkenyl, alkynyl, or alkoxy is meant to include groups where there are ten or fewer atoms in the substituent, preferably six or fewer. A "lower alkyl", for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, preferably from 5 to 7.

The term "sulfate" is art-recognized and refers to the group —OSO₃H, or a pharmaceutically acceptable salt thereof.

The term "sulfonamido" is art-recognized and refers to the group represented by the general formulae

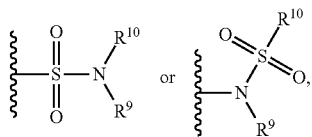

wherein $R^9$ and $R^{10}$ independently represents hydrogen or hydrocarbyl.

The term "sulfoxide" is art-recognized and refers to the group —S(O)—.

The term "sulfonate" is art-recognized and refers to the group SO₃H, or a pharmaceutically acceptable salt thereof.

The term "sulfone" is art-recognized and refers to the group —S(O)₂—.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate.

The term "thioalkyl", as used herein, refers to an alkyl group substituted with a thiol group.

The term "thioester", as used herein, refers to a group —C(O)SR⁹ or —SC(O)R⁹ wherein R⁹ represents a hydrocarbyl.

The term "thioether", as used herein, is equivalent to an ether, wherein the oxygen is replaced with a sulfur.

The term "urea" is art-recognized and may be represented by the general formula

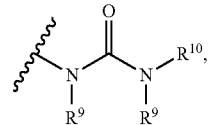

wherein $R^9$ and $R^{10}$ independently represent hydrogen or a hydrocarbyl.

The term "modulate" as used herein includes the inhibition or suppression of a function or activity (such as cell proliferation) as well as the enhancement of a function or activity.

The phrase "pharmaceutically acceptable" is art-recognized. In certain embodiments, the term includes compositions, excipients, adjuvants, polymers and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable salt" or "salt" is used herein to refer to an acid addition salt or a basic addition salt which is suitable for or compatible with the treatment of patients.

The term "pharmaceutically acceptable acid addition salt" as used herein means any non-toxic organic or inorganic salt of any base compounds represented by Formula I. Illustrative inorganic acids which form suitable salts include hydrochloric, hydrobromic, sulfuric and phosphoric acids, as well as metal salts such as sodium monohydrogen orthophosphate and potassium hydrogen sulfate. Illustrative organic acids that form suitable salts include mono-, di-, and tricarboxylic acids such as glycolic, lactic, pyruvic, malonic, succinic, glutaric, fumaric, malic, tartaric, citric, ascorbic, maleic, benzoic, phenylacetic, cinnamic and salicylic acids, as well as sulfonic acids such as p-toluene sulfonic and methanesulfonic acids. Either the mono or di-acid salts can be formed, and such salts may exist in either a hydrated, solvated or substantially anhydrous form. In general, the acid addition salts of compounds of Formula I are more soluble in water and various hydrophilic organic solvents, and generally demonstrate higher melting points in comparison to their free base forms. The selection of the appropriate salt will be known to one skilled in the art. Other non-pharmaceutically acceptable salts, e.g., oxalates, may be used, for example, in the isolation of compounds of Formula I for laboratory use, or for subsequent conversion to a pharmaceutically acceptable acid addition salt.

The term "pharmaceutically acceptable basic addition salt" as used herein means any non-toxic organic or inorganic base addition salt of any acid compounds represented by Formula I or any of their intermediates. Illustrative inorganic bases which form suitable salts include lithium, sodium, potassium, calcium, magnesium, or barium hydroxide. Illustrative organic bases which form suitable salts include aliphatic, alicyclic, or aromatic organic amines such as methylamine, trimethylamine and picoline or ammonia. The selection of the appropriate salt will be known to a person skilled in the art.

Many of the compounds useful in the methods and compositions of this disclosure have at least one stereogenic center in their structure. This stereogenic center may be present in a R or a S configuration, said R and S notation is used in correspondence with the rules described in Pure Appl. Chem. (1976), 45, 11-30. The disclosure contemplates all stereoisomeric forms such as enantiomeric and diastereoisomeric forms of the compounds, salts, prodrugs or mixtures thereof (including all possible mixtures of stereoisomers). See, e.g., WO 01/062726.

Furthermore, certain compounds which contain alkenyl groups may exist as Z (zusammen) or E (entgegen) isomers. In each instance, the disclosure includes both mixture and separate individual isomers.

"Prodrug" or "pharmaceutically acceptable prodrug" refers to a compound that is metabolized, for example hydrolyzed or oxidized, in the host after administration to form the compound of the present disclosure (e.g., compounds of formula I). Typical examples of prodrugs include compounds that have biologically labile or cleavable (protecting) groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, or dephosphorylated to produce the active compound. Examples of prodrugs using ester or phosphoramidate as biologically labile or cleavable (protecting) groups are disclosed in U.S. Pat. Nos. 6,875,751, 7,585,851, and 7,964,580, the disclosures of which are incorporated herein by reference. The prodrugs of this disclosure are metabolized to produce a compound of Formula I. The present disclosure includes within its scope, prodrugs of the compounds described herein. Conventional procedures for the selection and preparation of suitable prodrugs are described, for example, in "Design of Prodrugs" Ed. H. Bundgaard, Elsevier, 1985.

The phrase "pharmaceutically acceptable carrier" as used herein means a pharmaceutically acceptable material, composition or vehicle, such as a liquid or solid filter, diluent, excipient, solvent or encapsulating material useful for formulating a drug for medicinal or therapeutic use.

The term "Log of solubility", "Log S" or "log S" as used herein is used in the art to quantify the aqueous solubility of a compound. The aqueous solubility of a compound significantly affects its absorption and distribution characteristics. A low solubility often goes along with a poor absorption. Log S value is a unit stripped logarithm (base 10) of the solubility measured in mol/liter.

EXAMPLES

The representative examples which follow are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples which follow and the references to the scientific and patent literature cited herein. It should further be appreciated that the contents of those cited references are incorporated herein by reference to help illustrate the state of the art. The following examples contain important additional information, exemplification and guidance which can be adapted to the practice of this invention in its various embodiments and equivalents thereof.

Example 1: Synthesis of Exemplary Compounds of the Disclosure

General Procedure A.

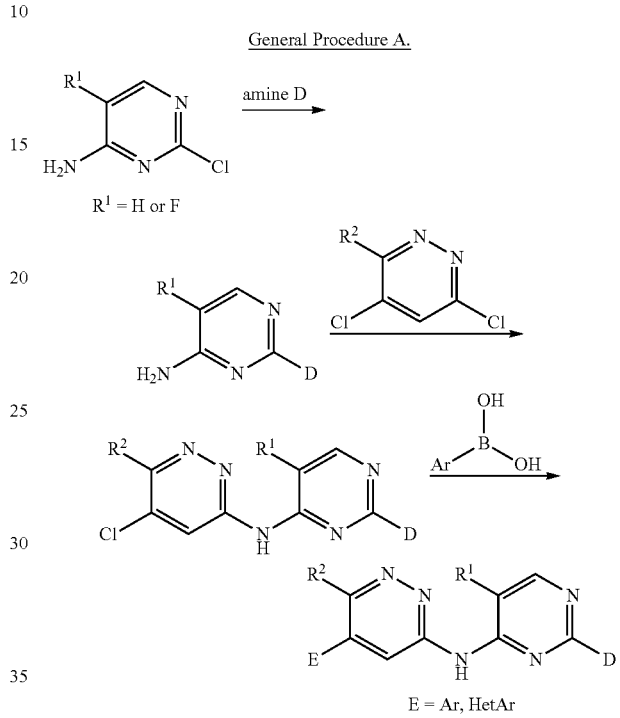

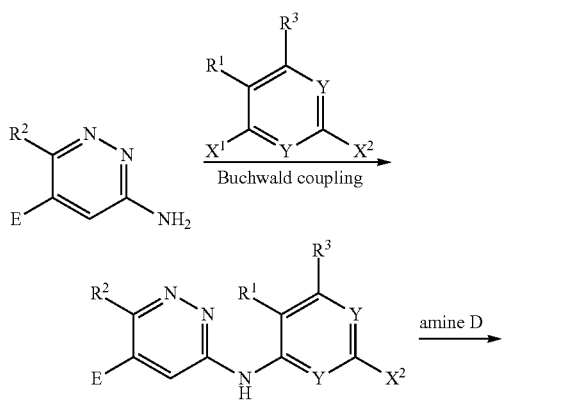

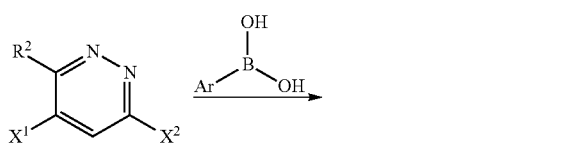

-continued
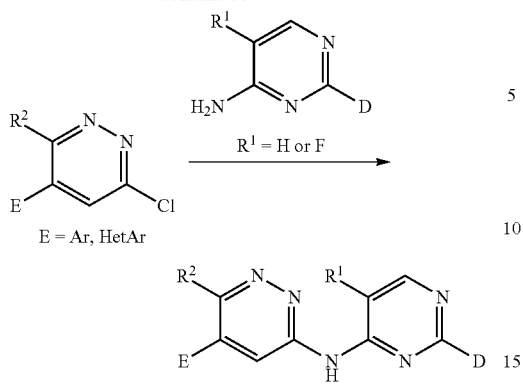
E = Ar, HetAr
R[1] = H or F
Representative Examples for D:
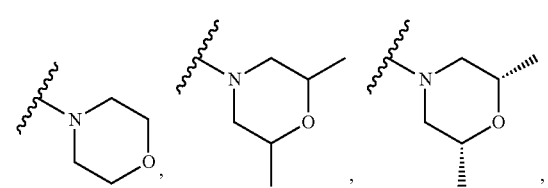
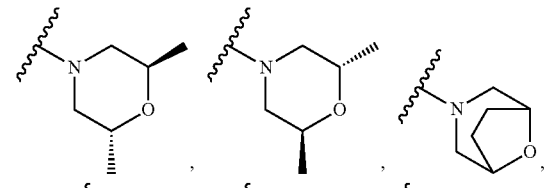
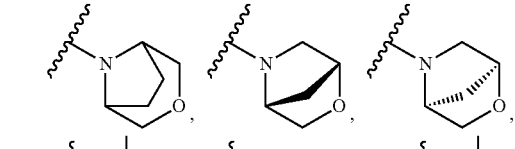
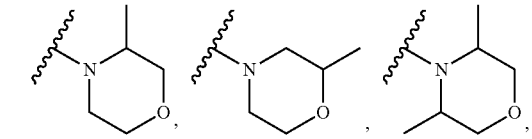
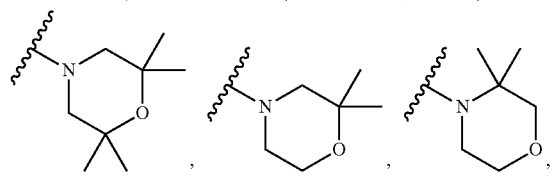
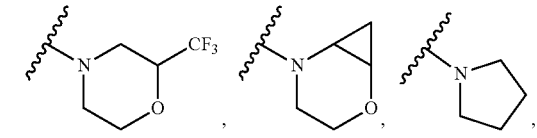
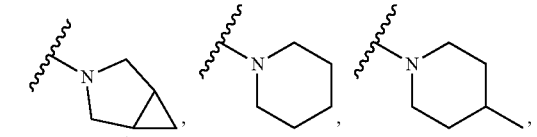
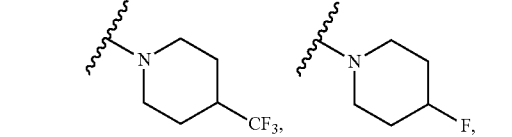
-continued
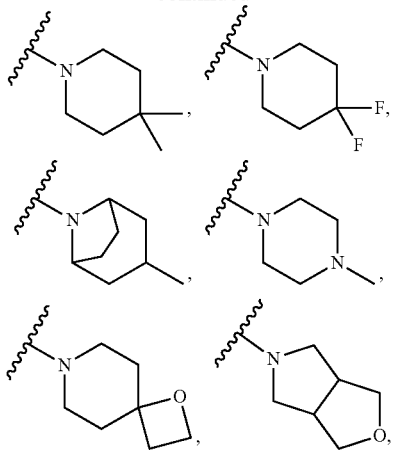
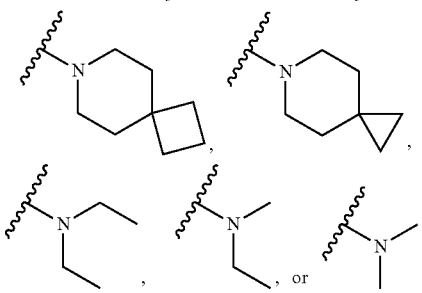
Representative examples for E:
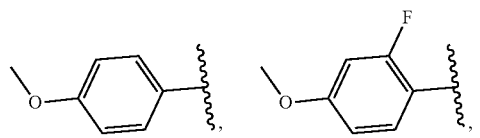
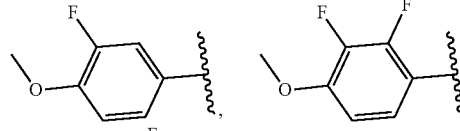
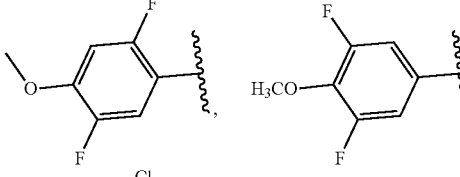
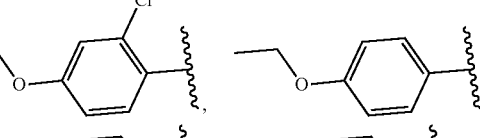
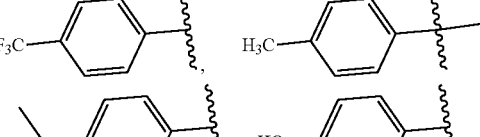
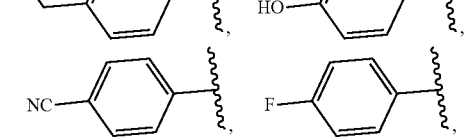

275
-continued

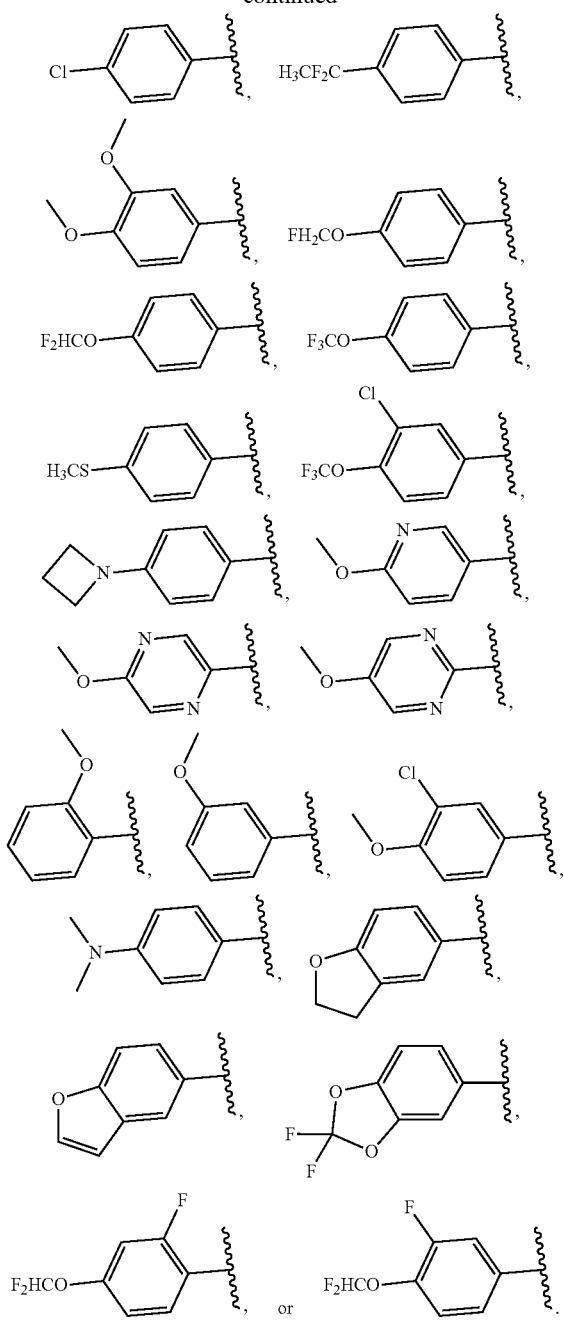

Synthesis of 2-((2R,6S)-2,6-dimethylmorpholino)pyrimidin-4-amine

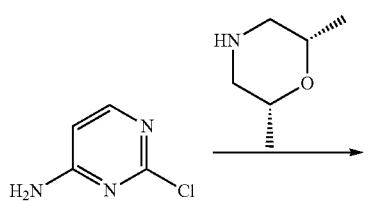

276
-continued

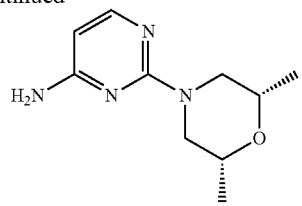

The mixture of compound 2-chloropyrimidin-4-amine (2.0 g, 15.4 mmol, 1.0 eq), compound (2R,6S)-2,6-dimethylmorpholine (5.33 g, 46.3 mmol, 3.0 eq) and DIEA (10.0 g, 77.0 mmol, 5.0 eq) in IPA (40 mL) was stirred at 80° C. for 16 h under $N_2$. The reaction was concentrated under reduced pressure. The residue was partitioned between ethyl acetate (90 mL) and water (150 mL). The separated organic layer was washed with water, dried over anhydrous Na2SO4 and evaporated to dryness. The residue was purified by column chromatography (PE:EA=5:1 to DCM:MeOH=40:1) to give 2-((2R,6S)-2,6-dimethylmorpholino)pyrimidin-4-amine (3.1 g, 97%) as a white solid. LCMS: 209.03 [M+1]$^+$; $^1$H NMR (400 MHz, CD$_3$OD) δ 7.76 (d, J=5.9 Hz, 1H), 5.86 (d, J=5.9 Hz, 1H), 4.49-4.36 (m, 2H), 3.61 (ddd, J=10.5, 6.3, 2.5 Hz, 2H), 3.38 (s, 1H), 2.48 (dd, J=13.2, 10.7 Hz, 2H), 1.22 (d, J=6.2 Hz, 6H).

Synthesis of 2-((2R,6S)-2,6-dimethylmorpholino)-5-fluoropyrimidin-4-amine

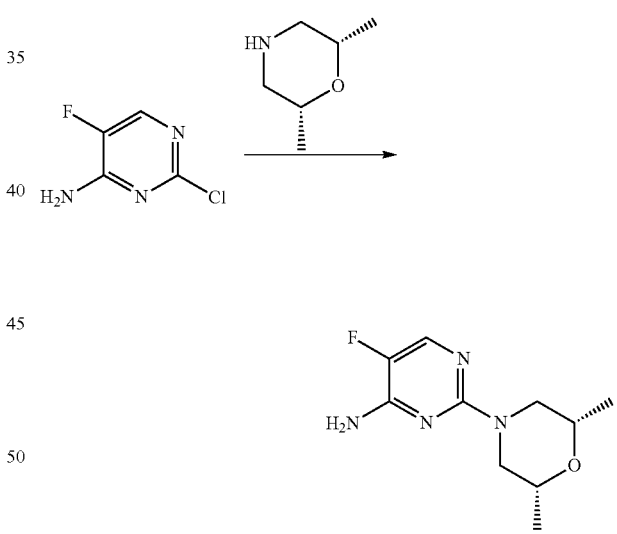

To a solution of compound 2-chloro-5-fluoropyrimidin-4-amine (50 g, 338.9 mmol, 1.0 eq.), compound (2R,6S)-2,6-dimethylmorpholine (78 g, 667.8 mmol, 2.0 eq) in IPA (500 mL) was added DIEA (87.6 g, 667.8 mmol, 2.0 eq.), and the reaction mixture was stirred at 80° C. for 16 h. The result mixture was concentrated under reduced pressure. The residue was purified by silica gel chromatography eluted with PE:EtOAc=20:1 to give 2-((2R,6S)-2,6-dimethylmorpholino)-5-fluoropyrimidin-4-amine (47 g, 61%) as a white solid. LCMS: 227.12 [M+H]$^+$; $^1$H NMR (400 MHz, DMSO-d$_6$): δ 7.76 (d, J=3.5 Hz, 1H), 6.83 (s, 2H), 4.28 (d, J=12.0 Hz, 2H), 3.46 (dd, J=7.9, 6.3 Hz, 2H), 2.32 (dd, J=12.7, 10.9 Hz, 2H), 1.07 (d, J=6.2 Hz, 6H).

Synthesis of 2-((2S,6S)-2,6-dimethylmorpholino)-5-fluoropyrimidin-4-amine

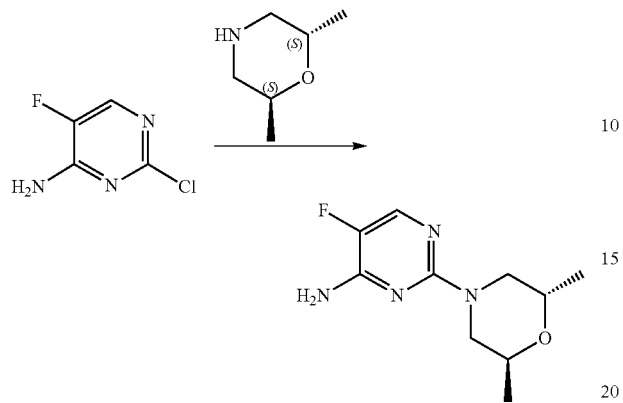

To a solution of compound 2-chloro-5-fluoropyrimidin-4-amine (325 mg, 2.2 mmol, 1.5 eq) and compound (2S,6S)-2,6-dimethylmorpholine (170 mg, 1.47 mmol, 1.0 eq) in IPA (3 mL) was added DIEA (569 mg, 4.4 mmol, 2.0 eq). The reaction mixture was stirred at 80° C. for 16 h. The resulting mixture was concentrated under reduced pressure. The residue was purified by Prep-TLC using DCM/MeOH=40/1 to give 2-((2S,6S)-2,6-dimethylmorpholino)-5-fluoropyrimidin-4-amine (92 mg, 18%) as a white solid. LCMS: 227.10 [M+1]+; $^1$H NMR (400 MHz, DMSO-$d_6$) δ 7.76 (d, J=3.5 Hz, 1H), 6.82 (s, 2H), 3.96-3.83 (m, 2H), 3.61 (dd, J=12.9, 3.2 Hz, 2H), 3.24 (dd, J=12.9, 6.2 Hz, 2H), 1.07 (d, J=6.4 Hz, 6H).

Synthesis of 2-((2R,6R)-2,6-dimethylmorpholino)-5-fluoropyrimidin-4-amine

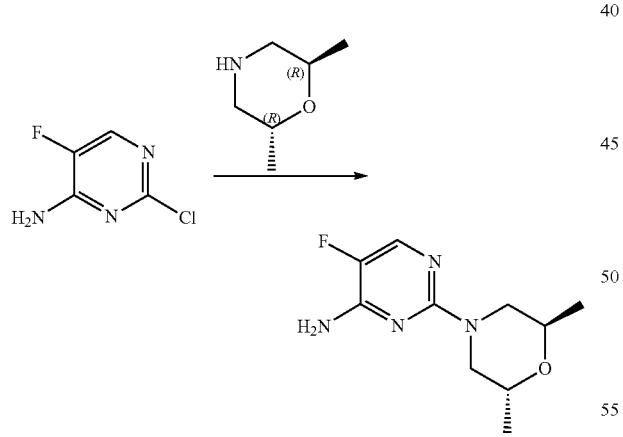

To a solution of compound 2-chloro-5-fluoropyrimidin-4-amine (200 mg, 1.36 mmol, 1.0 eq) in IPA (4 mL) was added compound (2R,6R)-2,6-dimethylmorpholine (391 mg, 3.40 mmol, 2.5 eq) and DIEA (526 mg, 4.08 mmol, 3.0 eq), The reaction mixture was stirred at 80° C. for 16 hrs. The mixture was concentrated under reduced pressure. The residue was purified by column chromatography on silica gel eluted with (DCM/MeOH/NH$_3$·H$_2$O=50/1/0.5) to afford 2-((2R,6R)-2,6-dimethylmorpholino)-5-fluoropyrimidin-4-amine (70 mg, white solid). LC-MS: 227.12[M+1]+; $^1$H NMR (400 MHz, DMSO-$d_6$) δ 7.77 (d, J=3.6 Hz, 1H), 6.84 (s, 2H), 3.92 (td, J=6.3, 3.5 Hz, 2H), 3.63 (dd, J=12.9, 3.3 Hz, 2H), 3.26 (dd, J=12.9, 6.2 Hz, 2H), 1.08 (d, J=6.4 Hz, 6H).

Synthesis of 5-fluoro-2-(pyrrolidin-1-yl)pyrimidin-4-amine

To a solution of 2-chloro-5-fluoropyrimidin-4-amine (200 mg, 1.36 mmol, 1.0 eq) in IPA (4 mL) was added pyrrolidine (290 mg, 4.08 mmol, 3.0 eq) and DIEA (526 mg, 4.08 mmol, 3.0 eq). The reaction mixture was stirred at 80° C. for 16 hrs. The mixture was concentrated under reduced pressure. The residue was purified by column chromatography on silica gel eluted with (PE/EA=1/1) to afford 5-fluoro-2-(pyrrolidin-1-yl)pyrimidin-4-amine (230 mg, white solid). LC-MS: 183.1[M+1]+; $^1$H NMR (400 MHz, DMSO-$d_6$) δ 7.75 (d, J=3.8 Hz, 1H), 6.72 (s, 2H), 3.35 (t, J=6.6 Hz, 4H), 1.84 (t, J=6.6 Hz, 4H).

Synthesis of 2-(2-oxa-5-azabicyclo[4.1.0]heptan-5-yl)-5-fluoropyrimidin-4-amine

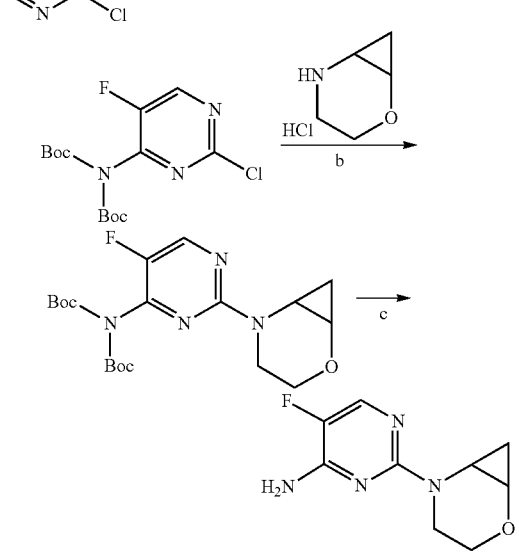

Step a: To a solution of 2-chloro-5-fluoropyrimidin-4-amine (300 mg, 2.03 mmol 1.0 eq), Boc$_2$O (1.77 g, 8.13 mmol 4.0 eq) and TEA (821 mg, 8.13 mmol 4.0 eq) in DCM (3 mL) was added DMAP (12 mg, 0.10 mmol 0.05 eq) at RT. The reaction mixture was stirred at RT for 2 h. The resulting mixture was concentrated under reduced pressure. The residue was purified by silica gel chromatography eluted with PE:EtOAc=100:1 to give bis-N-Boc protected compound (600 mg, 85%) as a white solid. $^1$H NMR (400 MHz, CDCl$_3$) δ 8.49 (s, 1H), 1.44 (s, 18H).

Step b: To a solution of bis-N-Boc protected compound (512 mg, 1.47 mmol, 1.0 eq) 2-oxa-5-azabicyclo[4.1.0]heptane hydrochloride (200 mg, 1.47 mmol, 1.0 eq) in DIEA (3 mL) was added. The reaction mixture was stirred at 100° C. for 16 h. The resulting mixture was concentrated under reduced pressure. The residue was purified by Prep-TLC with PE/EA=3/1 to give the product (110 mg, crude) as a white solid. LCMS: 411.35 [M+1]$^+$ Step c: To a solution of bis-N-Boc product from step b (110 mg crude, 0.268 mmol, 1.0 eq) in Dioxane (1 mL) was added HCl/Dioxane (4M, 1 mL). The reaction mixture was stirred at 40° C. for 16 h. The resulting mixture was concentrated under reduced pressure. The residue was partitioned between ethylacetate (50 mL) and saturated Na$_2$CO$_3$ solution (50 mL). The separated organic layer was dried over (Na2SO4 or MgSO4) and evaporated to dryness. The residue was purified by Prep-TLC with DCM/MeOH=40/1 to give 2-(2-oxa-5-azabicyclo[4.1.0]heptan-5-yl)-5-fluoropyrimidin-4-amine (12 mg, 21%) as a white solid. $^1$H NMR (400 MHz, CDCl3) δ 7.90 (d, J=3.0 Hz, 1H), 4.85 (s, 2H), 3.85-3.65 (m, 3H), 3.40 (dt, J=7.4, 4.4 Hz, 2H), 2.92 (td, J=6.9, 5.0 Hz, 1H), 0.92 (q, J=6.8 Hz, 1H), 0.57 (ddd, J=6.9, 4.8, 3.6 Hz, 1H).

Synthesis of (2R,6S)-4-(4,6-difluoropyrimidin-2-yl)-2,6-dimethylmorpholine

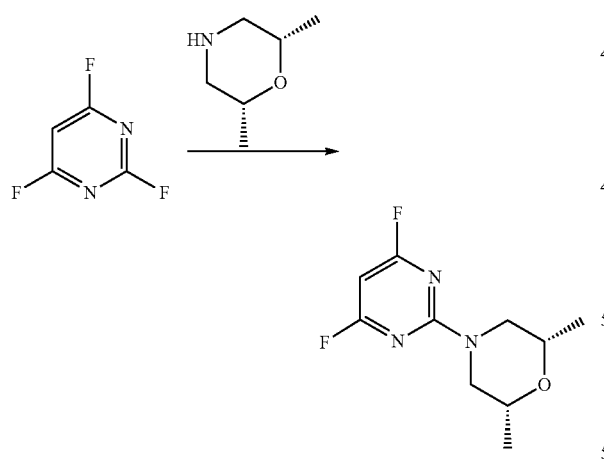

To a solution of 2,4,6-trifluoropyrimidine (300 mg, 2.24 mmol, 1.0 eq), K$_2$CO$_3$ (619 mg, 4.48 mmol, 2.0 eq) in ACN (30 mL) was added (2R,6S)-2,6-dimethylmorpholine (258 mg, 2.24 mmol, 1.0 eq). The reaction mixture was stirred for over 10 min under ice-cooling and stirred at room temperature for another 1 hr. The mixture was concentrated under vacuum to give a residue, which was purified by column chromatography on silica gel eluted with (PE/EA=100/1 to 50/1) to afford (2R,6S)-4-(4,6-difluoropyrimidin-2-yl)-2,6-dimethylmorpholine (250 mg, 49%) as a white solid. $^1$H NMR (400 MHz, CDCl$_3$) δ 5.68 (t, J=1.6 Hz, 1H), 4.43 (dd, J=13.2, 1.3 Hz, 2H), 3.58 (m, J=12.5, 6.2, 2.4 Hz, 2H), 2.61 (dd, J=13.4, 10.8 Hz, 2H), 1.23 (d, J=6.2 Hz, 6H).

Synthesis of 5-chloro-N-(2-((2R,6S)-2,6-dimethylmorpholino) pyrimidin-4-yl)pyridazin-3-amine

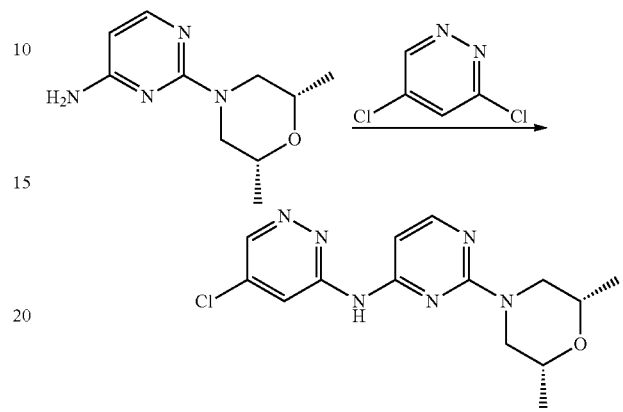

To a solution of 2-((2R,6S)-2,6-dimethylmorpholino)pyrimidin-4-amine (700 mg, 3.36 mmol, 1.0 eq), 3,5-dichloropyridazine (500 mg, 3.36 mmol, 1.0 eq), Xantphos (197 mg, 0.34 mmol, 0.1 eq) and Cs$_2$CO$_3$ (2.2 g, 6.72 mmol, 2.0 eq) in dioxane (10 mL) was added Pd$_2$(dba)$_3$ (97 mg, 0.17 mmol, 0.05 eq) at RT under N$_2$. Then the reaction mixture was stirred at 110° C. for 16 h under N$_2$. The reaction was concentrated under reduced pressure. The residue was partitioned between ethyl acetate (90 mL) and water (150 mL). The separated organic layer was washed with water, dried over anhydrous Na2SO4 and evaporated to dryness. The residue was purified by column chromatography (PE:EA=5:1 to DCM:MeOH=40:1) to give 5-chloro-N-(2-((2R,6S)-2,6-dimethylmorpholino)pyrimidin-4-yl)pyridazin-3-amine (200 mg, 18.5%) as a yellow solid. LCMS: 321.00 [M+1]$^+$ Synthesis of 5-chloro-N-(2-((2R,6S)-2,6-dimethylmorpholino)-5-fluoropyrimidin-4-yl)pyridazin-3-amine

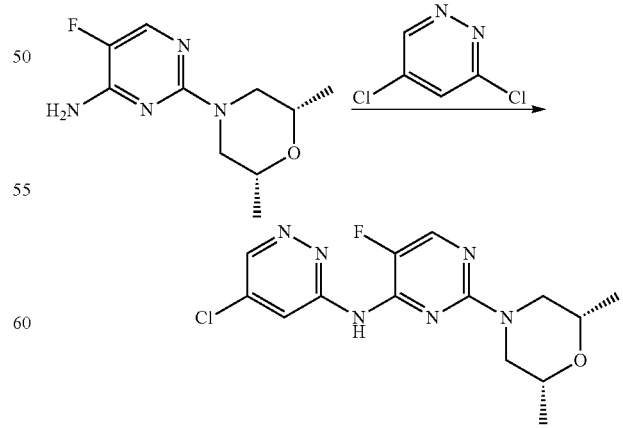

To a solution of 2-((2R,6S)-2,6-dimethylmorpholino)-5-fluoropyrimidin-4-amine (35.5 g, 157.08 mmol, 1.0 eq), 3,5-dichloropyridazine (35 g, 234.90 mmol, 1.5 eq), Xantphos (4.54 g, 7.85 mmol, 0.05 eq) and Cs$_2$CO$_3$ (153.5 g, 471.15 mmol, 3.0 eq) in Tol. (500 mL) was added Pd(dppf)Cl$_2$ (5.75 g, 7.86 mmol, 0.05 eq) at RT under N$_2$. The reaction mixture was stirred at 80° C. for 16 h. The reaction was concentrated under reduced pressure. The residue was partitioned between ethyl acetate (500 mL) and water. The separated organic layer was washed with water, dried over Na$_2$SO$_4$ and evaporated to dryness. The residue was purified by silica gel chromatography eluted with PE:EtOAc=5:1 to give 5-chloro-N-(2-((2R,6S)-2,6-dimethylmorpholino)-5-fluoropyrimidin-4-yl)pyridazin-3-amine (29 g, 55%) as a yellow solid. LCMS: 339.11 [M+H]$^+$; $^1$H NMR (400 MHz, DMSO-d$_6$): δ 10.69 (s, 1H), 9.05 (s, 1H), 8.47 (d, J=2.0 Hz, 1H), 8.17 (d, J=3.2 Hz, 1H), 4.20 (d, J=12.5 Hz, 2H), 3.52 (d, J=7.3 Hz, 2H), 2.51 (s, 2H), 1.10 (d, J=6.1 Hz, 6H).

Synthesis of 5-chloro-N-(2-((2S,6S)-2,6-dimethyl-morpholino)-5-fluoropyrimidin-4-yl)pyridazin-3-amine

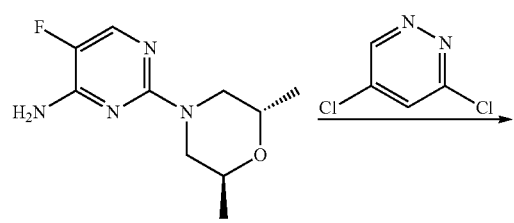

To a solution of 2-((2S,6S)-2,6-dimethylmorpholino)-5-fluoropyrimidin-4-amine (92 mg, 0.41 mmol, 1.0 eq), 3,5-dichloropyridazine (91 mg, 0.61 mmol, 1.5 eq), Xantphos (12 mg, 0.02 mmol, 0.05 eq) and Cs$_2$CO$_3$ (398 mg, 1.22 mmol, 3.0 eq) in Tol (3 mL) was added Pd(dppf)Cl$_2$ (15 mg, 0.02 mmol, 0.05 eq) at RT under N$_2$. Then the reaction mixture was stirred at 80° C. for 16 h under N$_2$. The reaction was concentrated under reduced pressure. The residue was partitioned between ethylacetate (30 mL) and water (50 mL). The separated organic layer was washed with water, dried over (Na2SO4 or MgSO4) and evaporated to dryness. The residue was purified by Prep-TLC with PE/EA=2/1 to give 5-chloro-N-(2-((2S,6S)-2,6-dimethylmorpholino)-5-fluoropyrimidin-4-yl)pyridazin-3-amine (75 mg, 54%) as a yellow solid. LCMS: 339.10 [M+1]$^+$; $^1$H NMR (400 MHz, DMSO-d$_6$) δ 10.68 (s, 1H), 9.06 (d, J=2.1 Hz, 1H), 8.44 (d, J=2.2 Hz, 1H), 8.17 (d, J=3.3 Hz, 1H), 4.01-3.91 (m, 2H), 3.67 (dd, J=13.0, 3.3 Hz, 2H), 3.33 (m, 1H), 3.29 (m, 1H), 1.10 (d, J=6.4 Hz, 6H).

Synthesis of 5-chloro-N-(2-((2R,6R)-2,6-dimethyl-morpholino)-5-fluoropyrimidin-4-yl)pyridazin-3-amine

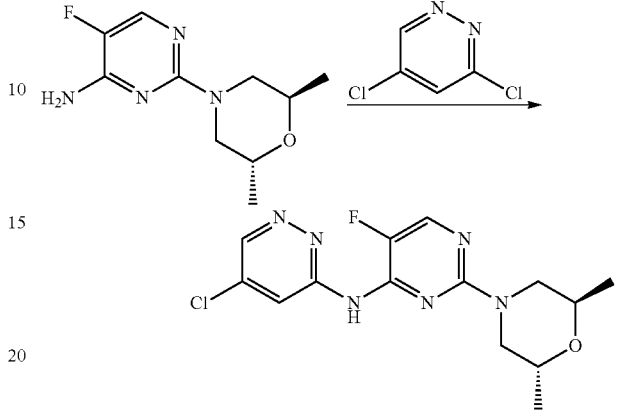

To a solution of 2-((2R,6R)-2,6-dimethylmorpholino)-5-fluoropyrimidin-4-amine (70 mg, 0.31 mmol, 1.0 eq) in in toluene (4 mL) was added 3,5-dichloropyridazine (46 mg, 0.31 mmol, 1.0 eq), Cs$_2$CO$_3$ (202 mg, 0.62 mmol, 2.0 eq), Xantphos (18 mg, 0.031 mmol, 0.1 eq) and Pd(dppf)Cl$_2$ (23 mg, 0.031 mmol, 0.1 eq). The reaction mixture was stirred at 80° C. for 16 h under N$_2$. 50 mL H$_2$O was poured into the mixture and extracted with EtOAc (20 mL×3), dried over anhydrous Na$_2$SO$_4$, filtered and concentrated under reduced pressure. The residue was purified by column chromatography on silica gel eluted with (PE/EA=2/1) to afford 5-chloro-N-(2-((2R,6R)-2,6-dimethylmorpholino)-5-fluoropyrimidin-4-yl)pyridazin-3-amine (50 mg). LC-MS: 339.05 [M+1]$^+$

Synthesis of 5-chloro-N-(5-fluoro-2-(pyrrolidin-1-yl)pyrimidin-4-yl)pyridazin-3-amine

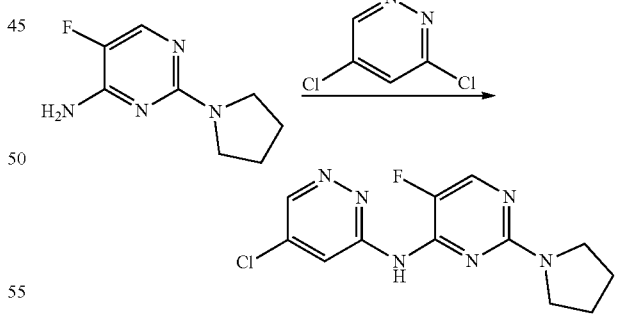

To a solution of 5-fluoro-2-(pyrrolidin-1-yl)pyrimidin-4-amine (230 mg, 1.26 mmol, 1.0 eq) in toluene (5 mL) was added 3,5-dichloropyridazine (188 mg, 1.26 mmol, 1.0 eq), Cs$_2$CO$_3$ (819 mg, 2.52 mmol, 2.0 eq), Xantphos (73 mg, 0.126 mmol, 0.1 eq) and Pd(dppf)Cl$_2$ (92 mg, 0.126 mmol, 0.1 eq). The reaction mixture was stirred at 80° C. for 16 h under N$_2$. 50 mL H$_2$O was poured into the mixture and extracted with EtOAc (20 mL×3), dried over anhydrous Na$_2$SO$_4$, filtered and concentrated under reduced pressure. The residue was purified by column chromatography on silica gel eluted with (PE/EA=2/1) to afford 5-chloro-N-(5-fluoro-2-(pyrrolidin-1-yl)pyrimidin-4-yl)pyridazin-3-amine (50 mg, crude). LC-MS: 295.00 [M+1]+

Synthesis of N-(2-(2-oxa-5-azabicyclo[4.1.0]heptan-5-yl)-5-fluoropyrimidin-4-yl)-5-chloropyridazin-3-amine

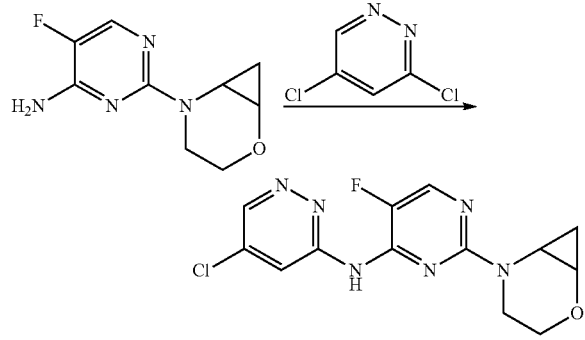

To a solution of 2-(2-oxa-5-azabicyclo[4.1.0]heptan-5-yl)-5-fluoropyrimidin-4-amine (12 mg, 0.06 mmol, 1.0 eq), 3,5-dichloropyridazine (13 mg, 0.09 mmol, 1.5 eq), Xantphos (2 mg, 0.003 mmol, 0.05 eq) and Cs$_2$CO$_3$ (59 mg, 0.18 mmol, 3.0 eq) in Tol (3 mL) was added Pd(dppf)Cl$_2$ (2 mg, 0.003 mmol, 0.05 eq) at RT. Then, the reaction mixture was stirred at 80° C. for 16 h under N$_2$. The reaction was concentrated under reduced pressure. The residue was partitioned between ethylacetate (50 mL) and water. The separated organic layer was washed with water, dried over (Na$_2$SO$_4$ or MgSO$_4$) and evaporated to dryness. The residue was purified by Prep-TLC with PE/EA=1/1 to give N-(2-(2-oxa-5-azabicyclo[4.1.0]heptan-5-yl)-5-fluoropyrimidin-4-yl)-5-chloropyridazin-3-amine (10 mg, 54%) as a white solid. LCMS: 323.07 [M+1]+; $^1$H NMR (400 MHz, CDCl$_3$) δ 9.12 (s, 1H), 8.85 (s, 1H), 8.10 (s, 2H), 3.88 (m, 3H), 3.46 (m, J=25.7 Hz, 2H), 2.88 (s, 1H), 1.08 (d, J=6.2 Hz, 1H), 0.66 (s, 1H).

Synthesis of 5-chloro-N-(2-((2R,6S)-2,6-dimethyl-morpholino)-5-fluoropyrimidin-4-yl)-6-methylpyridazin-3-amine

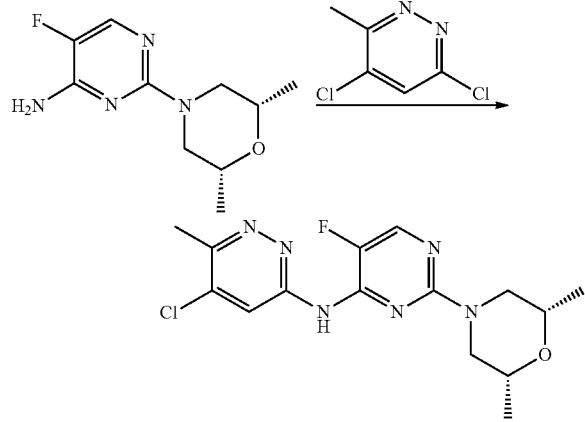

The reaction mixture of 2-((2R,6S)-2,6-dimethylmorpholino)-5-fluoropyrimidin-4-amine (100 mg, 0.44 mmol, 1.0 eq), 4,6-dichloro-3-methylpyridazine (71 mg, 0.44 mmol, 1.0 eq), Xantphos (35 mg, 0.044 mmol, 0.1 eq), Pd$_2$(dba)$_3$ (56 mg, 0.044 mmol, 0.1 eq) and CS$_2$CO$_3$ (380 mg, 0.88 mmol, 2.0 eq) in toluene (5 mL) was stirred at 110° C. for 16 hrs under N$_2$. The mixture was concentrated under reduced pressure. The residue was purified by column chromatography on silica gel eluted with (PE/EA=7/1 to 4/1) to give 5-chloro-N-(2-((2R,6S)-2,6-dimethylmorpholino)-5-fluoropyrimidin-4-yl)-6-methylpyridazin-3-amine (70 mg, 45%) as a white solid. $^1$H NMR (400 MHz, CDCl$_3$): δ 8.70 (s, 1H), 8.04 (s, 1H), 7.92 (s, 1H), 4.35 (d, J=12.9 Hz, 2H), 3.67 (s, 2H), 2.74 (s, 3H), 2.65 (t, J=11.5 Hz, 2H), 1.28 (d, J=6.1 Hz, 6H).

Synthesis of N-(2-((2R,6S)-2,6-dimethylmorpholino)pyrimidin-4-yl)-5-(2-fluoro-4-methoxyphenyl)pyridazin-3-amine—Compound 3

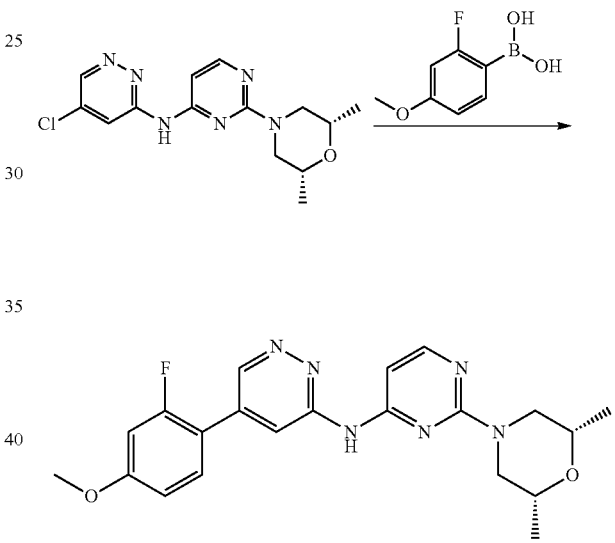

To a solution of 5-chloro-N-(2-((2R,6S)-2,6-dimethylmorpholino)pyrimidin-4-yl)pyridazin-3-amine (100 mg, 0.31 mmol, 1.0 eq), (2-fluoro-4-methoxyphenyl)boronic acid (80 mg, 0.47 mmol, 1.5 eq) and K$_2$CO$_3$ (86 mg, 0.62 mmol, 2.0 eq) in Dioxane/H$_2$O (5 mL/0.5 mL) was added Pd(PPh$_3$)$_4$ (36 mg, 0.031 mmol, 0.1 eq) at RT under N$_2$. Then the reaction mixture was stirred at 110° C. for 16 h under N$_2$. The reaction was concentrated under reduced pressure. The residue was partitioned between ethyl acetate (50 mL) and water (100 mL). The separated organic layer was washed with water, dried over anhydrous Na2SO4 and evaporated to dryness. The residue was purified by column chromatography (PE:EA=5:1 to 1:1) to give N-(2-((2R,6S)-2,6-dimethylmorpholino)pyrimidin-4-yl)-5-(2-fluoro-4-methoxyphenyl)pyridazin-3-amine (70 mg, 74.7%) as a brown solid. LCMS: 411.05 [M+1]+; $^1$H NMR (400 MHz, CD$_3$OD) δ 9.03 (d, J=2.3 Hz, 1H), 8.68 (s, 1H), 8.04 (d, J=5.6 Hz, 1H), 7.83 (t, J=8.9 Hz, 1H), 6.91 (d, J=8.6 Hz, 1H), 6.81 (dd, J=13.0, 2.3 Hz, 1H), 6.17 (d, J=5.7 Hz, 1H), 4.40 (d, J=13.1 Hz, 2H), 3.85 (s, 3H), 3.65-3.57 (m, 2H), 2.59-2.49 (m, 2H), 1.17 (d, J=6.2 Hz, 6H).

Synthesis of 5-(4-(difluoromethoxy)phenyl)-N-(2-((2R,6S)-2,6-dimethylmorpholino)pyrimidin-4-yl)pyridazin-3-amine—Compound 20

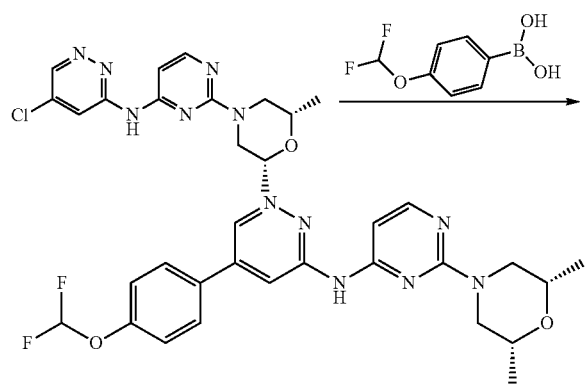

To a solution of 5-chloro-N-(2-((2R,6S)-2,6-dimethylmorpholino)pyrimidin-4-yl)pyridazin-3-amine (75 mg, 0.23 mmol, 1.0 eq) in dioxane/H$_2$O (2 mL/0.2 mL) was added (4-(difluoromethoxy)phenyl)boronic acid (80 mg, 0.46 mmol, 2.0 eq), K$_3$PO$_4$ (149 mg, 0.7 mmol, 3.0 eq) and Pd(dppf)Cl$_2$ (17 mg, 0.023 mmol, 0.1 eq), The reaction mixture was stirred at 110° C. for 16 hrs under N$_2$. The reaction mixture was concentrated under reduced pressure. The residue was purified by prep-TLC (PE/EA=0/1) to afford 5-(4-(difluoromethoxy)phenyl)-N-(2-((2R,6S)-2,6-dimethylmorpholino)pyrimidin-4-yl)pyridazin-3-amine as a white solid (68 mg, 68%). LCMS: [M+1]: 429.10; $^1$H NMR (400 MHz, CD$_3$OD) δ 9.12 (s, 1H), 8.72 (s, 1H), 8.10 (d, J=5.5 Hz, 1H), 8.02 (d, J=8.6 Hz, 2H), 7.31 (d, J=8.4 Hz, 2H), 6.94 (t, J=73.6 Hz, 1H), 6.21 (d, J=5.6 Hz, 1H), 4.45 (d, J=12.5 Hz, 2H), 3.65 (m, 2H), 2.67-2.57 (m, 2H), 1.19 (d, J=6.2 Hz, 6H).

Synthesis of 5-(4-(difluoromethoxy)phenyl)-N-(2-((2R,6S)-2,6-dimethylmorpholino)-5-fluoropyrimidin-4-yl)pyridazin-3-amine—Compound 80

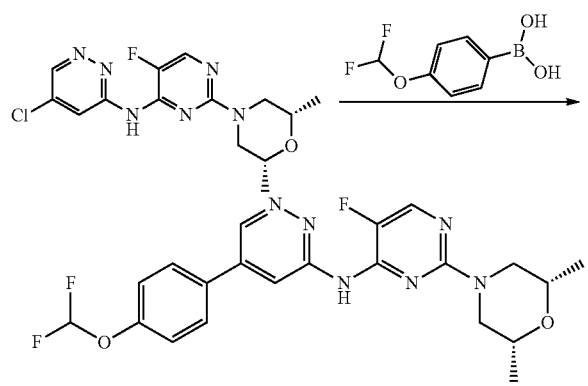

To a solution of 5-chloro-N-(2-((2R,6S)-2,6-dimethylmorpholino)-5-fluoropyrimidin-4-yl)pyridazin-3-amine (9 g, 26.57 mmol, 1.0 eq), (4-(difluoromethoxy)phenyl)boronic acid (9 g, 53.13 mmol, 2.0 eq) and K$_3$PO$_4$ (16.9 g, 79.7 mmol, 3.0 eq) in Dioxane/H$_2$O (10:1, 90 mL/10 mL) was added Pd(dppf)Cl$_2$ (1.94 g, 2.66 mmol, 0.05 eq) at RT under N$_2$. Then the reaction mixture was stirred at 110° C. for 16 h. The reaction was concentrated under reduced pressure. The residue was partitioned between ethyl acetate (90 mL) and water. The separated organic layer was washed with water, dried over Na$_2$SO$_4$ and evaporated to dryness. The residue was purified by silica gel chromatography eluted with PE:EtOAc=2:1 to give 5-(4-(difluoromethoxy)phenyl)-N-(2-((2R,6S)-2,6-dimethylmorpholino)-5-fluoropyrimidin-4-yl)pyridazin-3-amine (5.2 g, 44%) as a yellow solid. LCMS: 447.35 [M+H]$^+$; $^1$H NMR (400 MHz, DMSO-d$_6$): δ 10.42 (s, 1H), 9.31 (s, 1H), 8.61 (s, 1H), 8.16 (d, J=3.0 Hz, 1H), 7.95 (d, J=8.6 Hz, 2H), 7.55-7.12 (m, 3H), 4.20 (d, J=12.5 Hz, 2H), 3.49 (t, 2H), 2.42 (d, J=12.6 Hz, 2H), 0.96 (d, J=5.0 Hz, 6H).

Synthesis of 5-(4-(difluoromethoxy)phenyl)-N-(2-((2S,6S)-2,6-dimethylmorpholino)-5-fluoropyrimidin-4-yl)pyridazin-3-amine—Compound 91

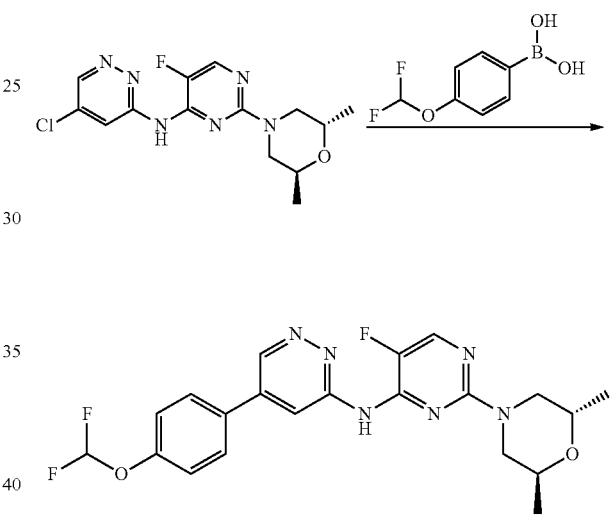

To a solution of 5-chloro-N-(2-((2S,6S)-2,6-dimethylmorpholino)-5-fluoropyrimidin-4-yl)pyridazin-3-amine (75 mg, 0.22 mmol, 1.0 eq), (4-(difluoromethoxy)phenyl)boronic acid (76 mg, 0.44 mmol, 2.0 eq) and K$_3$PO$_4$ (141 mg, 0.66 mmol, 3.0 eq) in Dioxane/H$_2$O (2 mL/0.2 mL) was added Pd(dppf)Cl$_2$ (16 mg, 0.02 mmol, 0.1 eq) at RT under N$_2$. Then the reaction mixture was stirred at 110° C. for 16 h under N$_2$. The reaction was concentrated under reduced pressure. The residue was partitioned between ethyl acetate (50 mL) and water (50 mL). The separated organic layer was washed with water, dried over (Na2SO4 or MgSO4) and evaporated to dryness. The residue was purified by Prep-TLC with PE/EA=1/1 to give 5-(4-(difluoromethoxy)phenyl)-N-(2-((2S,6S)-2,6-dimethylmorpholino)-5-fluoropyrimidin-4-yl)pyridazin-3-amine (63 mg, 64%) as a yellow solid. LCMS: 447.35 [M+1]$^+$; $^1$H NMR (400 MHz, CD$_3$OD) δ 9.17 (s, 1H), 8.83 (s, 1H), 8.03 (s, 1H), 7.86 (d, J=8.6 Hz, 2H), 7.33 (d, J=8.3 Hz, 2H), 6.95 (t, J=73.3 Hz, 1H), 4.02 (s, 2H), 3.75 (d, J=13.0 Hz, 2H), 3.40 (dd, J=12.8, 6.3 Hz, 2H), 1.11 (d, J=6.3 Hz, 6H).

Synthesis of 5-(4-(difluoromethoxy)phenyl)-N-(2-((2R,6R)-2,6-dimethylmorpholino)-5-fluoropyrimidin-4-yl)pyridazin-3-amine—Compound 90

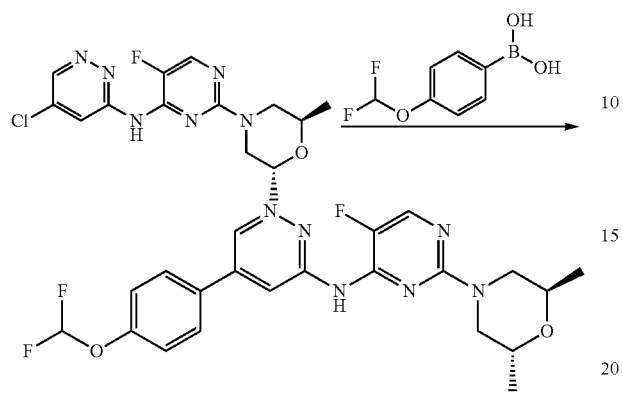

To a solution of 5-chloro-N-(2-((2R,6R)-2,6-dimethylmorpholino)-5-fluoropyrimidin-4-yl)pyridazin-3-amine (50 mg, 0.15 mmol, 1.0 eq) in in toluene/H$_2$O (3 mL/1 mL) was added (4-(difluoromethoxy)phenyl)boronic acid (43 mg, 0.23 mmol, 1.5 eq), K$_3$PO$_4$ (64 mg, 0.30 mmol, 2.0 eq) and Pd(dppf)Cl$_2$ (11 mg, 0.015 mmol, 0.1 eq). The reaction mixture was stirred at 110° C. for 16 hrs under N$_2$. 50 mL H$_2$O was poured into the mixture and extracted with EtOAc (15 mL×3), dried over anhydrous Na$_2$SO$_4$, filtered and concentrated under reduced pressure. The residue was purified by column chromatography on silica gel eluted with (PE/EA=1/1) to afford the compound 5-(4-(difluoromethoxy)phenyl)-N-(2-((2R,6R)-2,6-dimethylmorpholino)-5-fluoropyrimidin-4-yl)pyridazin-3-amine as a yellow oil (21 mg). LC-MS: 447.20[M+1]$^+$; $^1$H NMR (400 MHz, CD$_3$OD) δ 9.16 (d, J=2.0 Hz, 1H), 8.81 (d, J=2.0 Hz, 1H), 8.02 (d, J=3.3 Hz, 1H), 7.89-7.81 (m, 2H), 7.33 (d, J=8.6 Hz, 2H), 6.97 (t, J=73.5 Hz, 1H), 4.08-3.98 (m, 2H), 3.75 (dd, J=12.9, 3.3 Hz, 2H), 3.40 (dd, J=12.9, 6.5 Hz, 2H), 1.13 (d, J=6.4 Hz, 6H).

Synthesis of 5-(4-(difluoromethoxy)phenyl)-N-(5-fluoro-2-(pyrrolidin-1-yl)pyrimidin-4-yl)pyridazin-3-amine—Compound 104

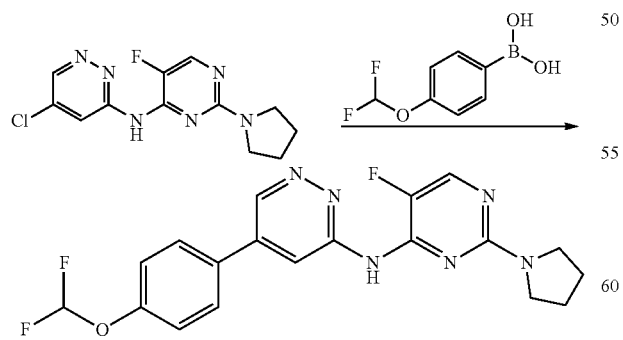

To a solution of 5-chloro-N-(5-fluoro-2-(pyrrolidin-1-yl)pyrimidin-4-yl)pyridazin-3-amine (50 mg, 0.17 mmol, 1.0 eq) in in toluene/H$_2$O (3 mL/1 mL) was added (4-(difluoromethoxy)phenyl)boronic acid (48 mg, 0.26 mmol, 1.5 eq), K$_3$PO$_4$ (72 mg, 0.0.34 mmol, 2.0 eq) and Pd(dppf)Cl$_2$ (13 mg, 0.017 mmol, 0.1 eq). The reaction mixture was stirred at 110° C. for 16 hrs under N$_2$. 50 mL H$_2$O was poured into the mixture and extracted with EtOAc (15 mL×3), dried over anhydrous Na$_2$SO$_4$, filtered and concentrated under reduced pressure. The residue was purified by prep-HPLC to afford the compound 5-(4-(difluoromethoxy)phenyl)-N-(5-fluoro-2-(pyrrolidin-1-yl)pyrimidin-4-yl)pyridazin-3-amine as a yellow solid (5 mg). LC-MS: 403.10[M+1]$^+$; $^1$H NMR (400 MHz, CD$_3$OD) δ 9.12 (dd, J=17.1, 2.0 Hz, 2H), 8.13 (s, 1H), 7.96 (d, J=3.8 Hz, 1H), 7.84 (d, J=8.8 Hz, 2H), 7.32 (d, J=8.7 Hz, 2H), 6.99 (t, J=73.5 Hz, 1H), 3.50 (s, 4H), 2.00 (dd, J=7.8, 5.6 Hz, 4H).

Synthesis of N-(2-(2-oxa-5-azabicyclo[4.1.0]heptan-5-yl)-5-fluoropyrimidin-4-yl)-5-(4-(difluoromethoxy)phenyl)pyridazin-3-amine—Compound 103

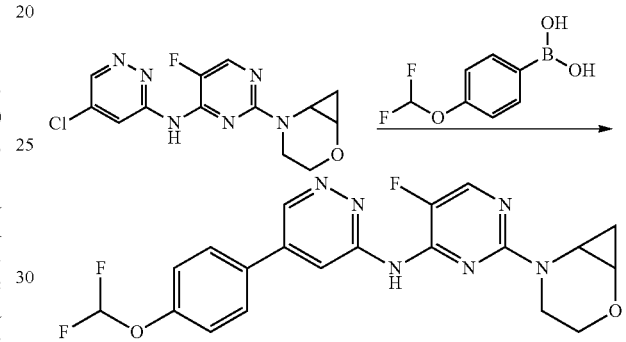

To a solution of N-(2-(2-oxa-5-azabicyclo[4.1.0]heptan-5-yl)-5-fluoropyrimidin-4-yl)-5-chloropyridazin-3-amine (10 mg, 0.03 mmol, 1.0 eq), (4-(difluoromethoxy)phenyl)boronic acid (10 mg, 0.06 mmol, 2.0 eq) and K$_3$PO$_4$ (19 mg, 0.09 mmol, 3.0 eq) in Dioxane/H$_2$O (1 mL/0.1 mL) was added Pd(dppf)Cl$_2$ (2 mg, 0.003 mmol, 0.1 eq) at RT. Then the reaction mixture was stirred at 110° C. for 16 h under N$_2$. The reaction was concentrated under reduced pressure. The residue was partitioned between ethyl acetate (50 mL) and water. The separated organic layer was dried over (Na$_2$SO$_4$ or MgSO$_4$) and evaporated to dryness. The residue was purified by Prep-TLC with PE/EA=1/1 to give N-(2-(2-oxa-5-azabicyclo[4.1.0]heptan-5-yl)-5-fluoropyrimidin-4-yl)-5-(4-(difluoromethoxy)phenyl)pyridazin-3-amine (63 mg, 64%) as a yellow solid. LCMS: 431.30 [M+1]$^+$; $^1$H NMR (400 MHz, CDCl$_3$) δ 9.09 (s, 2H), 8.12 (s, 2H), 7.62 (d, J=7.4 Hz, 2H), 7.26 (s, 1H), 6.59 (t, J=72.9 Hz, 1H), 3.81 (d, J=13.6 Hz, 3H), 3.51 (d, J=27.5 Hz, 2H), 2.92 (s, 1H), 0.87 (s, 1H), 0.62 (s, 1H).

Synthesis of 5-(4-(difluoromethoxy)phenyl)-N-(2-((2R,6S)-2,6-dimethylmorpholino)-5-fluoropyrimidin-4-yl)-6-methylpyridazin-3-amine—Compound 508

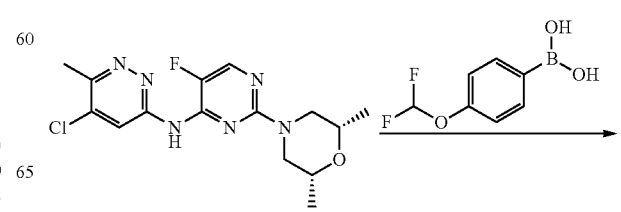

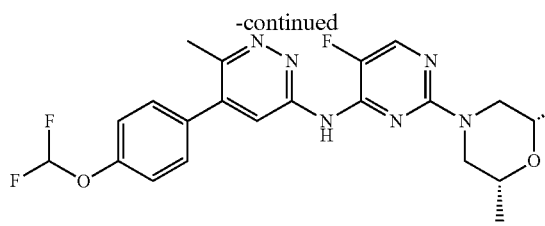

To a solution of 5-chloro-N-(2-((2R,6S)-2,6-dimethylmorpholino)-5-fluoropyrimidin-4-yl)-6-methylpyridazin-3-amine (70 mg, 0.20 mmol, 1.0 eq) in toluene (4 mL) was added (4-(difluoromethoxy)phenyl)boronic acid (38 mg, 0.20 mmol, 1.0 eq), $K_3PO_4$ (85 mg, 0.40 mmol, 2.0 eq) and Pd(dppf)$Cl_2$ (15 mg, 0.020 mmol, 0.1 eq). The reaction mixture was stirred at 110° C. for 16 hrs under $N_2$. The mixture was extracted with EtOAc (20 mL×3), dried over anhydrous $Na_2SO_4$, filtered and concentrated under reduced pressure. The residue was purified by column chromatography on silica gel eluted with (PE/EA=2/1) to afford the compound 5-(4-(difluoromethoxy)phenyl)-N-(2-((2R,6S)-2,6-dimethylmorpholino)-5-fluoropyrimidin-4-yl)-6-methylpyridazin-3-amine (25 mg, 27%) as a white solid. LC-MS: 461.15 [M+1]$^+$; $^1$H NMR (400 MHz, $CD_3OD$) δ 8.56 (s, 1H), 8.03 (d, J=3.3 Hz, 1H), 7.57 (d, J=8.6 Hz, 2H), 7.33 (d, J=8.6 Hz, 2H), 6.95 (t, J=73.6 Hz, 1H), 4.21 (d, J=12.9 Hz, 2H), 3.60-3.47 (m, 2H), 2.60 (s, 3H), 2.44 (dd, J=12.8, 10.8 Hz, 2H), 1.02 (d, J=6.2 Hz, 6H).

Synthesis of 5-(4-(difluoromethoxy)phenyl)pyridazin-3-amine

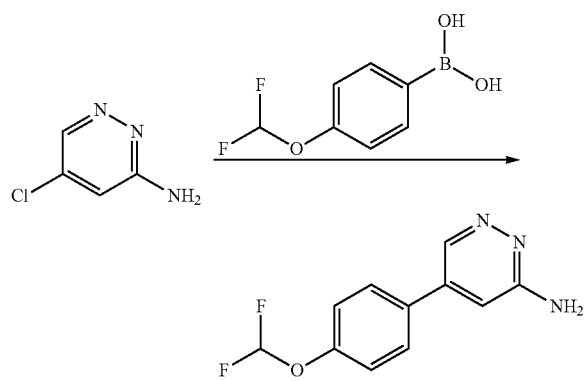

To a solution of 5-chloropyridazin-3-amine (500 mg, 3.86 mmol, 1.0 eq), (4-(difluoromethoxy)phenyl)boronic acid (1.45 g, 7.7 mmol, 2.0 eq) and $K_3PO_4$ (2.46 g, 11.58 mmol, 3.0 eq) in Dioxane/$H_2O$ (20 mL/2 mL) was added Pd(dppf)$Cl_2$ (283 mg, 0.39 mmol, 0.1 eq) at RT under $N_2$. Then the reaction mixture was stirred at 110° C. for 16 h under $N_2$. The reaction was concentrated under reduced pressure. The residue was partitioned between ethyl acetate (100 mL) and water (100 mL). The separated organic layer was washed with water, dried over ($Na_2SO_4$ or MgSO4) and evaporated to dryness. The residue was purified by silica gel chromatography eluted with DCM/MeOH=80:1 to give 5-(4-(difluoromethoxy)phenyl)pyridazin-3-amine (780 mg, 85%) as yellow solid. LCMS: 237.07 [M+1]$^+$; $^1$H NMR (400 MHz, DMSO) δ 8.76 (s, 1H), 7.78 (d, J=8.6 Hz, 2H), 7.53-7.10 (m, 3H), 6.92 (s, 1H), 6.40 (s, 2H).

Synthesis of 5-(4-(difluoromethoxy)phenyl)-2-methoxypyridin-3-amine

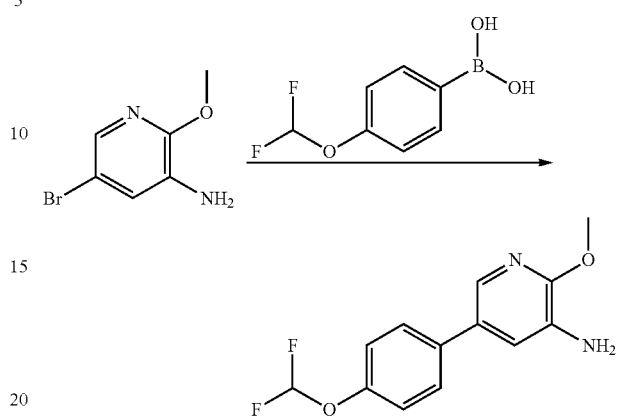

Pd(dppf)$Cl_2$ (220 mg, 0.3 mmol, 0.1 eq) was added into a solution of (4-(difluoromethoxy)phenyl)boronic acid (564 mg, 3.0 mmol, 1.0 eq), 5-bromo-2-methoxypyridin-3-amine (609 mg, 3.0 mmol, 1.0 eq) and $K_3PO_4$ (1.27 g, 6.0 mmol, 2.0 eq) in dioxane/$H_2O$ (8 mL/2 mL) under $N_2$. Then the reaction mixture was stirred at 110° C. for 16 hrs under $N_2$. The mixture was concentrated under reduced pressure. The residue was purified by column chromatography on silica gel eluted with (PE/EA=6/1 to 4/1) to give 5-(4-(difluoromethoxy)phenyl)-2-methoxypyridin-3-amine (800 mg, white solid). $^1$H NMR (400 MHz, $CDCl_3$) δ 7.74 (d, J=2.1 Hz, 1H), 7.52-7.45 (m, 2H), 7.17 (d, J=8.6 Hz, 2H), 7.05 (d, J=2.1 Hz, 1H), 6.53 (t, J=73.9 Hz, 1H), 4.02 (s, 3H), 3.87 (s, 2H).

Synthesis of N-(2-bromopyridin-4-yl)-5-(4-(difluoromethoxy)phenyl)pyridazin-3-amine

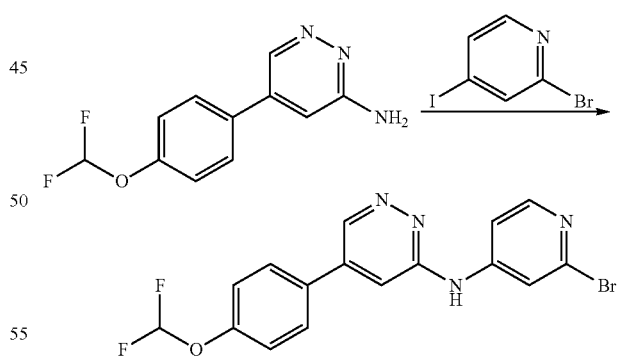

To a solution of 5-(4-(difluoromethoxy)phenyl)pyridazin-3-amine (100 mg, 0.42 mmol, 1.0 eq) in toluene (4 mL) was added 2-bromo-4-iodopyridine (180 mg, 0.063 mmol, 1.5 eq), $Cs_2CO_3$ (273 mg, 0.82 mmol, 2.0 eq), Xantphos (24 mg, 0.042 mmol, 0.1 eq) and $Pd_2(dba)_3$ (39 mg, 0.042 mmol, 0.1 eq). The reaction mixture was stirred at 100° C. for 16 hrs under $N_2$. 50 mL $H_2O$ was poured into the mixture was extracted with EtOAc (20 mL×3), dried over anhydrous $Na_2SO_4$, filtered and concentrated under reduced pressure. The residue was purified by column chromatography on silica gel eluted with (DCM/MeOH=30/1) to afford the N-(2-bromopyridin-4-yl)-5-(4-(difluoromethoxy)phenyl)pyridazin-3-amine (80 mg, yellow solid). LC-MS: 393.00 [M+1]$^+$ Synthesis of N-(2-chloro-5-fluoropyridin-4-yl)-5-(4-(difluoromethoxy)phenyl)pyridazin-3-amine

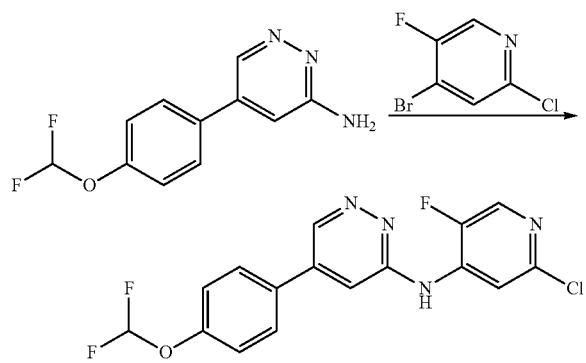

To a solution of compound 5-(4-(difluoromethoxy)phenyl)pyridazin-3-amine (100 mg, 0.42 mmol, 1.0 eq), 4-bromo-2-chloro-5-fluoropyridine (134 mg, 0.64 mmol, 1.5 eq), Xantphos (25 mg, 0.04 mmol, 0.1 eq) and Cs$_2$CO$_3$ (414 mg, 1.27 mmol, 3.0 eq) in Dioxane (2 mL) was added Pd$_2$(dba)$_3$ (39 mg, 0.04 mmol, 0.1 eq) at RT under N$_2$. Then the reaction mixture was stirred at 80° C. for 16 h. The reaction was concentrated under reduced pressure. The residue was partitioned between ethylacetate (500 mL) and water. The separated organic layer was washed with water, dried over (Na2SO4 or MgSO4) and evaporated to dryness. The residue was purified by Prep-TLC with DCM/MeOH=20/1 to give N-(2-chloro-5-fluoropyridin-4-yl)-5-(4-(difluoromethoxy)phenyl)pyridazin-3-amine (135 mg, 87%) as yellow solid. LCMS: 366.05 [M+1]$^+$; $^1$H NMR (400 MHz, DMSO) δ 9.84 (s, 1H), 9.30 (s, 1H), 8.78 (d, J=6.1 Hz, 1H), 8.33 (d, J=1.9 Hz, 1H), 7.94-7.81 (m, 3H), 7.56-7.15 (m, 3H).

Synthesis of N-(6-chloro-3-fluoropyridin-2-yl)-5-(4-(difluoromethoxy)phenyl)pyridazin-3-amine

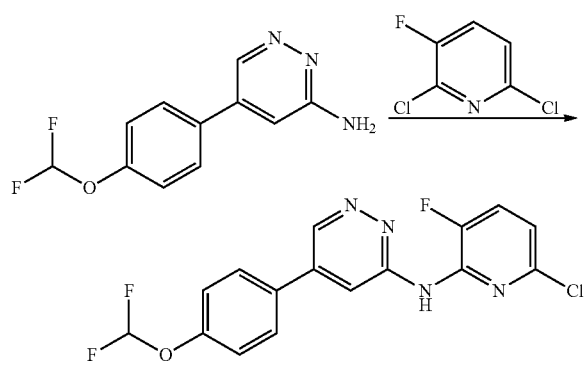

To a solution of 5-(4-(difluoromethoxy)phenyl)pyridazin-3-amine (100 mg, 0.42 mmol, 1.0 eq) in toluene (4 mL) was added 2,6-dichloro-3-fluoropyridine (105 mg, 0.42 mmol, 1.0 eq), Cs$_2$CO$_3$ (273 mg, 0.82 mmol, 2.0 eq), Xantphos (24 mg, 0.042 mmol, 0.1 eq) and Pd$_2$(dba)$_3$ (39 mg, 0.042 mmol, 0.1 eq). The reaction mixture was stirred at 100° C. for 16 h under N$_2$. 50 mL H$_2$O was poured into the mixture and extracted with EtOAc (20 mL×3), dried over anhydrous Na$_2$SO$_4$, filtered and concentrated under reduced pressure. The residue was purified by column chromatography on silica gel eluted with (DCM/MeOH=30/1) to afford the N-(6-chloro-3-fluoropyridin-2-yl)-5-(4-(difluoromethoxy)phenyl)pyridazin-3-amine (100 mg, white solid). LC-MS: 367.00 [M+1]$^+$; $^1$H NMR (400 MHz, DMSO-d6) δ 10.28 (s, 1H), 9.26 (s, 1H), 8.24 (s, 1H), 7.92 (d, J=8.4 Hz, 2H), 7.56-7.10 (m, 4H).

Synthesis of 2-chloro-N-(5-(4-(difluoromethoxy)phenyl)-2-methoxypyridin-3-yl)pyrimidin-4-amine

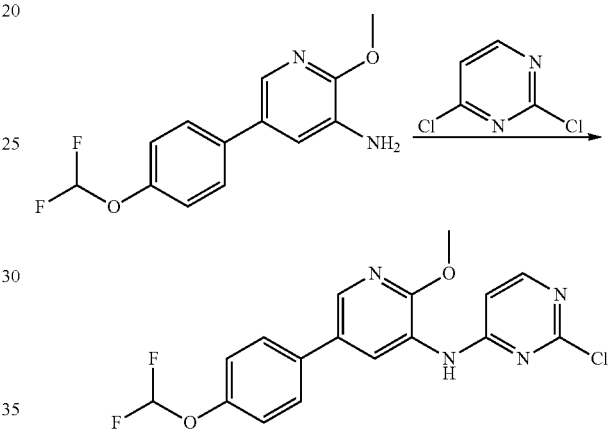

The mixture of 5-(4-(difluoromethoxy)phenyl)-2-methoxypyridin-3-amine (300 mg, 1.12 mmol, 1.0 eq), 2,4-dichloropyrimidine (184 mg, 1.24 mmol, 1.1 eq) and DIEA (434 mg, 3.36 mmol, 3.0 eq) in DMSO (5 mL) was stirred at 80° C. for 16 hrs. The mixture was poured into 60 mL H$_2$O, extracted with EtOAc (20 mL×3), dried over anhydrous Na$_2$SO$_4$, filtered and concentrated under reduced pressure. The residue was purified by column chromatography on silica gel eluted with (PE/EA=3/1) to afford 2-chloro-N-(5-(4-(difluoromethoxy)phenyl)-2-methoxypyridin-3-yl)pyrimidin-4-amine (150 mg). LC-MS: 379.00 [M+1]$^+$.

Synthesis of 2-chloro-N-(5-(4-(difluoromethoxy)phenyl)-2-methoxypyridin-3-yl)-5-fluoropyrimidin-4-amine

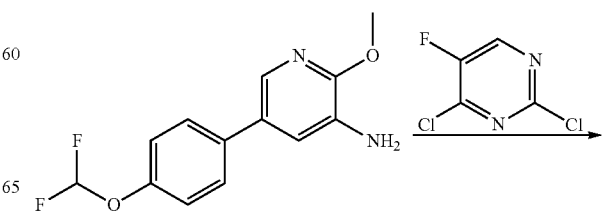

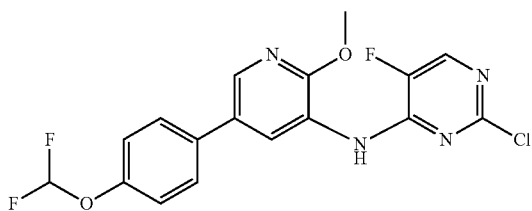

The mixture of 5-(4-(difluoromethoxy)phenyl)-2-methoxypyridin-3-amine (300 mg, 1.12 mmol, 1.0 eq), 2,4-dichloro-5-fluoropyrimidine (207 mg, 1.24 mmol, 1.1 eq) and DIEA (434 mg, 3.36 mmol, 3.0 eq) in DMSO (5 mL) was stirred at 80° C. for 16 hrs. The mixture was poured into 60 mL H$_2$O, extracted with EtOAc (20 mL×3), dried over anhydrous Na$_2$SO$_4$, filtered and concentrated under reduced pressure. The residue was purified by column chromatography on silica gel eluted with (PE/EA=3/1) to afford 2-chloro-N-(5-(4-(difluoromethoxy)phenyl)-2-methoxy-pyridin-3-yl)-5-fluoropyrimidin-4-amine (300 mg, crude). LC-MS: 397.00 [M+1]$^+$.

Synthesis of 5-(4-(difluoromethoxy)phenyl)-N-(2-((2R,6S)-2,6-dimethylmorpholino)pyridin-4-yl)pyridazin-3-amine—Compound 428

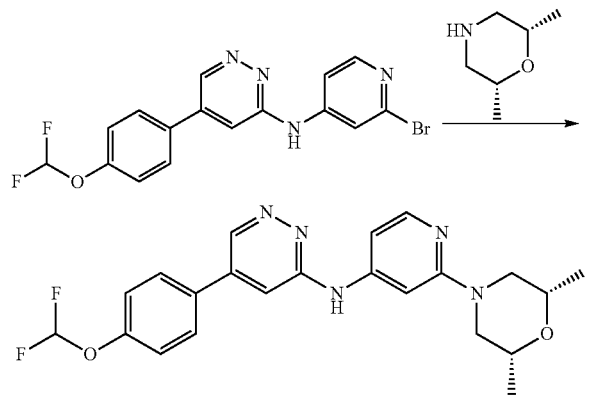

To a solution of N-(2-bromopyridin-4-yl)-5-(4-(difluoromethoxy)phenyl)-pyridazin-3-amine (80 mg, 0.20 mmol, 1.0 eq) in toluene (4 mL) was added (2R,6S)-2,6-dimethylmorpholine (47 mg, 0.40 mmol, 2.0 eq), Cs$_2$CO$_3$ (130 mg, 0.4 mmol, 2.0 eq), Xantphos (12 mg, 0.020 mmol, 0.1 eq) and Pd$_2$(dba)$_3$ (18 mg, 0.020 mmol, 0.1 eq). The reaction mixture was stirred at 100° C. for 16 hrs under N$_2$. 50 mL H$_2$O was poured into the mixture and extracted with EtOAc (20 mL×3), dried over anhydrous Na$_2$SO$_4$, filtered and concentrated under reduced pressure. The residue was purified by prep-HPLC to afford the compound 5-(4-(difluoromethoxy)phenyl)-N-(2-((2R,6S)-2,6-dimethylmorpholino)pyridin-4-yl)pyridazin-3-amine (2.1 mg). LC-MS: 428.30 [M+1]$^+$; $^1$H NMR (400 MHz, CD$_3$OD) δ 9.15 (s, 1H), 7.97 (s, 1H), 7.87 (d, J=7.4 Hz, 3H), 7.45 (s, 1H), 7.35 (d, J=8.8 Hz, 2H), 6.96 (m, J=81.4, 65.7 Hz, 2H), 3.99 (d, J=12.4 Hz, 2H), 3.77 (s, 2H), 2.66 (s, 2H), 1.28 (d, J=6.0 Hz, 6H).

Synthesis of 5-(4-(difluoromethoxy)phenyl)-N-(2-((2R,6S)-2,6-dimethylmorpholino)-5-fluoropyridin-4-yl)pyridazin-3-amine—Compound 469

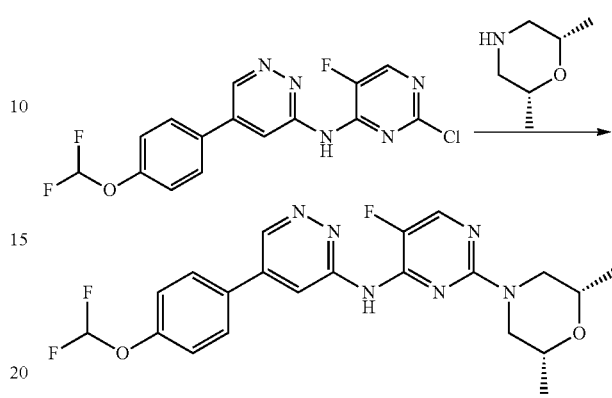

To a solution of N-(2-chloro-5-fluoropyridin-4-yl)-5-(4-(difluoromethoxy)phenyl)pyridazin-3-amine (135 mg, 0.37 mmol, 1.0 eq), (2R,6S)-2,6-dimethylmorpholine (85 mg, 0.74 mmol, 1.0 eq) in NMP (5 mL) was added DIEA (143 mg, 1.11 mmol, 3.0 eq), the reaction mixture was stirred at 200° C. for 2 h under microwave. The reaction mixture was partitioned between ethyl acetate (500 mL) and water. The separated organic layer was washed with saturated brine, dried over (Na$_2$SO$_4$ or MgSO$_4$) and evaporated to dryness. The residue was purified by Prep-TLC with DCM/MeOH=40/1 and Prep-HPLC to give 5-(4-(difluoromethoxy)phenyl)-N-(2-((2R,6S)-2,6-dimethylmorpholino)-5-fluoropyridin-4-yl)pyridazin-3-amine (6 mg, 3.7%) as white solid. LCMS: 445.17 [M+1]$^+$; $^1$H NMR (400 MHz, CD$_3$OD) δ 9.10 (s, 1H), 8.29 (d, J=5.9 Hz, 1H), 7.87 (dd, J=23.4, 5.9 Hz, 3H), 7.64 (d, 1H), 7.32 (d, J=8.6 Hz, 2H), 6.94 (t, J=73.5 Hz, 1H), 3.97 (d, J=12.0 Hz, 2H), 3.70 (d, J=6.4 Hz, 2H), 2.49-2.37 (m, 2H), 1.23 (d, J=6.2 Hz, 6H).

Synthesis of 5-(4-(difluoromethoxy)phenyl)-N-(6-((2R,6S)-2,6-dimethylmorpholino)-3-fluoropyridin-2-yl)pyridazin-3-amine—Compound 223

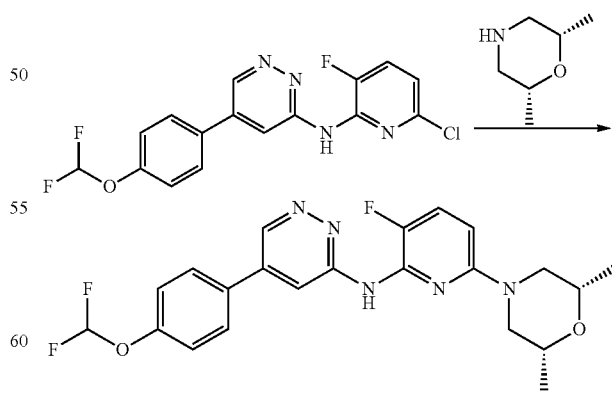

To a solution of N-(6-chloro-3-fluoropyridin-2-yl)-5-(4-(difluoromethoxy)phenyl)pyridazin-3-amine (100 mg, 0.27 mmol, 1.0 eq) was added (2R,6S)-2,6-dimethylmorpholine (95 mg, 0.82 mmol, 3.0 eq), in NMP (4 mL) was added DIEA (109 mg, 0.82 mmol, 3.0 eq). The reaction mixture was stirred at 200° C. microwave for 1. 50 mL H2O was poured into the mixture and extracted with EtOAc (20 mL×3), dried over anhydrous Na₂SO₄, filtered and concentrated under reduced pressure. The residue was purified by prep-HPLC to afford the compound 5-(4-(difluoromethoxy)phenyl)-N-(6-((2R,6S)-2,6-dimethylmorpholino)-3-fluoropyridin-2-yl)pyridazin-3-amine (15 mg). LC-MS: 446.20 [M+1]⁺; ¹H NMR (400 MHz, CD₃OD) δ 9.03 (s, 1H), 8.75 (s, 1H), 7.81 (d, J=8.2 Hz, 2H), 7.34 (dd, J=21.2, 9.2 Hz, 3H), 6.94 (t, J=73.6 Hz, 1H), 6.30 (d, J=8.8 Hz, 1H), 3.86 (d, J=12.2 Hz, 2H), 3.64 (s, 2H), 2.38 (t, J=11.4 Hz, 2H), 1.08 (d, J=6.1 Hz, 6H).

Synthesis of N-(5-(4-(difluoromethoxy)phenyl)-2-methoxypyridin-3-yl)-2-((2R,6S)-2,6-dimethylmorpholino)pyrimidin-4-amine—Compound 305

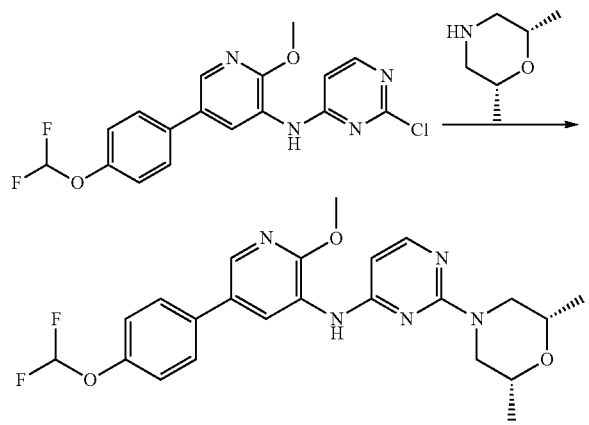

To a solution of 2-chloro-N-(5-(4-(difluoromethoxy)phenyl)-2-methoxypyridin-3-yl)pyrimidin-4-amine (150 mg, 0.40 mmol, 1.0 eq) in IPA (4 mL) was added (2R,6S)-2,6-dimethylmorpholine (137 mg, 1.20 mmol, 3.0 eq), DIEA (154 mg, 1.20 mmol, 3.0 eq). Then the reaction mixture was stirred at 90° C. overnight under N₂. The mixture was concentrated under reduced pressure. The residue was purified by column chromatography on silica gel eluted with (PE/EA=5/1 to 2/1) to give N-(5-(4-(difluoromethoxy)phenyl)-2-methoxypyridin-3-yl)-2-((2R,6S)-2,6-dimethylmorpholino)pyrimidin-4-amine (50 mg, white solid). LC-MS: 458.15 [M+1]⁺; ¹H NMR (400 MHz, CD₃OD) δ 8.95 (d, J=2.2 Hz, 1H), 7.94 (dd, J=16.0, 4.0 Hz, 2H), 7.60 (d, J=8.6 Hz, 2H), 7.22 (d, J=8.6 Hz, 2H), 6.85 (t, J=74.0 Hz, 1H), 6.27 (d, J=5.8 Hz, 1H), 4.36 (d, J=13.0 Hz, 2H), 4.06 (s, 3H), 3.56 (d, J=6.2 Hz, 2H), 2.57-2.46 (m, 2H), 1.07 (d, J=6.2 Hz, 6H).

Synthesis of 5-(4-(difluoromethoxy)phenyl)-3-((2-((2R,6S)-2,6-dimethylmorpholino)pyrimidin-4-yl)amino)pyridin-2(1H)-one—Compound 264

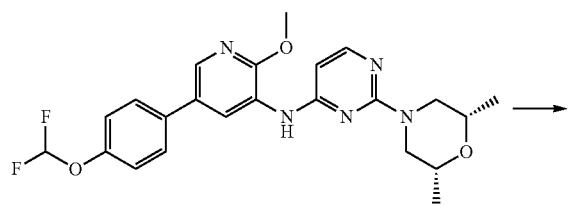

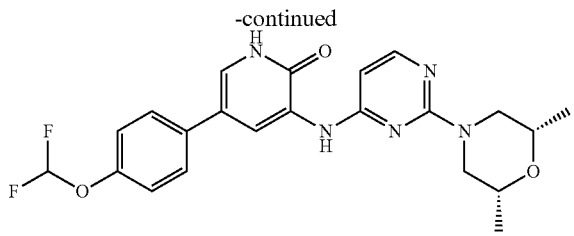

To a solution of N-(5-(4-(difluoromethoxy)phenyl)-2-methoxypyridin-3-yl)-2-((2R,6S)-2,6-dimethylmorpholino)pyrimidin-4-amine (50 mg, 0.109 mmol, 1.0 eq) in DMF (1.5 mL) was added LiBr (95 mg, 1.090 mmol, 10.0 eq), then the reaction mixture was stirred at 120° C. overnight under N₂. H₂O (7 mL) was added, and extracted with EA (10 m L*3), dried with Na₂SO₄. The filtrate was concentrated under reduced pressure. The residue was purified by HPLC to give 5-(4-(difluoromethoxy)phenyl)-3-((2-((2R,6S)-2,6-dimethylmorpholino)pyrimidin-4-yl)amino)pyridin-2(1H)-one (5 mg, white solid). LC-MS: 444.20 [M+1]⁺; ¹H NMR (400 MHz, CD₃OD) δ 8.92 (d, J=2.4 Hz, 1H), 7.95 (d, J=5.8 Hz, 1H), 7.54 (d, J=8.7 Hz, 2H), 7.22 (dd, J=16.5, 5.5 Hz, 3H), 6.84 (t, J=70.2 Hz, 2H), 6.27 (d, J=5.8 Hz, 2H), 4.38 (d, J=11.3 Hz, 2H), 3.58 (d, J=6.3 Hz, 2H), 2.55 (dd, J=13.0, 10.7 Hz, 2H), 1.11 (d, J=6.2 Hz, 6H); ¹⁹F NMR (400 MHz, DMSO-d₆) δ −83.55, δ −83.74.

Synthesis of N-(5-(4-(difluoromethoxy)phenyl)-2-methoxypyridin-3-yl)-2-((2R,6S)-2,6-dimethylmorpholino)-5-fluoropyrimidin-4-amine—Compound 387

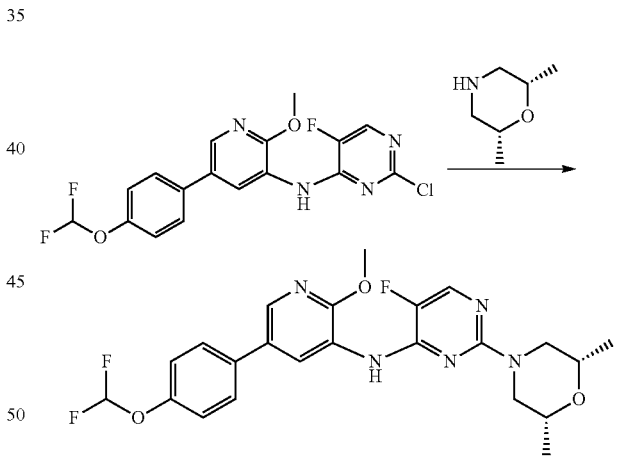

To a solution of 2-chloro-N-(5-(4-(difluoromethoxy)phenyl)-2-methoxypyridin-3-yl)-5-fluoropyrimidin-4-amine (300 mg, 0.76 mmol, 1.0 eq) in IPA (4 mL) was added (2R,6S)-2,6-dimethylmorpholine (261 mg, 2.27 mmol, 3.0 eq) and DIEA (293 mg, 2.27 mmol, 3.0 eq). Then the reaction mixture was stirred at 90° C. overnight under N₂. The mixture was concentrated under reduced pressure. The residue was purified by column chromatography on silica gel eluted with (PE/EA=5/1 to 2/1) to give N-(5-(4-(difluoromethoxy)phenyl)-2-methoxypyridin-3-yl)-2-((2R,6S)-2,6-dimethylmorpholino)-5-fluoropyrimidin-4-amine (200 mg, white solid). LC-MS: 476.35 [M+1]⁺; ¹H NMR (400 MHz, CDCl₃) δ 9.01 (s, 1H), 7.98 (d, J=17.6 Hz, 2H), 7.55 (d, J=8.2 Hz, 2H), 7.40 (s, 1H), 7.20 (d, J=8.3 Hz, 2H), 6.53

(t, J=73.6 Hz, 1H), 4.37 (d, J=13.0 Hz, 2H), 4.11 (s, 3H), 3.64 (s, 2H), 2.60 (t, J=11.7 Hz, 2H), 1.19 (d, J=6.1 Hz, 6H).

Synthesis of 5-(4-(difluoromethoxy)phenyl)-3-((2-((2R,6S)-2,6-dimethylmorpholino)-5-fluoropyrimidin-4-yl)amino)pyridin-2(1H)-one—Compound 346

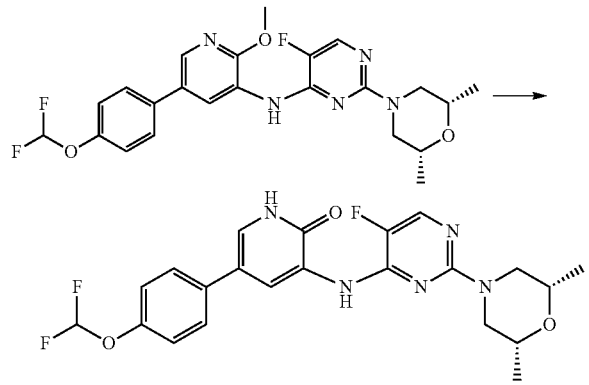

To a solution of N-(5-(4-(difluoromethoxy)phenyl)-2-methoxypyridin-3-yl)-2-((2R,6S)-2,6-dimethylmorpholino)-5-fluoropyrimidin-4-amine (50 mg, 0.105 mmol, 1.0 eq) in DMF (1.5 mL) was added LiBr (92 mg, 1.050 mmol, 10.0 eq), then the reaction mixture was stirred at 120° C. overnight under N$_2$. H$_2$O (7 mL) was added, extracted with EA (10 m L*3), dried with Na$_2$SO$_4$. The residue was concentrated under reduced pressure. The residue was purified by TLC (DCM/MeOH=20/1) to give 5-(4-(difluoromethoxy)phenyl)-3-((2-((2R,6S)-2,6-dimethylmorpholino)-5-fluoropyrimidin-4-yl)amino)pyridin-2(1H)-one (7 mg, white solid). LC-MS: 462.10 [M+1]$^+$; $^1$H NMR (400 MHz, DMSO-d$_6$) δ 12.38 (s, 1H), 8.73 (s, 1H), 8.19-8.10 (m, 2H), 7.62 (d, J=8.6 Hz, 2H), 7.44 (s, 1H), 7.19 (dd, J=41.4, 32.7 Hz, 3H), 4.39-4.22 (m, 2H), 3.64-3.51 (m, 2H), 2.60-2.52 (m, 2H), 1.14-1.03 (m, 6H); $^{19}$F NMR (400 MHz, DMSO-d$_6$) δ −82.26, δ −82.46, δ −169.61.

Synthesis of 5-(4-(difluoromethoxy)phenyl)-N-(2-((2R,6S)-2,6-dimethylmorpholino)-6-fluoropyrimidin-4-yl)pyridazin-3-amine—Compound 131

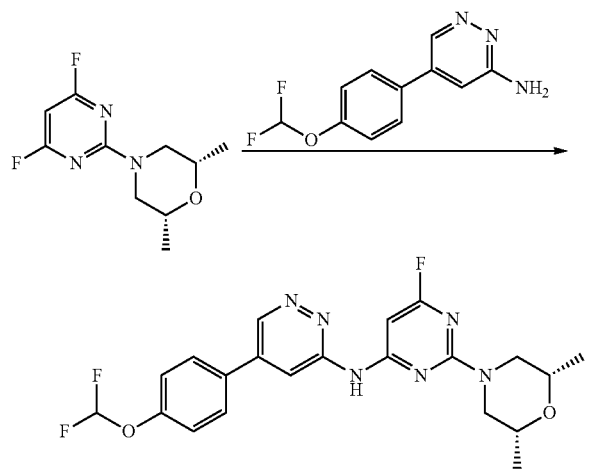

To a solution of 5-(4-(difluoromethoxy)phenyl)pyridazin-3-amine (52 mg, 0.22 mmol, 1.0 eq) in DMF (1 mL) was added NaH (13 mg, 0.33 mmol, 1.5 eq) at 0° C. The mixture was stirred for 0.5 h at 0° C., then (2R,6S)-4-(4,6-difluoropyrimidin-2-yl)-2,6-dimethylmorpholine (50 mg, 0.26 mmol, 1.2 eq) in DMF (0.5 mL) was added. The reaction mixture was stirred at room temperature for 2 h. 30 mL H$_2$O was poured into the mixture and extracted with EtOAc (20 mL×3). The organic phase was combined, washed with brine, dried over anhydrous Na$_2$SO$_4$, filtered and concentrated under reduced pressure to give a residue. The residue was purified by prep-TLC (PE/EA=1/1) to afford 5-(4-(difluoromethoxy)phenyl)-N-(2-((2R,6S)-2,6-dimethylmorpholino)-6-fluoropyrimidin-4-yl)pyridazin-3-amine (20 mg, yield: 20%) as a white solid. LCMS: [M+1]: 447.30; $^1$H NMR (400 MHz, DMSO-d$_6$) δ 10.69 (s, 1H), 9.25 (s, 1H), 8.49 (s, 1H), 7.92 (d, J=8.6 Hz, 2H), 7.54-7.15 (m, 3H), 6.30 (s, 1H), 4.29 (d, J=12.4 Hz, 2H), 3.53 (s, 2H), 2.55 (s, 2H), 1.05 (s, 6H).

Synthesis of 6-chloro-4-(4-(difluoromethoxy)phenyl)-3-methoxy-pyridazine

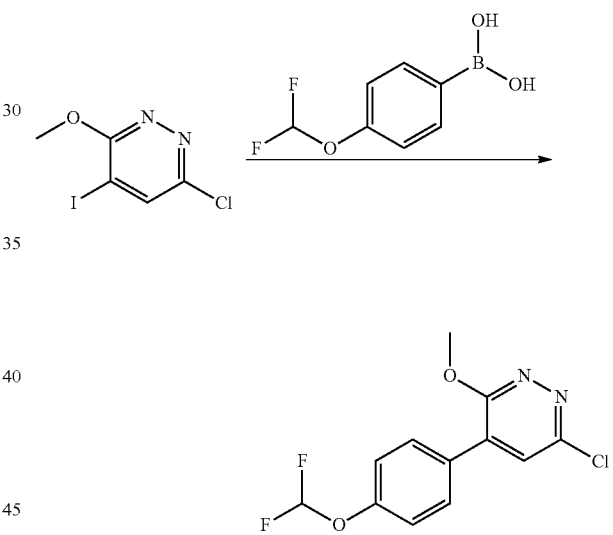

To a solution of 6-chloro-4-iodo-3-methoxypyridazine (200 mg, 0.74 mmol, 1.0 eq), (4-(difluoromethoxy)phenyl)boronic acid (139 mg, 0.74 mmol, 1.0 eq) and K$_3$PO$_4$ (471 mg, 2.22 mmol, 3.0 eq) in Dioxane/H$_2$O (6 mL/0.6 mL) was added Pd(dppf)Cl$_2$ (16 mg, 0.07 mmol, 0.1 eq) at room temperature under N$_2$. Then the reaction mixture was stirred at 80° C. for 16 h. The reaction was concentrated under reduced pressure. The residue was partitioned between ethyl acetate (90 mL) and water (150 mL). The separated organic layer was washed with water, dried over anhydrous Na2SO4 and evaporated to dryness. The residue was purified by Prep-TLC with PE/EA=5/1 to give 6-chloro-4-(4-(difluoromethoxy)phenyl)-3-methoxy-pyridazine (120 mg, 57%) as a yellow solid. LCMS: 287.03 [M+1]$^+$; $^1$H NMR (400 MHz, DMSO) δ 7.88 (s, 1H), 7.78 (d, J=8.3 Hz, 2H), 7.54-7.09 (m, 3H), 4.04 (s, 3H).

Synthesis of 5-(4-(difluoromethoxy)phenyl)-N-(2-((2R,6S)-2,6-dimethylmorpholino)-5-fluoropyrimidin-4-yl)-6-methoxypyridazin-3-amine—Compound 526

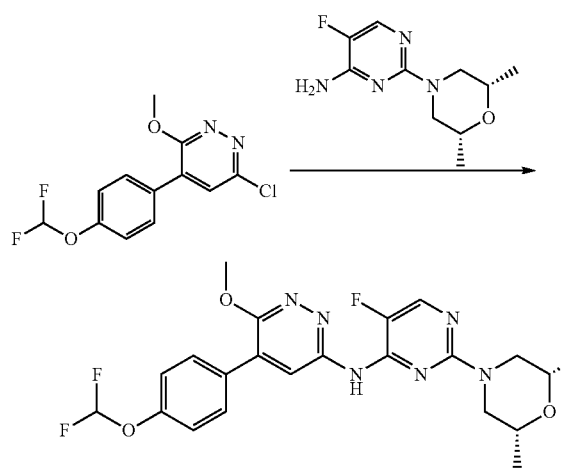

To a solution of 6-chloro-4-(4-(difluoromethoxy)phenyl)-3-methoxypyridazine (120 mg, 0.42 mmol, 1.0 eq), 2-((2R,6S)-2,6-dimethylmorpholino)-5-fluoropyrimidin-4-amine (142 mg, 0.63 mmol, 1.5 eq), Xantphos (25 mg, 0.04 mmol, 0.1 eq) and Cs$_2$CO$_3$ (409 mg, 1.26 mmol, 3.0 eq) in Dioxane (2 mL) was added Pd$_2$(dba)$_3$ (39 mg, 0.04 mmol, 0.1 eq) at RT under N$_2$. Then the reaction mixture was stirred at 80° C. for 16 h. The reaction was concentrated under reduced pressure. The residue was partitioned between ethylacetate (50 mL) and water (100 mL). The separated organic layer was washed with water, dried over anhydrous Na$_2$SO$_4$ and evaporated to dryness. The residue was purified by Prep-TLC with PE/EA=2/1 to give 5-(4-(difluoromethoxy)phenyl)-N-(2-((2R,6S)-2,6-dimethyl morpholino)-5-fluoropyrimidin-4-yl)-6-methoxypyridazin-3-amine (63 mg, 32%) as yellow solid. LC-MS: 477.35 [M+1]$^+$; $^1$H NMR (400 MHz, DMSO) δ 10.25 (s, 1H), 8.31 (s, 1H), 8.09 (s, 1H), 7.75 (d, J=8.6 Hz, 2H), 7.50-7.11 (m, 3H), 4.09 (s, 2H), 4.02 (s, 3H), 3.41 (s, 2H), 2.34 (t, J=11.5 Hz, 2H), 0.88 (s, 6H).

Synthesis of 5-(4-(difluoromethoxy)phenyl)-N3-(2-((2R,6S)-2,6-dimethylmorpholino)-5-fluoropyrimidin-4-yl)pyridazine-3,6-diamine—Compound 598

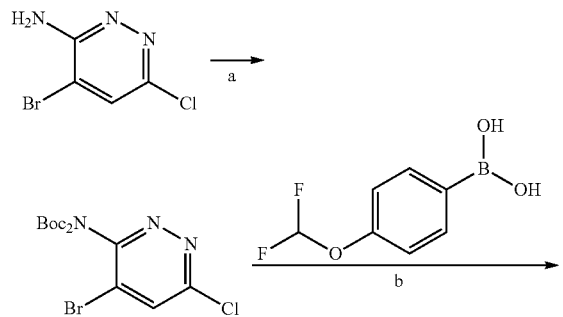

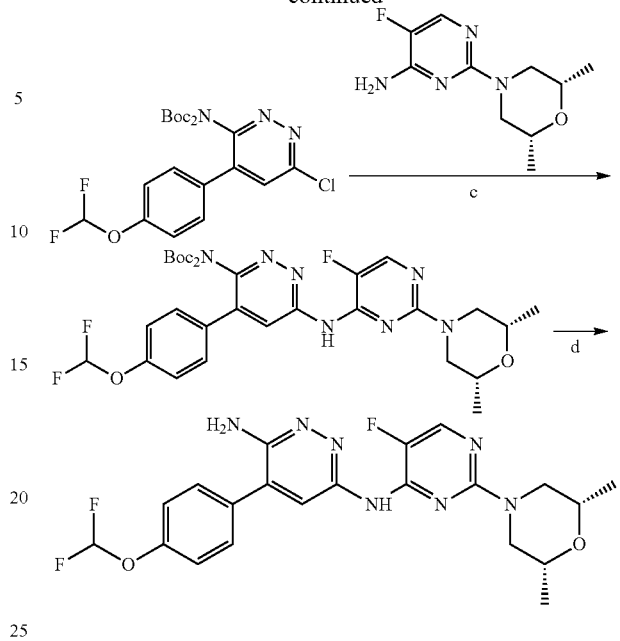

Step a: To a solution of 4-bromo-6-chloropyridazin-3-amine (1.2 g, 5.77 mmol, 1.0 eq) in THF (10 mL) was added Boc$_2$O (2.5 g, 11.54 mmol, 2.0 eq), TEA (1.75 g, 17.31 mmol, 3.0 eq). The reaction mixture was stirred at 60° C. for 3 hrs. 100 mL H$_2$O was poured into the mixture and extracted with EtOAc (30 mL×3), dried over anhydrous Na$_2$SO$_4$, filtered and concentrated under reduced pressure. The residue was purified by column chromatography on silica gel eluted with (PE/EA=10/1 to 5/1) to afford the bis-N-Boc product (1.2 g, white solid). LC-MS: 408.02[M+1]$^+$; $^1$H NMR (400 MHz, CDCl$_3$) δ 7.86 (s, 1H), 1.41 (s, 18H).

Step b: To a solution of bis-N-Boc compound (408 mg, 1.0 mmol, 1.0 eq) in toluene/H$_2$O (5 mL/1 mL) was added (4-(difluoromethoxy)phenyl)boronic acid (188 mg, 1.0 mmol, 1.0 eq), K$_3$PO$_4$ (636 mg, 3.0 mmol, 3.0 eq) and Pd(dppf)Cl$_2$ (73 mg, 0.1 mmol, 0.1 eq), The reaction mixture was stirred at 110° C. for 16 hrs under N$_2$. Then it was concentrated under reduced pressure. The residue was purified by prep-TLC (PE/EA=3/1) to afford the bis-N-Boc protected 6-chloro-4-(4-(difluoromethoxy)phenyl)pyridazin-3-amine (255 mg, crude). LCMS: [M+1]: 472.15

Step c: To a solution of bis-N-Boc protected 6-chloro-4-(4-(difluoromethoxy)phenyl)pyridazin-3-amine (150 mg, 0.32 mmol, 1.0 eq) in toluene (5 mL) was added 2-((2R,6S)-2,6-dimethylmorpholino)-5-fluoropyrimidin-4-amine (72 mg, 0.32 mmol, 1.0 eq), Cs$_2$CO$_3$ (208 mg, 0.64 mmol, 2.0 eq), Xantphos (19 mg, 0.032 mmol, 0.1 eq) and Pd(dppf)Cl$_2$ (24 mg, 0.032 mmol, 0.1 eq), The reaction mixture was stirred at 100° C. for 16 hrs under N$_2$. Then it was concentrated under reduced pressure. The residue was purified by prep-TLC (PE/EA=3/1) to afford the coupling product (90 mg). LCMS: [M+1]: 662.2; $^1$H NMR (400 MHz, CDCl$_3$) δ 8.77 (s, 1H), 8.17 (s, 1H), 8.06 (s, 1H), 7.50 (d, J=7.4 Hz, 2H), 7.26-7.23 (m, 2H), 6.55 (t, J=72.0 Hz, 1H), 4.26 (d, J=12.0 Hz, 2H), 3.59 (s, 2H), 2.56 (t, J=12.2 Hz, 2H), 1.32 (s, 18H), 1.12 (d, J=6.0 Hz, 6H).

Step d: Boc-protected compound (90 mg, 0.136 mmol, 1.0 eq) was added into HCl/EA (4M, 5 mL). The reaction mixture was stirred at 40° C. for 1 hrs. Then it was concentrated under reduced pressure. 50 mL NaHCO$_3$(aq)

was poured into the residue and extracted with EtOAc (30 mL×3), dried over anhydrous Na$_2$SO$_4$, filtered and concentrated under reduced pressure. The residue was purified by prep-TLC (PE/EA=1/1) to afford final product 5-(4-(difluoromethoxy)phenyl)-N$^3$-(2-((2R,6S)-2,6-dimethylmorpholino)-5-fluoropyrimidin-4-yl)pyridazine-3,6-diamine (19 mg). LCMS: [M+1]: 462.15; $^1$H NMR (400 MHz, CD$_3$OD) δ 8.46 (s, 1H), 8.18 (d, J=4.0 Hz, 1H), 7.68 (d, J=8.1 Hz, 2H), 7.40 (d, J=8.1 Hz, 2H), 6.99 (t, J=73.2 Hz, 1H), 4.06 (d, J=13.0 Hz, 2H), 3.58 (s, 2H), 2.64 (t, J=11.8 Hz, 2H), 1.05 (d, J=5.2 Hz, 6H).

Synthesis of 4-(4-(difluoromethoxy)phenyl)-N6-(2-((2R,6S)-2,6-dimethylmorpholino)-5-fluoropyrimidin-4-yl)-N3-methylpyridazine-3,6-diamine—Compound 544

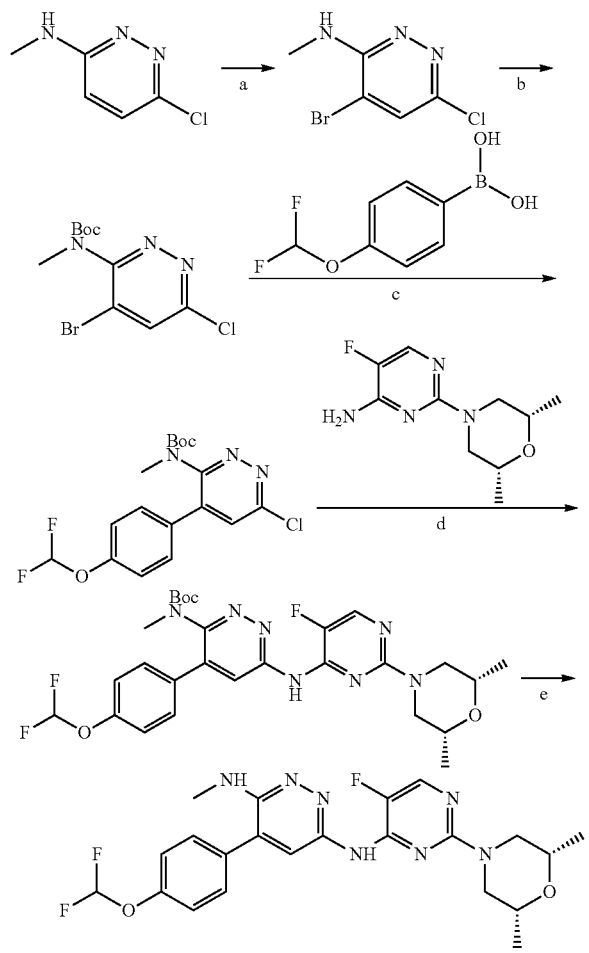

Step a: To a solution of 6-chloro-N-methylpyridazin-3-amine (1.0 g, 7.0 mmol, 1.0 eq) in AcOH/H$_2$O (5 mL/5 mL) was added Br$_2$ (3.36 g, 21 mmol, 3.0 eq), KBr (2.5 g, 21 21 mmol, 3.0 eq) and KOAc (1.03 g, 10.5 mmol, 1.5 eq). The reaction mixture was stirred at 80° C. for 16 hrs. 100 mL H$_2$O was poured into the mixture and extracted with EtOAc (35 mL×3), dried over anhydrous Na$_2$SO$_4$, filtered and concentrated under reduced pressure. The residue was purified by column chromatography on silica gel eluted with (PE/EA=5/1 to 2/1) to afford 4-bromo-6-chloro-N-methylpyridazin-3-amine (400 mg, crude). LC-MS: 221.94[M+1]$^+$; $^1$H NMR (400 MHz, DMSO-d6) δ 7.99 (s, 1H), 6.98 (s, 1H), 2.90 (d, J=3.9 Hz, 3H).

Step b: To a solution of 4-bromo-6-chloro-N-methylpyridazin-3-amine (400 mg, 1.79 mmol, 1.0 eq) in THF (7 mL) was added Boc$_2$O (782 mg, 3.59 mmol, 2.0 eq), TEA (542 mg, 5.37 mmol, 3.0 eq) and DMAP (22 mg, 0.179 mg, 0.1 eq). The reaction mixture was stirred at 60° C. for 3 hrs. 100 mL H$_2$O was poured into the mixture and extracted with EtOAc (30 mL×3), dried over anhydrous Na$_2$SO$_4$, filtered and concentrated under reduced pressure. The residue was purified by column chromatography on silica gel eluted with (PE/EA=10/1) to afford tert-butyl (4-bromo-6-chloropyridazin-3-yl)(methyl)carbamate (640 mg, colorless oil). LC-MS: 321.99[M+1]$^+$ Step c: To a solution of tert-butyl (4-bromo-6-chloropyridazin-3-yl)(methyl)carbamate (320 mg, 1.0 mmol, 1.0 eq) in toluene/H$_2$O (5 mL/1 mL) was added (4-(difluoromethoxy)phenyl)boronic acid (188 mg, 1.0 mmol, 1.0 eq), K$_3$PO$_4$ (636 mg, 3.0 mmol, 3.0 eq) and Pd(dppf)Cl$_2$ (73 mg, 0.1 mmol, 0.1 eq), The reaction mixture was stirred at 110° C. for 16 hrs under N$_2$. Then it was concentrated under reduced pressure. The residue was purified by prep-TLC (PE/EA=3/1) to afford tert-butyl (6-chloro-4-(4-(difluoromethoxy)phenyl)pyridazin-3-yl)(methyl)carbamate (70 mg). LCMS: [M+1]: 386.1; $^1$H NMR (400 MHz, CDCl$_3$) δ 7.52-7.40 (m, 3H), 7.27 (d, J=7.1 Hz, 2H), 6.56 (t, J=73.0 Hz, 1H), 3.48 (s, 3H), 1.08 (s, 3H).

Step d: To a solution of tert-butyl (6-chloro-4-(4-(difluoromethoxy)phenyl)pyridazin-3-yl)(methyl)carbamate (70 mg, 0.18 mmol, 1.0 eq) in toluene (5 mL) was added 2-((2R,6S)-2,6-dimethylmorpholino)-5-fluoropyrimidin-4-amine (41 mg, 0.18 mmol, 1.0 eq), Cs$_2$CO$_3$ (117 mg, 0.36 mmol, 2.0 eq), Xantphos (11 mg, 0.018 mmol, 0.1 eq) and Pd(dppf)Cl$_2$ (14 mg, 0.018 mmol, 0.1 eq). The reaction mixture was stirred at 100° C. for 16 hrs under N$_2$. Then it was concentrated under reduced pressure. The residue was purified by prep-TLC (PE/EA=2/1) to afford the tert-butyl (4-(4-(difluoromethoxy)phenyl)-6-((2-((2R,6S)-2,6-dimethylmorpholino)-5-fluoropyrimidin-4-yl)amino)pyridazin-3-yl)(methyl)carbamate (50 mg, yellow oil. LCMS: [M+1]: 576.2; $^1$H NMR (400 MHz, CDCl$_3$) δ 8.71 (s, OH), 8.06 (d, J=14.0 Hz, 1H), 7.47 (s, 2H), 6.53 (t, J=73.0 Hz, 1H), 4.27 (s, 2H), 3.59 (s, 2H), 3.43 (s, 3H), 2.56 (t, J=11.7 Hz, 2H), 1.10 (d, J=37.3 Hz, 5H).

Step e: tert-butyl (4-(4-(difluoromethoxy)phenyl)-6-((2-((2R,6S)-2,6-dimethylmorpholino)-5-fluoropyrimidin-4-yl)amino)pyridazin-3-yl)(methyl)carbamate (50 mg, 0.087 mmol, 1.0 eq) was added into HCl/EA (4M, 5 mL). The reaction mixture was stirred at 40° C. for 1 hrs. Then it was concentrated under reduced pressure. 50 mL NaHCO$_3$ (aq) was poured into the residue and extracted with EtOAc (30 mL×3), dried over anhydrous Na$_2$SO$_4$, filtered and concentrated under reduced pressure. The residue was purified by prep-TLC (PE/EA=1/1) to afford 4-(4-(difluoromethoxy)phenyl)-N-(2-((2R,6S)-2,6-dimethylmorpholino)-5-fluoropyrimidin-4-yl)-N$^3$-methylpyridazine-3,6-diamine (18.5 mg). LCMS: [M+1]: 476.20; $^1$H NMR (400 MHz, CD$_3$OD) δ 8.33 (s, 1H), 8.02 (s, 1H), 7.61 (d, J=8.3 Hz, 2H), 7.36 (d, J=8.6 Hz, 2H), 6.96 (t, J=73.3 Hz, 1H), 4.20 (d, J=13.0 Hz, 2H), 3.52 (s, 2H), 3.02 (s, 3H), 2.42 (t, J=11.5 Hz, 2H), 1.03 (d, J=6.1 Hz, 6H).

Synthesis of methyl 4-(4-(difluoromethoxy)phenyl)-6-((2-((2R,6S)-2,6-dimethylmorpholino)-5-fluoropyrimidin-4-yl)amino)pyridazine-3-carboxylate—Compound 616

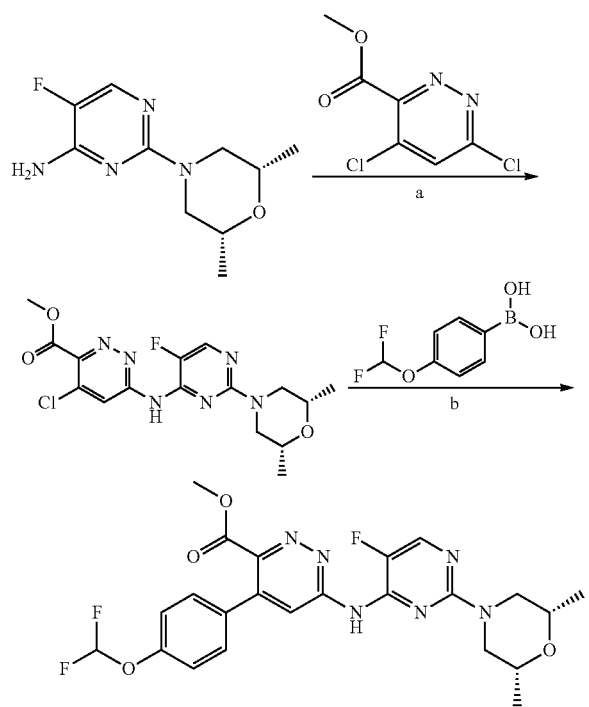

Step a: To a solution of 2-((2R,6S)-2,6-dimethylmorpholino)-5-fluoropyrimidin-4-amine (2 g, 8.85 mmol, 1.0 eq), methyl 4,6-dichloropyridazine-3-carboxylate (2.7 g, 13.27 mmol, 1.5 eq), Xantphos (512 g, 0.88 mmol, 0.1 eq) and $Cs_2CO_3$ (8.6 g, 26.55 mmol, 3.0 eq) in Toluene (20 mL) was added $Pd_2(dba)_3$ (810 mg, 0.88 mmol, 0.1 eq) at RT. Then the reaction mixture was stirred at 80° C. for 16 h under $N_2$. The reaction was concentrated under reduced pressure. The residue was partitioned between ethylacetate (100 mL) and water. The separated organic layer was washed with water, dried over $Na_2SO_4$ and evaporated to dryness. The residue was purified by silica gel chromatography eluted with PE:EA=2:1 to give methyl 4-chloro-6-((2-((2R,6S)-2,6-dimethylmorpholino)-5-fluoropyrimidin-4-yl)amino)pyridazine-3-carboxylate (2.05 g, 58%) as a white solid. $^1$H NMR (400 MHz, DMSO) δ 11.15 (s, 1H), 8.63 (s, 1H), 8.23 (d, J=2.8 Hz, 1H), 4.21 (d, J=12.1 Hz, 2H), 3.93 (s, 3H), 3.53 (d, J=6.3 Hz, 2H), 2.52 (m, 2H), 1.11 (d, J=6.1 Hz, 6H).

Step b: To a solution of methyl 4-chloro-6-((2-((2R,6S)-2,6-dimethylmorpholino)-5-fluoropyrimidin-4-yl)amino)pyridazine-3-carboxylate (2 g, 5.05 mmol, 1.0 eq), (4-(difluoromethoxy)phenyl)boronic acid (1.3 g, 7.58 mmol, 1.5 eq) and $K_3PO_4$ (3.2 g, 15.15 mmol, 3.0 eq) in Dioxane/$H_2O$ (40 mL/4 mL) was added $Pd(dppf)Cl_2$ (370 mg, 0.51 mmol, 0.1 eq) at RT. Then the reaction mixture was stirred at 110° C. for 16 h under $N_2$. The reaction was concentrated under reduced pressure. The residue was partitioned between ethylacetate (100 mL) and water. The separated organic layer was washed with water, dried over $Na_2SO_4$ and evaporated to dryness. The residue was purified by silica gel chromatography eluted with DCM/MeOH=200:1 to give methyl 4-(4-(difluoromethoxy)phenyl)-6-((2-((2R,6S)-2,6-dimethylmorpholino)-5-fluoropyrimidin-4-yl)amino)pyridazine-3-carboxylate (1.4 g, 55%) as a yellow solid. LCMS: 505.35 [M+1]$^+$; $^1$H NMR (400 MHz, DMSO) δ 10.93 (s, 1H), 8.55 (s, 1H), 8.21 (d, J=3.1 Hz, 1H), 7.54-7.15 (m, 5H), 4.11 (s, 2H), 3.76 (s, 3H), 3.44 (s, 2H), 2.43-2.34 (t, 2H), 0.93 (s, 6H).

Synthesis of 4-(4-(difluoromethoxy)phenyl)-6-((2-((2R,6S)-2,6-dimethylmorpholino)-5-fluoropyrimidin-4-yl)amino)pyridazine-3-carboxylic acid—Compound 562

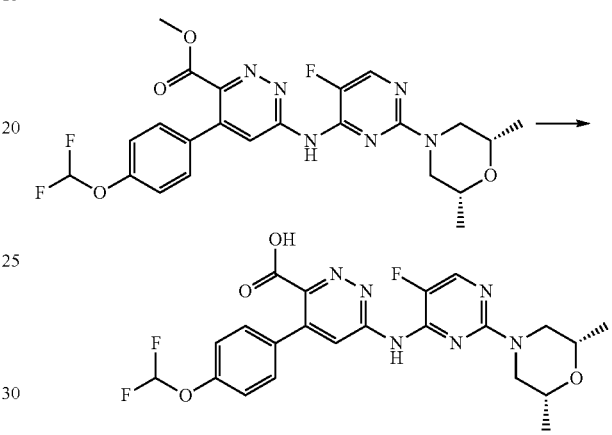

To a solution of methyl 4-(4-(difluoromethoxy)phenyl)-6-((2-((2R,6S)-2,6-dimethylmorpholino)-5-fluoropyrimidin-4-yl)amino)pyridazine-3-carboxylate (1.3 g, 2.58 mmol, 1.0 eq) in THF/$H_2O$ (5 mL/5 mL) was added LiOH·$H_2O$ (433 mg, 10.32 mmol, 4.0 eq). The reaction mixture was stirred at 25° C. for 16 h. The reaction mixture was partitioned between ethylacetate (100 mL) and 1N aq. HCl (100 mL). The separated organic layer was washed with water, dried over Na2SO4 and evaporated to dryness. The residue was added MeOH (10 mL) stirred at RT for 1 h. Then the mixture was filtered, the cake was diluted with MeOH (10 mL×2), dried under reduced pressure to afford 4-(4-(difluoromethoxy)phenyl)-6-((2-((2R,6S)-2,6-dimethylmorpholino)-5-fluoropyrimidin-4-yl)amino)pyridazine-3-carboxylic acid (700 mg, 55%) as a white solid. LCMS: 491.30 [M+1]$^+$; $^1$H NMR (400 MHz, DMSO) δ 13.74 (s, 1H), 10.82 (s, 1H), 8.51 (s, 1H), 8.20 (d, J=3.1 Hz, 1H), 7.56-7.14 (m, J=8.6 Hz, 5H), 4.12 (s, 2H), 3.44 (s, 2H), 2.42-2.35 (t, 2H), 0.93 (s, 6H).

Synthesis of 1-(4-(4-(difluoromethoxy)phenyl)-6-((2-((2R,6S)-2,6-dimethylmorpholino)-5-fluoropyrimidin-4-yl)amino)pyridazin-3-yl)ethan-1-one—Compound 580

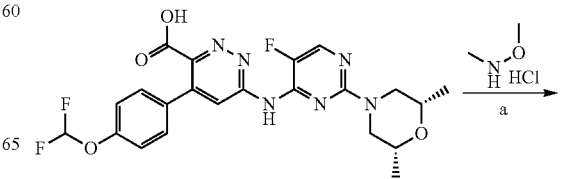

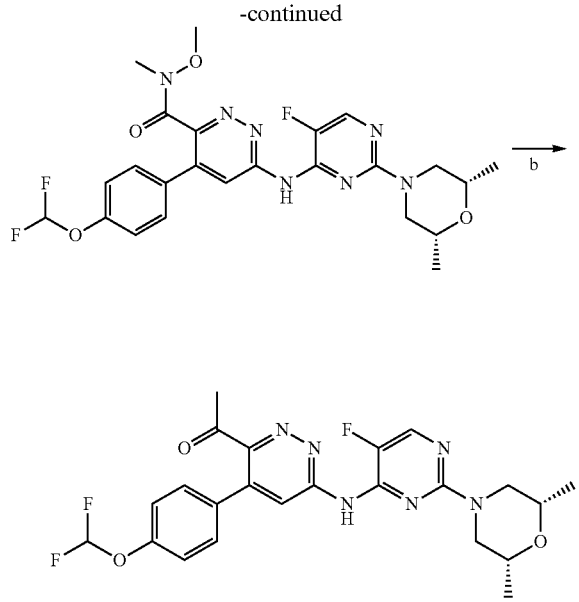

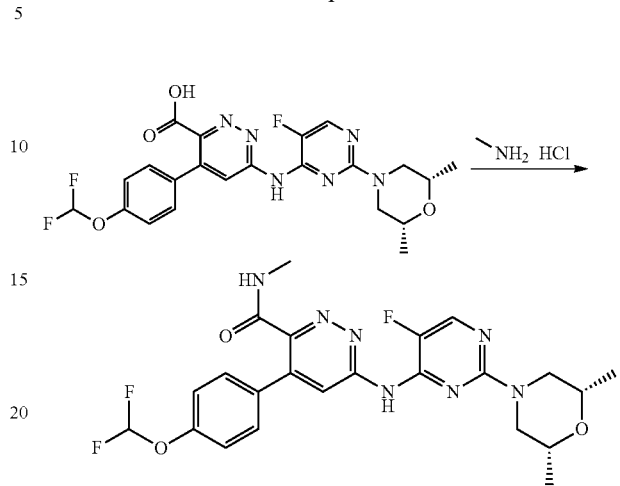

Synthesis of 4-(4-(difluoromethoxy)phenyl)-6-((2-((2R,6S)-2,6-dimethylmorpholino)-5-fluoropyrimidin-4-yl)amino)-N-methylpyridazine-3-carboxamide—Compound 634

Step a: To a solution of 4-(4-(difluoromethoxy)phenyl)-6-((2-((2R,6S)-2,6-dimethylmorpholino)-5-fluoropyrimidin-4-yl)amino)pyridazine-3-carboxylic acid (100 mg, 0.2 mmol, 1.0 eq) and HATU (93 mg, 0.24 mmol, 1.2 eq) in DMF (2 mL) was added N,O-dimethylhydroxylamine hydrochloride (24 mg, 0.24 mmol, 1.2 eq) and DIEA (79 mg, 0.60 mmol, 3.0 eq). Then the mixture stirred at RT for 16 h. The reaction mixture was partitioned between ethylacetate (50 mL) and water. The separated organic layer was washed with water, dried over Na₂SO₄ and evaporated to dryness. The residue was purified by Prep-TLC with DCM/MeOH=20/1 to give 4-(4-(difluoromethoxy)phenyl)-6-((2-((2R,6S)-2,6-dimethylmorpholino)-5-fluoropyrimidin-4-yl)amino)-N-methoxy-N-methylpyridazine-3-carboxamide (80 mg, 74%) as a white solid. ¹H NMR (400 MHz, DMSO) δ 10.70 (s, 1H), 8.56 (s, 1H), 8.19 (d, J=3.1 Hz, 1H), 7.55 (d, J=8.6 Hz, 2H), 7.32 (d, J=8.8 Hz, 3H), 4.14 (d, J=11.5 Hz, 2H), 3.53 (s, 3H), 3.48-3.41 (m, 2H), 3.20 (s, 3H), 2.41 (t, J=12.7 Hz, 2H), 0.92 (s, 6H).

Step b: To a solution of 4-(4-(difluoromethoxy)phenyl)-6-((2-((2R,6S)-2,6-dimethylmorpholino)-5-fluoropyrimidin-4-yl)amino)-N-methoxy-N-methylpyridazine-3-carboxamide (80 mg, 0.15 mmol, 1.0 eq) in THF (1 mL) was added MeMgBr (0.18 mL, 0.18 mmol, 1.2 eq) at 0° C. under N₂. The reaction mixture was stirred at RT for 2 h. An aqueous solution of NH4Cl (50 mL) was added the reaction mixture. The aqueous layer was extracted with ethylacetate (50 mL) twice. The combined organic layers were dried over Na2SO4 and evaporated to dryness. The residue was purified by Prep-TLC with DCM/MeOH=20/1 to give 1-(4-(4-(difluoromethoxy)phenyl)-6-((2-((2R,6S)-2,6-dimethylmorpholino)-5-fluoropyrimidin-4-yl)amino)pyridazin-3-yl)ethan-1-one (40 mg, 55%) as a white solid. LCMS: 489.20 [M+1]⁺; ¹H NMR (400 MHz, DMSO) δ 10.92 (s, 1H), 8.42 (s, 1H), 8.22 (d, J=3.2 Hz, 1H), 7.49 (d, J=8.8 Hz, 2H), 7.22 (m, J=41.2, 32.6 Hz, 3H), 4.10 (s, 2H), 3.43 (s, 2H), 2.73 (s, 3H), 2.41-2.33 (t, 2H), 0.93 (s, 6H).

To a solution of 4-(4-(difluoromethoxy)phenyl)-6-((2-((2R,6S)-2,6-dimethylmorpholino)-5-fluoropyrimidin-4-yl)amino)pyridazine-3-carboxylic acid (100 mg, 0.2 mmol, 1.0 eq) and HATU (93 mg, 0.24 mmol, 1.2 eq) in DMF (2 mL) was added methylamine hydrochloride (17 mg, 0.24 mmol, 1.2 eq) and DIEA (79 mg, 0.60 mmol, 3.0 eq). Then the mixture stirred at RT for 16 h. The reaction mixture was partitioned between ethylacetate (30 mL) and water. The separated organic layer was washed with water, dried over Na₂SO₄ and evaporated to dryness. The residue was purified by Prep-TLC with DCM/MeOH=20/1 to give 4-(4-(difluoromethoxy)phenyl)-6-((2-((2R,6S)-2,6-dimethylmorpholino)-5-fluoropyrimidin-4-yl)amino)-N-methylpyridazine-3-carboxamide (70 mg, 68%) as a white solid. LC-MS: 504.40[M+1]⁺; ¹H NMR (400 MHz, DMSO) δ 10.73 (s, 1H), 8.79 (d, J=4.5 Hz, 1H), 8.45 (s, 1H), 8.19 (d, J=3.2 Hz, 1H), 7.52 (t, J=6.6 Hz, 2H), 7.24 (m, J=41.1, 32.6 Hz, 3H), 4.11 (s, 2H), 3.43 (s, 2H), 2.72 (d, J=4.6 Hz, 3H), 2.42-2.35 (t, 2H), 0.92 (s, 6H).

Synthesis of N-(5-bromo-2-fluoropyridin-3-yl)-2-chloropyrimidin-4-amine

The mixture of 5-bromo-2-fluoropyridin-3-amine (500 mg, 2.6 mmol, 1.0 eq), 2,4-dichloropyrimidine (770 mg, 5.2 mmol, 2.0 eq) in DIEA (0.5 mL) was stirred 119° C. for 16 h. DCM (5 mL) was added and the residue was purified by column chromatography on silica gel eluted with (DCM/MeOH=200/1 to 50/1) to give the crude. The crude was purified by prep-TLC (DCM/MeOH=20/1) to afford N-(5-bromo-2-fluoropyridin-3-yl)-2-chloropyrimidin-4-amine (50 mg crude) as a white solid. LC-MS: [M+1]$^+$: 303.05.

Synthesis of N-(5-bromo-2-fluoropyridin-3-yl)-2-((2R,6S)-2,6-dimethylmorpholino)pyrimidin-4-amine

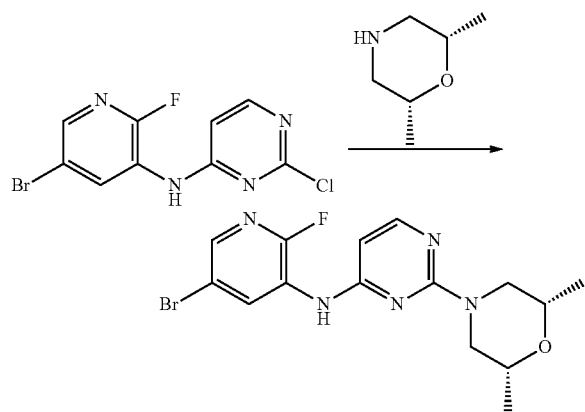

The mixture of N-(5-bromo-2-fluoropyridin-3-yl)-2-chloropyrimidin-4-amine (50 mg, 0.17 mmol, 1.0 eq), (2R,6S)-2,6-dimethylmorpholine (38 mg, 0.33 mmol 2.0 eq) and DIEA (64 mg, 0.50 mmol, 3.0 eq) in IPA (1 mL) was stirred at 80° C. for 16 h. The mixture was concentrated under reduced pressure. The residue was purified by prep-TLC (DCM/MeOH=20/1) to afford N-(5-bromo-2-fluoropyridin-3-yl)-2-((2R,6S)-2,6-dimethylmorpholino)pyrimidin-4-amine (27 mg, crude). LC-MS: [M+1]$^+$: 382.15.

Synthesis of N-(5-(4-(difluoromethoxy)phenyl)-2-fluoropyridin-3-yl)-2-((2R,6S)-2,6-dimethylmorpholino)pyrimidin-4-amine—Compound 182

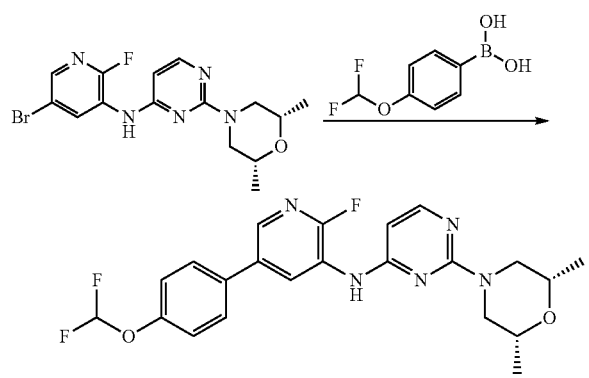

To a solution of N-(5-bromo-2-fluoropyridin-3-yl)-2-((2R,6S)-2,6-dimethylmorpholino)pyrimidin-4-amine (27 mg, 0.07 mmol, 1.0 eq), (4-(difluoromethoxy)phenyl)boronic acid (26 mg, 0.14 mmol 2.0 eq), K$_3$PO$_4$ (45 mg, 0.21 mmol, 3.0 eq) in dioxane/H$_2$O (1 mL/0.1 mL) was added Pd(dppf)Cl$_2$ (5 mg, 0.007 mmol, 0.1 eq) under N$_2$. The reaction mixture was stirred at 110° C. for 16 hrs under N$_2$. Then it was concentrated under reduced pressure. The residue was purified by prep-TLC (DCM/MeOH=20/1) to afford N-(5-(4-(difluoromethoxy)phenyl)-2-fluoropyridin-3-yl)-2-((2R,6S)-2,6-dimethylmorpholino)pyrimidin-4-amine (2.5 mg). LCMS: [M+1]$^+$: 446.30; $^1$H NMR (400 MHz, DMSO-d$_6$): δ=9.40 (s, 1H), 9.06 (d, J=9.3, 1H), 8.09 (s, 1H), 8.04 (d, J=5.6, 1H), 7.75 (d, J=8.6, 2H), 7.50-7.10 (m, 3H), 6.37 (d, J=5.5, 1H), 4.31 (s, 2H), 3.49 (s, 2H), 2.44 (d, J=11.1, 2H), 0.98 (s, 6H).

Methods of making and using related compounds are disclosed in PCT/TR2019/050164, PCT/TR2019/050951, and U.S. 63/173,796; the contents of each of these applications is fully incorporated by reference herein.

Example 2: Exemplary Biological Activity of Compounds of the Disclosure

Cell Culture and Reagents

Human breast carcinoma cell line, MDA-MB-231 and human endometrial cancer cell line, HEC-59 were purchased from ATCC (American Type Culture Collection; USA). MDA-MB-231 cells were cultured in Dulbecco's modified Eagle's medium (Lonza, NJ, USA), and HEC-59 were grown in Iscove's Modified Dulbecco's Medium (Lonza, NJ, USA), supplemented with 10% fetal bovine serum (FBS, Lonza), 1% non-essential amino acid (NEAA), 2 mM L-glutamine (Sigma Aldrich, MO, USA) and 50 U/ml penicillin/streptomycin (P/S). All cell lines were tested regularly using MycoAlert Mycoplasma Detection Kit (Lonza). The cumulative length of the cells between thawing and use in the experiments was less than 20 passages.

Cell Viability Assay Protocol 4000 cells/well of MDA-MB-231 and HEC-59 cells were seeded in a 96 well plate in 80 μL media/well. Approximately 18 hours later, 3× drug solutions were prepared by serial dilution (100, 10, 5, 1, 0.5, 0.3, 0.1, 0.05, 0.01 μM), and the drug containing media was added to each well with a volume of 40 μL. For MDA-MB-231, 3 days after drug treatment, the SRB or CTG assay was performed. HEC59, the drug containing media was renewed at day 4. After 7 days total, the SRB or CTG assay was performed.

TABLE 3

| Cell viability data in MDA-MB-231 and HEC-59 | | |
| --- | --- | --- |
| Compound | MDA-MB-231 IC$_{50}$ | HEC-59 IC$_{50}$ |
| 80 | 0.398 | 0.236 |
| 90 | 0.533 | 1.101 |
| 91 | 0.328 | 0.200 |
| 103 | >10 | >10 |
| 104 | 0.345 | 0.086 |
| 131 | 0.181 | 0.142 |
| 182 | 1.089 | 0.290 |
| 223 | 0.084 | 0.061 |
| 264 | 0.202 | 0.121 |
| 305 | >10 | >10 |
| 346 | 1.049 | 0.784 |
| 387 | >10 | >10 |
| 428 | 0.794 | >10 |
| 469 | 0.645 | 1.298 |
| 508 | >10 | 7.264 |
| 526 | >10 | 1.178 |
| 544 | >10 | 2.722 |
| 562 | >10 | >10 |
| 580 | >10 | >10 |
| 598 | 0.805 | 9.854 |
| 616 | >10 | >10 |
| 634 | >10 | >10 |

Example 3: Further Exemplary Biological Activity of Compounds of the Disclosure Six-to-eight-week-old female athymic Balb/c nude mice were housed with a temperature-controlled and 12-hour light/12-hour dark cycle environment. For in vivo colon cancer tumor growth, $5 \times 10^6$ RKO cells were prepared in 100 μl of DMEM and injected into right flank of female nude mice. Mouse weight and tumor volume were measured twice a week. Tumor volumes were calculated as length× width²×0.5. Once the tumor volume had reached about 150-175 mm³, xenografts were randomized into groups (8 mice per group). Animals were treated with vehicle, Compound 80 or oxaliplatin as mentioned in the table. The formulation for vehicle and Compound 80 was 50% PEG400 and 20% Cremophor RH40 final (50% of 40% Cremophor) in Acetate buffer, PH=4. Oxaliplatin was prepared in glucose solution. The mice were sacrificed after around 3 weeks or if the tumors reached a predefined tumor volume cut-off of 2500 mm³. Compound 80 showed strong tumor growth inhibition in a dose-dependent manner in the RKO xenograft with a TGI of 85% at the highest dose (FIG. 1).

| Group # | Compound | Mice/ group | Dose (mg/ kg) | Dose Vol (μl/g) | Route | Regimen | Of doses |
|---|---|---|---|---|---|---|---|
| 1 | Vehicle | 8 | — | 4 | PO | BID | 20 Days |
| 2 | 80 | 8 | 20 | 4 | PO | BID | 20 Days |
| 3 | 80 | 8 | 30 | 4 | PO | BID | 20 Days |
| 4 | 80 | 8 | 50 | 4 | PO | QD | 20 Days |
| 5 | Oxaliplatin | 8 | 5 | 4 | IP | Twice a week | 20 Days |

Compound 80 was tested in other xenograft models using the following cell lines: triple negative breast cancer cell line, MDA-MB-231, ovarian cancer cell line, SKOV-3 and endometrium cell line, HEC-59. For the SKOV-3 xenograft, $1.5 \times 10^7$ SKOV-3 cells in 200 μl of 1:1 DMEM: Matrigel (Thermo Fisher, NJ, USA) and for the MDA-MB-231 xenograft, $1.5 \times 10^7$ MDA-MB-231 cells in 100 μl of 1:1 DMEM: Matrigel (Thermo Fisher, NJ, USA) for was injected in the right flank of six-to-eight-week-old female athymic Balb/c nude mice. When the tumor volume reached mean of ~200 mm³ mice for SKOV-3 xenografts and between 150-175 mm³ for MDA-MB-231 xenografts, mice were randomized in a group of 8, and treatment was initiated vehicle, 20 mpk BID, 25 mpk BID and 30 mpk BID of Compound 80. For the HEC-59 xenografts, $1. \times 10^7$ HEC-59 cells in in 100 μl of DMEM (Lonza, NJ, USA) was injected in the right flank of six-to-eight-week-old female athymic Balb/c nude mice. When the tumor volume reached mean of ~150 mm³ mice were randomized in a group of 8 mice, and treatment was initiated vehicle, 20 mpk BID, 40 mpk QD and 30/40 mpk BID of Compound 80. Statistically significant tumor growth inhibition or regression was observed.

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

We claim:

1. A compound represented by formula Mc or a pharmaceutically acceptable salt thereof:

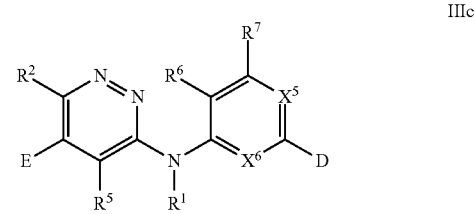

IIIc wherein:
E is aryl, heteroaryl, or heterocyclyl;
D is

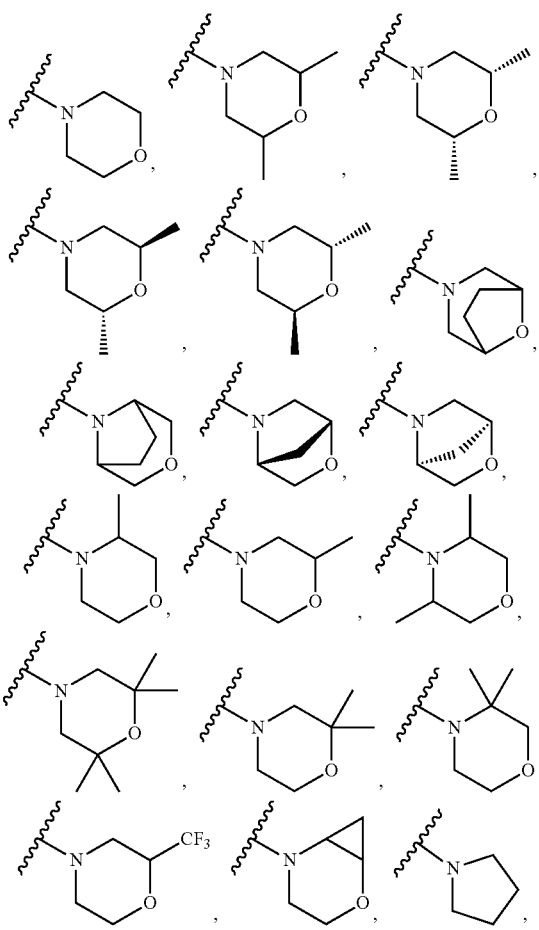

311

-continued

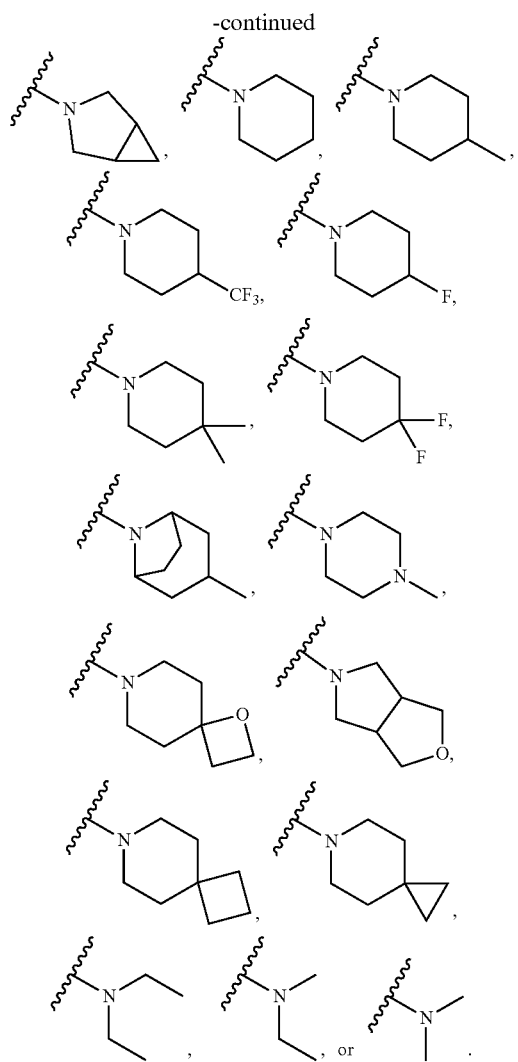

$X^5$ is N or $CR^8$;

$X^6$ is N or $CR^9$;

$R^1$ is H, alkyl, or benzyl;

$R^2$, $R^5$, $R^6$, $R^7$, $R^8$, and $R^9$ are each independently H, alkyl, alkenyl, alkynyl, halo, hydroxyl, carboxy, acyl, acetyl, ester, thioester, alkoxy, phosphoryl, amino, amido, cyano, nitro, azido, alkylthio, alkenyl, alkynyl, cycloalkyl, alkylsulfonyl, or sulfonamido.

2. The compound of claim 1, wherein $R^1$ is H.

3. The compound of claim 1, wherein $R^2$ is H, alkyl, halo, hydroxyl, alkoxy, amino, amido, acetyl, carboxy, or ester.

4. The compound of claim 1, wherein $R^6$ is H, hydroxyl, halo, alkyl, or alkoxy.

5. The compound of claim 1, wherein $R^6$ is halo.

6. The compound of claim 1, wherein $R^7$ is H, alkyl, halo, acyl, or amido.

7. The compound of claim 1, wherein $R^7$ is H.

8. The compound of claim, 1, wherein $X^5$ and $X^6$ are each N.

9. The compound of claim, 1, wherein $X^5$ is CH and $X^6$ is N.

312

10. The compound of claim 1, wherein D is

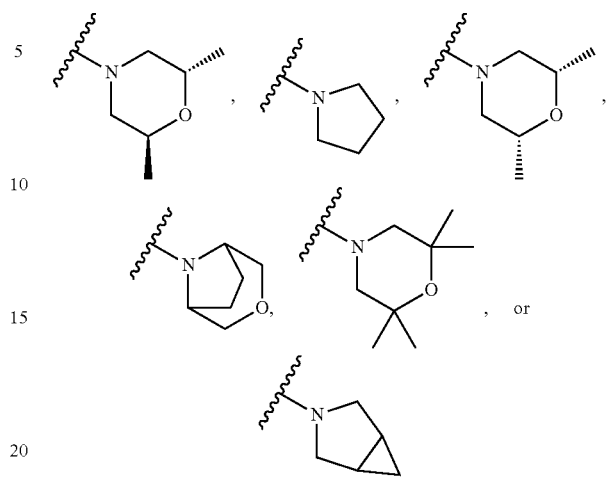

11. The compound of claim 1, wherein E has a structure represented by formula VIa, VIb, or VIc:

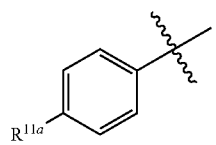
VIa

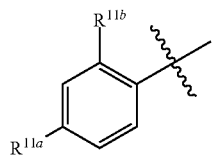
VIb

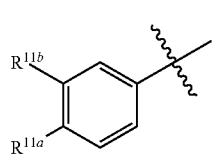
VIc wherein $R^{11a}$ and $R^{11b}$ are each independently selected from hydrogen, deuterium, alkyl, alkenyl, alkynyl, halo, hydroxyl, carboxyl, acyl, acetyl, ester, thioester, alkoxy, phosphoryl, amino, amido, cyano, nitro, azido, alkylthio, alkenyl, alkynyl, cycloalkyl, alkylsulfonyl, and sulfonamido.

12. The compound of 10, wherein $R^{11a}$ is difluoromethoxy.

13. The compound of 10, wherein $R^{11a}$ is halo.

14. The compound of claim 1, wherein E is

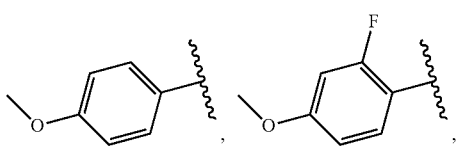

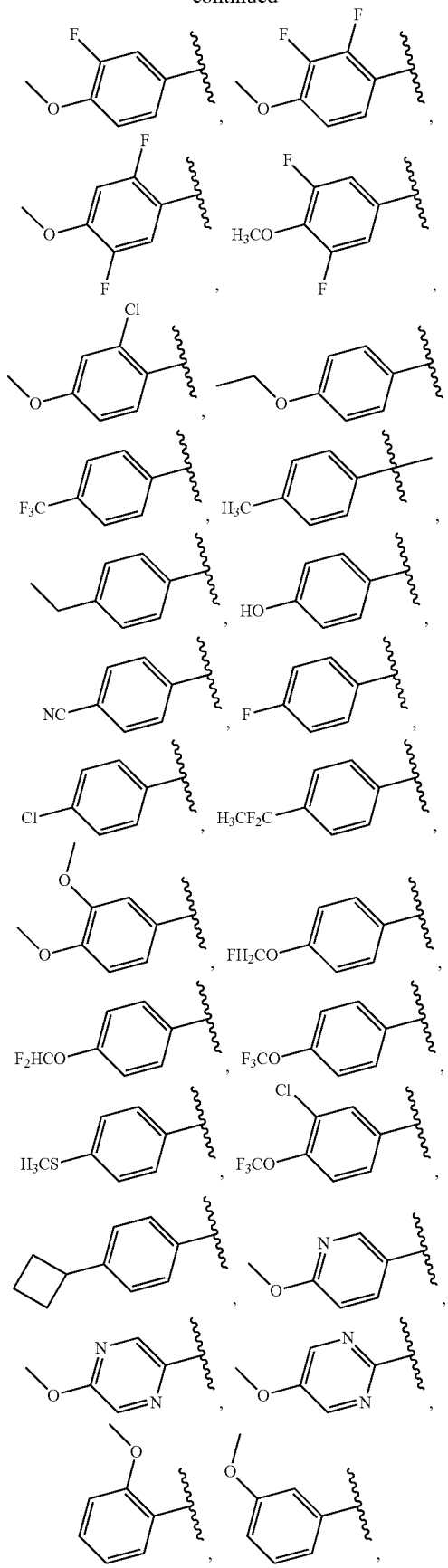

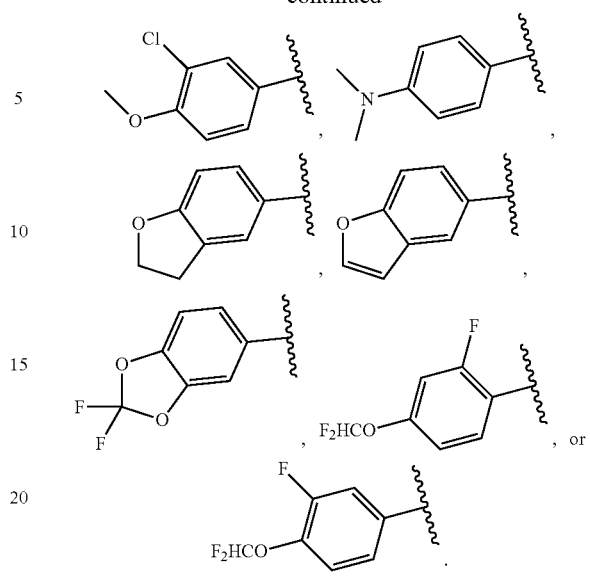

15. The compound of claim 1, wherein the compound is represented by formula VIIb, or a pharmaceutically acceptable salt thereof:

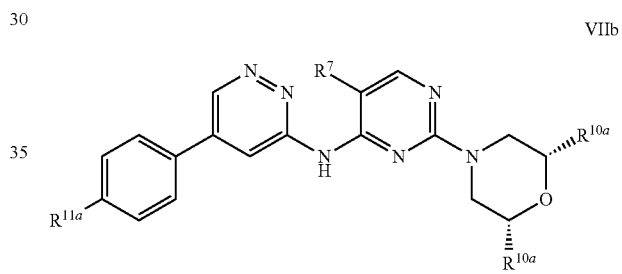

wherein:
- $R^7$ is H, alkyl, alkenyl, alkynyl, halo, hydroxyl, oxo, carboxyl, acyl, acetyl, ester, thioester, alkoxy, phosphoryl, amino, amido, cyano, nitro, azido, alkylthio, alkenyl, alkynyl, cycloalkyl, alkylsulfonyl, or sulfonamide;
- $R^{10a}$ and $R^{10b}$ are each methyl; and
- $R^{11a}$ is hydrogen, deuterium, alkyl, alkenyl, alkynyl, halo, hydroxyl, carboxyl, acyl, acetyl, ester, thioester, alkoxy, phosphoryl, amino, amido, cyano, nitro, azido, alkylthio, alkenyl, alkynyl, cycloalkyl, alkylsulfonyl, or sulfonamido.

16. The compound of claim 1, wherein the compound is selected from

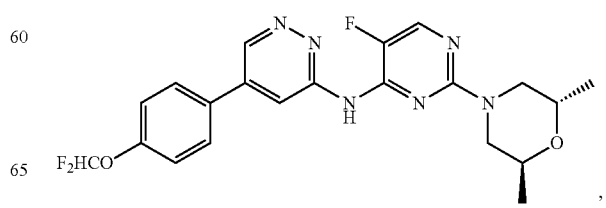

-continued
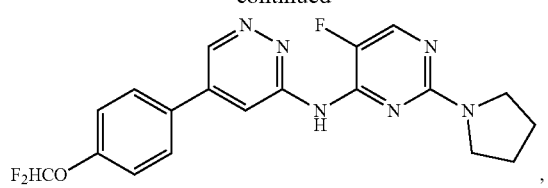
,
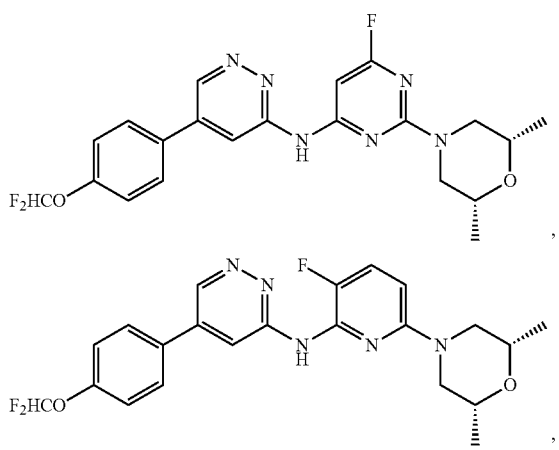
,
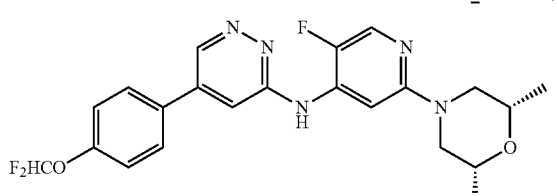
,
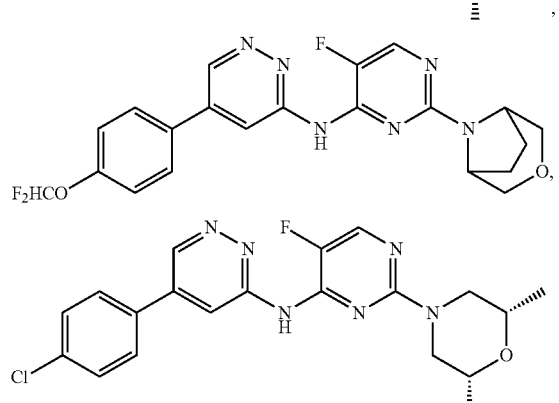
,
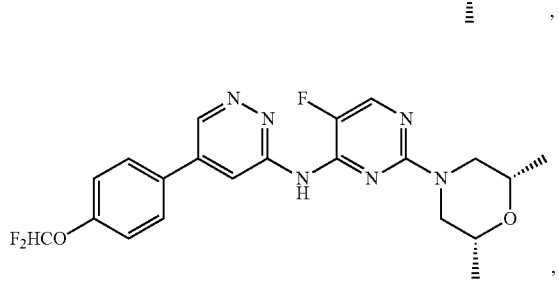
, and
-continued
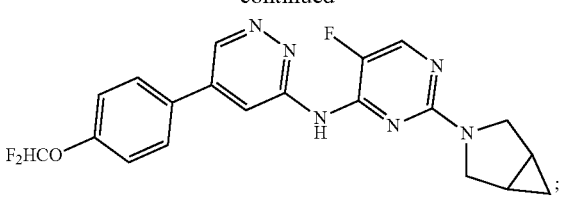
;
or a pharmaceutically acceptable salt thereof.
17. The compound of claim 16, wherein the compound is
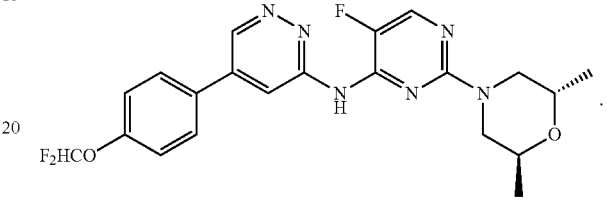
.
18. The compound of claim 16, wherein the compound is
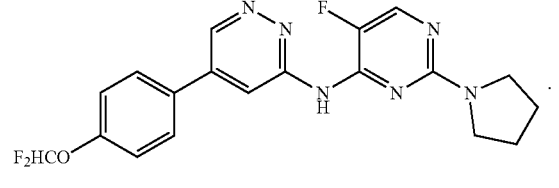 [SMILES: Fc1cnc(N2CCCC2)nc1Nc1cc(-c2ccc(OC(F)F)cc2)cnn1]
.
19. The compound of claim 16, wherein the compound is
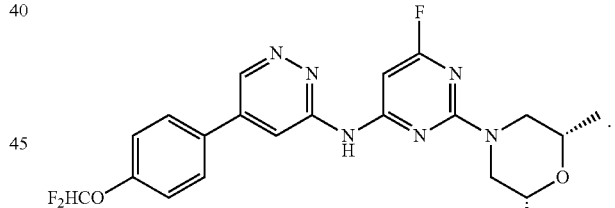
.
20. The compound of claim 16, wherein the compound is
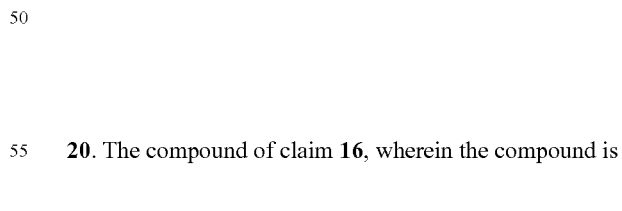
.

21. The compound of claim 16, wherein the compound is
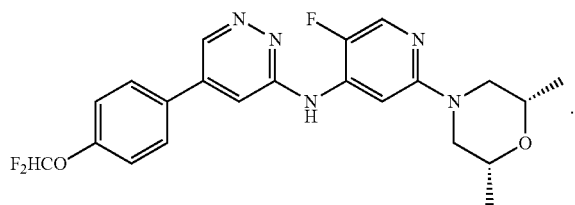
22. The compound of claim 16, wherein the compound is
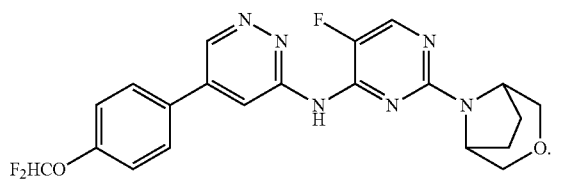 [SMILES: Fc1cnc(N2C3CCC2COC3)nc1Nc1cc(-c2ccc(OC(F)F)cc2)cnn1]
23. The compound of claim 16, wherein the compound is
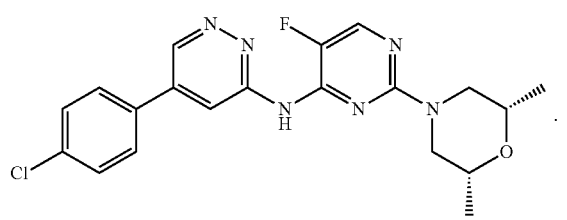 [SMILES: C[C@@H]1CN(c2ncc(F)c(Nc3cc(-c4ccc(Cl)cc4)cnn3)n2)C[C@H](C)O1]
24. The compound of claim 16, wherein the compound is
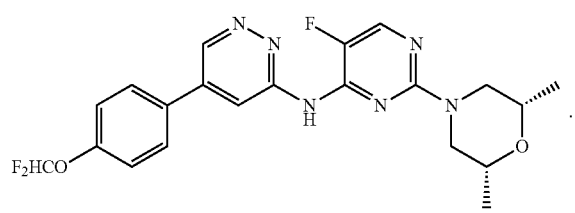 [SMILES: C[C@@H]1CN(c2ncc(F)c(Nc3cc(-c4ccc(OC(F)F)cc4)cnn3)n2)C[C@H](C)O1]
25. The compound of claim 16, wherein the compound is
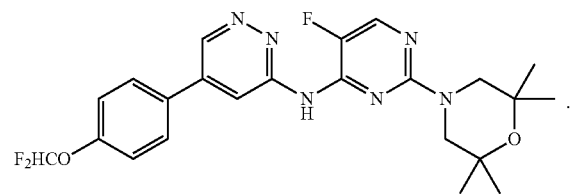 [SMILES: CC1(C)CN(c2ncc(F)c(Nc3cc(-c4ccc(OC(F)F)cc4)cnn3)n2)CC(C)(C)O1]
26. The compound of claim 16, wherein the compound is
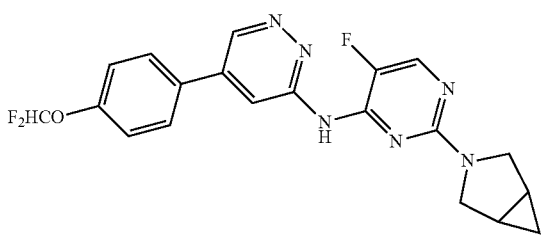
27. The compound of claim 1, wherein E is
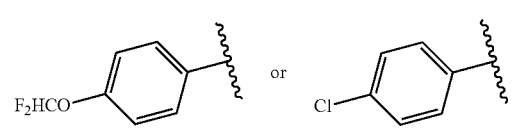
28. The compound of claim 1, wherein:
D is
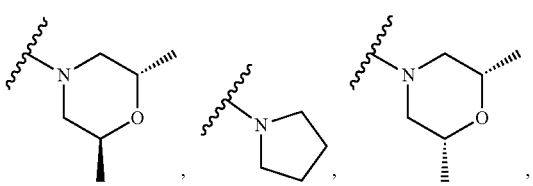
* * * * *